US012622813B2

(12) United States Patent
DiGrazia

(10) Patent No.: US 12,622,813 B2
(45) Date of Patent: May 12, 2026

(54) WOUND AND BANDAGE PROTECTION SYSTEM AND METHOD

(71) Applicant: Jennifer DiGrazia, Brooklyn, NY (US)

(72) Inventor: Jennifer DiGrazia, Brooklyn, NY (US)

( * ) Notice: Subject to any disclaimer, the term of this patent is extended or adjusted under 35 U.S.C. 154(b) by 301 days.

(21) Appl. No.: 17/060,950

(22) Filed: Oct. 1, 2020

(65) Prior Publication Data

US 2021/0085527 A1     Mar. 25, 2021

Related U.S. Application Data

(60) Division of application No. 15/831,692, filed on Dec. 5, 2017, now Pat. No. 12,427,068, which is a continuation of application No. 13/807,404, filed as application No. PCT/US2011/042216 on Jun. 28, 2011, now Pat. No. 9,833,361, which is a
(Continued)

(51) Int. Cl.
| | |
|---|---|
| *A61F 13/00* | (2024.01) |
| *A61D 9/00* | (2006.01) |
| *A61F 13/01* | (2024.01) |
| *A61F 13/02* | (2006.01) |
(Continued)

(52) U.S. Cl.
CPC .......... *A61F 13/01021* (2024.01); *A61D 9/00* (2013.01); *A61F 13/0203* (2013.01); *A61F 13/0273* (2013.01); *A61F 15/004* (2013.01); *A61F 2013/00544* (2013.01)

(58) Field of Classification Search
USPC ........................................... 602/3
See application file for complete search history.

(56) References Cited

U.S. PATENT DOCUMENTS

| | | | |
|---|---|---|---|
| 250,154 A | 11/1881 | Master | |
| 679,918 A | 8/1901 | Shears | |
(Continued)

FOREIGN PATENT DOCUMENTS

| | | |
|---|---|---|
| CH | 676197 | 12/1990 |
| CN | 2538314 | 3/2003 |
(Continued)

OTHER PUBLICATIONS

Final OA Dated Oct. 8, 2013 in Corresponding U.S. Appl. No. 13/004,866.
(Continued)

*Primary Examiner* — Kim M Lewis
(74) *Attorney, Agent, or Firm* — Shore IP Group, PLLC; Eric J. Strianese

(57) ABSTRACT

A wound/bandage protector configured as a wrap, a sock/ mitten, or a bandage may be made out of stretchable material. The wrap may have one or more fastening straps as well as possibly a first catch fastening surface. The sock/ mitten may have a fastening strap and a sheath. The wrap, the sock/mitten, and the bandages may have apertures and aperture covers. In addition, the wound/bandage protectors as well as the bandages may have diamond or triangular gauze configurations with the gauze pad having three or four primary corners, the primary corners of the gauze pad in most instances being oriented towards edges of the body portion or length or width tangents of the body portion, preferably mid-points or mid-sections of the length or width tangents or body portion edges.

16 Claims, 66 Drawing Sheets

Related U.S. Application Data continuation-in-part of application No. 13/004,866, filed on Jan. 11, 2011, now abandoned, and a continuation-in-part of application No. 12/826,644, filed on Jun. 29, 2010, now Pat. No. 8,591,447.

(60) Provisional application No. 61/453,341, filed on Mar. 16, 2011, provisional application No. 61/360,873, filed on Jul. 1, 2010.

(51) Int. Cl.
　　*A61F 13/0203*　　　(2024.01)
　　*A61F 15/00*　　　　(2006.01)

(56) References Cited

U.S. PATENT DOCUMENTS

| | | | |
|---|---|---|---|
| 697,637 | A | 4/1902 | Lee |
| 1,457,858 | A | 6/1923 | Ruddell |
| 1,610,089 | A | 12/1926 | Heitler |
| 2,233,209 | A | 2/1941 | Herzog |
| 2,273,873 | A | 2/1942 | Klein |
| 2,310,082 | A | 2/1943 | Holbrooke |
| 2,321,363 | A | 6/1943 | Crowley et al. |
| 2,367,690 | A | 1/1945 | Purdy |
| 2,632,443 | A | 3/1953 | Lesher |
| 2,823,672 | A | 2/1958 | Schlardermundt |
| 2,897,961 | A | 8/1959 | Bush |
| 2,924,331 | A | 2/1960 | Hoey |
| 3,245,406 | A | 4/1966 | Chardack |
| 3,297,034 | A | 1/1967 | Peavy |
| 3,419,003 | A | 12/1968 | Krauss et al. |
| 3,442,270 | A | 5/1969 | Steinman et al. |
| 3,476,109 | A | 11/1969 | Hurney |
| 3,504,672 | A | 4/1970 | Moon et al. |
| 3,561,436 | A | 2/1971 | Gaylord et al. |
| 3,657,741 | A | 4/1972 | Blanco |
| 3,667,462 | A | 6/1972 | Moon |
| 3,741,203 | A * | 6/1973 | Liman ................... A61F 15/004 |
| | | | 602/3 |
| 3,784,014 | A | 1/1974 | Turner |
| 3,874,014 | A | 4/1975 | Davey |
| 3,880,161 | A | 4/1975 | Fossel |
| 3,954,105 | A | 5/1976 | Nordby et al. |
| 3,970,079 | A | 7/1976 | Gaylord |
| 4,036,220 | A | 7/1977 | Bellasalma |
| 4,088,136 | A | 5/1978 | Hasslinger et al. |
| 4,126,130 | A | 11/1978 | Cowden et al. |
| 4,254,765 | A * | 3/1981 | Brown ................... A61F 15/004 |
| | | | 602/3 |
| 4,263,906 | A | 4/1981 | Finley |
| D265,423 | S | 7/1982 | Abraham et al. |
| 4,355,635 | A | 10/1982 | Bihl et al. |
| 4,399,816 | A | 8/1983 | Spangler |
| 4,461,098 | A | 7/1984 | Diegelman |
| 4,530,350 | A * | 7/1985 | Brown ................... A61F 13/041 |
| | | | 602/3 |
| 4,641,643 | A | 2/1987 | Greer |
| 4,665,909 | A | 5/1987 | Trainor |
| 4,671,787 | A | 6/1987 | Widman |
| 4,724,831 | A | 2/1988 | Huntjens |
| 4,727,864 | A | 3/1988 | Wiesenthal et al. |
| 4,881,276 | A * | 11/1989 | Swan ............... A41D 19/01529 |
| | | | 2/167 |
| 4,907,579 | A | 3/1990 | Kum |
| 4,909,243 | A | 3/1990 | Frank et al. |
| 4,911,151 | A | 3/1990 | Rankin et al. |
| 4,911,156 | A | 3/1990 | Libertucci |
| 4,991,234 | A | 2/1991 | Greenberg |
| 5,085,210 | A | 2/1992 | Smith, III |
| 5,086,763 | A | 2/1992 | Hathman |
| 5,137,508 | A | 8/1992 | Engman |
| 5,244,523 | A | 9/1993 | Tollini |
| D340,985 | S | 11/1993 | Arginsky |
| 5,271,745 | A | 12/1993 | Fentress et al. |
| 5,342,286 | A | 8/1994 | Kelly et al. |
| 5,354,261 | A | 10/1994 | Clark et al. |
| 5,395,302 | A * | 3/1995 | Botha ................... A61F 15/004 |
| | | | 128/849 |
| 5,449,340 | A | 9/1995 | Tollini |
| 5,456,660 | A | 10/1995 | Reich et al. |
| 5,495,828 | A | 3/1996 | Solomon et al. |
| 5,513,658 | A | 5/1996 | Goseki |
| 5,538,500 | A | 7/1996 | Peterson |
| 5,562,107 | A | 10/1996 | Lavender et al. |
| 5,591,122 | A | 1/1997 | Yewer, Jr. |
| 5,592,953 | A | 1/1997 | Delao |
| D383,544 | S | 9/1997 | Heckathorn |
| 5,662,599 | A | 9/1997 | Reich et al. |
| 5,702,356 | A | 12/1997 | Hathman |
| D389,244 | S | 1/1998 | Dunshee et al. |
| 5,720,713 | A * | 2/1998 | Hutchison ............. A61F 15/008 |
| | | | 604/179 |
| 5,735,807 | A | 4/1998 | Cropper |
| 5,755,698 | A | 5/1998 | Kagan et al. |
| 5,786,365 | A | 7/1998 | Heitsch et al. |
| 5,817,038 | A * | 10/1998 | Orange ................. A61F 13/041 |
| | | | 602/62 |
| 5,820,578 | A | 10/1998 | Johansen |
| 5,843,018 | A | 12/1998 | Shesol et al. |
| 5,843,025 | A | 12/1998 | Shaari |
| D404,134 | S | 1/1999 | Dunshee |
| D404,135 | S | 1/1999 | Dunshee |
| 5,865,776 | A | 2/1999 | Springs |
| 5,873,365 | A | 2/1999 | Brown |
| 5,876,365 | A | 3/1999 | Hart |
| 5,897,519 | A | 4/1999 | Shesol et al. |
| 5,918,599 | A | 7/1999 | Shesol |
| 5,919,180 | A | 7/1999 | Raimondo |
| 5,921,949 | A | 7/1999 | Dray |
| 5,964,721 | A | 10/1999 | Augustine |
| 5,994,613 | A | 11/1999 | Cummings et al. |
| 6,000,366 | A | 12/1999 | Reeping |
| 6,013,097 | A | 1/2000 | Augustine et al. |
| 6,032,289 | A | 3/2000 | Villapiano |
| 6,059,834 | A | 5/2000 | Springs |
| 6,070,557 | A | 6/2000 | Hibbert |
| 6,164,279 | A | 12/2000 | Tweedle |
| D437,217 | S | 2/2001 | Bloor et al. |
| 6,186,097 | B1 | 2/2001 | Brockmann et al. |
| 6,191,338 | B1 | 2/2001 | Haller |
| 6,255,552 | B1 | 7/2001 | Cummings et al. |
| 6,257,240 | B1 | 7/2001 | Shesol |
| 6,258,051 | B1 | 7/2001 | Shesol et al. |
| 6,274,787 | B1 | 8/2001 | Downing |
| 6,293,917 | B1 | 9/2001 | Augustine et al. |
| 6,307,118 | B1 | 10/2001 | Reich |
| D454,956 | S | 3/2002 | Visintainer |
| 6,399,852 | B1 | 6/2002 | Barron |
| D461,250 | S | 8/2002 | Berry |
| D463,564 | S | 9/2002 | Siegwart et al. |
| 6,512,159 | B1 | 1/2003 | Shesol et al. |
| 6,526,920 | B1 | 3/2003 | Griffin |
| D474,842 | S | 5/2003 | Wolsing et al. |
| D476,412 | S | 6/2003 | Berry |
| 6,659,970 | B1 | 12/2003 | Woodworth et al. |
| 6,664,434 | B2 | 12/2003 | Cominsky |
| 6,681,404 | B1 | 1/2004 | Adlard et al. |
| D492,786 | S | 7/2004 | Saim et al. |
| 6,762,337 | B2 | 7/2004 | Boukanov et al. |
| 6,892,733 | B2 | 5/2005 | Clinton |
| 6,894,204 | B2 | 5/2005 | Dunshee |
| 6,932,785 | B1 | 8/2005 | Shesol |
| 7,004,922 | B1 | 2/2006 | Shesol |
| 7,025,738 | B2 | 4/2006 | Hall |
| 7,091,394 | B2 | 8/2006 | Kolte et al. |
| 7,118,545 | B2 | 10/2006 | Boyde |
| 7,160,262 | B2 | 1/2007 | Wicks |
| D544,607 | S | 6/2007 | Henry et al. |
| 7,264,602 | B1 | 9/2007 | Longsworth |
| D573,260 | S | 7/2008 | Dunshee |
| 7,576,257 | B2 | 8/2009 | La Greca, Sr. |
| D601,707 | S | 10/2009 | Chouiller |
| D604,423 | S | 11/2009 | Dunshee |

(56) References Cited

U.S. PATENT DOCUMENTS

| | | | |
|---|---|---|---|
| D617,463 | S | 6/2010 | Tokumoto et al. |
| D618,811 | S | 6/2010 | Navies |
| D622,404 | S | 8/2010 | Williams |
| 7,780,615 | B1 | 8/2010 | Shesol |
| D625,018 | S | 10/2010 | Smith et al. |
| 8,529,481 | B1 | 9/2013 | Lois |
| 8,591,447 | B2 | 11/2013 | Digrazia |
| 9,833,361 | B2 | 12/2017 | DiGrazia |
| 2002/0115955 | A1 | 8/2002 | De Sena |
| 2003/0036716 | A1 | 2/2003 | Knutson et al. |
| 2003/0139696 | A1 | 7/2003 | Boukanov et al. |
| 2003/0149389 | A1 | 8/2003 | Daneshvar |
| 2003/0153861 | A1 | 8/2003 | Royer |
| 2004/0133144 | A1 | 7/2004 | Crichton |
| 2004/0199092 | A1* | 10/2004 | Biewend ............... A61F 15/004 |
| | | | 602/3 |
| 2004/0260224 | A1 | 12/2004 | Binder et al. |
| 2004/0267179 | A1 | 12/2004 | Lerman |
| 2005/0010154 | A1 | 1/2005 | Wright et al. |
| 2005/0192524 | A1 | 9/2005 | Lipshaw et al. |
| 2005/0261617 | A1 | 11/2005 | Hall |
| 2006/0116621 | A1* | 6/2006 | Barker ................. A61F 15/008 |
| | | | 602/56 |
| 2006/0116622 | A1 | 6/2006 | Pike |
| 2006/0258966 | A1* | 11/2006 | Hargrave .............. A61F 5/3753 |
| | | | 602/5 |
| 2007/0010775 | A1 | 1/2007 | Lutri |
| 2007/0033711 | A1 | 2/2007 | Achtelstetter |
| 2007/0078364 | A1 | 4/2007 | Davis Belcher |
| 2007/0232974 | A1 | 10/2007 | Serola |
| 2008/0015483 | A1 | 1/2008 | Kilbey |
| 2008/0039760 | A1 | 2/2008 | Lesko |
| 2008/0103451 | A1 | 5/2008 | Schaefer, Jr. et al. |
| 2008/0120754 | A1* | 5/2008 | Raymond ........ A41D 19/01558 |
| | | | 2/167 |
| 2008/0127907 | A1 | 6/2008 | Purtell et al. |
| 2008/0312572 | A1 | 12/2008 | Reisinger |
| 2009/0049710 | A1* | 2/2009 | Barnett .................... A43B 3/04 |
| | | | 36/50.1 |
| 2009/0221945 | A1 | 9/2009 | Andersson et al. |
| 2010/0100024 | A1 | 4/2010 | Reid |
| 2010/0331747 | A1* | 12/2010 | Ferenc ................. A61F 13/041 |
| | | | 602/3 |
| 2011/0137223 | A1* | 6/2011 | Daniel .................... A61L 15/12 |
| | | | 602/76 |
| 2011/0277283 | A1 | 11/2011 | Ward, IV |
| 2011/0319798 | A1 | 12/2011 | DiGrazia |
| 2012/0203152 | A1 | 8/2012 | Thompson |
| 2013/0102944 | A1 | 4/2013 | DiGrazia |
| 2013/0123679 | A1 | 5/2013 | DiGrazia |
| 2018/0092778 | A1 | 4/2018 | Di Grazia |

FOREIGN PATENT DOCUMENTS

| | | |
|---|---|---|
| DE | 10231701 | 2/2004 |
| FR | 2843539 | 2/2004 |
| GB | 319215 | 12/1930 |
| GB | 2358141 | 7/2001 |
| JP | 11216158 | 8/1999 |
| NZ | 280249 | 10/1997 |
| UA | 3297034 | 1/1967 |
| WO | 9406382 | 3/1994 |
| WO | 9500087 | 1/1995 |
| WO | 0238096 | 5/2002 |
| WO | 02053075 | 7/2002 |
| WO | 2006053222 | 5/2006 |
| WO | 2010015227 | 2/2010 |

OTHER PUBLICATIONS

US OA Dated Apr. 30, 2015 in Corresponding U.S. Appl. No. 13/732,355.

US OA Dated Oct. 26, 2016 in Corresponding U.S. Appl. No. 13/732,355.

US OA Dated Feb. 7, 2013 in Corresponding U.S. Appl. No. 13/004,866.

IPER Dated Jul. 9, 2015 for PCT/US2013/078532.

PCT International Search Report and Written Opinion of the International Searching Authority for PCT Application PCT/US2011/042216, mailing date—Apr. 6, 2012, 18 pages.

Bowswear, LLC, Pringed Jul. 18, 2013, Bowsewear, LLC announces "Healers Veterinary dressings"—a new class of products that changes the way pet lovers bandage and protect their pets injuries, http://sites.webed.me/healers/press-releases/howsewearllc-announces-%E2%80%9Chealers-veterinary-dressings%E2%80%93-a-new-class-of-products-that-changes-the-way-pet-lovers-bandage-and-protect-their-pets-injuries/, 2 pages.

amazom.com, Inc., Printed Jul. 18, 2013, HEALERS Medical Dog Boots and Gauze Pads, Blue, http://www.amazom.com/HEALERS-Medical-Dog-Boots-Bandages/dp/B006KJ4D2/ref=sr_1_3?s=pet-supplies&ie=UTF8&qid=1373028156, 1 page.

Office Action Dated Sep. 30, 2022 in Related U.S. Appl. No. 17/060,912.

Office Action Dated Apr. 26, 2023 in Corresponding U.S. Appl. No. 15/831,692.

Office Action Dated Mar. 9, 2023 in Corresponding U.S. Appl. No. 16/576,128.

Final Office Action Dated Oct. 18, 2023 in Corresponding U.S. Appl. No. 16/576,128.

Final Office Action Dated Oct. 25, 2023 in Corresponding U.S. Appl. No. 17/060,912.

* cited by examiner

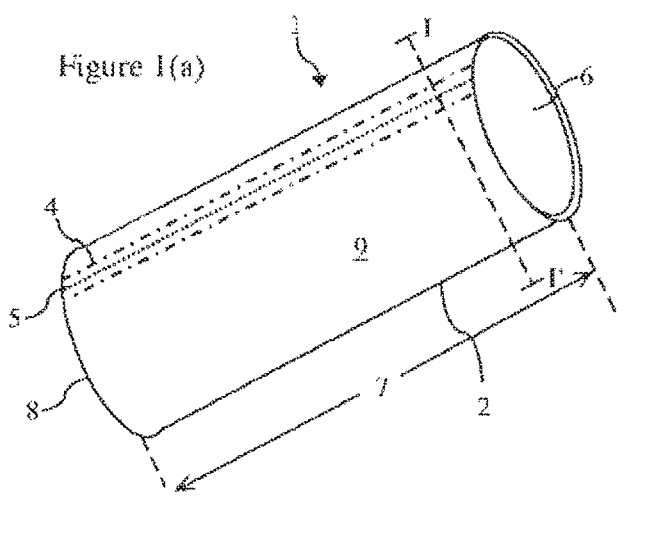
Figure 1(a)
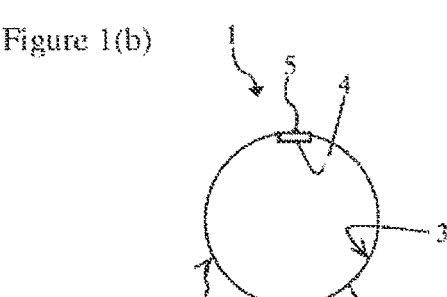
Figure 1(b)
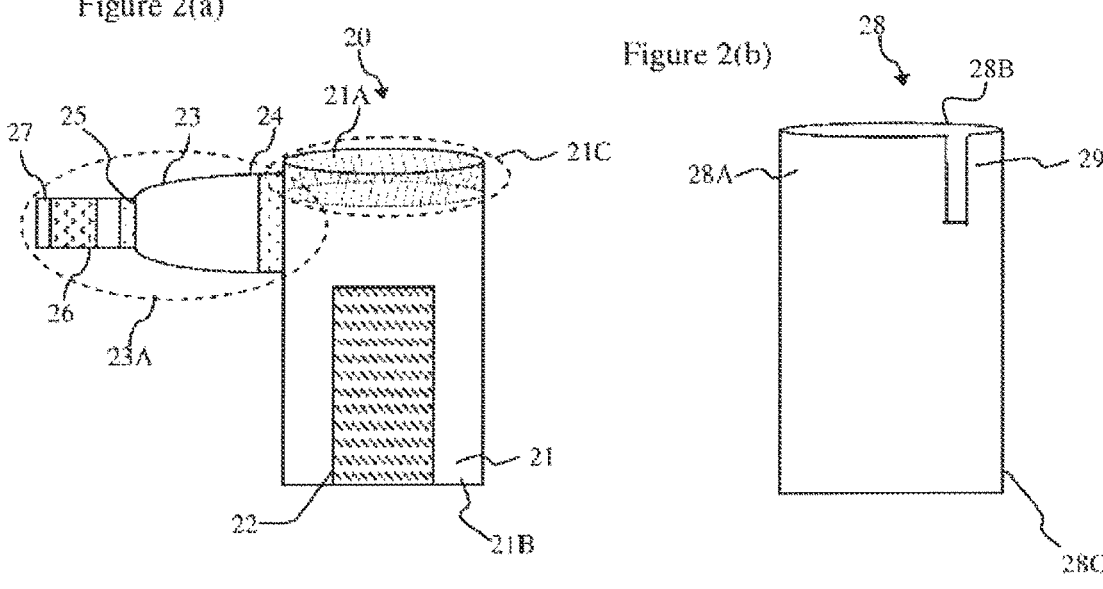
Figure 2(a)
Figure 2(b)

Figure 3(a)
Figure 3(b)
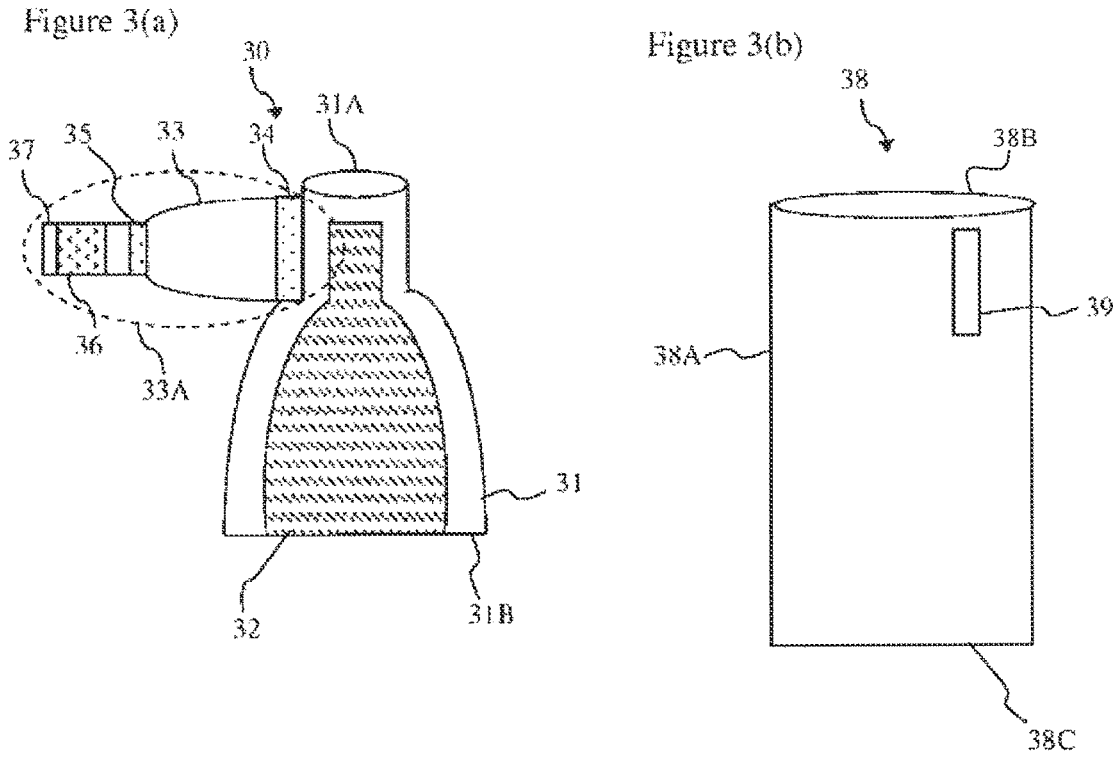
Figure 4
Figure 5
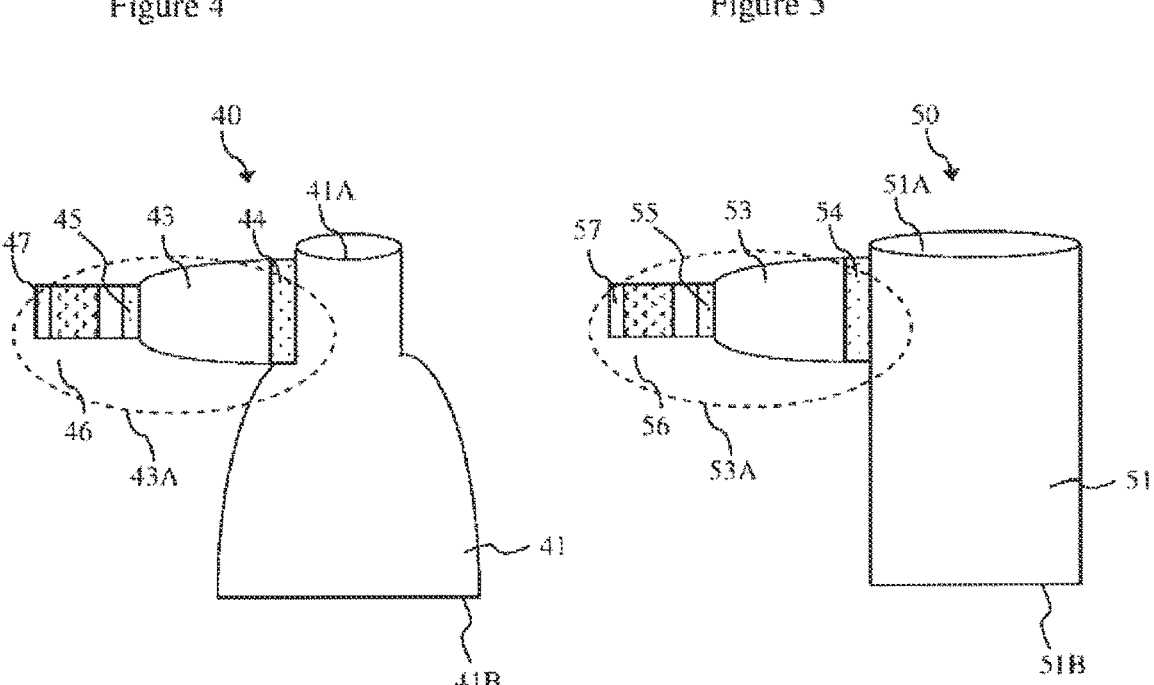

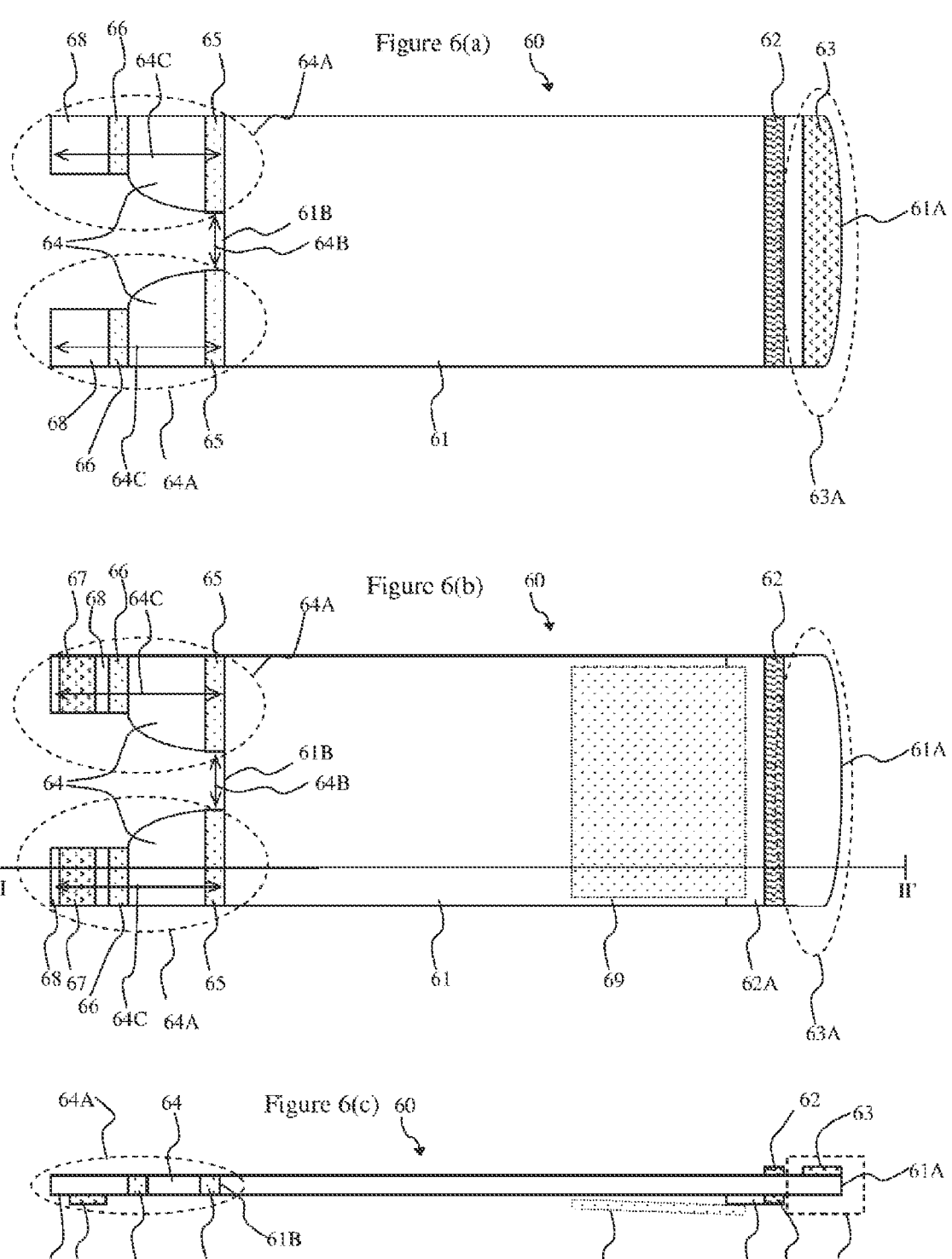

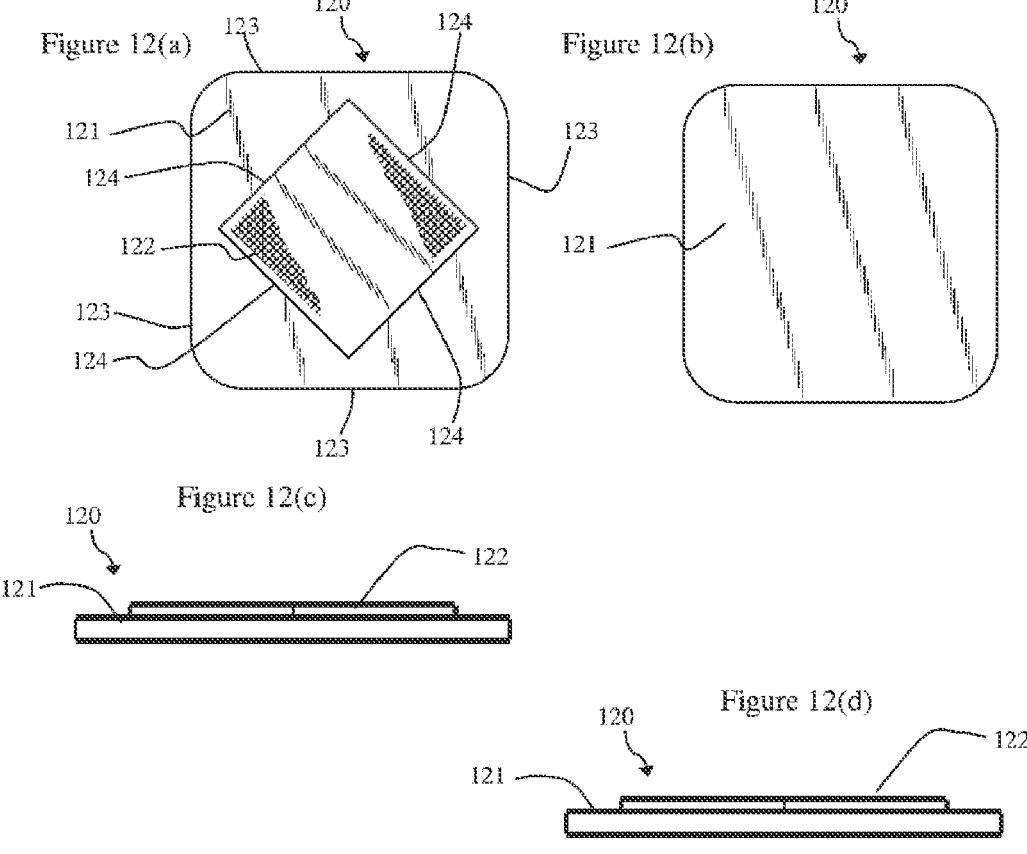
Figure 12(a)
Figure 12(b)
Figure 12(c)
Figure 12(d)
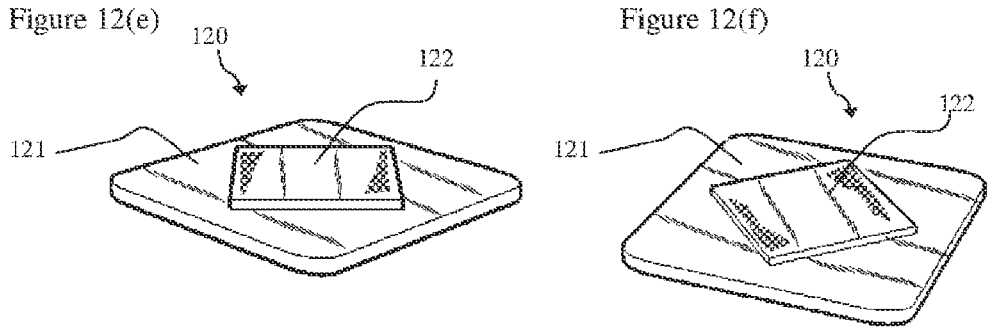
Figure 12(e)
Figure 12(f)

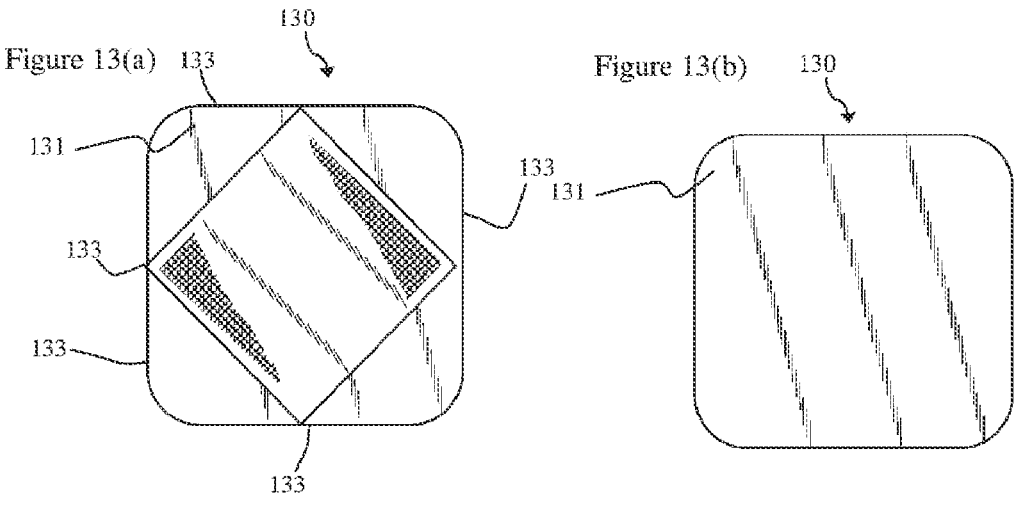
Figure 13(a)
Figure 13(b)
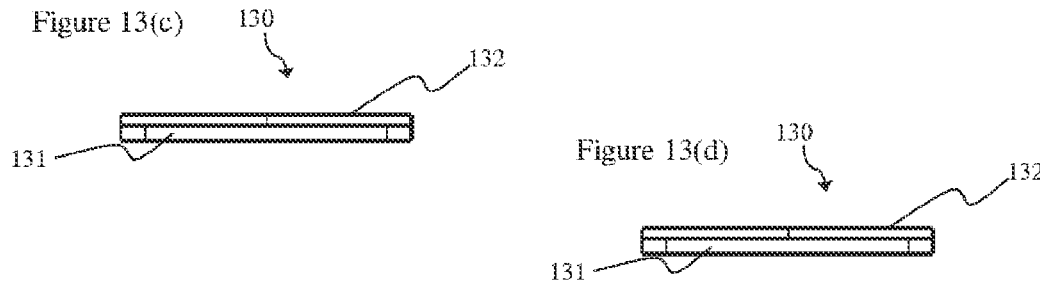
Figure 13(c)
Figure 13(d)
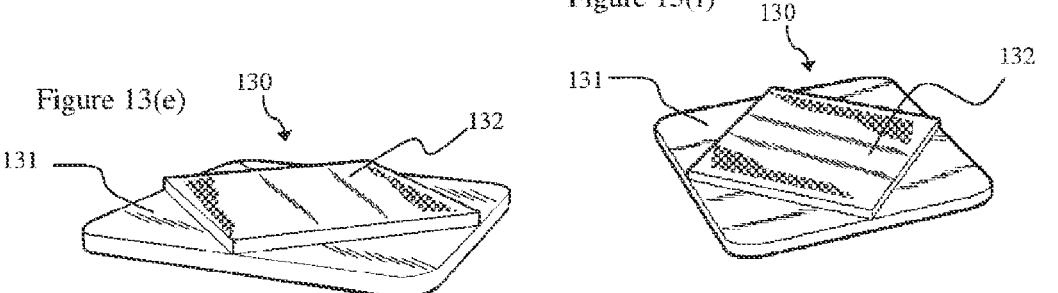
Figure 13(e)
Figure 13(f)

Figure 14(a)
140
141
142
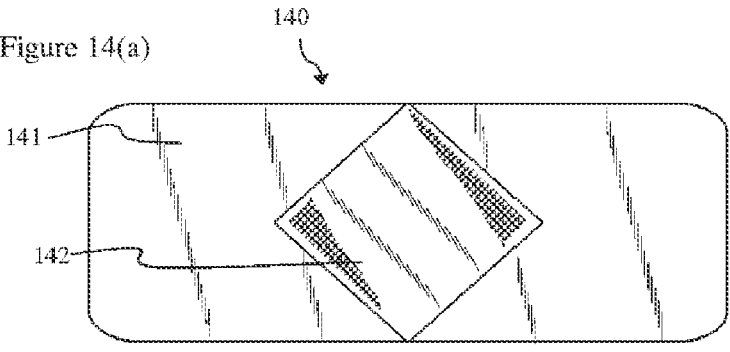
Figure 14(b)
140
141
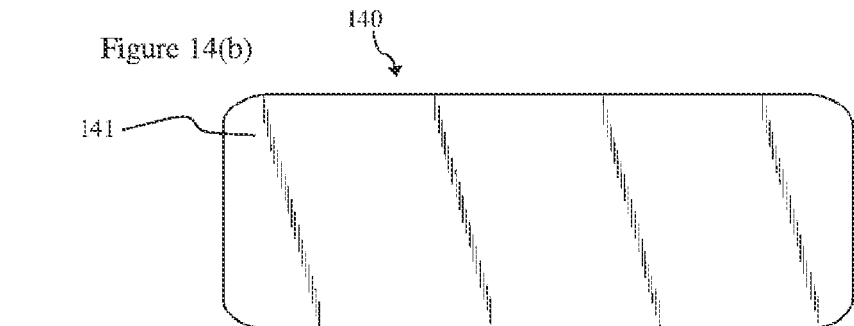
Figure 14(c)          140
141
142
Figure 14(d)          140
141
142
Figure 14(e)
141
140
142
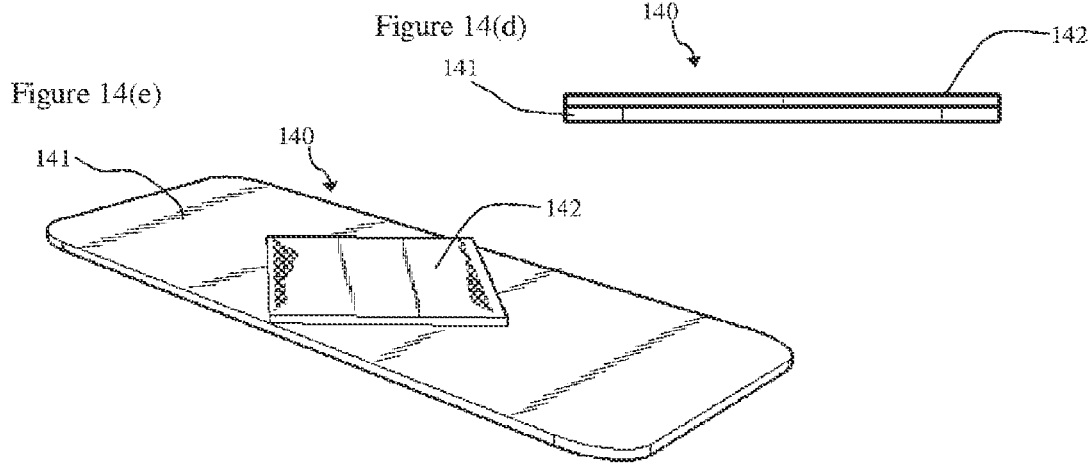

Figure 15(a)
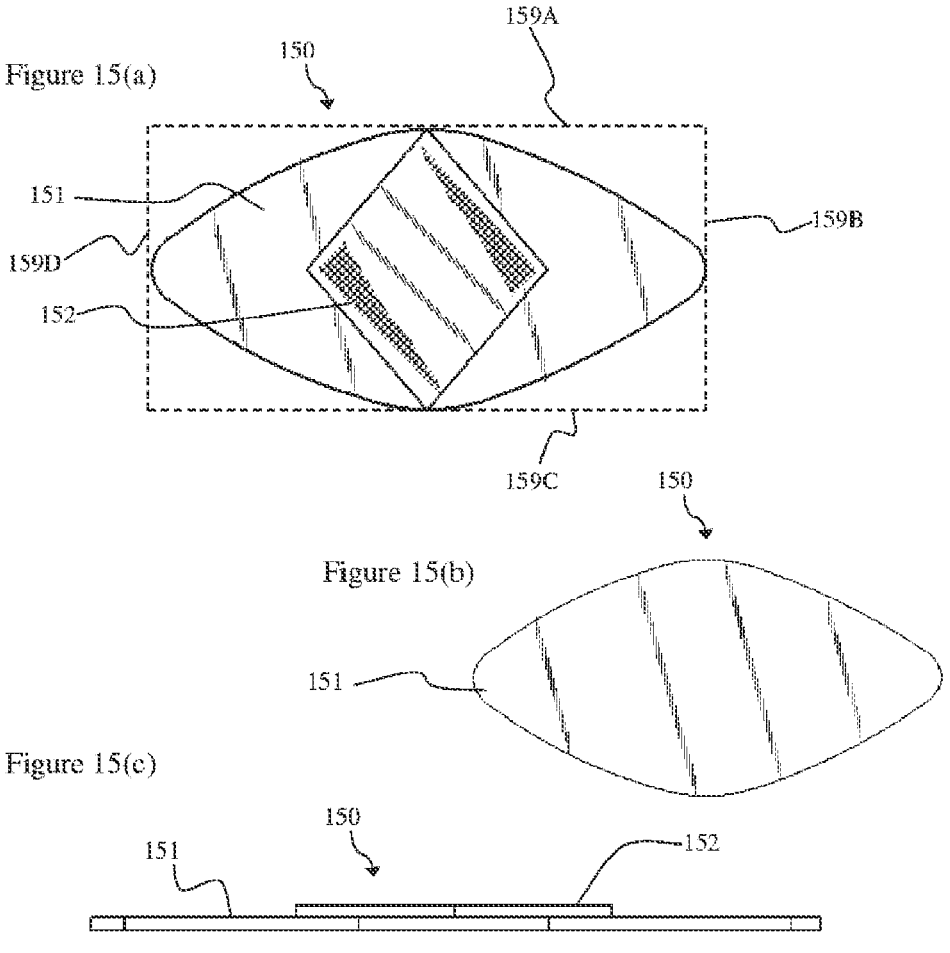
Figure 15(b)
Figure 15(c)
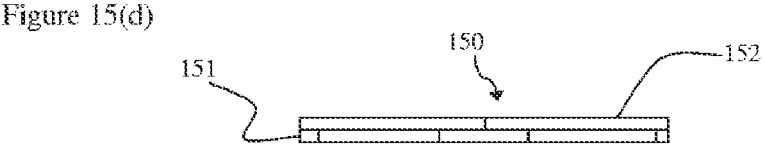
Figure 15(d)
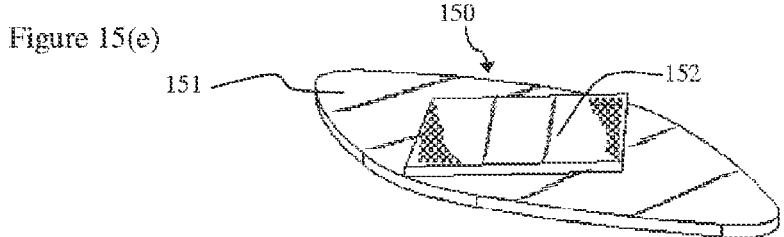
Figure 15(e)

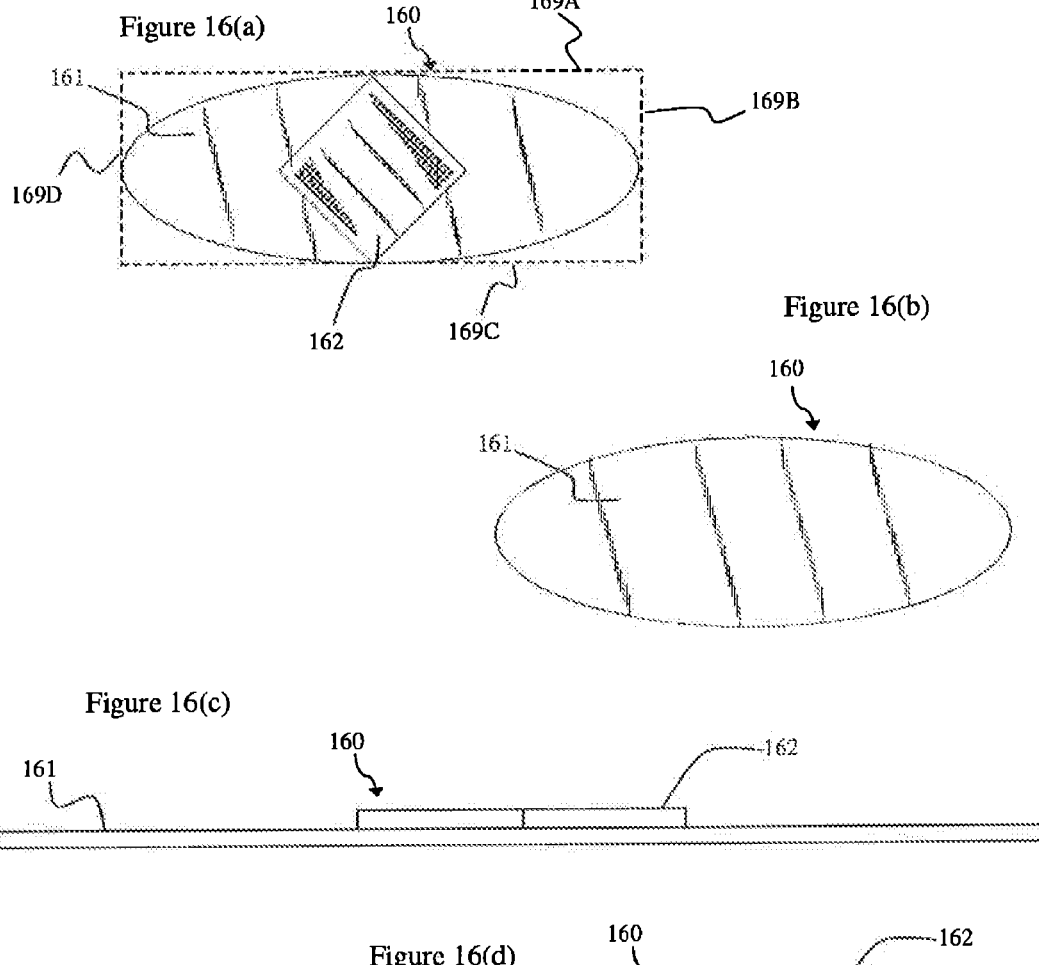
Figure 16(a)
169A
160
161
169B
169D
162
169C
Figure 16(b)
160
161
Figure 16(c)
161
160
162
Figure 16(d)
160
162
Figure 16(e)
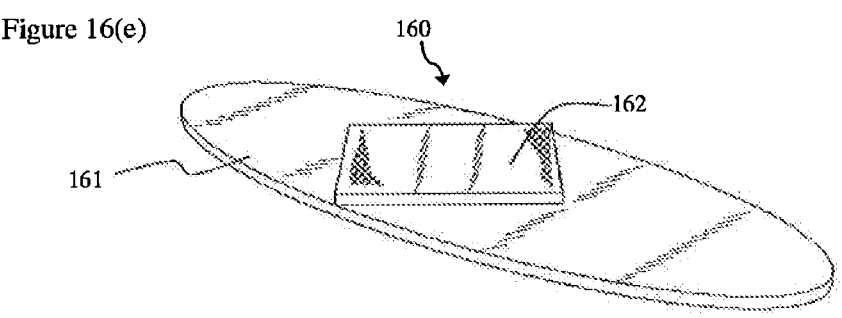
160
162
161

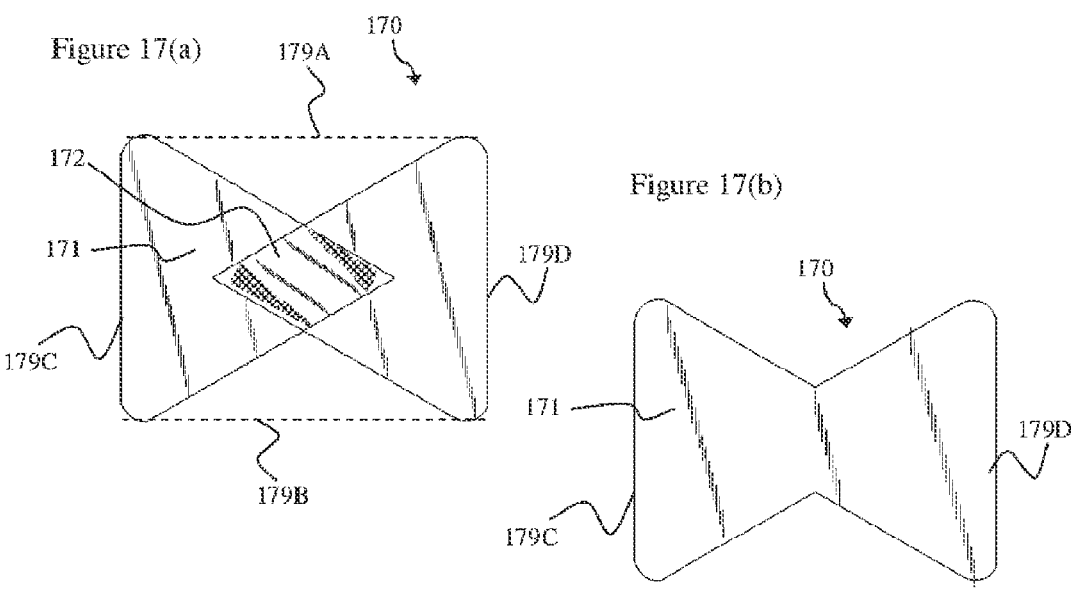
Figure 17(a)
Figure 17(b)
Figure 17(c)
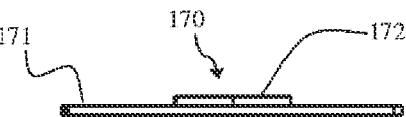
Figure 17(d)
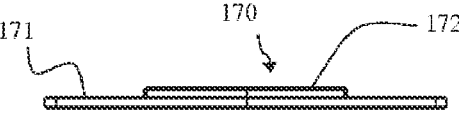
Figure 17(e)

Figure 18(a)
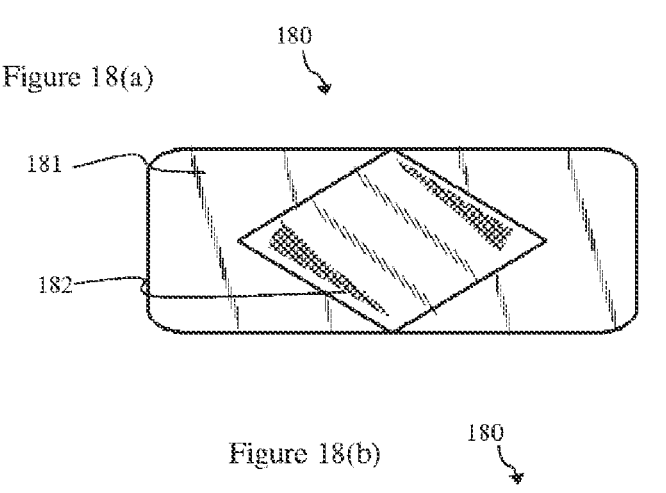
Figure 18(b)
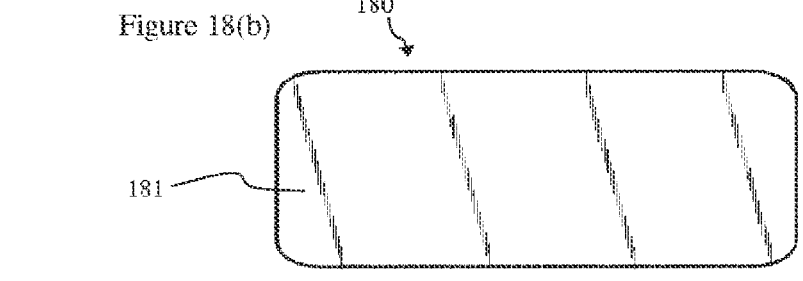
Figure 18(c)
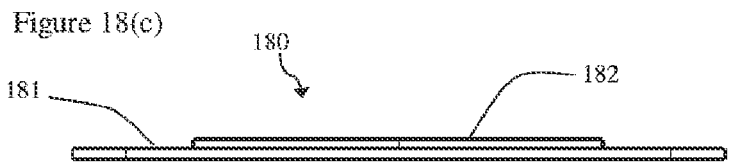
Figure 18(d)
Figure 18(e)
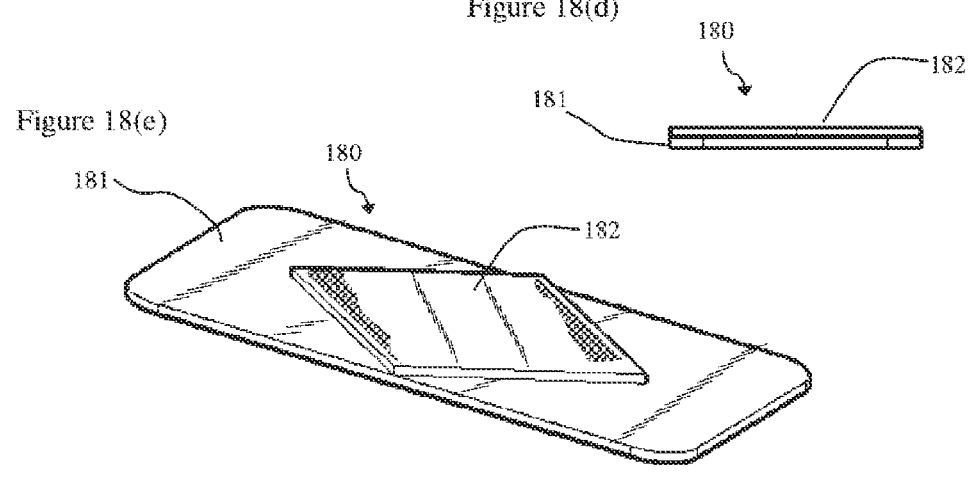

Figure 19(c)
190
192
191
Figure 19(d)
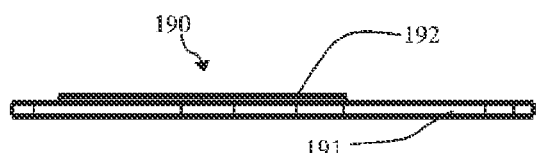
190
192
191
Figure 19(e)
190
192
191
Figure 19(f)
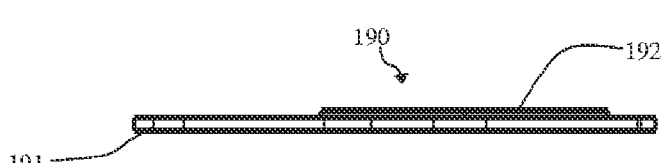
190
192
191
190
Figure 19(g)
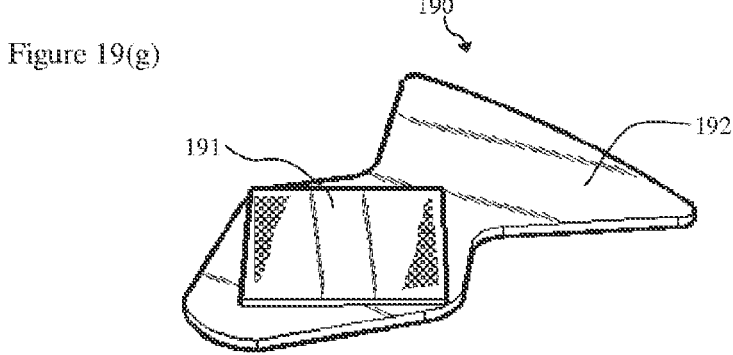
191
192

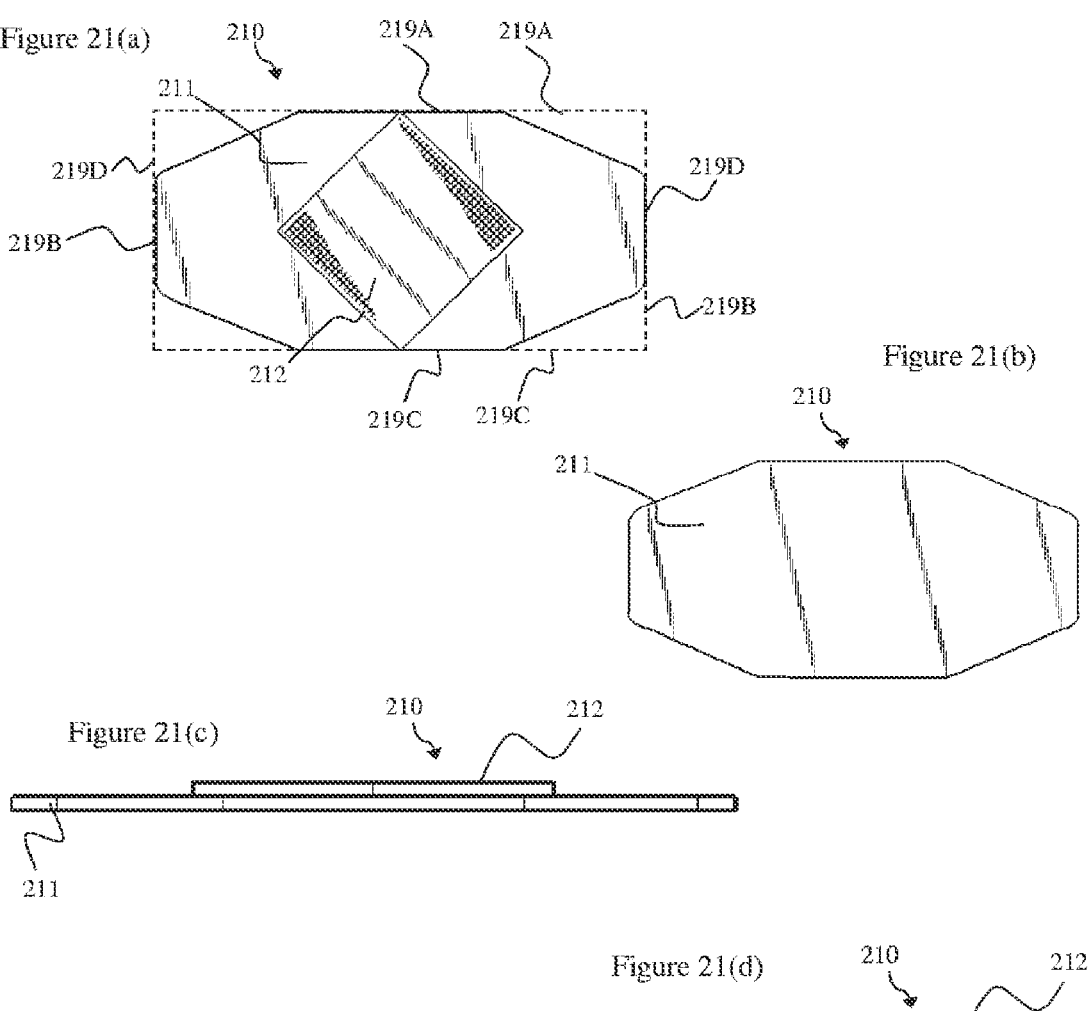
Figure 21(a)
Figure 21(b)
Figure 21(c)
Figure 21(d)
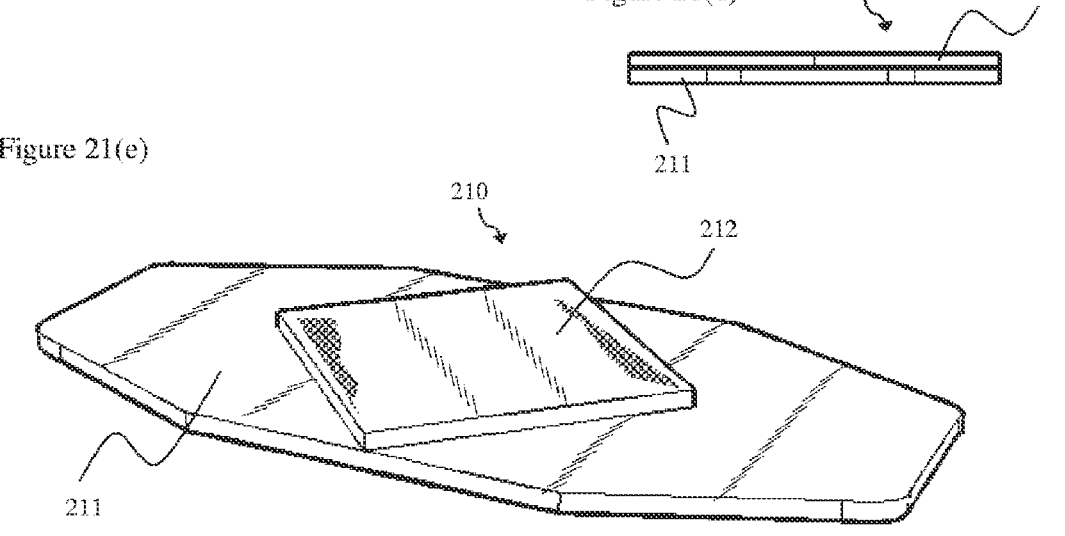
Figure 21(e)

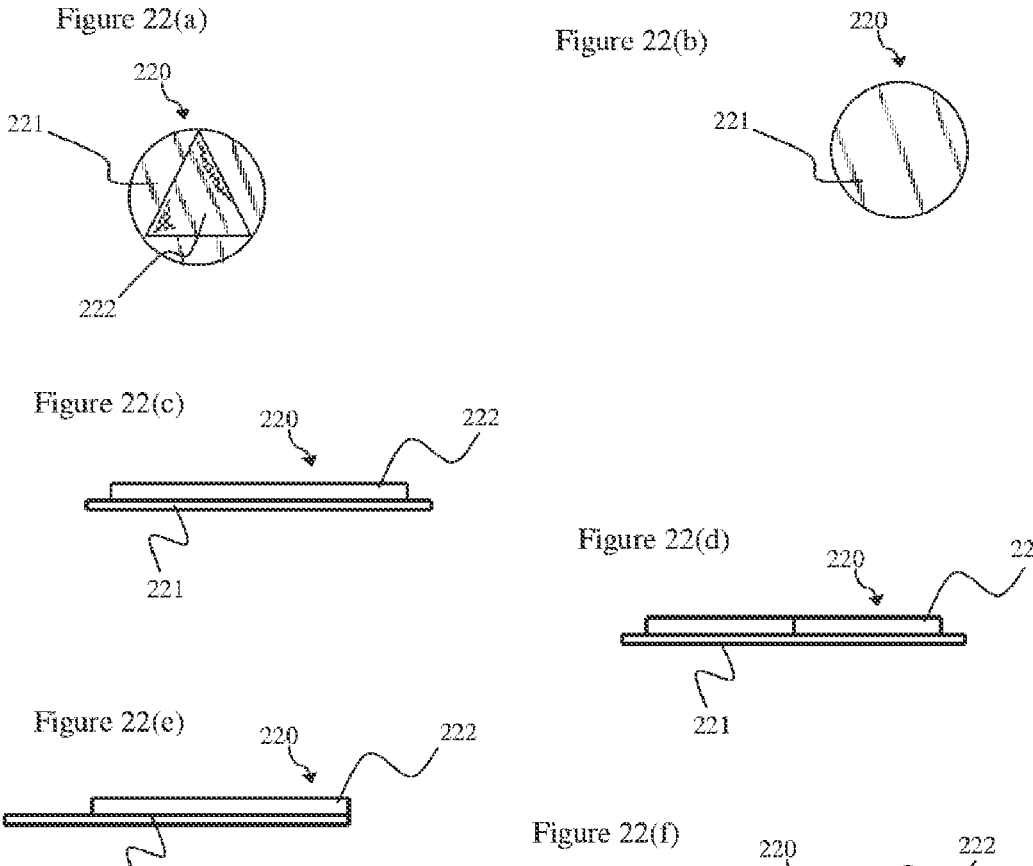
Figure 22(a)
Figure 22(b)
Figure 22(c)
Figure 22(d)
Figure 22(e)
Figure 22(f)
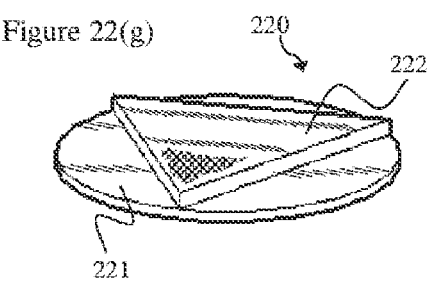
Figure 22(g)

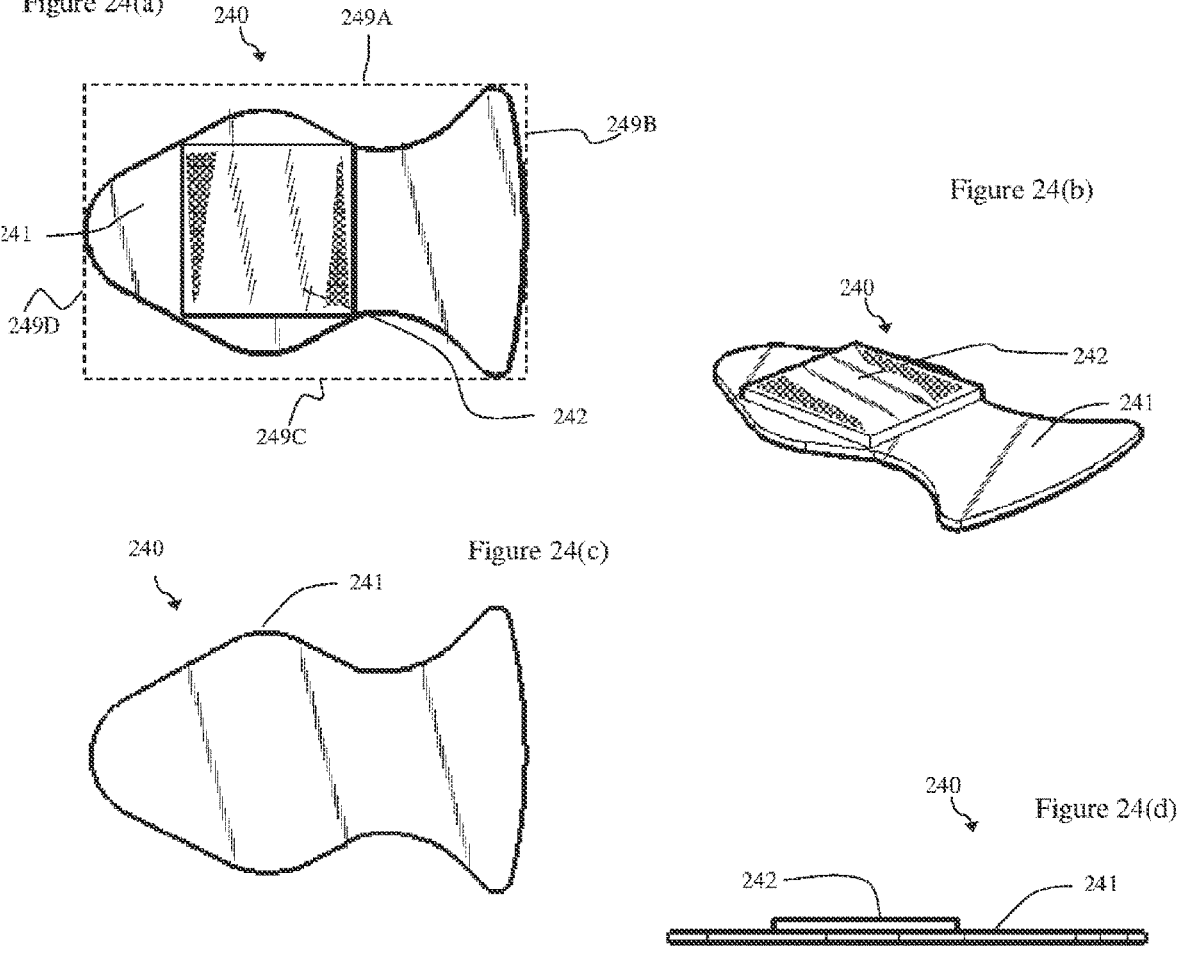
Figure 24(a)
Figure 24(b)
Figure 24(c)
Figure 24(d)
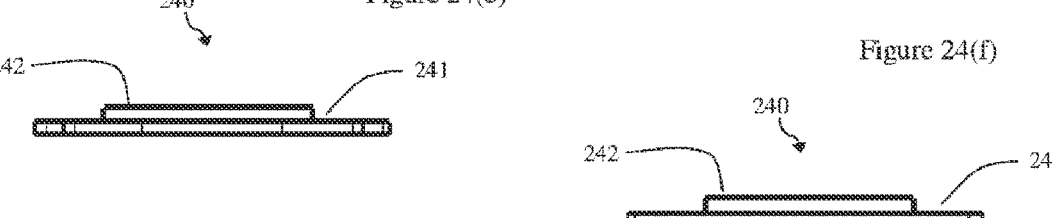
Figure 24(e)
Figure 24(f)

Figure 27(a)
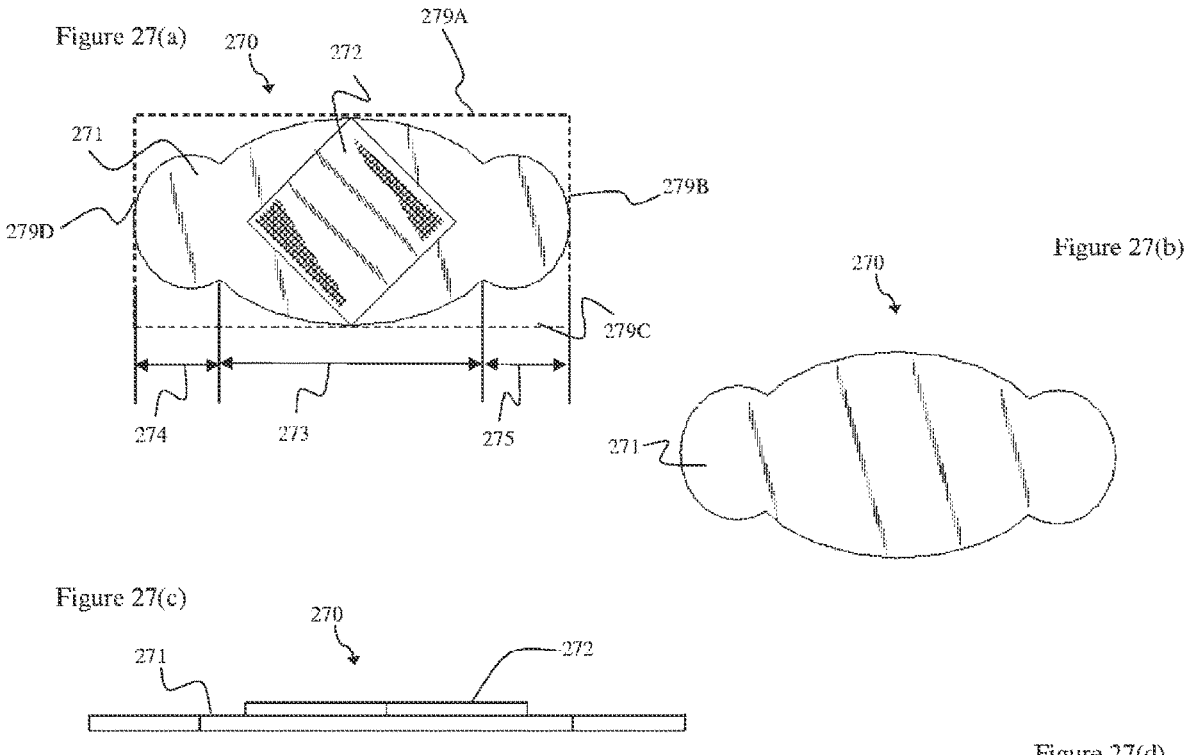
Figure 27(b)
Figure 27(c)
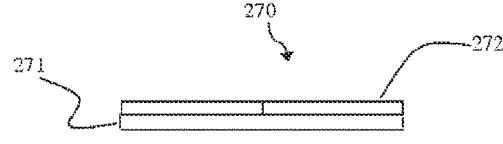
Figure 27(d)
Figure 27(e)
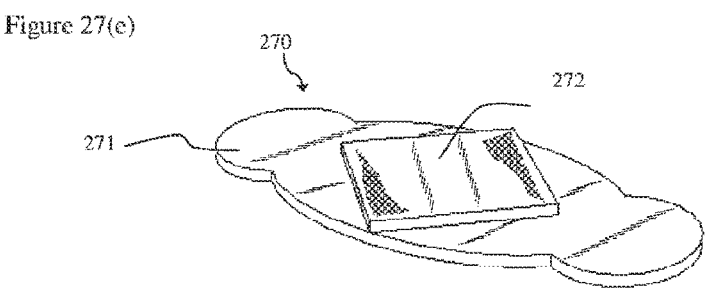

Figure 30(a)
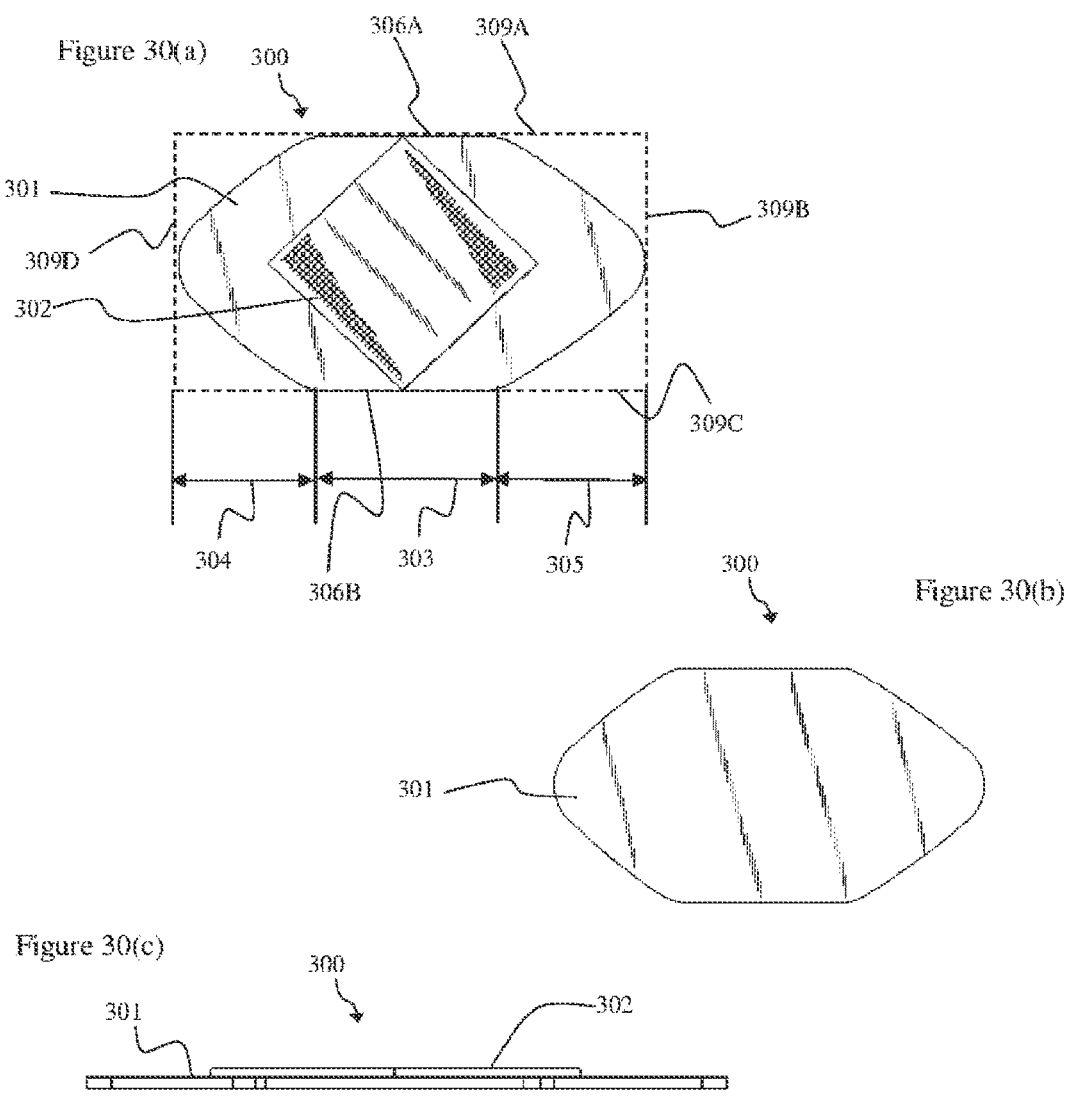
Figure 30(b)
Figure 30(c)
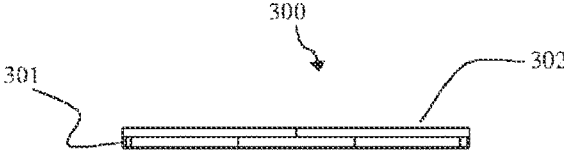
Figure 30(d)
Figure 30(e)
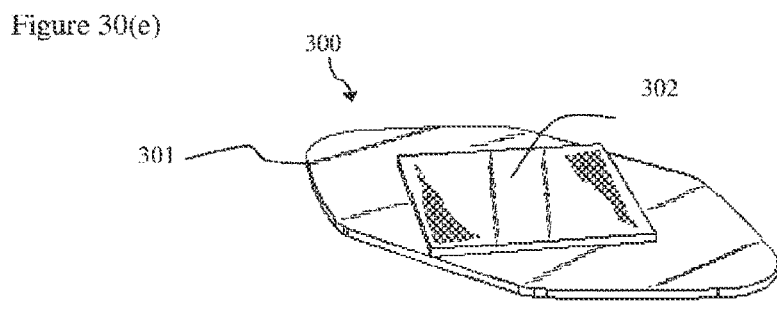

340

349A

341

349B

342

349C

349D

344

343

345

340

341

340

341

342

340

341

342

340

342

341

Figure 37(a)
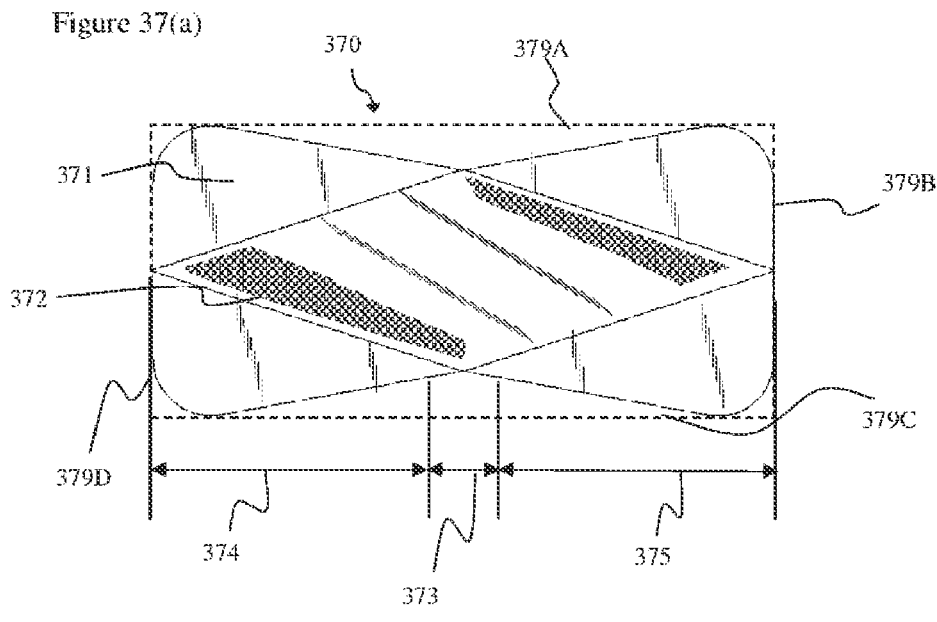
Figure 37(b)
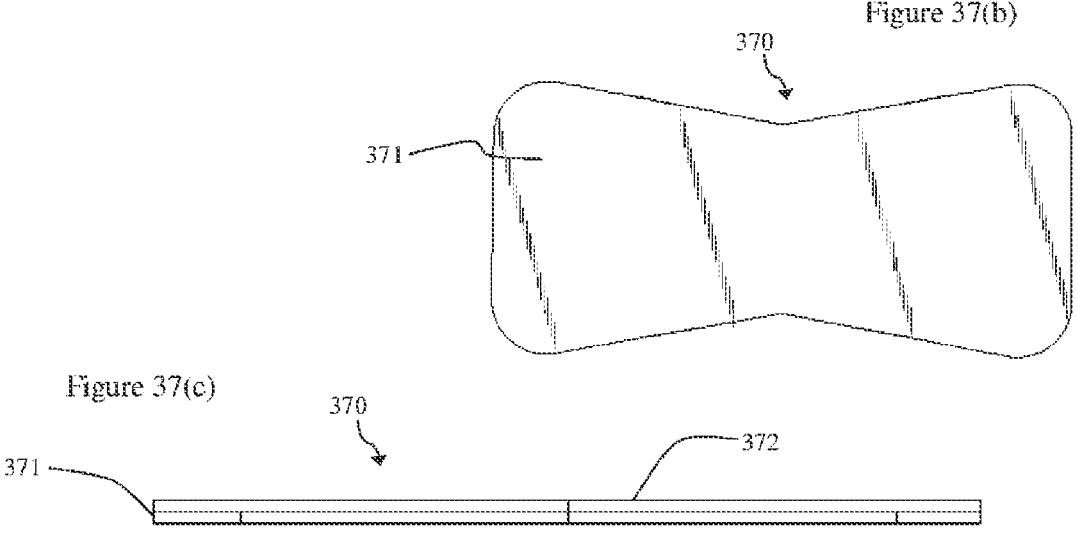
Figure 37(c)
Figure 37(d)
Figure 37(e)
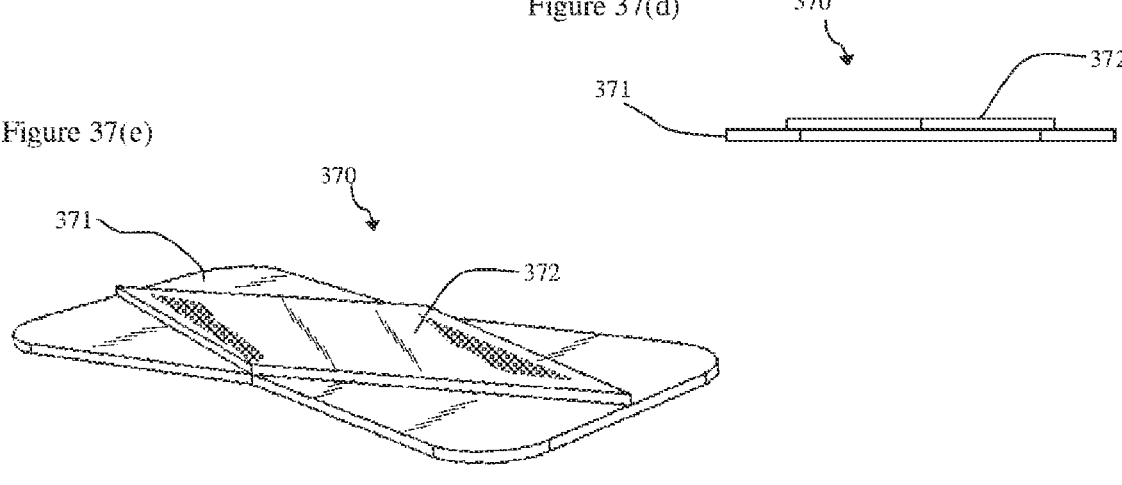

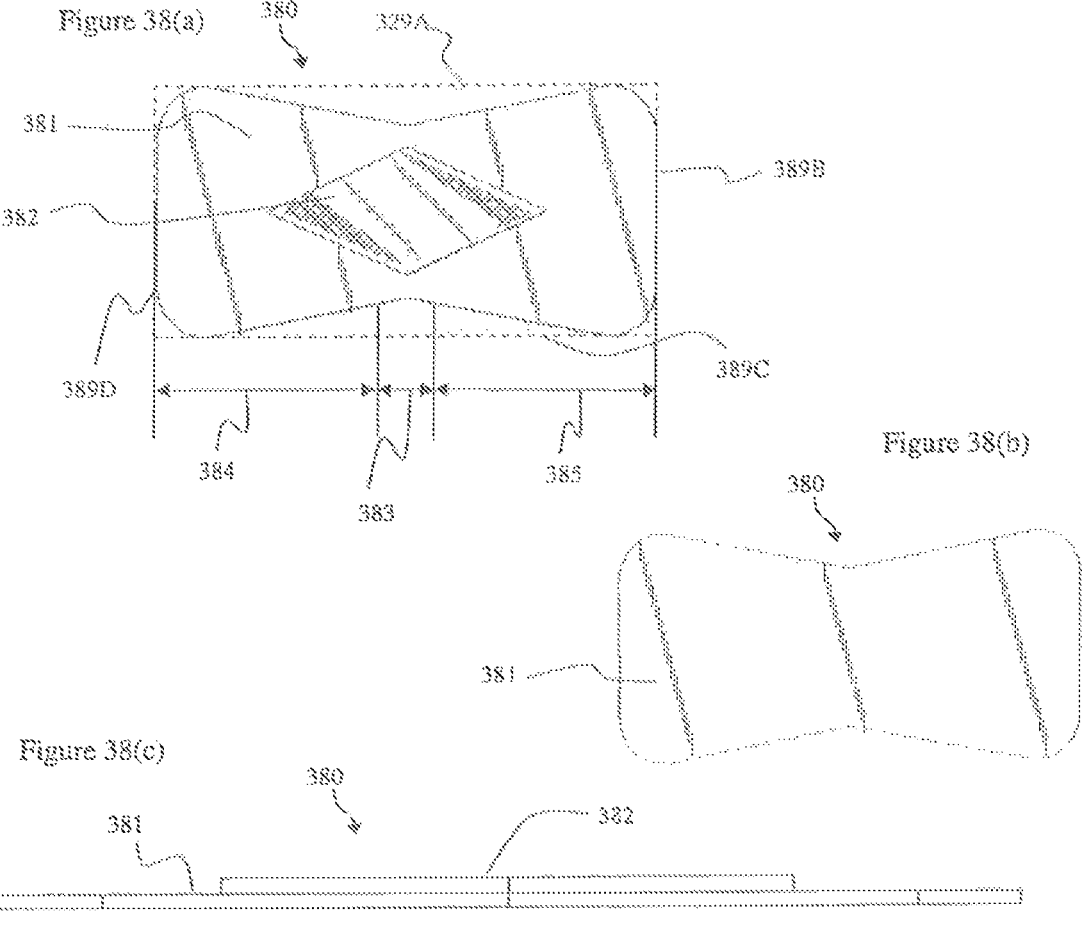
Figure 38(a)
Figure 38(b)
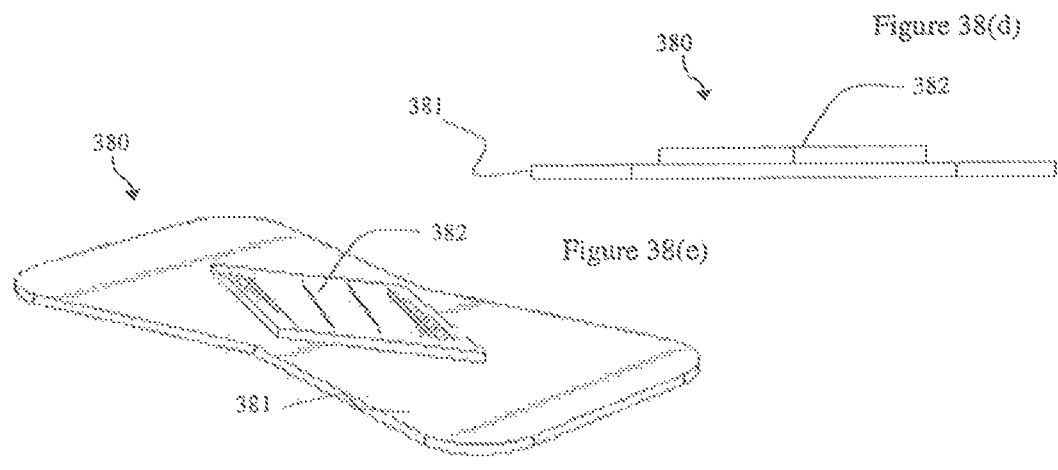
Figure 38(c)
Figure 38(d)
Figure 38(e)

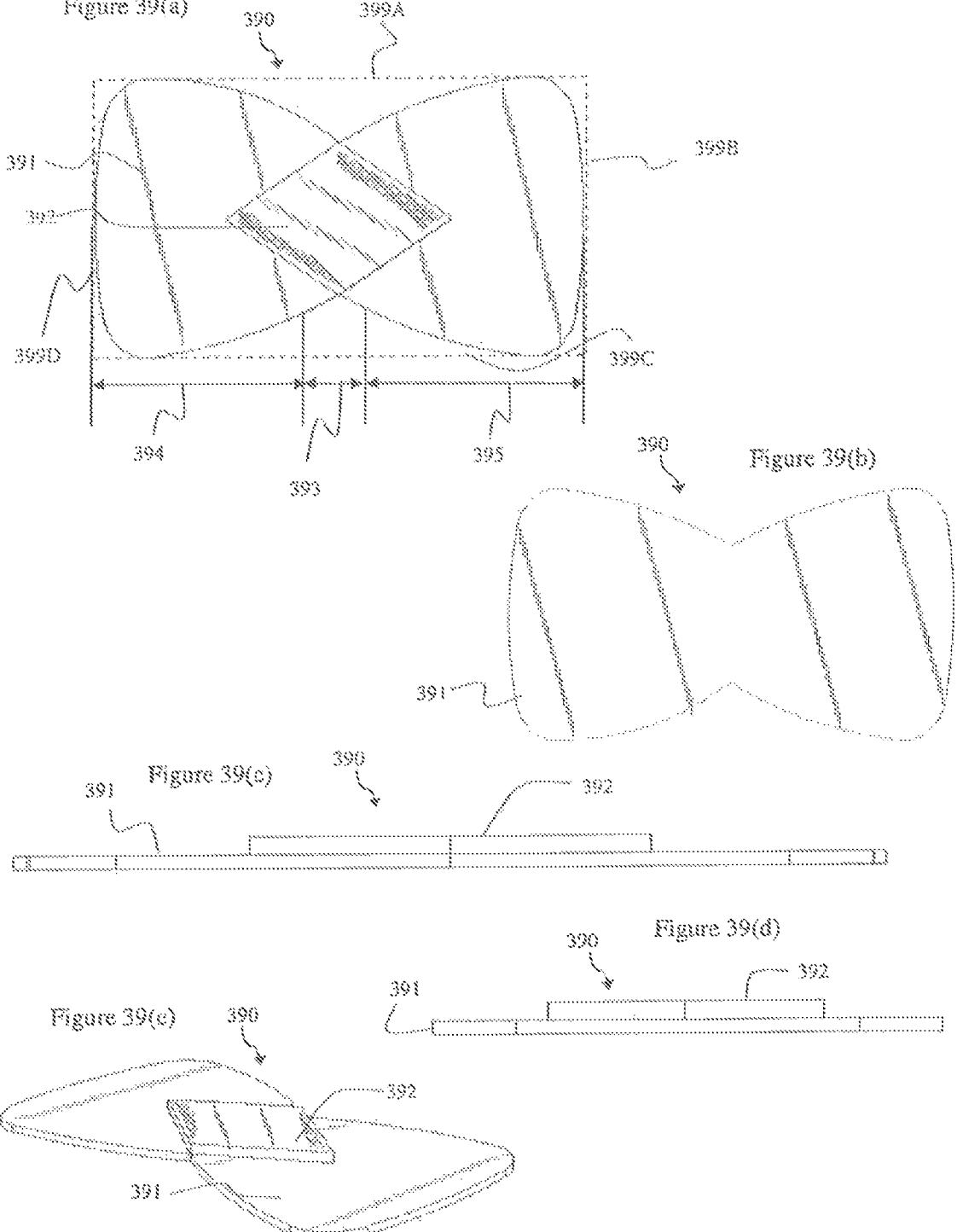

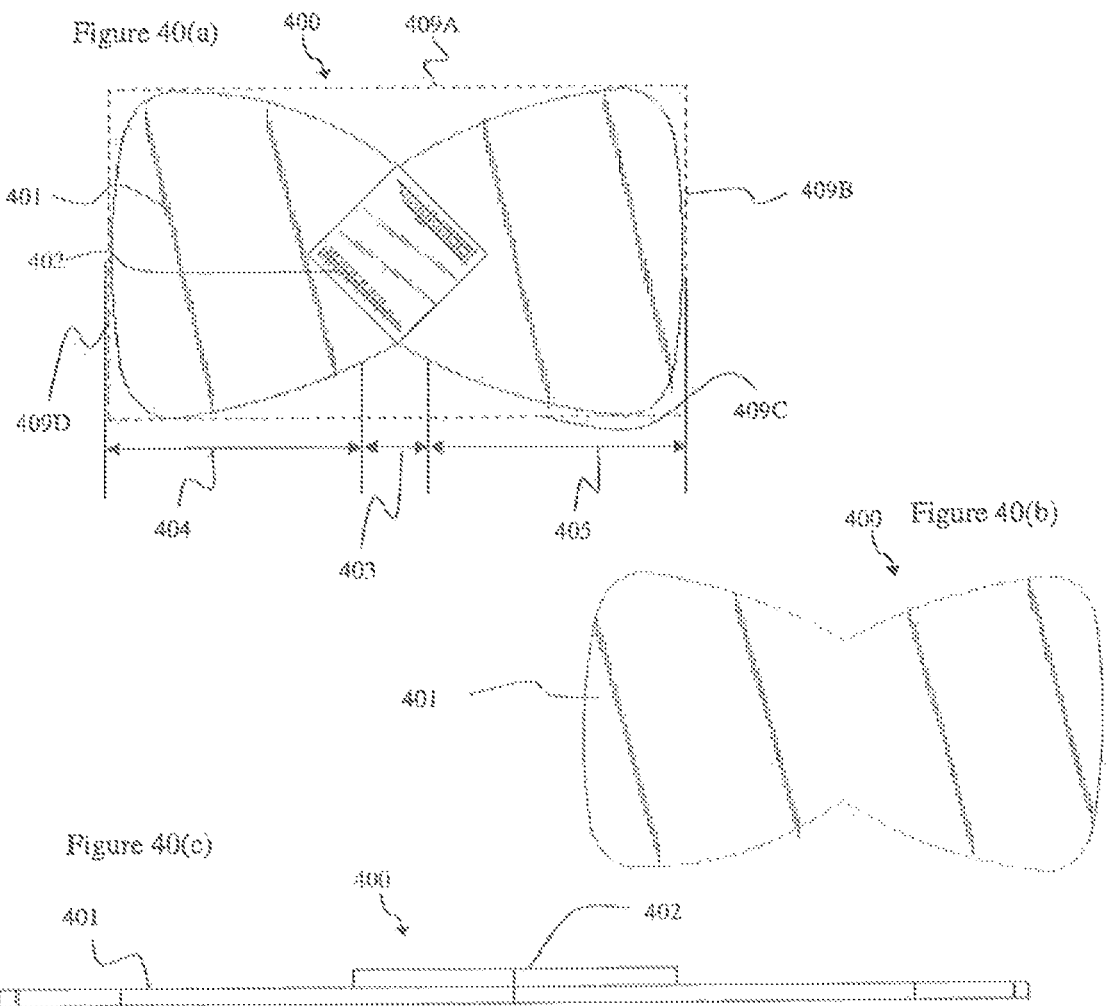
Figure 40(a)
Figure 40(b)
Figure 40(c)
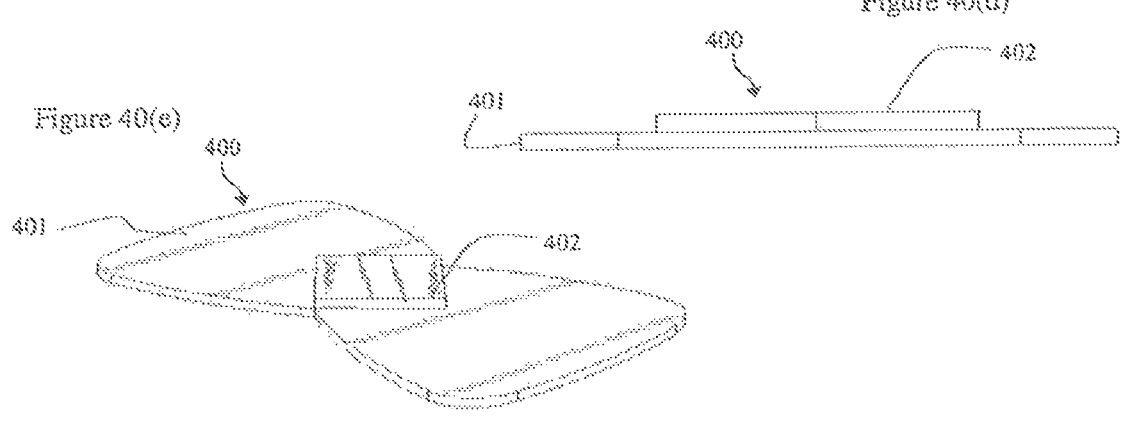
Figure 40(d)
Figure 40(e)

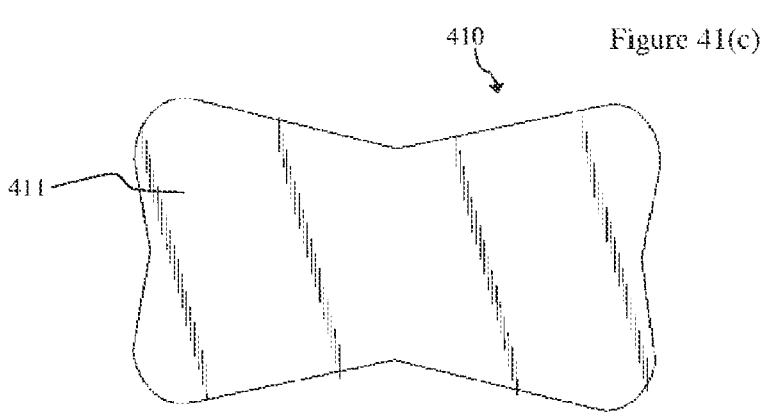
Figure 41(c)
Figure 41(d)
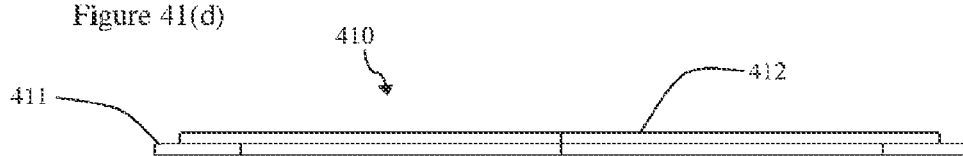
Figure 41(e)
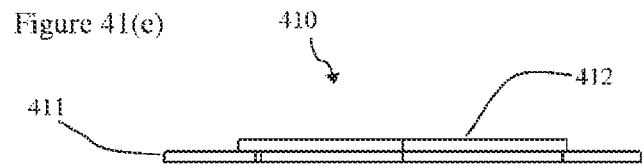
Figure 41(f)
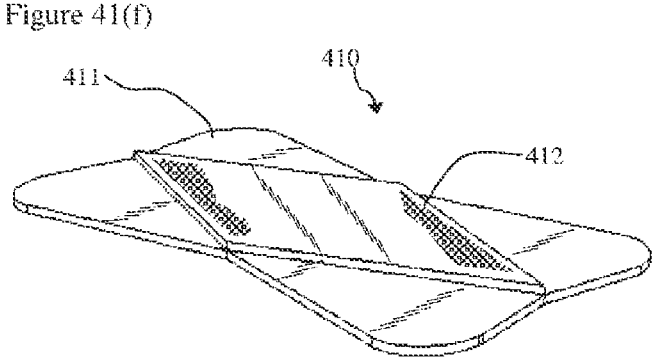

Figure 42(a)
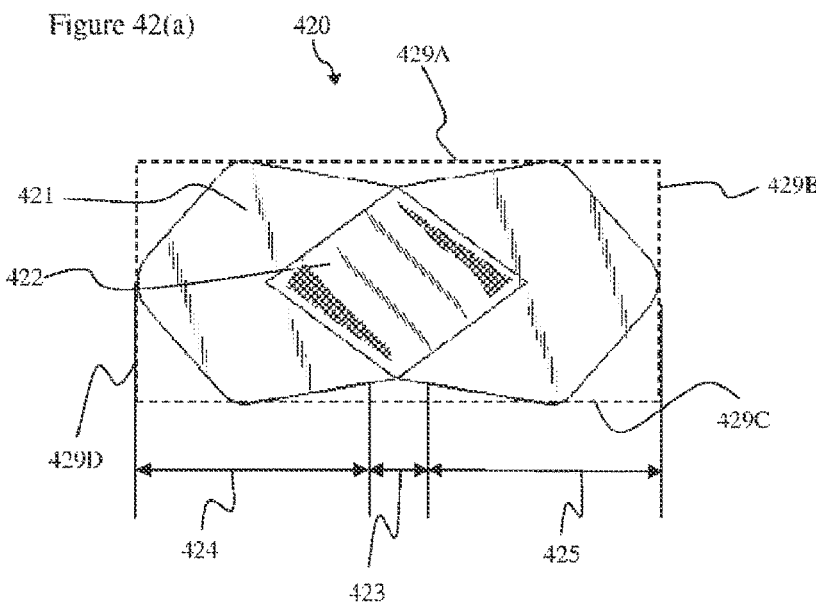
Figure 42(b)
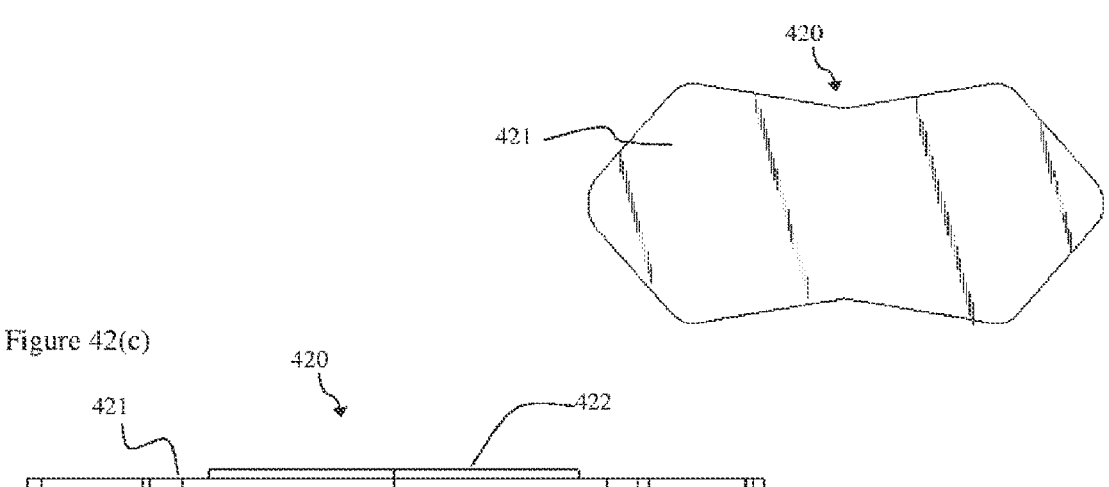
Figure 42(c)
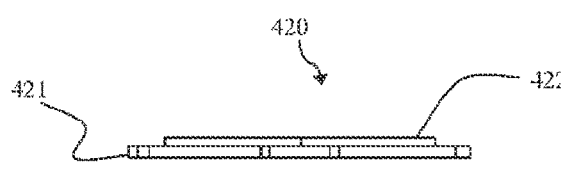
Figure 42(d)
Figure 42(e)
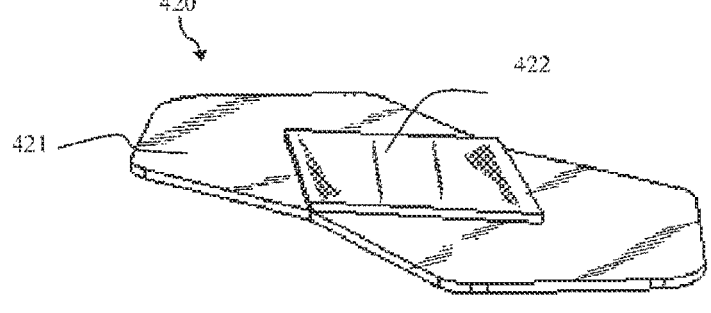

Figure 44(a)
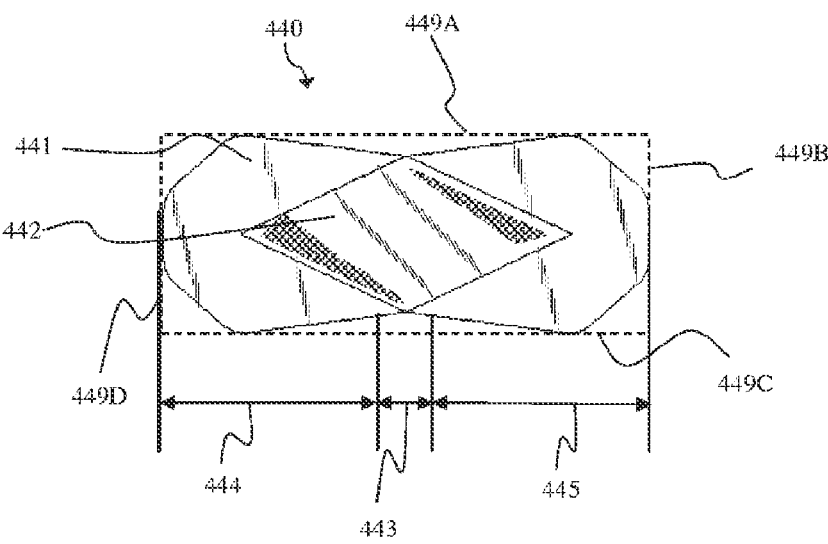
Figure 44(b)
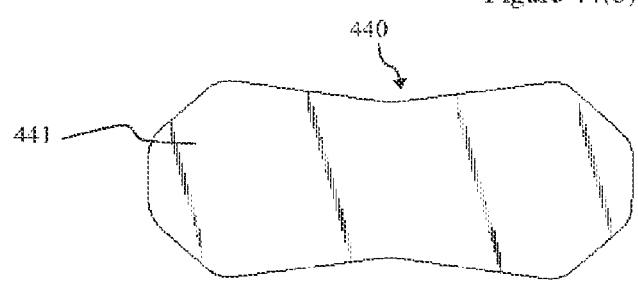
Figure 44(c)
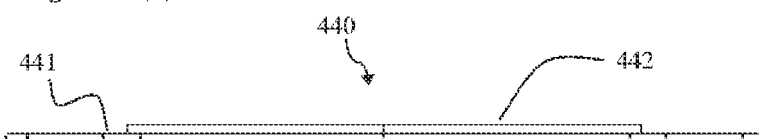
Figure 44(d)
Figure 44(e)
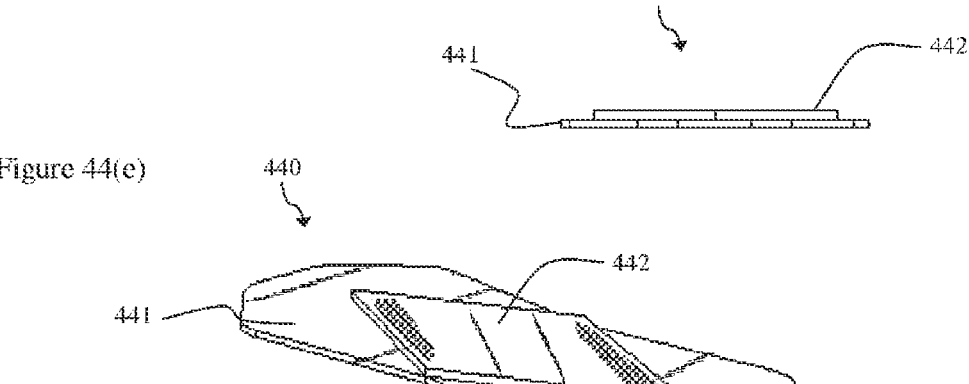

Figure 45(a)
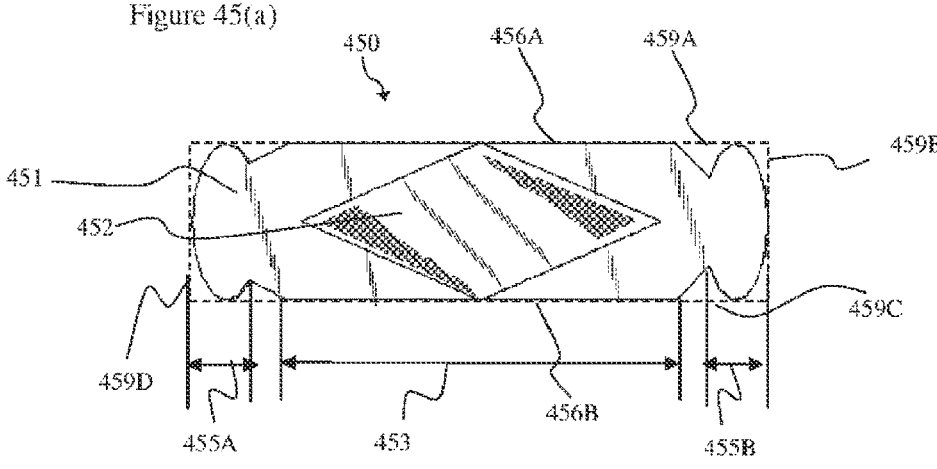
Figure 45(b)
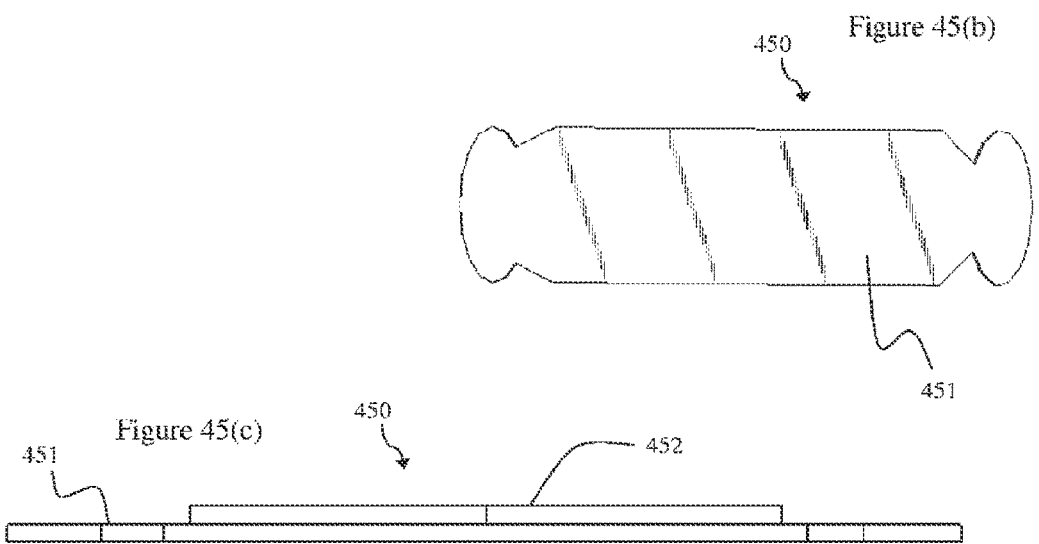
Figure 45(c)
Figure 45(d)
Figure 45(e)
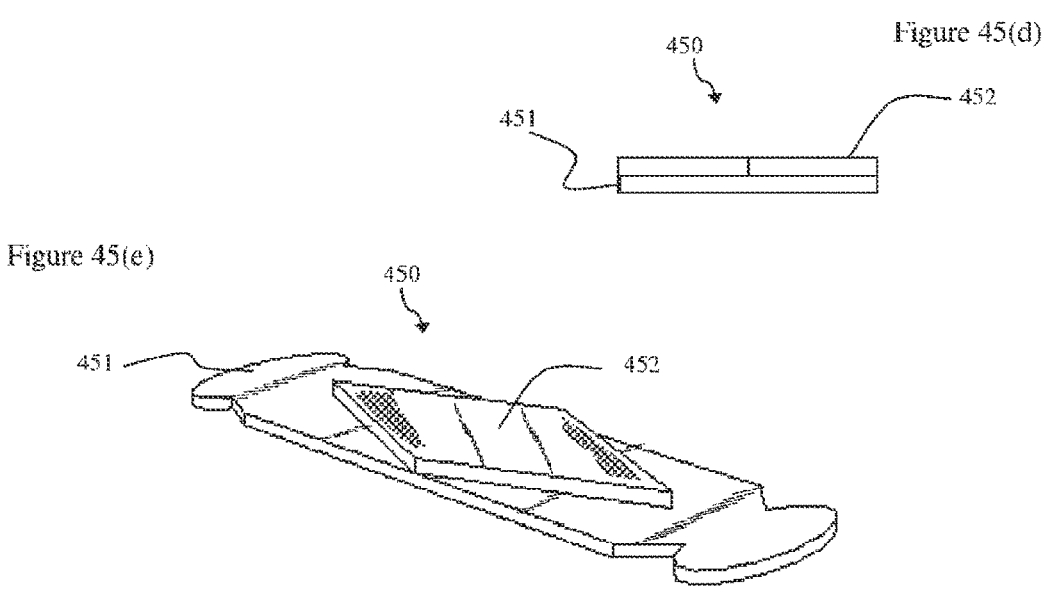

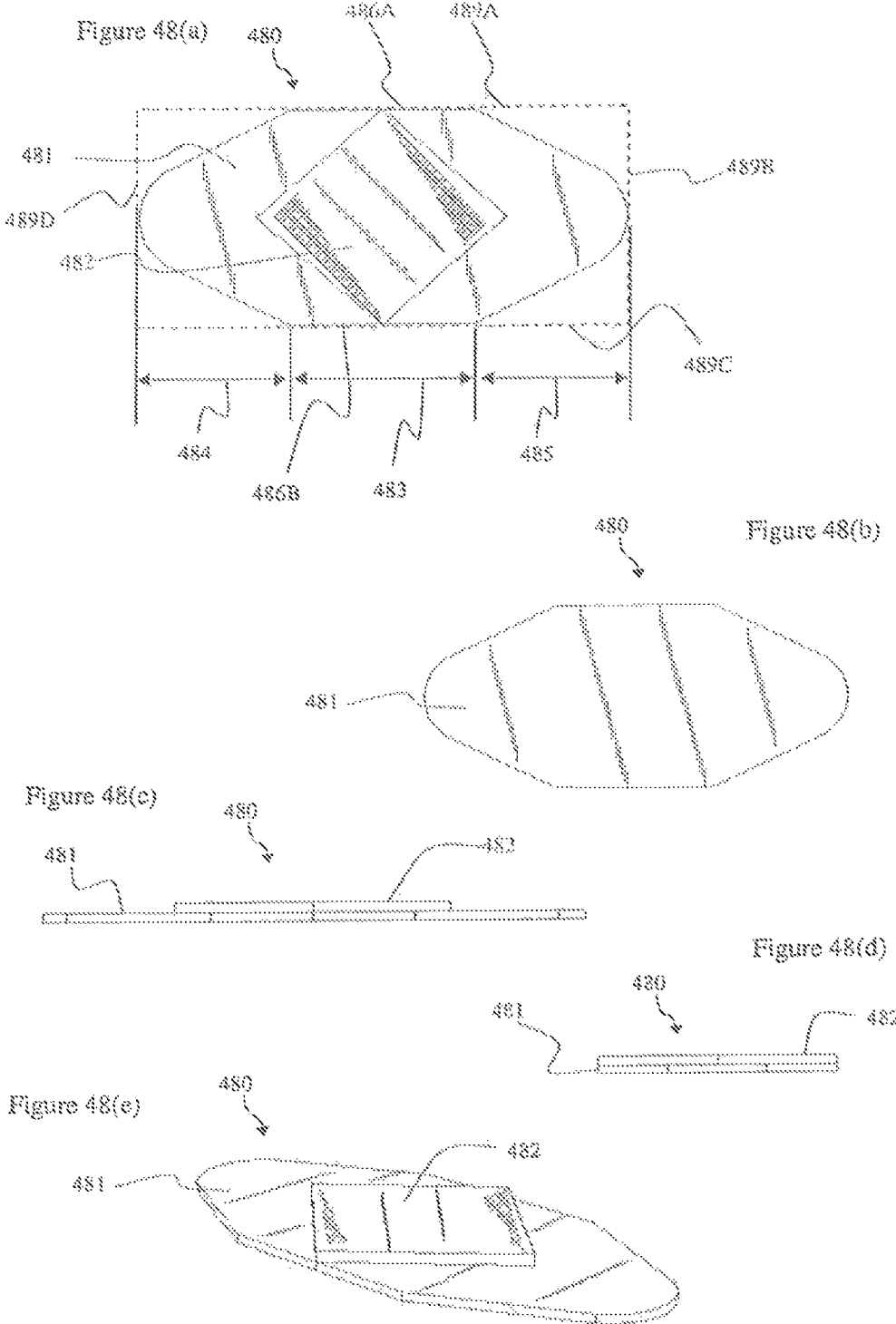

490

491

491 490 492

490 492

491

Figure 50(a)
500
501
502
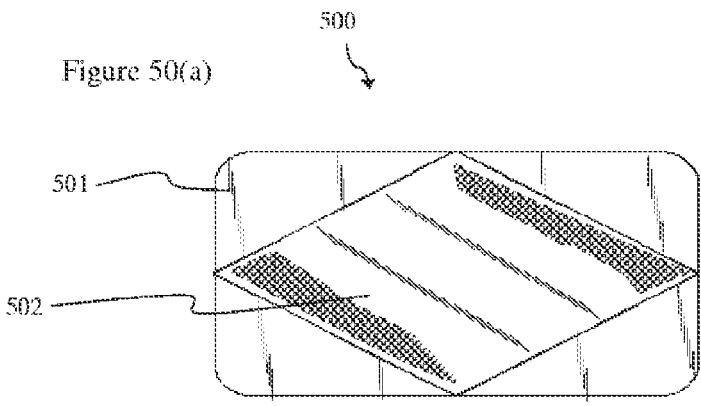
500
Figure 50(b)
501
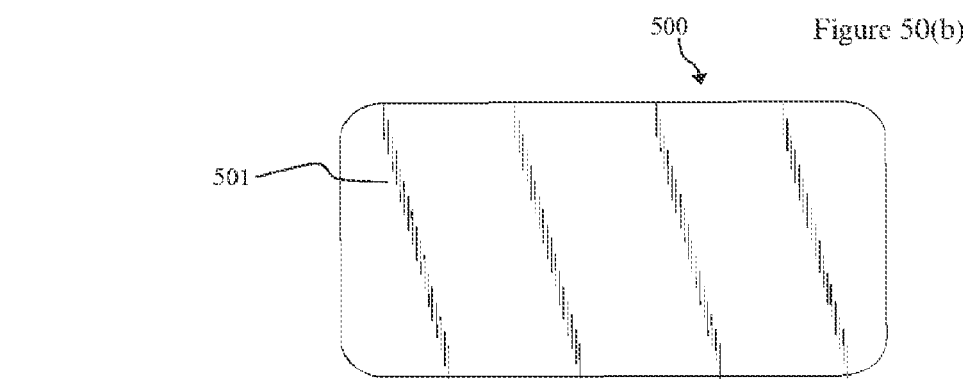
Figure 50(c)
500
501
502
Figure 50(d)
500
501
502
Figure 50(e)
500
501
502
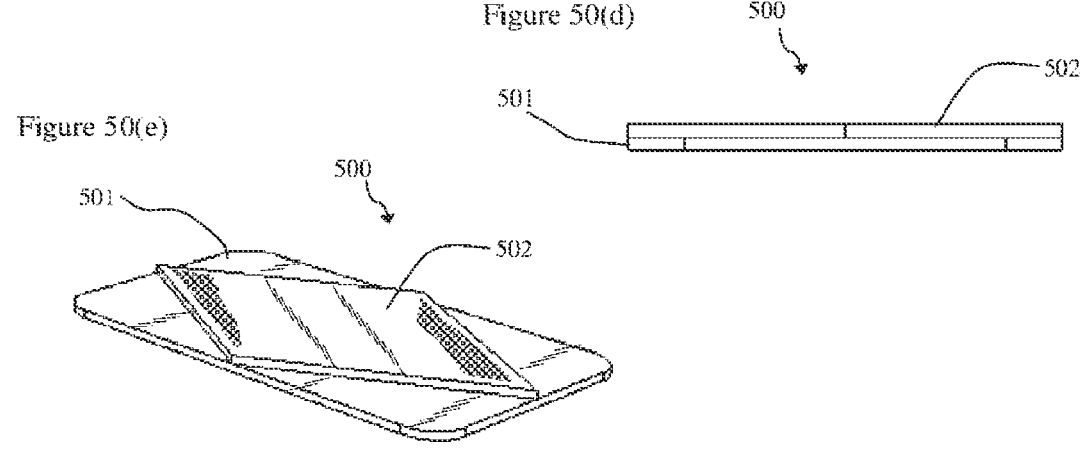

510

519A

511

512

519D

519B

519C

516A · 515A · 515B · 516B

514A

513

514B

510

511

510

511

512

510

511

512

510

511

512

510

512

511

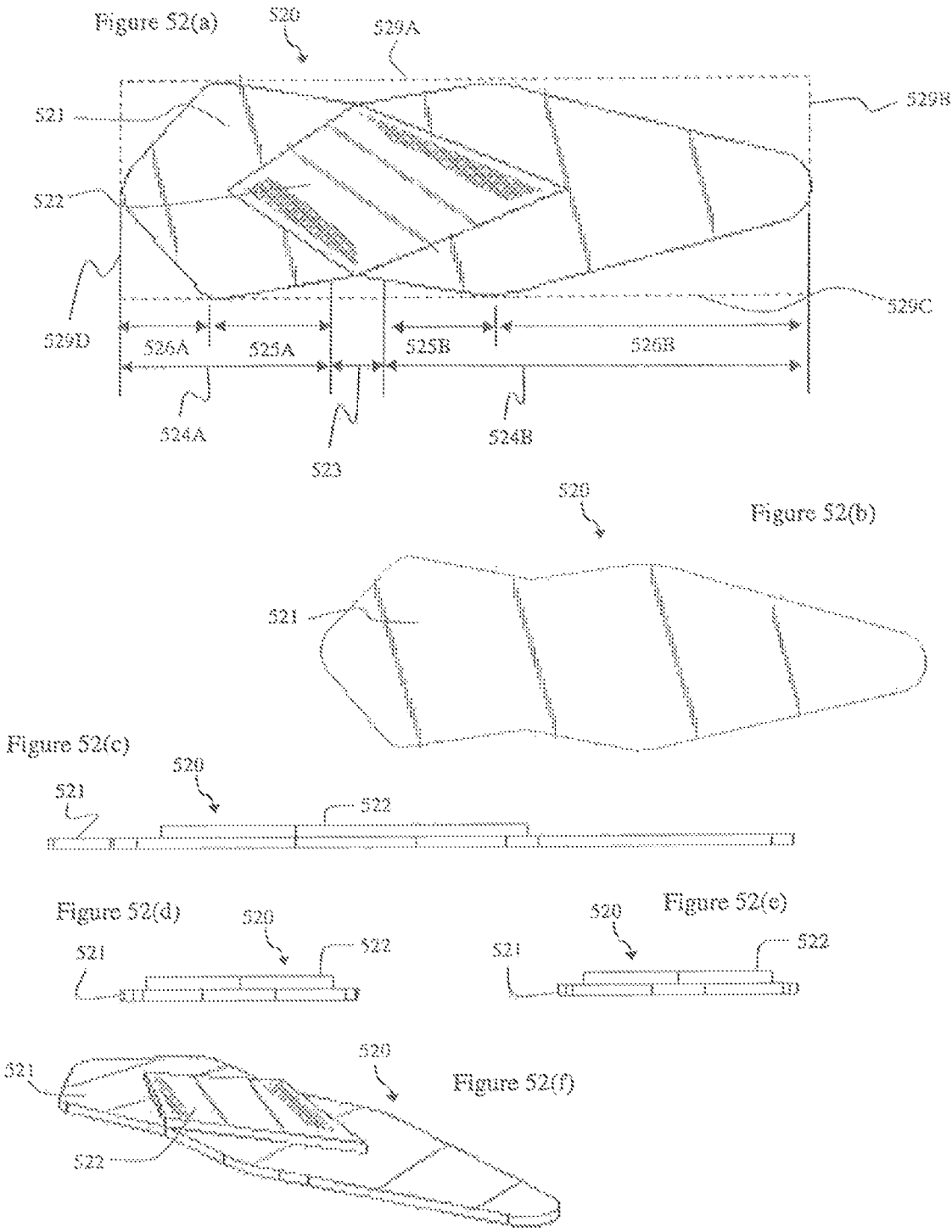

530

531

532

VIII                                                                                    VIII'

Figure 58(a)
580
582
581
XII                    XII'
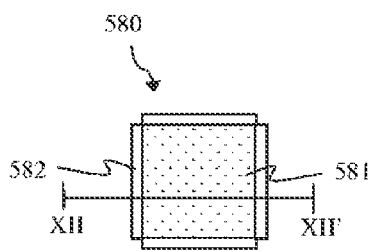
Figure 58(b)
580
582
581
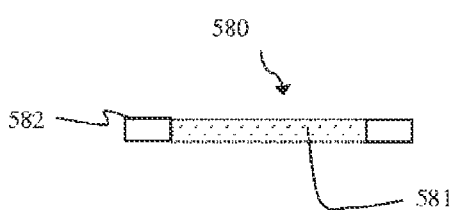
Figure 59(a)
590
592
591
XIII                    XIII'
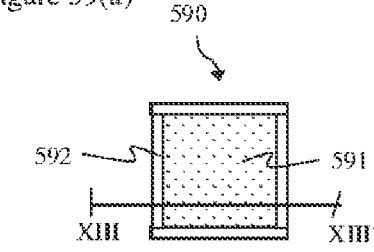
Figure 59(b)
300B
592B
591B
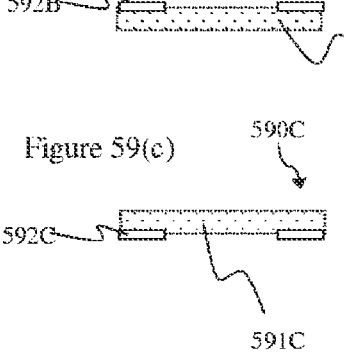
Figure 59(c)
590C
592C
591C
Figure 59(d)
590D
592D
591D
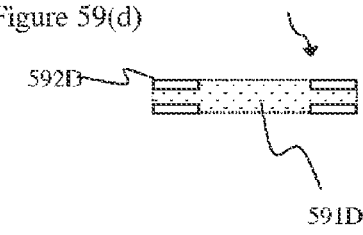
Figure 59(e)
590E
592E
591E
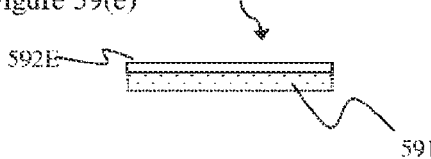

Figure 66(a)
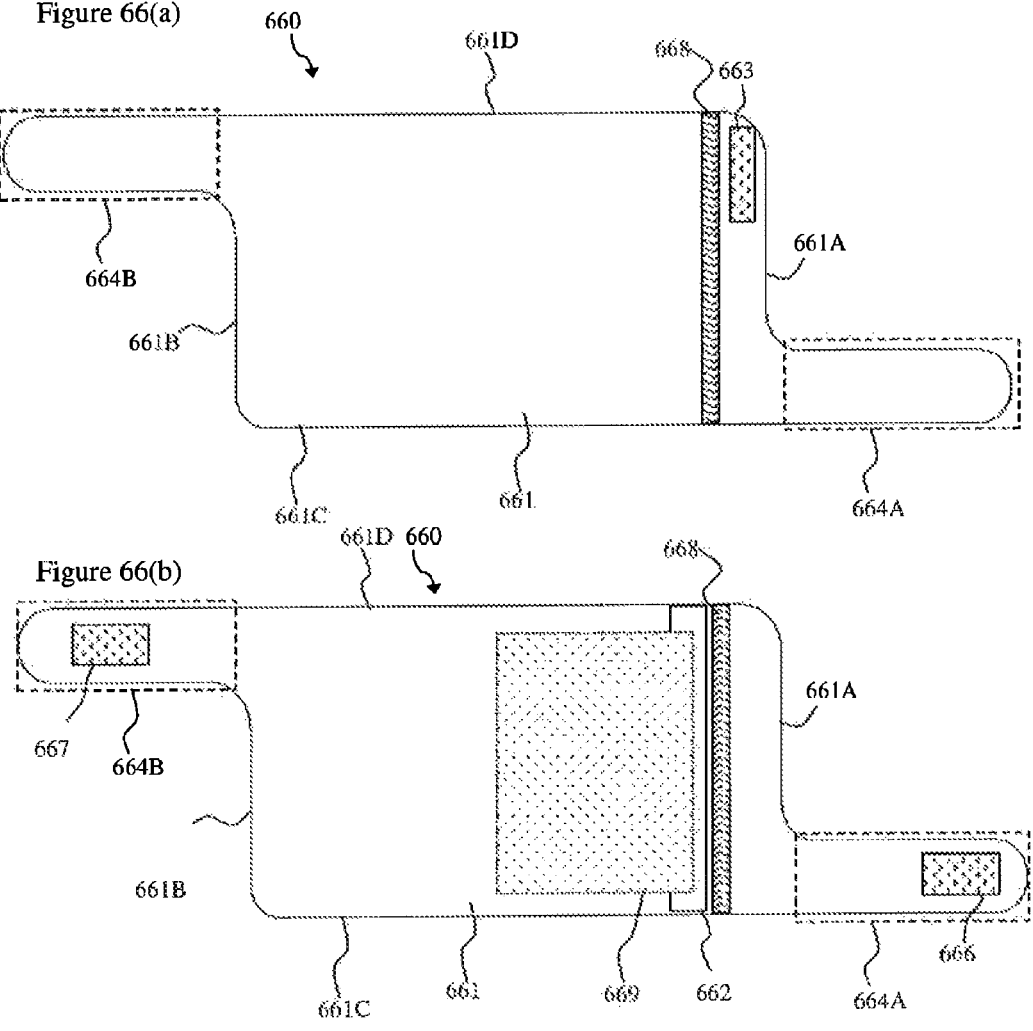
Figure 66(b)
Figure 66(c)
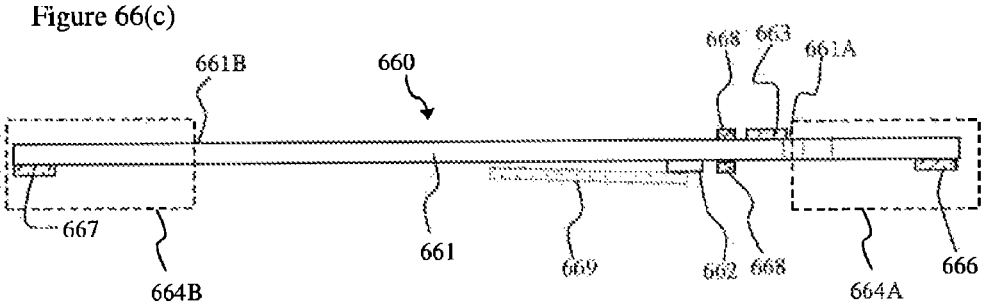

WOUND AND BANDAGE PROTECTION SYSTEM AND METHOD

CROSS-REFERENCE TO RELATED APPLICATIONS

This application is a Divisional Application of U.S. application Ser. No. 15/831,692 filed Dec. 5, 2017, which is a Continuation Application of U.S. application Ser. No. 13/807,404 filed Dec. 28, 2012, which is a national stage filing under 35 U.S.C. 371 of PCT/US2011/042216 filed Jun. 28, 2011, which claims priority to U.S. Provisional Application Ser. No. 61/453,341 filed Mar. 16, 2011, is a Continuation-in-Part Application of U.S. application Ser. No. 13/004,866 filed Jan. 11, 2011, claims priority to U.S. Provisional Application Ser. No. 61/360,873 filed Jul. 1, 2010, and is a Continuation-in-Part Application of U.S. application Ser. No. 12/826,644 filed Jun. 29, 2010 (now U.S. Pat. No. 8,591,447), the disclosures of which are herein incorporated by reference in their entireties.

TECHNICAL FIELD

The invention generally relates to a wound and bandage protection system that is designed to resolve many issues of durability, comfort and ease of application that are not adequately resolved by current wound and bandage protection systems. The invention also relates to a method of using the wound and bandage protection system for wound care.

BACKGROUND ART

Traditional solutions for wound care involve use of gauze and bandages affixed to skin with adhesive, which need to be replaced completely when redressing the wound. This type of wound dressing has numerous shortcomings, in particular for animals with fur. Bandages affixed with adhesive restrict patient movement, and are uncomfortable. Removing the adhesive from skin can be painful, and removing it from fur is not only uncomfortable for an animal, but is also time consuming, and therefore very impractical. However, veterinarians and pet supply stores today almost exclusively sell or use bandages designed for humans for purposes of pet wound care.

One alternative for wound care are self-adhesive wraps that adhere to themselves via a sticky adhesive quality of the wrap material, without sticking to skin or fur. However, a major drawback of these bandages is that they lose the ability to stick when wet or when dirty. The wraps can become undone and unusable in a matter of seconds if licked or tampered with. Therefore, while a good solution for human wound care, these wraps are still impractical for pet wound care.

An additional reason for the need for a comfortable bandage for animals is because they are very prone to infection when healing from a wound, due to the instinct of the animals to lick the location of the wound, leading to the introduction of bacteria and germs to the wound. The animal will also lick and possibly gnaw on bandages as well. Dogs, for example, like the taste of adhesive. The current solution of veterinarians is to place a cone collar around the animal's neck. However, the cone is big, cumbersome and a nuisance for both pet and owner. A dog will swing its head wildly while trying to get the collar off. In the process they can injure themselves; they also find it difficult to navigate when moving about. They also bang into things and knock down everything that is not attached. The cone is a very unpleasant solution.

Therefore, there is a need for a bandaging system that reduces pull on skin and fur, will attach quickly and effortlessly, stay on securely, and be removable and exchangeable without pain.

Furthermore, throughout the history of bandage making, a common problem has plagued the adhesive bandage industry. In order to properly protect a wound, it should be covered and insulated from outside infectants. However, most adhesive bandages do not adequately protect a wound when applied. Makers of older bandages tried to size the gauze pad to allow for a thin strip of adhesive around the gauze pad to adhere to the skin around the wound. However, the strip of adhesive around the gauze pad would often buckle or come loose altogether, and not keep the wound properly sealed, and possibly cause discomfort. Recently companies have tried other solutions. Band-Aid® brand has given up on sealing the wound and has extended the gauze to the edge of the adhesive to maximize the amount of gauze available to cover the wound. Nexcare® has created bandages with extremely small gauze in relation to the bandage, allowing for a better seal, but providing less gauze in the exchange. Furthermore, these bandages tend not to perform well on joints, where the areas of adhesive do not conform to the bending of the limbs without causing a large amount of buckling of the gauze. Therefore, there is a need for a bandaging system to prevent buckling and loosening of the adhesive around the gauze pad of an adhesive bandage, particularly with regard to application of bandages to joints, while at the same time maximizing the amount of gauze available to cover the wound.

DISCLOSURE OF INVENTION

The present invention provides a wound/bandage protection system and a method of use thereof. An exemplary embodiment of a super-stretch tube according to the present invention is disclosed. The super-stretch tube has a strip that extends along a length of the super-stretch tube from a first open end to a second open end of the super-stretch tube at least along an inside surface of the super-stretch tube. The super-stretch tube is preferably made of a super-stretchable elastic non-woven material.

In a first exemplary embodiment of a wound/bandage protector according to the present invention, the wound/bandage protector may be comprised of a body portion, a first-catch fastening surface and a first fastening strap. The body portion is configured as a wrap with a first end, a second end, a wound facing side and a non-wound facing side. The first-catch fastening surface is on an end region, which is proximal to the first end of the body portion, of the wound facing side of the body portion. The first-catch fastening surface is configured so as to be capable of fastening with at least a portion of the non-wound facing side of the body portion. Alternatively, the wound/bandage protector may be configured without the first-catch fastening surface.

The first fastening strap extends from the second end of the body portion and at least a portion of a wound facing side surface of the first fastening strap is configured so as to be capable of fastening with at least a portion of the non-wound facing side of the body portion or a non-wound facing side of the first fastening strap. In one alternative embodiment, the body portion and the first fastening strap may be comprised of the same integral piece of material.

The wound/bandage protector according to the present invention may be configured to be stretchable in a lengthwise direction defined by the first end of the body portion and the second end of the body portion. The first fastening strap of the wound/bandage protector may have a first strap part that is stretchable, and a second strap part. In such an embodiment of the wound/bandage protector according to the present invention, the second strap part may include the portion of the first fastening strap that is capable of fastening with at least a portion of the non-wound facing side of the body portion or the non-wound facing side of the first fastening strap. An elastic modulus of the first strap part may be greater than an elastic modulus of the body portion.

Furthermore, the wound/bandage protector according to the present invention may also have a second fastening strap extending from the second end of the body portion. At least a portion of a wound facing side surface of the second fastening strap is configured so as to be capable of fastening with at least a portion of the non-wound facing side of the body portion and/or a non-wound facing side of the second fastening strap. The second fastening strap may have a first strap part and a second strap part configured in the manner discussed above in reference to the first fastening strap. An elastic modulus of the second fastening strap first strap part may be configured to be greater than an elastic modulus of the body portion.

The wound/bandage protector according to the present invention may also have a strip. The strip may be on the body portion proximal to the first end and extend widthwise. Alternatively, the strip may extend along the length of the body proximal to a top or bottom edge of the body portion. Moreover, multiple strips may be provided, such as strips along both the top and bottom edge of the body portion. The strip may be comprised of a rubberized material exposed on at least the wound facing side of the body portion.

The wound/bandage protector according to the present invention may have a gauze port on the wound facing side of the body portion proximal to the first end of the body portion. The gauze port may be configured to attach to only a small portion of a gauze pad proximal to one side of the gauze pad. The gauze port may be configured so as to allow repeated removable attachment of the gauze pad. The wound/bandage protector may also include a gauze pad. The gauze pad may be configured to attach to the gauze port. Alternatively, the gauze pad may be configured so as to remain adjacent but unattached to the non-wound facing side of the body portion. In such an alternative exemplary embodiment, the gauze pad may have a rubberized or tacky frame on a wound-facing and/or non-wound-facing side of the gauze pad.

The wound/bandage protector according to the present invention may have a strip provided on the body portion preferably between the gauze port and the first end of the body portion. If there is no gauze port, the strip is preferably located proximal to the first end of the body portion. The strip may be comprised of a rubberized material that is exposed at least on the wound facing side of the body portion. Alternatively, all or a portion of the wound-facing side of the body portion may have a tacky surface.

A wound/bandage protector according to the present invention, may have a cover. In such an embodiment of the wound/bandage protector according to the present invention, the body portion has an aperture, and the cover and the aperture are sized so as to allow the cover to completely close the aperture. The body portion may be configured with a shelf surrounding the aperture, and the cover is sized so as to close the aperture by extending at least partially onto the shelf. The wound/bandage protector according to this exemplary embodiment may further comprise a non-stretchable or substantially non-stretchable rim provided on the non-wound-facing side surface of the body portion surrounding the aperture. The surface of the rim is sized and configured so as to allow for removable attachment of the cover.

A wound/bandage protector according to the present invention, may have dead-zones periodically provided along the length of the body portion. The dead zones may be configured to extend widthwise with respect to the length of the bandage and provided, preferably, at least every 3 inches along the length of the body portion.

A wound/bandage protector according to the present invention, may have a gauze panel positioned on or integrated into the body portion proximal to the first end of the body portion. The gauze panel may be configured so as to allow for attachment and/or repeated attachment of a gauze pad on the wound-facing side of the body portion. The gauze panel may be sized so as to allow all or substantially all of the gauze pad to be attached or removably attached to the gauze panel. The gauze panel and the part of the body portion on which the gauze panel is positioned or integrated may be configured as a dead zone. Alternatively, the gauze pad and the gauze panel may be comprised of stretchable material.

In one exemplary embodiment of a bandage according to the present invention, the bandage is comprised of a stretchable body portion with a stretchable gauze pad affixed to the wound-facing side of the body portion. The body portion has adhesive on at least a portion of a wound facing side or, alternatively, the body portion is comprised of self adherent material, such as Coban™.

In another exemplary embodiment of a bandage according to the present invention, the bandage has a body portion and a gauze pad on a wound-facing side of the body portion. The gauze pad is shaped and positioned on the body portion in such manner that the bandage is configured as a "diamond gauze" adhesive bandage. The body portion has adhesive on at least a portion of a wound facing side or, alternatively, the body portion is comprised of self adherent material.

In another exemplary embodiment of a bandage according to the present invention, the bandage is a "diamond gauze" bandage that has a body portion and a gauze pad. The body portion has adhesive on at least a portion of a wound facing side or, alternatively, the body portion is comprised of self adherent material. The gauze pad is shaped as a square, rhombus or parallelogram and oriented on the wound-facing side of the body portion in such manner that each of the corners of the gauze pad are oriented towards a different length tangent or width tangent of the adhesive bandage.

In another exemplary embodiment of a bandage according to the present invention the bandage further includes a cover. The body portion has an aperture, and the cover and the aperture are sized so as to allow the cover to completely close the aperture. The body portion may also be configured with a shelf surrounding the aperture. In such an embodiment, the cover is sized so as to close the aperture by extending at least partially onto the shelf.

In another exemplary embodiment of a wound/bandage protector according to the present invention, the wound/bandage protector may be comprised of a body, a fastening strap and a cover. The body is comprised of stretchable material and configured as a sock/mitten with a first end that is open, a second end that is closed, an internal wound facing side and an external non-wound facing side. The body may also have a panel with little or no stretch. The fastening strap is comprised of a first strap part and a second strap part. The first strap part is connected to the body and comprised of stretchable material. The second strap part is connected to the first strap part. At least a portion of a wound-facing side of the second strap part is configured so as to be capable of fastening with at least a portion of the external non-wound facing side of the body, at least a portion of a non-wound facing side of the first strap part, and at least a portion of a non-wound facing side of the second strap part. The fastening strap may also have a third strap part that is configured as a dead zone connecting the first strap part to the external non-wound facing side of the body. The fastening strap may also have a fourth strap part that is configured as a dead zone connecting the first strap part and the second strap part. Both the third strap part and the fourth strap part have a rubberized or tacky surface exposed on at least the wound facing side of the fastening strap.

The wound/bandage protector, according to this exemplary embodiment, may also include a sheath with a first open end, and a second closed end, the sheath sized and configured to fit over an entirety of the body of the wound/bandage protector. A slot or slit in the sheath is sized and positioned so as to allow the fastening strap to fit therethrough. The fastening strap is sized so as to be capable of extending around an outside of the sheath to secure both the body and the sheath to an appendage being bandaged by fastening the wound facing side of the second strap part to a non-wound facing side of the fastening strap.

In another exemplary embodiment of a bandage according to the present invention the bandage further includes a cover. The body portion has an aperture, and the cover and the aperture are sized so as to allow the cover to completely close the aperture. The body portion may also be configured with a shelf surrounding the aperture. In such an embodiment, the cover is sized so as to close the aperture by extending at least partially onto the shelf.

In another exemplary embodiment of a bandage according to the present invention, the bandage has a body portion a cover and a rim. The body portion has an aperture, and the cover and the aperture are sized so as to allow the cover to completely close the aperture. The rim, which is on a non-wound-facing side surface of the body portion surrounding the aperture, is preferably non-stretchable or substantially non-stretchable. The surface of the rim is sized and configured so as to allow for removable attachment of the cover.

In another exemplary embodiment of a bandage according to the present invention, the bandage has a body portion and a cover. The body portion has an aperture shaped as a square, rhombus or parallelogram that is oriented in such manner that each of the corners of the aperture are oriented towards a different length tangent or width tangent of the adhesive bandage. The cover is sized to completely close the aperture.

In another exemplary embodiment of a bandage according to the present invention, the bandage is a "triangular gauze" bandage that has a triangular shaped body portion and a triangular shaped gauze pad. The triangular shaped body portion has adhesive on at least a portion of a wound facing side. The triangular shaped gauze pad is oriented on the wound-facing side of the body portion in such manner that each of the corners of the gauze pad is oriented toward a different side of the adhesive bandage. The triangular shaped gauze pad may be oriented on the wound-facing side of the body portion in such manner that each of the corners of the gauze pad is oriented toward a mid-point or a mid-section of a different side of the adhesive bandage.

In another exemplary embodiment of a bandage according to the present invention, the bandage is a "triangular gauze"

bandage that has a circular shaped body portion and a triangular shaped gauze pad. The circular shaped body portion has adhesive on at least a portion of a wound facing side. The triangular shaped gauze pad is provided on the wound-facing side of the body portion.

In addition, the invention also relates to a kit that includes all or a subset of the bandages disclosed herein.

The present invention also discloses methods of protecting wounds using the wound/bandage protectors, bandages and super-stretch tubes, such as the exemplary embodiments of those disclosed herein. Thus, for example, a bandage with an aperture may be used to protect a wound by applying the bandage with the aperture opened, placing gauze and medicine on the wound; and closing the aperture of the bandage. The method may also be applied with wound/bandage protector with an aperture. In addition, a wound/bandage protector or super stretch tube may be positioned over the bandage or wound/bandage protector with the aperture. Similarly with all the bandages and wound/bandage protectors disclosed herein, the bandage or wound/bandage protector may first be placed over the wound and then a wound/bandage protector or super stretch tube may be positioned over the bandage or wound/bandage protector. In addition, the invention also relates to a kit that includes all or a set of the wound/bandage protectors, bandages, and/or super-stretch tubes, as disclosed herein.

BRIEF DESCRIPTION OF DRAWINGS

FIG. 1(a) is a perspective side view of an exemplary embodiment of a super-stretch tube according to the present invention;

FIG. 1(b) illustrates an exemplary embodiment of a cross-sectional view of the super-stretch tube taken along the line I-I' in FIG. 1(a);

FIG. 2(a) is a side view of an exemplary embodiment of a wound/bandage protector according to the present invention;

FIG. 2(b) is a side view of an exemplary embodiment of a protective sheath for the wound/bandage protector illustrated in FIG. 2(a);

FIG. 3(a) is a side view of an exemplary embodiment of a wound/bandage protector according to the present invention;

FIG. 3(b) is a side view of an exemplary embodiment of a protective sheath for the wound/bandage protector illustrated in FIG. 3(a);

FIG. 4 is a side view of an exemplary embodiment of a wound/bandage protector according to the present invention;

FIG. 5 is a side view of an exemplary embodiment of a wound/bandage protector according to the present invention;

FIG. 6(*a*) is a top non-wound facing side view of an exemplary embodiment of a wound/bandage protector according to the present invention;

FIG. 6(*b*) is a bottom wound facing side view of the exemplary embodiment of the wound/bandage protector illustrated in FIG. 6(*a*);

FIG. 6(*c*) is a side cross-sectional view of the exemplary embodiment of the wound/bandage protector illustrated in FIGS. 6(*a*) and (*b*) taken along the line II-II' in FIG. 6(*b*);

FIG. 7(*b*) is a bottom wound facing side view of the exemplary embodiment of the wound/bandage protector illustrated in FIG. 7(*a*);

FIG. 7(*c*) is a side cross-sectional view of the exemplary embodiment of the wound/bandage protector illustrated in FIGS. 7(*a*) and (*b*) taken along the line III-III' in FIG. 7(*b*);

FIG. 8(*b*) is a bottom wound facing side view of the exemplary embodiment of the wound/bandage protector illustrated in FIG. 8(*a*);

FIG. 8(*c*) is a side cross-sectional view of the exemplary embodiment of the wound/bandage protector illustrated in FIGS. 8(*a*) and (*b*) taken along the line IV-IV' in FIG. 8(*b*);

FIG. 9(*b*) is a bottom wound facing side view of the exemplary embodiment of the wound/bandage protector illustrated in FIG. 9(*a*);

FIG. 9(*c*) is a side cross-sectional view of the exemplary embodiment of the wound/bandage protector illustrated in FIGS. 9(*a*) and (*b*) taken along the line V-V' in FIG. 9(*b*);

FIG. 10(*b*) is a bottom wound facing side view of the exemplary embodiment of the wound/bandage protector illustrated in FIG. 10(*a*);

FIG. 10(*c*) is a side cross-sectional view of the exemplary embodiment of the wound/bandage protector illustrated in FIGS. 10(*a*) and (*b*) taken along the line VI-VI' in FIG. 10(*b*);

FIG. 11(*b*) is a bottom wound facing side view of the exemplary embodiment of the wound/bandage protector illustrated in FIG. 11(*a*);

FIG. 11(*c*) is a side cross-sectional view of the exemplary embodiment of the wound/bandage protector illustrated in FIGS. 11(*a*) and (*b*) taken along the line VII-VII' in FIG. 11(*b*);

FIG. 12(*a*) shows a bottom wound-facing side of an exemplary embodiment of a "diamond gauze" adhesive bandage according to the present invention;

FIG. 12(*b*) shows a top non-wound-facing side of the exemplary embodiment of the "diamond gauze" adhesive bandage illustrated in FIG. 12(*a*);

FIG. 12(*c*) shows a side view of the exemplary embodiment of the "diamond gauze" adhesive bandage illustrated in FIGS. 12(*a*) and (*b*) (the view from the other side is a mirror image);

FIG. 12(*d*) shows an end view of the exemplary embodiment of the "diamond gauze" adhesive bandage illustrated in FIGS. 12(*a*) and (*b*) (the view from the other side is a mirror image);

FIG. 12(*e*) shows a perspective view of the exemplary embodiment of the "diamond gauze" adhesive bandage illustrated in FIGS. 12(*a*) and (*b*);

FIG. 12(*f*) shows a second perspective view of the exemplary embodiment of the "diamond gauze" adhesive bandage illustrated in FIGS. 12(*a*) and (*b*);

FIG. 13(*a*) shows a bottom wound-facing side of an exemplary embodiment of a "diamond gauze" adhesive bandage according to the present invention;

FIG. 13(*b*) shows a top non-wound-facing side of the exemplary embodiment of the "diamond gauze" adhesive bandage illustrated in FIG. 13(*a*);

FIG. 13(*c*) shows a side view of the exemplary embodiment of the "diamond gauze" adhesive bandage illustrated in FIGS. 13(*a*) and (*b*) (the view from the other side is a mirror image);

FIG. 13(*d*) shows an end view of the exemplary embodiment of the "diamond gauze" adhesive bandage illustrated in FIGS. 13(*a*) and (*b*) (the view from the other side is a mirror image);

FIG. 13(*e*) shows a perspective view of the exemplary embodiment of the "diamond gauze" adhesive bandage illustrated in FIGS. 13(*a*) and (*b*);

FIG. 13(*f*) shows a second perspective view of the exemplary embodiment of the "diamond gauze" adhesive bandage illustrated in FIGS. 13(*a*) and (*b*);

FIG. 14(*a*) shows a bottom wound-facing side of an exemplary embodiment of a "diamond gauze" adhesive bandage according to the present invention;

FIG. 14(*b*) shows a top non-wound-facing side of the exemplary embodiment of the "diamond gauze" adhesive bandage illustrated in FIG. 14(*a*);

FIG. 14(*c*) shows a side view of the exemplary embodiment of the "diamond gauze" adhesive bandage illustrated in FIGS. 14(*a*) and (*b*) (the view from the other side is a mirror image);

FIG. 14(*d*) shows an end view of the exemplary embodiment of the "diamond gauze" adhesive bandage illustrated in FIGS. 14(*a*) and (*b*) (the view from the other side is a mirror image);

FIG. 14(*e*) shows a perspective view of the exemplary embodiment of the "diamond gauze" adhesive bandage illustrated in FIGS. 14(*a*) and (*b*);

FIG. 15(*a*) shows a bottom wound-facing side of an exemplary embodiment of a "diamond gauze" adhesive bandage according to the present invention;

FIG. 15(*b*) shows a top non-wound-facing side of the exemplary embodiment of the "diamond gauze" adhesive bandage illustrated in FIG. 15(*a*);

FIG. 15(*c*) shows a side view of the exemplary embodiment of the "diamond gauze" adhesive bandage illustrated in FIGS. 15(*a*) and (*b*) (the view from the other side is a mirror image);

FIG. 15(*d*) shows an end view of the exemplary embodiment of the "diamond gauze" adhesive bandage illustrated in FIGS. 15(*a*) and (*b*) (the view from the other side is a mirror image);

FIG. 15(*e*) shows a perspective view of the exemplary embodiment of the "diamond gauze" adhesive bandage illustrated in FIGS. 15(*a*) and (*b*);

FIG. 16(*a*) shows a bottom wound-facing side of an exemplary embodiment of a "diamond gauze" adhesive bandage according to the present invention;

FIG. 16(b) shows a top non-wound-facing side of the exemplary embodiment of the "diamond gauze" adhesive bandage illustrated in FIG. 16(a);

FIG. 16(c) shows a side view of the exemplary embodiment of the "diamond gauze" adhesive bandage illustrated in FIGS. 16(a) and (b) (the view from the other side is a mirror image);

FIG. 16(d) shows an end view of the exemplary embodiment of the "diamond gauze" adhesive bandage illustrated in FIGS. 16(a) and (b) (the view from the other side is a mirror image);

FIG. 16(e) shows a perspective view of the exemplary embodiment of the "diamond gauze" adhesive bandage illustrated in FIGS. 16(a) and (b);

FIG. 17(a) shows a bottom wound-facing side of an exemplary embodiment of a "diamond gauze" adhesive bandage according to the present invention;

FIG. 17(b) shows a top non-wound-facing side of the exemplary embodiment of the "diamond gauze" adhesive bandage illustrated in FIG. 17(a);

FIG. 17(c) shows a side view of the exemplary embodiment of the "diamond gauze" adhesive bandage illustrated in FIGS. 17(a) and (b) (the view from the other side is a mirror image);

FIG. 17(d) shows an end view of the exemplary embodiment of the "diamond gauze" adhesive bandage illustrated in FIGS. 17(a) and (b) (the view from the other side is a mirror image);

FIG. 17(e) shows a perspective view of the exemplary embodiment of the "diamond gauze" adhesive bandage illustrated in FIGS. 17(a) and (b);

FIG. 18(a) shows a bottom wound-facing side of an exemplary embodiment of a "diamond gauze" adhesive bandage according to the present invention;

FIG. 18(b) shows a top non-wound-facing side of the exemplary embodiment of the "diamond gauze" adhesive bandage illustrated in FIG. 18(a);

FIG. 18(c) shows a side view of the exemplary embodiment of the "diamond gauze" adhesive bandage illustrated in FIGS. 18(a) and (b) (the view from the other side is a mirror image);

FIG. 18(d) shows an end view of the exemplary embodiment of the "diamond gauze" adhesive bandage illustrated in FIGS. 18(a) and (b) (the view from the other side is a mirror image);

FIG. 18(e) shows a perspective view of the exemplary embodiment of the "diamond gauze" adhesive bandage illustrated in FIGS. 18(a) and (b);

FIG. 19(c) shows a first side view of the exemplary embodiment of the "diamond gauze" adhesive bandage illustrated in FIGS. 19(a) and (b);

FIG. 19(d) shows a second side view of the exemplary embodiment of the "diamond gauze" adhesive bandage illustrated in FIGS. 19(a) and (b);

FIG. 19(e) shows a first end view of the exemplary embodiment of the "diamond gauze" adhesive bandage illustrated in FIGS. 19(a) and (b);

FIG. 19(f) shows a second end view of the exemplary embodiment of the "diamond gauze" adhesive bandage illustrated in FIGS. 19(a) and (b);

FIG. 19(g) shows a perspective view of the exemplary embodiment of the "diamond gauze" adhesive bandage illustrated in FIGS. 19(a) and (b);

FIG. 21(a) shows a bottom wound-facing side of an exemplary embodiment of a "diamond gauze" adhesive bandage according to the present invention;

FIG. 21(b) shows a top non-wound-facing side of the exemplary embodiment of the "diamond gauze" adhesive bandage illustrated in FIG. 21(a);

FIG. 21(c) shows a side view of the exemplary embodiment of the "diamond gauze" adhesive bandage illustrated in FIGS. 21(a) and (b) (the view from the other side is a mirror image);

FIG. 21(d) shows an end view of the exemplary embodiment of the "diamond gauze" adhesive bandage illustrated in FIGS. 21(a) and (b) (the view from the other side is a mirror image);

FIG. 21(e) shows a perspective view of the exemplary embodiment of the "diamond gauze" adhesive bandage illustrated in FIGS. 21(a) and (b);

FIG. 22(a) shows a bottom wound-facing side of an exemplary embodiment of a "triangular gauze" adhesive bandage according to the present invention;

FIG. 22(b) shows a top non-wound-facing side of the exemplary embodiment of the "triangular gauze" adhesive bandage illustrated in FIG. 22(a);

FIG. 22(c) shows a first side view of the exemplary embodiment of the "triangular gauze" adhesive bandage illustrated in FIGS. 22(a) and (b);

FIG. 22(d) shows a second side view of the exemplary embodiment of the "triangular gauze" adhesive bandage illustrated in FIGS. 22(a) and (b);

FIG. 22(e) shows a first end view of the exemplary embodiment of the "triangular gauze" adhesive bandage illustrated in FIGS. 22(a) and (b);

FIG. 22(f) shows a second end view of the exemplary embodiment of the "triangular gauze" adhesive bandage illustrated in FIGS. 22(a) and (b);

FIG. 22(g) shows a perspective view of the exemplary embodiment of the "triangular gauze" adhesive bandage illustrated in FIGS. 22(a) and (b);

FIG. 23(*b*) shows a top non-wound-facing side of the exemplary embodiment of the "triangular gauze" adhesive bandage illustrated in FIG. 23(*a*);

FIG. 23(*c*) shows a first side view of the exemplary embodiment of the "triangular gauze" adhesive bandage illustrated in FIGS. 23(*a*) and (*b*);

FIG. 23(*d*) shows a second side view of the exemplary embodiment of the "triangular gauze" adhesive bandage illustrated in FIGS. 23(*a*) and (*b*);

FIG. 23(*e*) shows a first end view of the exemplary embodiment of the "triangular gauze" adhesive bandage illustrated in FIGS. 23(*a*) and (*b*);

FIG. 23(*f*) shows a second end view of the exemplary embodiment of the "triangular gauze" adhesive bandage illustrated in FIGS. 23(*a*) and (*b*);

FIG. 23(*g*) shows a perspective view of the exemplary embodiment of the "triangular gauze" adhesive bandage illustrated in FIGS. 23(*a*) and (*b*);

FIG. 24(*a*) shows a bottom wound-facing side of an exemplary embodiment of a "diamond gauze" bandage according to the present invention;

FIG. 24(*b*) shows a perspective view of the exemplary embodiment of the "diamond gauze" bandage illustrated in FIGS. 24(*a*) and (*c*);

FIG. 24(*c*) shows a top non-wound-facing side of the exemplary embodiment of the "diamond gauze" bandage illustrated in FIG. 24(*a*);

FIG. 24(*d*) shows a side view along a length tangent 249C of the exemplary embodiment of the "diamond gauze" bandage illustrated in FIGS. 24(*a*) and (*b*) (the view from the opposing length tangent 249A is a mirror image);

FIG. 24(*e*) shows a side view along a width tangent 249B of the exemplary embodiment of the "diamond gauze" bandage illustrated in FIGS. 24(*a*) and (*b*);

FIG. 24(*f*) shows a side view along a width tangent 249D of the exemplary embodiment of the "diamond gauze" bandage illustrated in FIGS. 24(*a*) and (*b*);

FIG. 25(*b*) shows a top view of an exemplary gauze pad configuration with convex sides for a "diamond gauze" bandage according to the present invention;

FIG. 25(*c*) shows a top view of an exemplary gauze pad configuration with undulating sides for a "diamond gauze" bandage according to the present invention;

FIG. 25(*d*) shows a top view of an exemplary gauze pad configuration with rounded corners for a "diamond gauze" bandage according to the present invention;

FIG. 25(*e*) shows a top view of an exemplary gauze pad configuration with a square shape for a "diamond gauze" bandage according to the present invention;

FIG. 25(*f*) shows a top view of an exemplary gauze pad configuration with an offset diamond shape for a "diamond gauze" bandage according to the present invention;

FIG. 25(*g*) shows a top view of an exemplary gauze pad configuration with a diamond or rhombus shape for a "diamond gauze" bandage according to the present invention;

FIG. 25(*h*) shows a top view of an exemplary gauze pad configuration with a kite shape for a "diamond gauze" bandage according to the present invention;

FIG. 25(*i*) shows a top view of an exemplary gauze pad configuration with a rectangular shape for a "diamond gauze" bandage according to the present invention;

FIG. 25(*j*) shows a top view of an exemplary gauze pad configuration with two opposing corners cut off for a "diamond gauze" bandage according to the present invention;

FIG. 25(*k*) shows a top view of an exemplary gauze pad configuration with four cut off corners for a "diamond gauze" bandage according to the present invention;

FIG. 25(*l*) shows a definition of length and width in terms of a horizontal axis and a vertical axis for a "diamond gauze" bandage according to the present invention;

FIG. 25(*m*) illustrates an exemplary preferred range of gauze pad orientation for a "diamond gauze" bandage according to the present invention;

FIG. 26(*a*) shows a bottom wound-facing side of an exemplary embodiment of a "diamond gauze" bandage according to the present invention;

FIG. 26(*b*) shows a top non-wound-facing side of the exemplary embodiment of the "diamond gauze" bandage illustrated in FIG. 26(*a*);

FIG. 26(*c*) shows a side view along a length tangent 269C of the exemplary embodiment of the "diamond gauze" bandage illustrated in FIGS. 26(*a*) and (*b*) (the view from the opposing length tangent 269A is a mirror image);

FIG. 26(*d*) shows a side view along a width tangent 269B of the exemplary embodiment of the "diamond gauze" bandage illustrated in FIGS. 26(*a*) and (*b*);

FIG. 26(*e*) shows a side view along a width tangent 269D of the exemplary embodiment of the "diamond gauze" bandage illustrated in FIGS. 26(*a*) and (*b*);

FIG. 26(*f*) shows a perspective view of the exemplary embodiment of the "diamond gauze" bandage illustrated in FIGS. 26(*a*) and (*b*);

FIG. 27(*a*) shows a bottom wound-facing side of an exemplary embodiment of a "diamond gauze" bandage according to the present invention;

FIG. 27(*b*) shows a top non-wound-facing side of the exemplary embodiment of the "diamond gauze" bandage illustrated in FIG. 27(*a*);

FIG. 27(*c*) shows a side view along a length tangent 279A of the exemplary embodiment of the "diamond gauze" bandage illustrated in FIGS. 27(*a*) and (*b*) (the view from the opposing length tangent 279C is a mirror image);

FIG. 27(*d*) shows a side view along a width tangent line 279B of the exemplary embodiment of the "diamond gauze" bandage illustrated in FIGS. 27(*a*) and (*b*) (the view from the opposing width tangent 279D is a mirror image);

FIG. 27(*e*) shows a perspective view of the exemplary embodiment of the "diamond gauze" bandage illustrated in FIGS. 27(*a*) and (*b*);

FIG. 28(*a*) shows a bottom wound-facing side of an exemplary embodiment of a "diamond gauze" bandage according to the present invention;

Figures 28B, 28C, 28D, 28E:
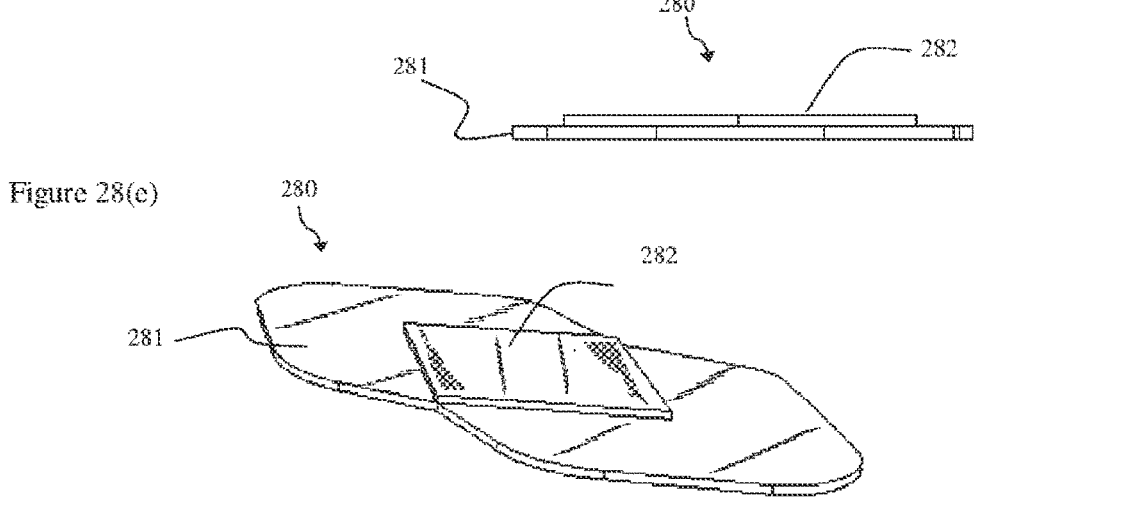
Figures 29A, 29B, 29C, 29D, 29E, 29F:
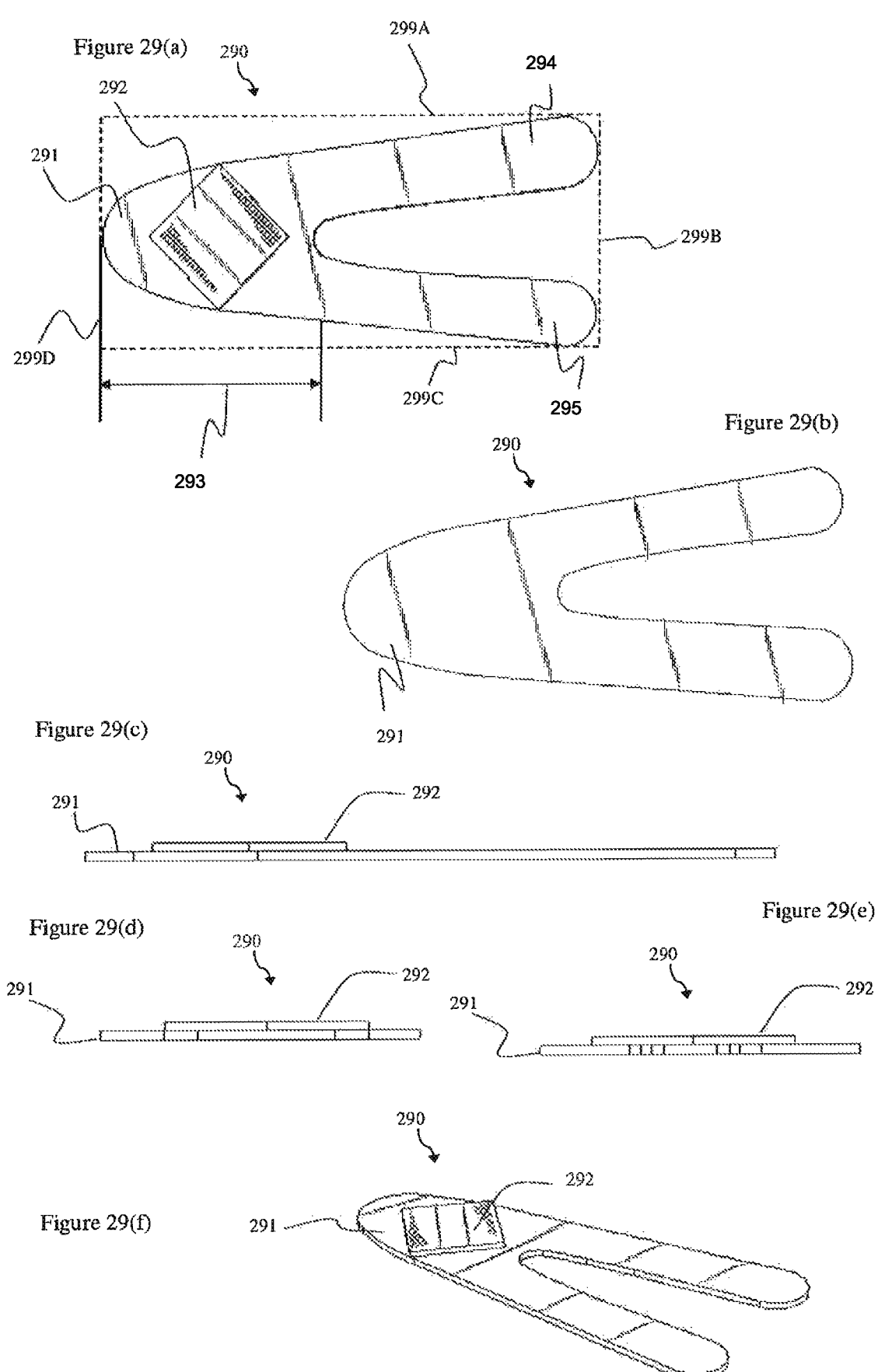
Figures 31A, 31B, 31C, 31D, 31E:
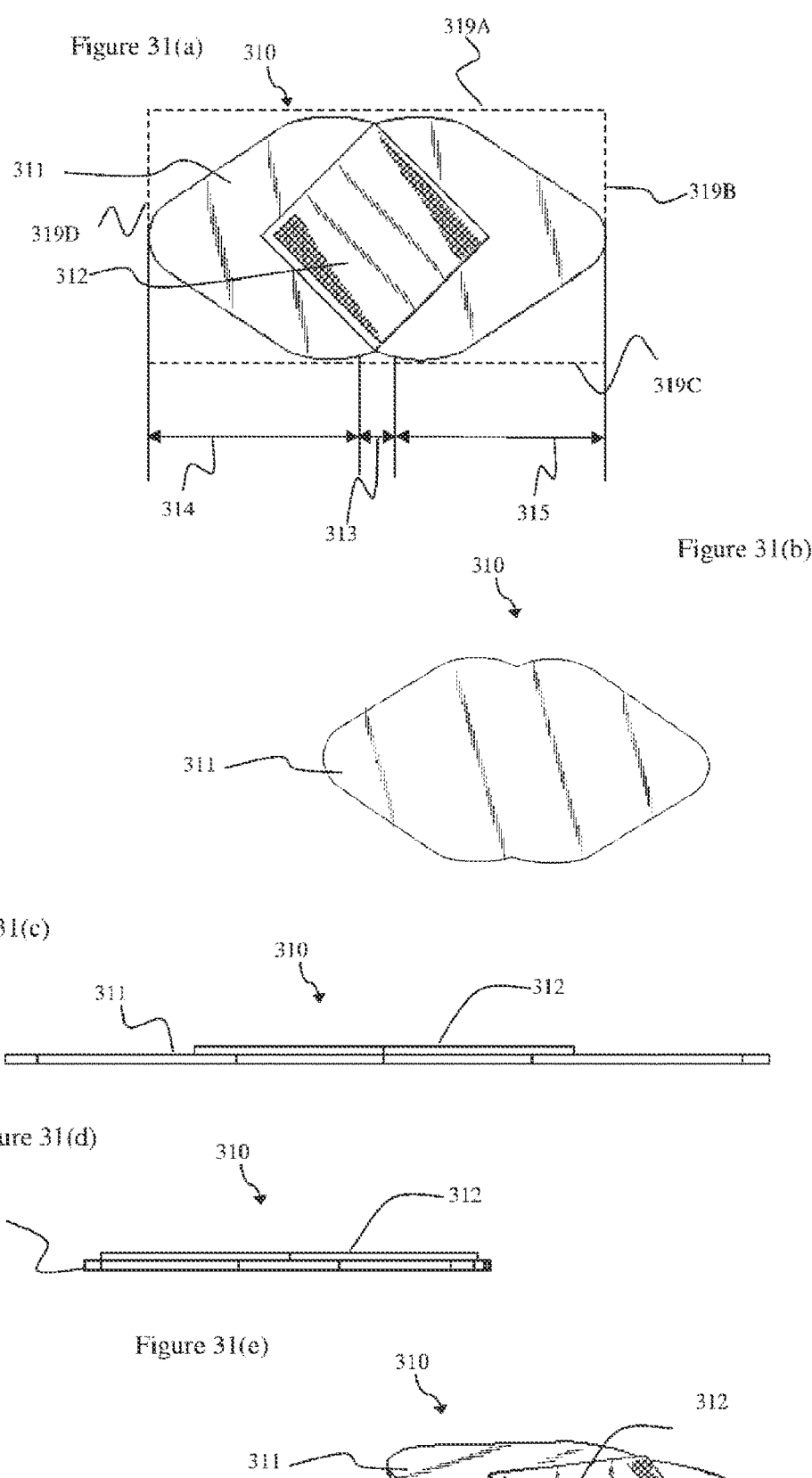
Figure 32A:
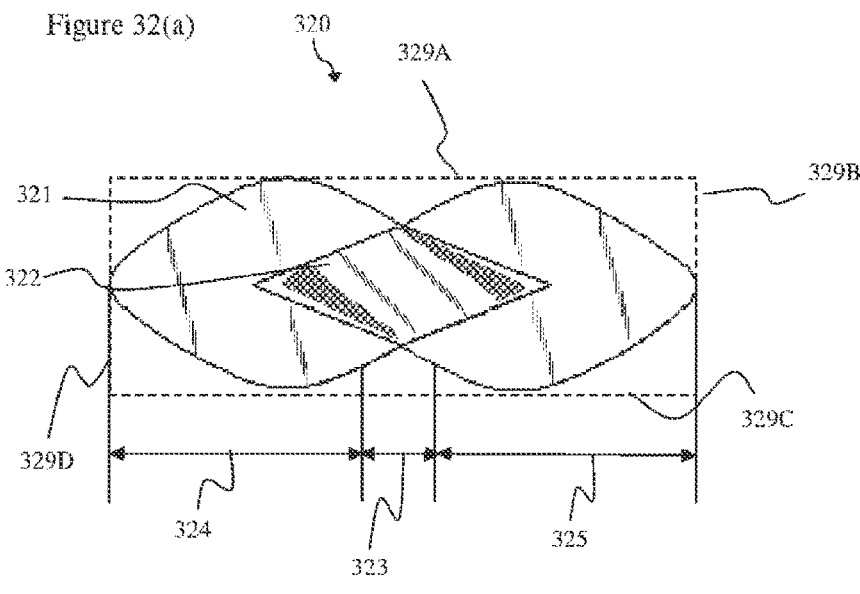
Figure 32B:
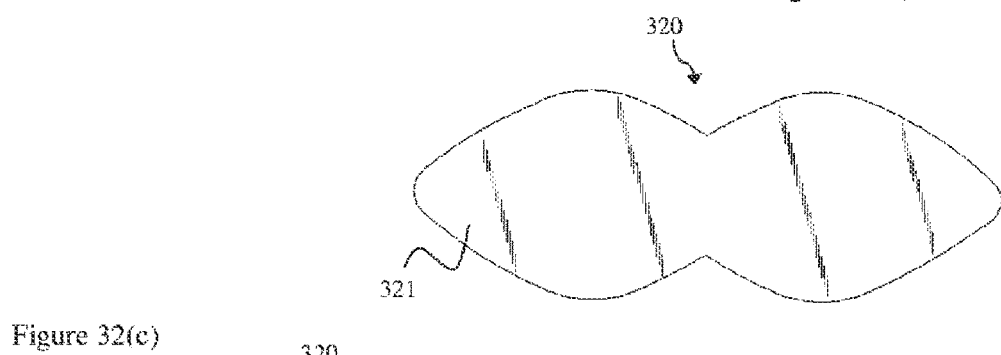
Figure 32C:
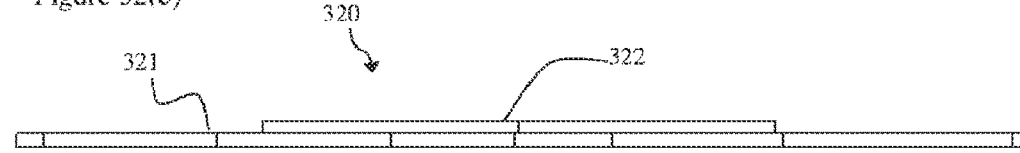
Figure 32D:
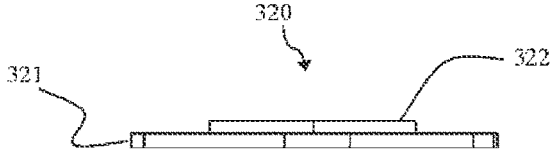
Figure 32E:
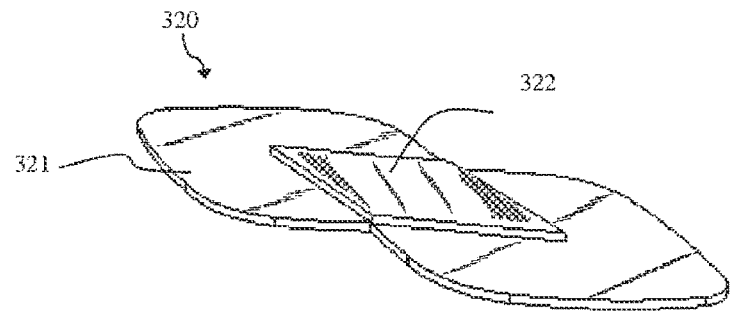
Figures 33A, 33B, 33C, 33D, 33E:
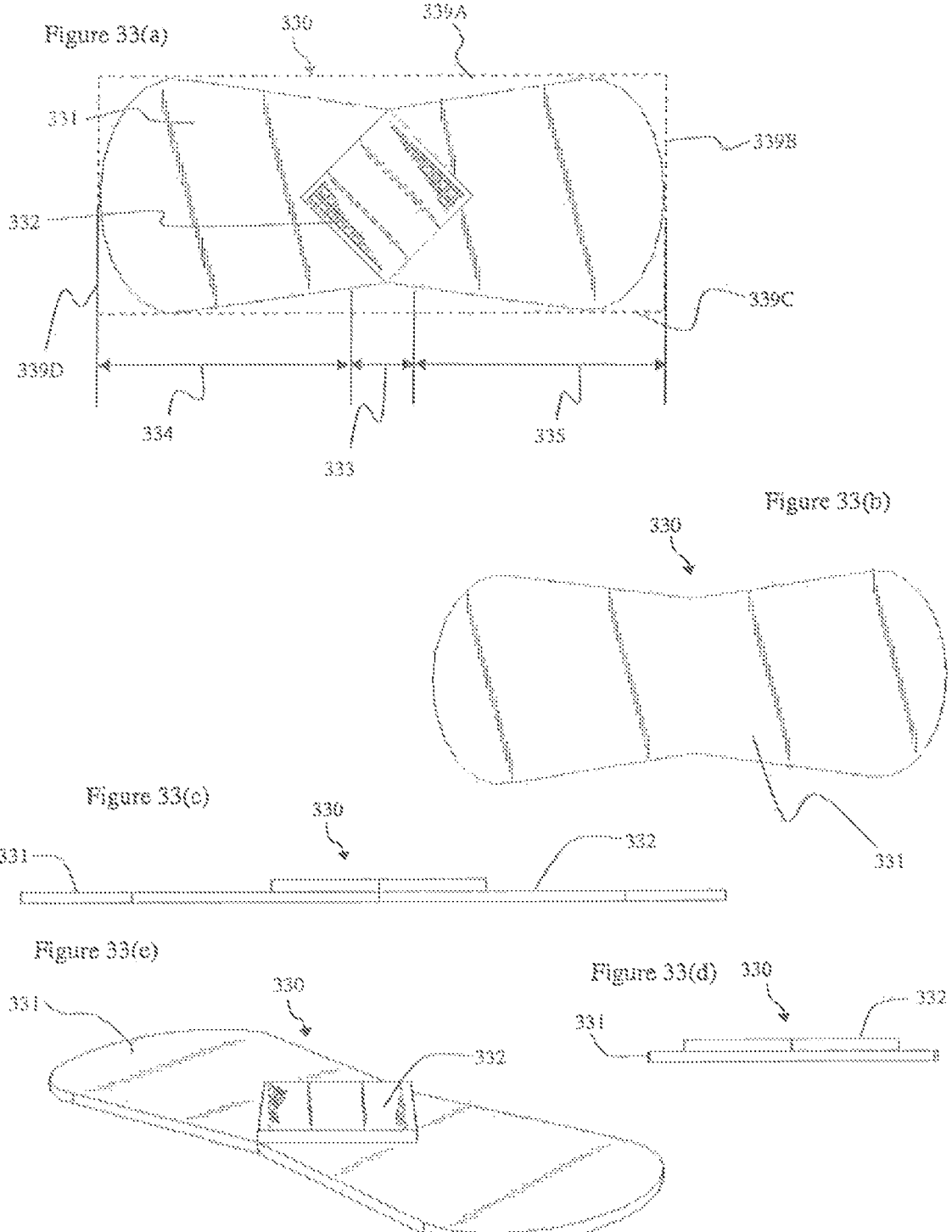
Figures 34A, 34B, 34C, 34D, 34E:
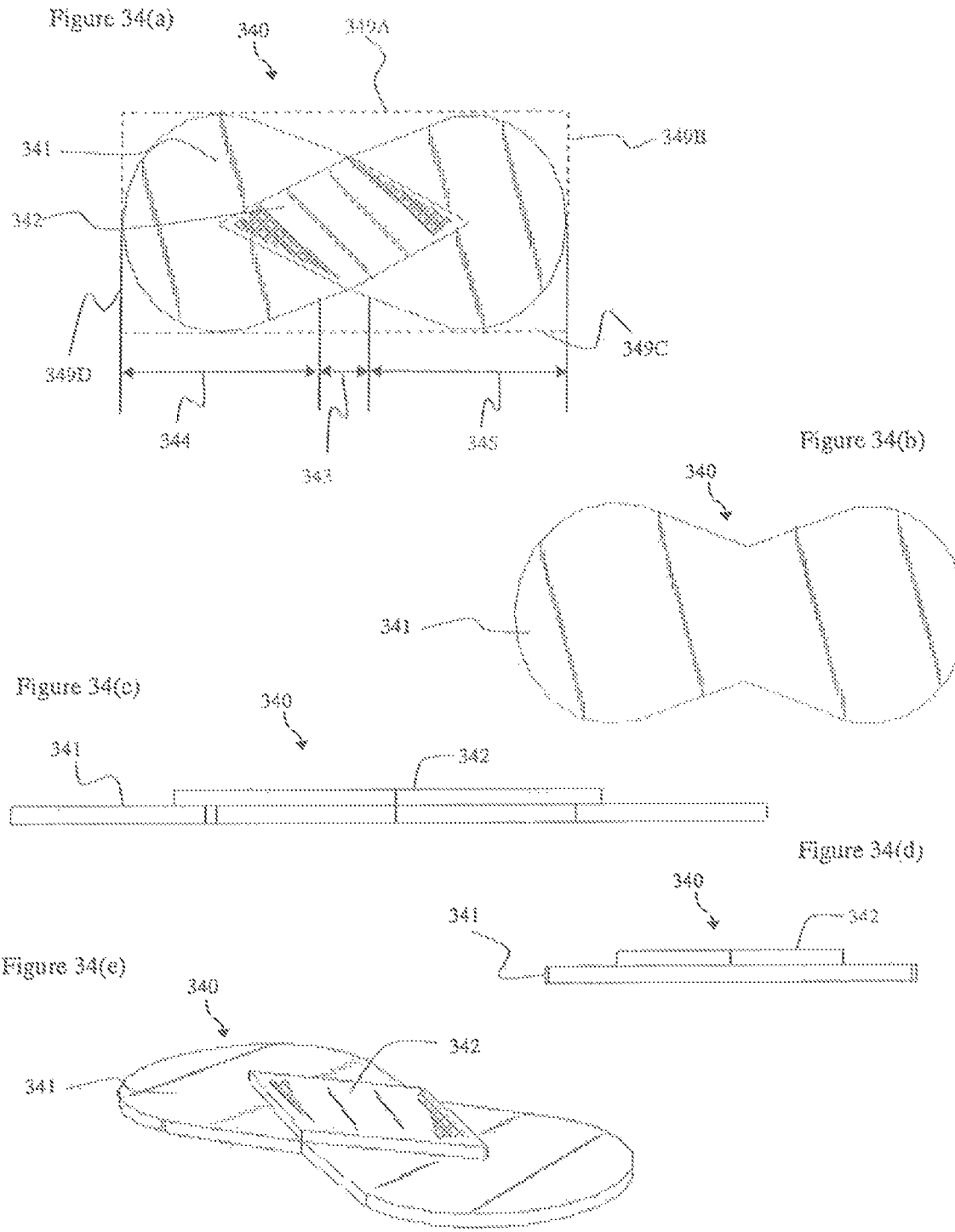
Figures 35A, 35B, 35C, 35D, 35E:
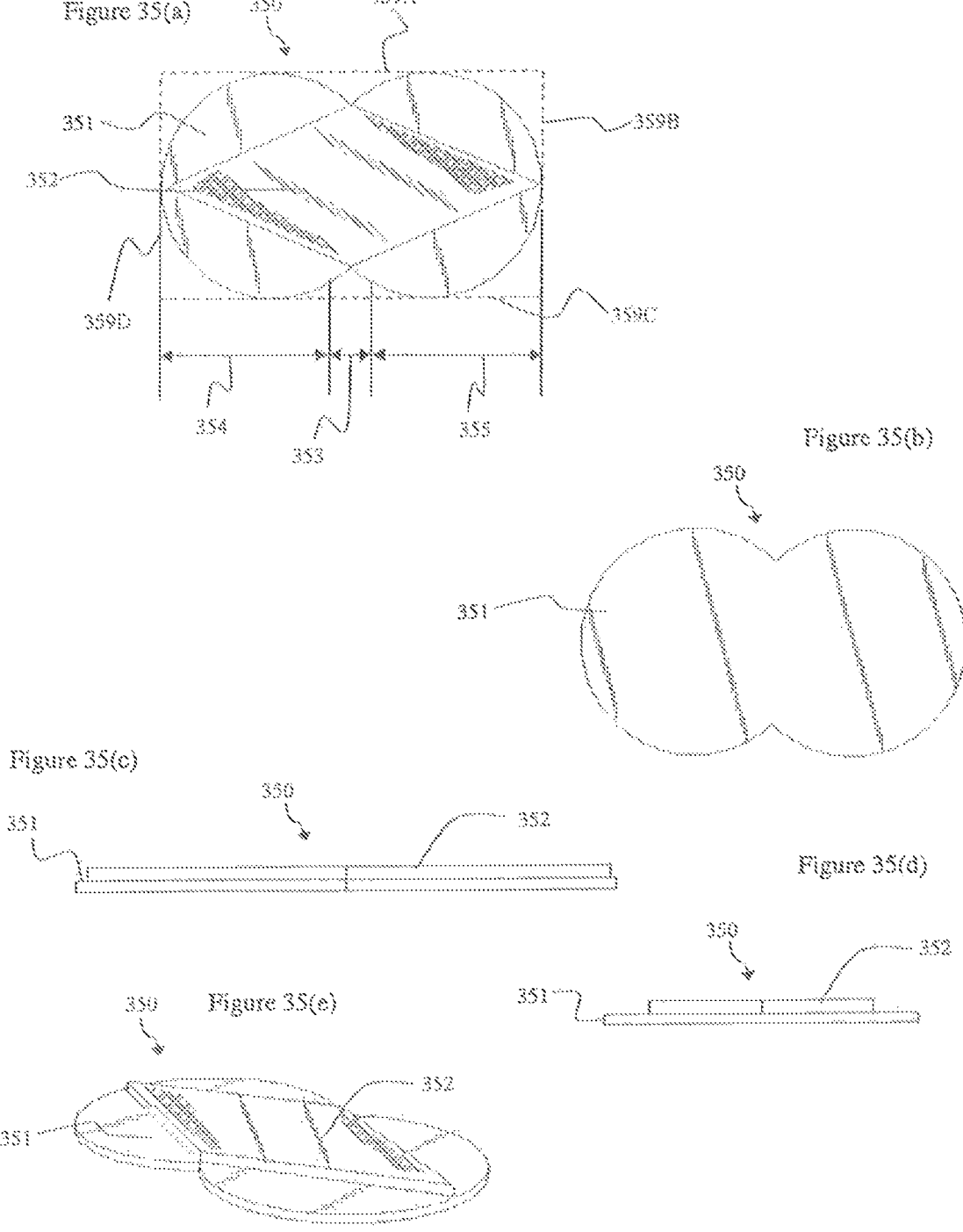
Figures 36A, 36B, 36C, 36D, 36E:
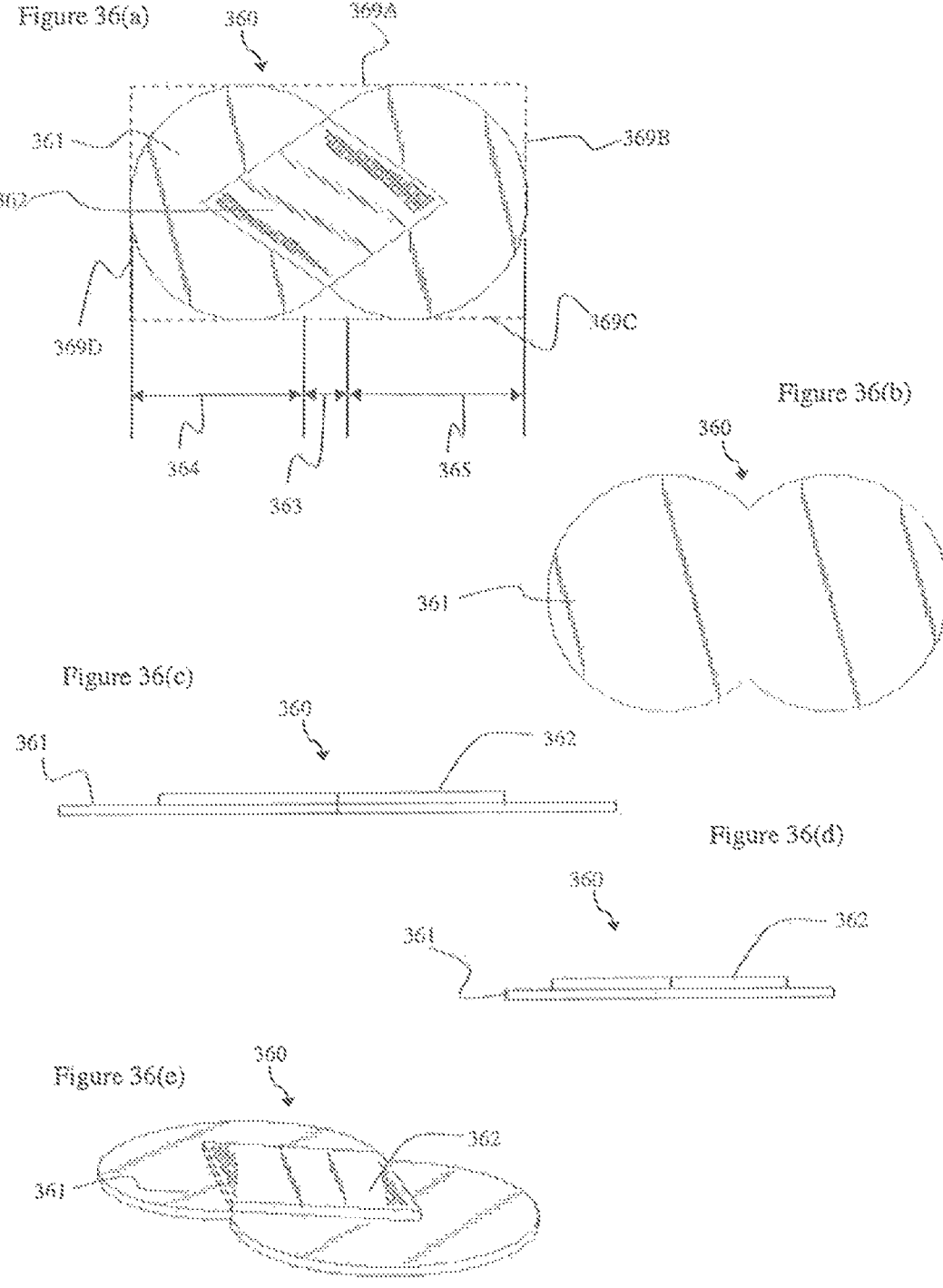
Figure 41A:
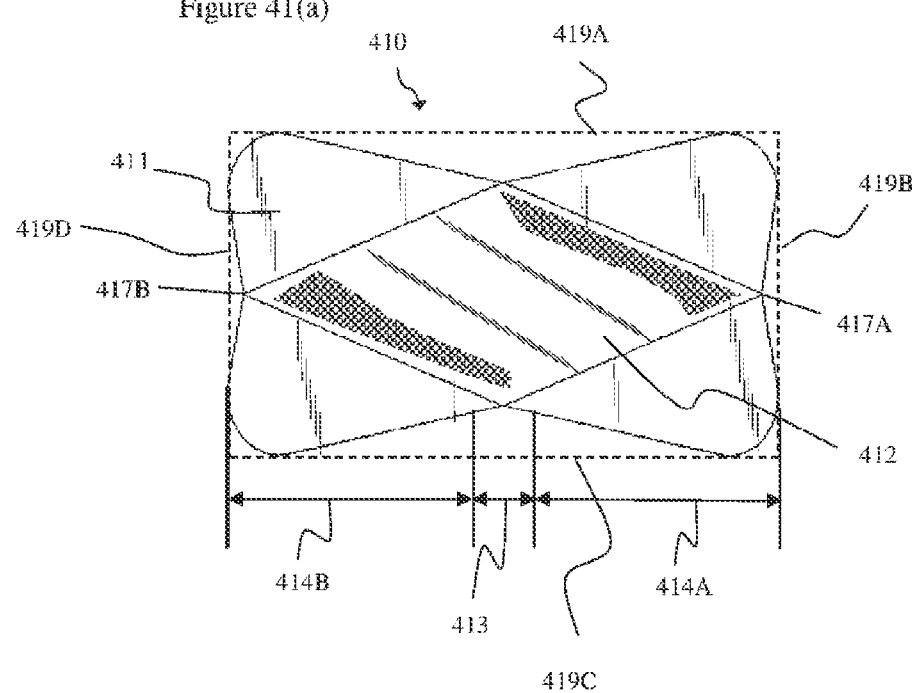
Figure 41B:
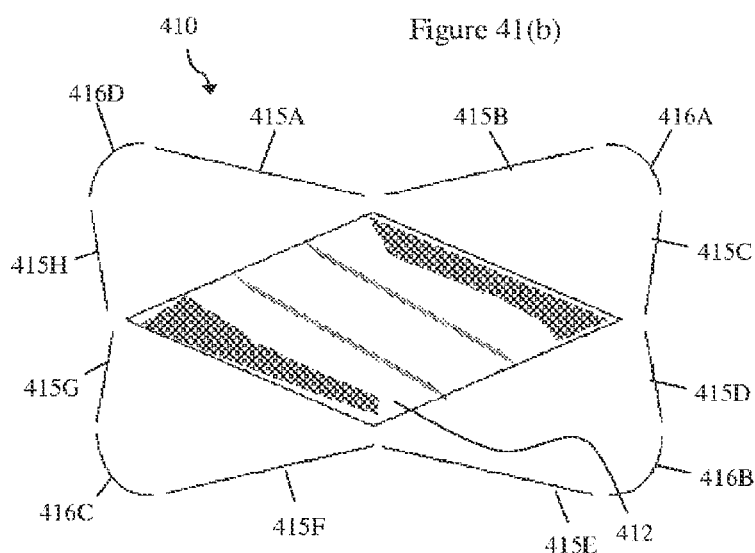
Figures 46A, 46B, 46C, 46D:
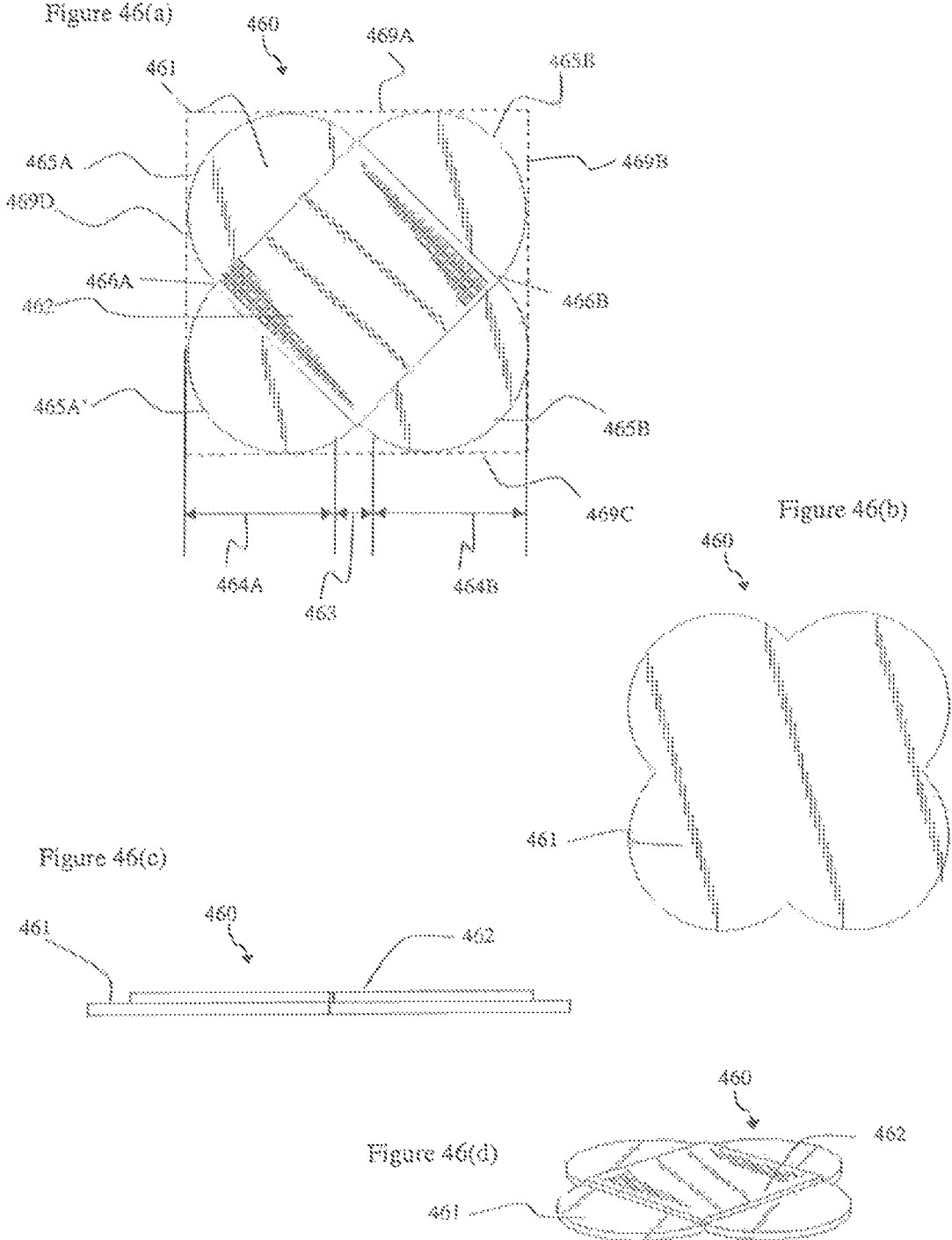
Figure 47A:
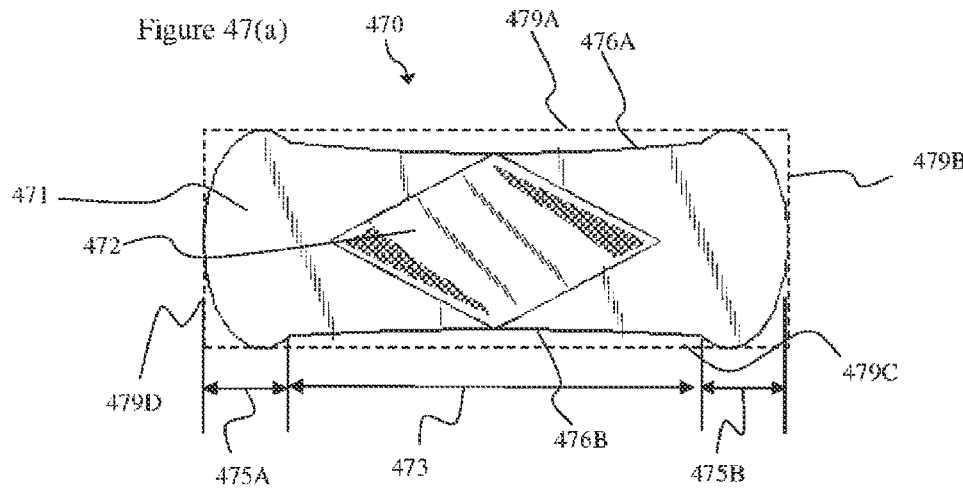
Figure 47B:
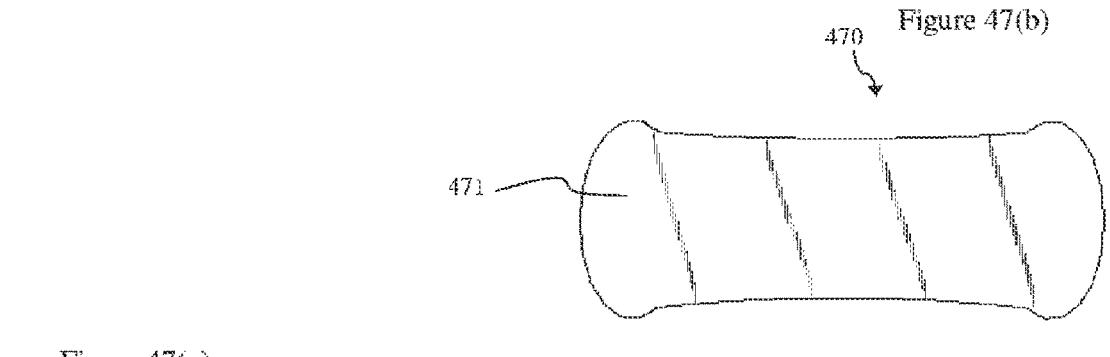
Figure 47C:
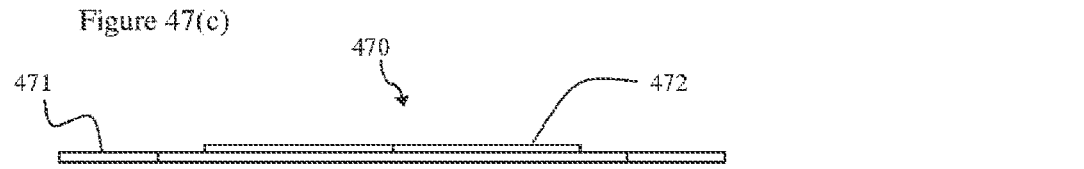
Figure 47D:
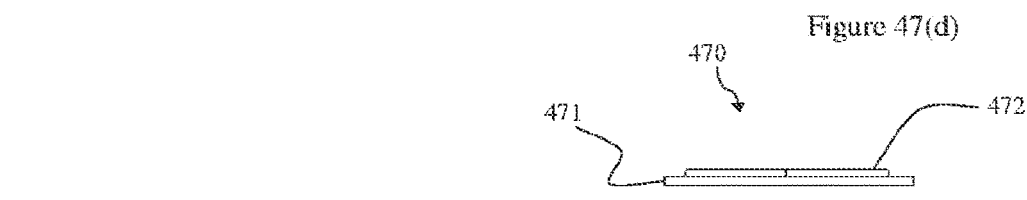
Figure 47E:
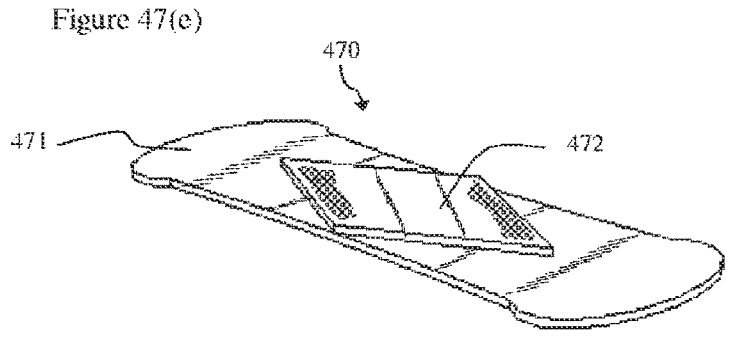
Figure 49A:
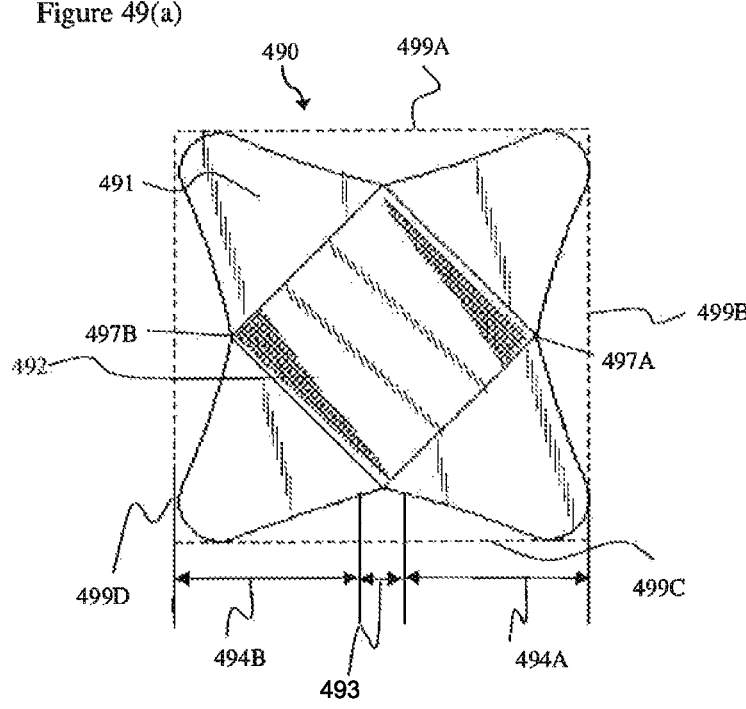
Figure 49B:
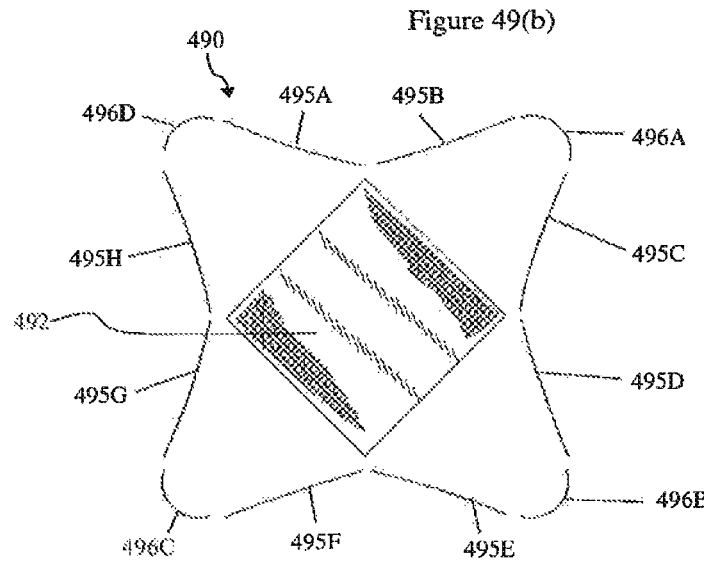
Figure 49C:
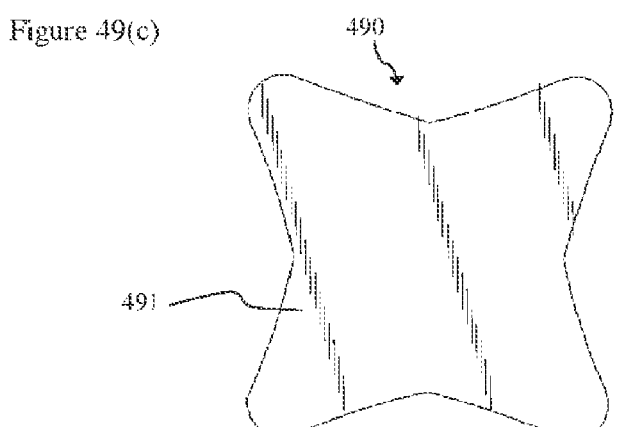
Figure 49D:
Figure 49E:
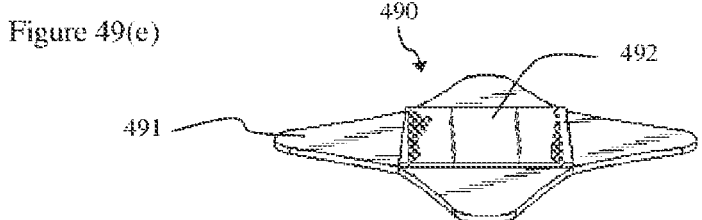
Figures 51A, 51B, 51C, 51D, 51E, 51F:
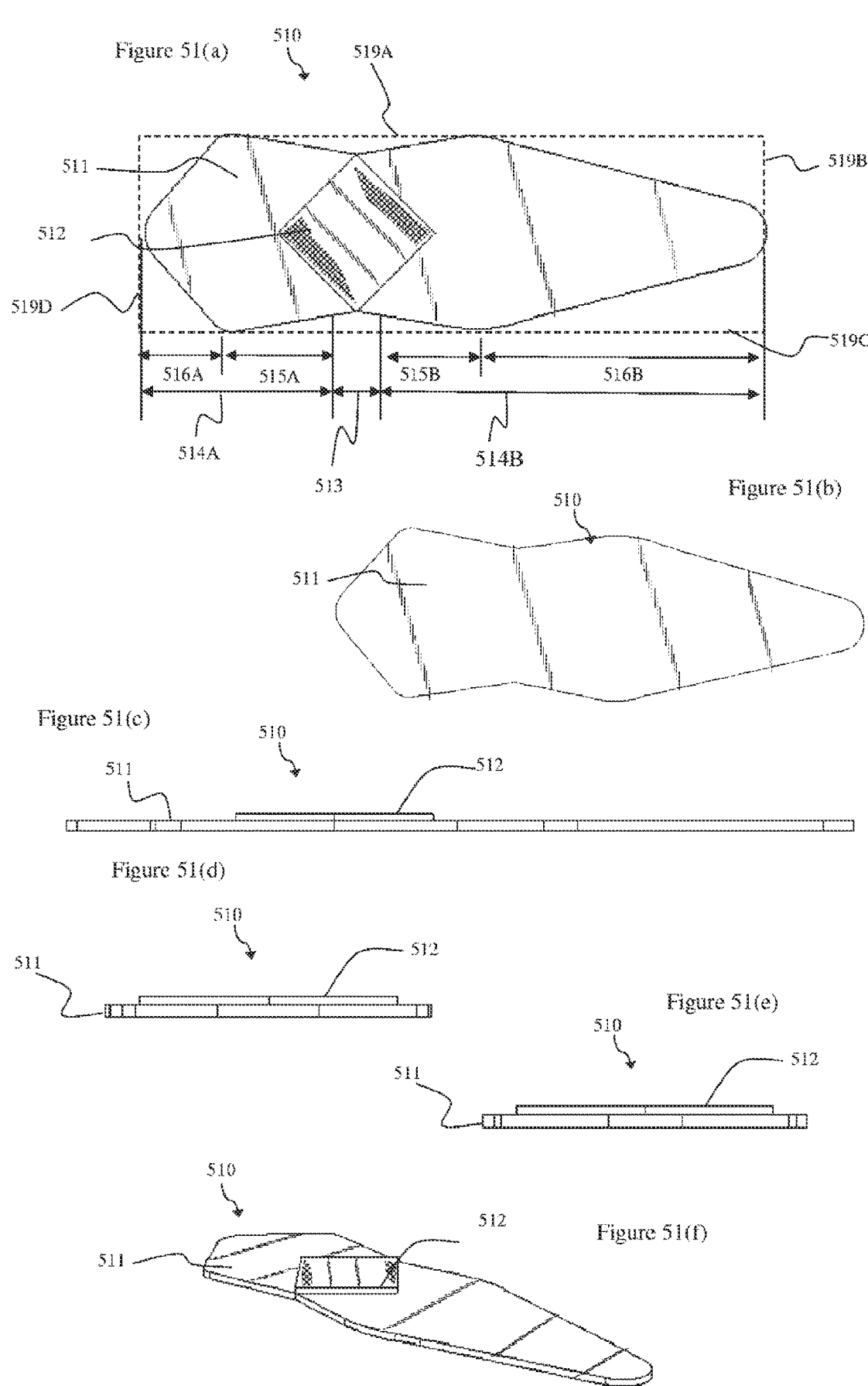
Figure 53A:
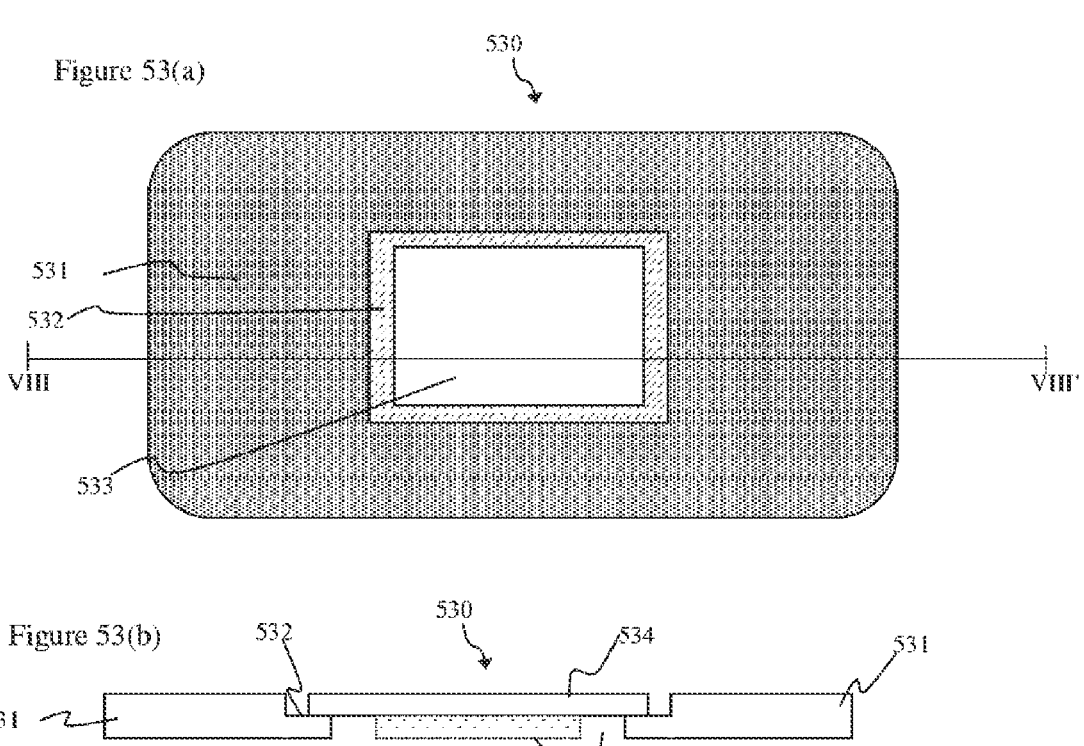

FIG. 28(*b*) shows a top non-wound-facing side of the exemplary embodiment of the "diamond gauze" bandage illustrated in FIG. 28(*a*);

FIG. 28(*c*) shows a side view along a length tangent 289A of the exemplary embodiment of the "diamond gauze" bandage illustrated in FIGS. 28(*a*) and (*b*) (the view from the opposing length tangent 289C is a mirror image);

FIG. 28(*d*) shows a side view along a width tangent 289B of the exemplary embodiment of the "diamond gauze" bandage illustrated in FIGS. 28(*a*) and (*b*) (the view from the opposing width tangent 289D is a mirror image);

FIG. 28(*e*) shows a perspective view of the exemplary embodiment of the "diamond gauze" bandage illustrated in FIGS. 28(*a*) and (*b*);

FIG. 29(*a*) shows a bottom wound-facing side of an exemplary embodiment of a "diamond gauze" bandage according to the present invention;

FIG. 29(*b*) shows a top non-wound-facing side of the exemplary embodiment of the "diamond gauze" bandage illustrated in FIG. 29(*a*);

FIG. 29(*c*) shows a side view along a length tangent 299C of the exemplary embodiment of the "diamond gauze" bandage illustrated in FIGS. 29(*a*) and (*b*) (the view from the opposing length tangent 299A is a mirror image);

FIG. 29(*d*) shows a side view along a width tangent 299D of the exemplary embodiment of the "diamond gauze" bandage illustrated in FIGS. 29(*a*) and (*b*);

FIG. 29(*e*) shows a side view along a width tangent line 299B of the exemplary embodiment of the "diamond gauze" bandage illustrated in FIGS. 29(*a*) and (*b*);

FIG. 29(*f*) shows a perspective view of the exemplary embodiment of the "diamond gauze" bandage illustrated in FIGS. 29(*a*) and (*b*);

FIG. 30(*a*) shows a bottom wound-facing side of an exemplary embodiment of a "diamond gauze" bandage according to the present invention;

FIG. 30(*b*) shows a top non-wound-facing side of the exemplary embodiment of the "diamond gauze" bandage illustrated in FIG. 30(*a*);

FIG. 30(*c*) shows a side view along a length tangent 309A of the exemplary embodiment of the "diamond gauze" bandage illustrated in FIGS. 30(*a*) and (*b*) (the view from the opposing tangent 309C is a mirror image);

FIG. 30(*d*) shows a side view along a width tangent 309B of the exemplary embodiment of the "diamond gauze" bandage illustrated in FIGS. 30(*a*) and (*b*) (the view from the opposing width tangent 309D is a minor image);

FIG. 30(*e*) shows a perspective view of the exemplary embodiment of the "diamond gauze" bandage illustrated in FIGS. 30(*a*) and (*b*);

FIG. 31(*a*) shows a bottom wound-facing side of an exemplary embodiment of a "diamond gauze" bandage according to the present invention;

FIG. 31(*b*) shows a top non-wound-facing side of the exemplary embodiment of the "diamond gauze" bandage illustrated in FIG. 31(*a*);

FIG. 31(*c*) shows a side view along a length tangent 319A of the exemplary embodiment of the "diamond gauze" bandage illustrated in FIGS. 31(*a*) and (*b*) (the view from the opposing length tangent 319C is a mirror image);

FIG. 31(*d*) shows a side view along a width tangent 319B of the exemplary embodiment of the "diamond gauze" bandage illustrated in FIGS. 31(*a*) and (*b*) (the view from the opposing width tangent 319D is a minor image);

FIG. 31(*e*) shows a perspective view of the exemplary embodiment of the "diamond gauze" bandage illustrated in FIGS. 31(*a*) and (*b*);

FIG. 32(*a*) shows a bottom wound-facing side of an exemplary embodiment of a "diamond gauze" bandage according to the present invention;

FIG. 32(*b*) shows a top non-wound-facing side of the exemplary embodiment of the "diamond gauze" bandage illustrated in FIG. 32(*a*);

FIG. 32(*c*) shows a side view along a length tangent 329A of the exemplary embodiment of the "diamond gauze" bandage illustrated in FIGS. 32(*a*) and (*b*) (the view from the opposing length tangent 329C is a mirror image);

FIG. 32(*d*) shows a side view along a width tangent 329B of the exemplary embodiment of the "diamond gauze" bandage illustrated in FIGS. 32(*a*) and (*b*) (the view from the opposing width tangent 329D is a minor image);

FIG. 32(*e*) shows a perspective view of the exemplary embodiment of the "diamond gauze" bandage illustrated in FIGS. 32(*a*) and (*b*);

FIG. 33(*a*) shows a bottom wound-facing side of an exemplary embodiment of a "diamond gauze" bandage according to the present invention;

FIG. 33(*b*) shows a top non-wound-facing side of the exemplary embodiment of the "diamond gauze" bandage illustrated in FIG. 33(*a*);

FIG. 33(*c*) shows a side view along a length tangent 339A of the exemplary embodiment of the "diamond gauze" bandage illustrated in FIGS. 33(*a*) and (*b*) (the view from the opposing length tangent 339C is a mirror image);

FIG. 33(*d*) shows a side view along a width tangent 339B of the exemplary embodiment of the "diamond gauze" bandage illustrated in FIGS. 33(*a*) and (*b*) (the view from the opposing width tangent 339D is a mirror image);

FIG. 33(*e*) shows a perspective view of the exemplary embodiment of the "diamond gauze" bandage illustrated in FIGS. 33(*a*) and (*b*);

FIG. 34(*a*) shows a bottom wound-facing side of an exemplary embodiment of a "diamond gauze" bandage according to the present invention;

FIG. 34(*b*) shows a top non-wound-facing side of the exemplary embodiment of the "diamond gauze" bandage illustrated in FIG. 34(*a*);

FIG. 34(*c*) shows a side view along a length tangent 349A of the exemplary embodiment of the "diamond gauze" bandage illustrated in FIGS. 34(*a*) and (*b*) (the view from the opposing length tangent 349C is a mirror image);

FIG. 34(*d*) shows a side view along a width tangent 349B of the exemplary embodiment of the "diamond gauze" bandage illustrated in FIGS. 34(*a*) and (*b*) (the view from the opposing tangent 349D is a mirror image);

FIG. 34(*e*) shows a perspective view of the exemplary embodiment of the "diamond gauze" bandage illustrated in FIGS. 34(*a*) and (*b*);

FIG. 35(*a*) shows a bottom wound-facing side of an exemplary embodiment of a "diamond gauze" bandage according to the present invention;

FIG. 35(*b*) shows a top non-wound-facing side of the exemplary embodiment of the "diamond gauze" bandage illustrated in FIG. 35(*a*);

FIG. 35(*c*) shows a side view along a length tangent 359A of the exemplary embodiment of the "diamond gauze" bandage illustrated in FIGS. 35(*a*) and (*b*) (the view from the opposing length tangent 359C is a mirror image);

FIG. 35(*d*) shows a side view along a width tangent 359B of the exemplary embodiment of the "diamond gauze" bandage illustrated in FIGS. 35(*a*) and (*b*) (the view from the opposing width tangent 359D is a minor image);

FIG. 35(*e*) shows a perspective view of the exemplary embodiment of the "diamond gauze" bandage illustrated in FIGS. 35(*a*) and (*b*);

FIG. 36(*a*) shows a bottom wound-facing side of an exemplary embodiment of a "diamond gauze" bandage according to the present invention;

FIG. 36(*b*) shows a top non-wound-facing side of the exemplary embodiment of the "diamond gauze" bandage illustrated in FIG. 36(*a*);

FIG. 36(*c*) shows a side view along a length tangent 369A of the exemplary embodiment of the "diamond gauze" bandage illustrated in FIGS. 36(*a*) and (*b*) (the view from the opposing length tangent 369C is a mirror image);

FIG. 36(*d*) shows a side view along a width tangent 369B of the exemplary embodiment of the "diamond gauze"

bandage illustrated in FIGS. 36(*a*) and (*b*) (the view from the opposing width tangent 369D is a minor image);

FIG. 36(*e*) shows a perspective view of the exemplary embodiment of the "diamond gauze" bandage illustrated in FIGS. 36(*a*) and (*b*);

FIG. 37(*a*) shows a bottom wound-facing side of an exemplary embodiment of a "diamond gauze" bandage according to the present invention;

FIG. 37(*b*) shows a top non-wound-facing side of the exemplary embodiment of the "diamond gauze" bandage illustrated in FIG. 37(*a*);

FIG. 37(*c*) shows a side view along a length tangent 379A of the exemplary embodiment of the "diamond gauze" bandage illustrated in FIGS. 37(*a*) and (*b*) (the view from the opposing length tangent 379C is a mirror image);

FIG. 37(*d*) shows a side view along a width tangent 379B of the exemplary embodiment of the "diamond gauze" bandage illustrated in FIGS. 37(*a*) and (*b*) (the view from the opposing width tangent 379D is a minor image);

FIG. 37(*e*) shows a perspective view of the exemplary embodiment of the "diamond gauze" bandage illustrated in FIGS. 37(*a*) and (*b*);

FIG. 38(*a*) shows a bottom wound-facing side of an exemplary embodiment of a "diamond gauze" bandage according to the present invention;

FIG. 38(*b*) shows a top non-wound-facing side of the exemplary embodiment of the "diamond gauze" bandage illustrated in FIG. 38(*a*);

FIG. 38(*c*) shows a side view along a length tangent 389A of the exemplary embodiment of the "diamond gauze" bandage illustrated in FIGS. 38(*a*) and (*b*) (the view from the opposing length tangent 389C is a mirror image);

FIG. 38(*d*) shows a side view along a width tangent 389B of the exemplary embodiment of the "diamond gauze" bandage illustrated in FIGS. 38(*a*) and (*b*) (the view from the opposing width tangent 389D is a mirror image);

FIG. 38(*e*) shows a perspective view of the exemplary embodiment of the "diamond gauze" bandage illustrated in FIGS. 38(*a*) and (*b*);

FIG. 39(*a*) shows a bottom wound-facing side of an exemplary embodiment of a "diamond gauze" bandage according to the present invention;

FIG. 39(*b*) shows a top non-wound-facing side of the exemplary embodiment of the "diamond gauze" bandage illustrated in FIG. 39(*a*);

FIG. 39(*c*) shows a side view along a length tangent 399A of the exemplary embodiment of the "diamond gauze" bandage illustrated in FIGS. 39(*a*) and (*b*) (the view from the opposing length tangent 399C is a mirror image);

FIG. 39(*d*) shows a side view along a width tangent 399B of the exemplary embodiment of the "diamond gauze" bandage illustrated in FIGS. 39(*a*) and (*b*) (the view from the opposing width tangent 399D is a mirror image);

FIG. 39(*e*) shows a perspective view of the exemplary embodiment of the "diamond gauze" bandage illustrated in FIGS. 39(*a*) and (*b*);

FIG. 40(*a*) shows a bottom wound-facing side of an exemplary embodiment of a "diamond gauze" bandage according to the present invention;

FIG. 40(*b*) shows a top non-wound-facing side of the exemplary embodiment of the "diamond gauze" bandage illustrated in FIG. 40(*a*);

FIG. 40(*c*) shows a side view along a length tangent 409A of the exemplary embodiment of the "diamond gauze" bandage illustrated in FIGS. 40(*a*) and (*b*) (the view from the opposing length tangent 409C is a mirror image);

FIG. 40(*d*) shows a side view along a width tangent 409B of the exemplary embodiment of the "diamond gauze" bandage illustrated in FIGS. 40(*a*) and (*b*) (the view from the opposing width tangent 409D is a minor image);

FIG. 40(*e*) shows a perspective view of the exemplary embodiment of the "diamond gauze" bandage illustrated in FIGS. 40(*a*) and (*b*);

FIG. 41(*a*) shows a bottom wound-facing side of an exemplary embodiment of a "diamond gauze" bandage according to the present invention;

FIG. 41(*b*) shows an exploded bottom wound-facing side of an exemplary embodiment of a "diamond gauze" bandage according to the present invention;

FIG. 41(*c*) shows a top non-wound-facing side of the exemplary embodiment of the "diamond gauze" bandage illustrated in FIG. 41(*a*);

FIG. 41(*d*) shows a side view along a length tangent 419A of the exemplary embodiment of the "diamond gauze" bandage illustrated in FIGS. 41(*a*) and (*b*) (the view from the opposing length tangent 419C is a mirror image);

FIG. 41(*e*) shows a side view along a width tangent 419B of the exemplary embodiment of the "diamond gauze" bandage illustrated in FIGS. 41(*a*) and (*b*) (the view from the opposing width tangent 419D is a minor image);

FIG. 41(*f*) shows a perspective view of the exemplary embodiment of the "diamond gauze" bandage illustrated in FIGS. 41(*a*) and (*b*);

FIG. 42(*a*) shows a bottom wound-facing side of an exemplary embodiment of a "diamond gauze" bandage according to the present invention;

FIG. 42(*b*) shows a top non-wound-facing side of the exemplary embodiment of the "diamond gauze" bandage illustrated in FIG. 42(*a*);

FIG. 42(*c*) shows a side view along a length tangent 429A of the exemplary embodiment of the "diamond gauze" bandage illustrated in FIGS. 42(*a*) and (*b*) (the view from the opposing length tangent 429C is a mirror image);

FIG. 42(*d*) shows a side view along a width tangent 429B of the exemplary embodiment of the "diamond gauze" bandage illustrated in FIGS. 42(*a*) and (*b*) (the view from the opposing width tangent 429D is a minor image);

FIG. 42(*e*) shows a perspective view of the exemplary embodiment of the "diamond gauze" bandage illustrated in FIGS. 42(*a*) and (*b*);

Figures 43A, 43B, 43C, 43D, 43E:
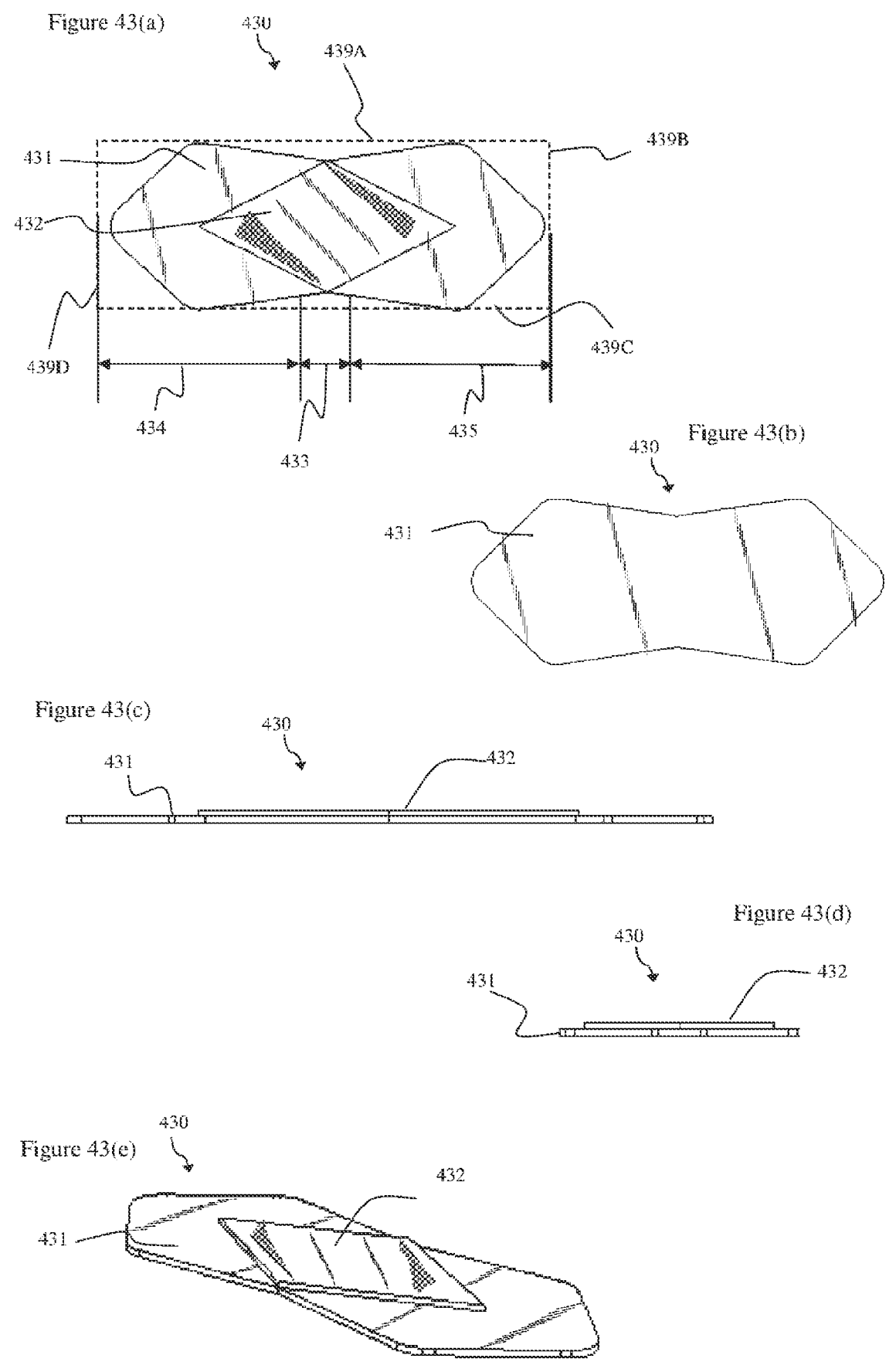

FIG. 43(*a*) shows a bottom wound-facing side of an exemplary embodiment of a "diamond gauze" bandage according to the present invention;

FIG. 43(*b*) shows a top non-wound-facing side of the exemplary embodiment of the "diamond gauze" bandage illustrated in FIG. 43(*a*);

FIG. 43(*c*) shows a side view along a length tangent 439A of the exemplary embodiment of the "diamond gauze" bandage illustrated in FIGS. 43(*a*) and (*b*) (the view from the opposing length tangent 439C is a mirror image);

FIG. 43(*d*) shows a side view along a width tangent 439B of the exemplary embodiment of the "diamond gauze" bandage illustrated in FIGS. 43(*a*) and (*b*) (the view from the opposing width tangent 439D is a mirror image);

FIG. 43(*e*) shows a perspective view of the exemplary embodiment of the "diamond gauze" bandage illustrated in FIGS. 43(*a*) and (*b*);

FIG. 44(*a*) shows a bottom wound-facing side of an exemplary embodiment of a "diamond gauze" bandage according to the present invention;

FIG. 44(*b*) shows a top non-wound-facing side of the exemplary embodiment of the "diamond gauze" bandage illustrated in FIG. 44(*a*);

FIG. 44(*c*) shows a side view along a length tangent 449A of the exemplary embodiment of the "diamond gauze" bandage illustrated in FIGS. 44(*a*) and (*b*) (the view from the opposing length tangent 449C is a mirror image);

FIG. 44(*d*) shows a side view along a width tangent 449B of the exemplary embodiment of the "diamond gauze" bandage illustrated in FIGS. 44(*a*) and (*b*) (the view from the opposing width tangent 449D is a mirror image);

FIG. 44(*e*) shows a perspective view of the exemplary embodiment of the "diamond gauze" bandage illustrated in FIGS. 44(*a*) and (*b*);

FIG. 45(*a*) shows a bottom wound-facing side of an exemplary embodiment of a "diamond gauze" bandage according to the present invention;

FIG. 45(*b*) shows a top non-wound-facing side of the exemplary embodiment of the "diamond gauze" bandage illustrated in FIG. 45(*a*);

FIG. 45(*c*) shows a side view along a length tangent 459A of the exemplary embodiment of the "diamond gauze" bandage illustrated in FIGS. 45(*a*) and (*b*) (the view from the opposing length tangent 459C is a mirror image);

FIG. 45(*d*) shows a side view along a width tangent 459B of the exemplary embodiment of the "diamond gauze" bandage illustrated in FIGS. 45(*a*) and (*b*) (the view from the opposing width tangent 459D is a minor image);

FIG. 45(*e*) shows a perspective view of the exemplary embodiment of the "diamond gauze" bandage illustrated in FIGS. 45(*a*) and (*b*);

FIG. 46(*a*) shows a bottom wound-facing side of an exemplary embodiment of a "diamond gauze" bandage according to the present invention;

FIG. 46(*b*) shows a top non-wound-facing side of the exemplary embodiment of the "diamond gauze" bandage illustrated in FIG. 46(*a*);

FIG. 46(*c*) shows a side view along a length tangent 469A of the exemplary embodiment of the "diamond gauze" bandage illustrated in FIGS. 46(*a*) and (*b*) (the view from the opposing length tangent 469C, as well as from width tangents 469B and 469D are identical);

FIG. 46(*d*) shows a perspective view of the exemplary embodiment of the "diamond gauze" bandage illustrated in FIGS. 46(*a*) and (*b*);

FIG. 47(*a*) shows a bottom wound-facing side of an exemplary embodiment of a "diamond gauze" bandage according to the present invention;

FIG. 47(*b*) shows a top non-wound-facing side of the exemplary embodiment of the "diamond gauze" bandage illustrated in FIG. 47(*a*);

FIG. 47(*c*) shows a side view along a length tangent 479A of the exemplary embodiment of the "diamond gauze" bandage illustrated in FIGS. 47(*a*) and (*b*) (the view from the opposing length tangent 479C is a mirror image);

FIG. 47(*d*) shows a side view along a width tangent 479B of the exemplary embodiment of the "diamond gauze" bandage illustrated in FIGS. 47(*a*) and (*b*) (the view from the opposing width tangent 479D is a minor image);

FIG. 47(*e*) shows a perspective view of the exemplary embodiment of the "diamond gauze" bandage illustrated in FIGS. 47(*a*) and (*b*);

FIG. 48(*a*) shows a bottom wound-facing side of an exemplary embodiment of a "diamond gauze" bandage according to the present invention;

FIG. 48(*b*) shows a top non-wound-facing side of the exemplary embodiment of the "diamond gauze" bandage illustrated in FIG. 48(*a*);

FIG. 48(*c*) shows a side view along a length tangent 489A of the exemplary embodiment of the "diamond gauze" bandage illustrated in FIGS. 48(*a*) and (*b*) (the view from the opposing length tangent 489C is a mirror image);

FIG. 48(*d*) shows a side view along a width tangent 489B of the exemplary embodiment of the "diamond gauze" bandage illustrated in FIGS. 48(*a*) and (*b*) (the view from the opposing width tangent 489D is a minor image);

FIG. 48(*e*) shows a perspective view of the exemplary embodiment of the "diamond gauze" bandage illustrated in FIGS. 48(*a*) and (*b*);

FIG. 49(*a*) shows a bottom wound-facing side of an exemplary embodiment of a "diamond gauze" bandage according to the present invention;

FIG. 49(*b*) shows an exploded bottom wound-facing side of an exemplary embodiment of a "diamond gauze" bandage according to the present invention;

FIG. 49(*c*) shows a top non-wound-facing side of the exemplary embodiment of the "diamond gauze" bandage illustrated in FIG. 49(*a*);

FIG. 49(*d*) shows a side view along a length tangent 499A of the exemplary embodiment of the "diamond gauze" bandage illustrated in FIGS. 49(*a*) and (*b*) (the view from the length tangent line 499C, as well as the views from width tangents 499B and 499D are identical to the view from length tangent 499A);

FIG. 49(*e*) shows a perspective view of the exemplary embodiment of the "diamond gauze" bandage illustrated in FIGS. 49(*a*) and (*b*);

FIG. 50(*a*) shows a bottom wound-facing side of an exemplary embodiment of a "diamond gauze" bandage according to the present invention;

FIG. 50(*b*) shows a top non-wound-facing side of the exemplary embodiment of the "diamond gauze" bandage illustrated in FIG. 50(*a*);

FIG. 50(*c*) shows a side view along a length of the exemplary embodiment of the "diamond gauze" bandage illustrated in FIGS. 50(*a*) and (*b*) (the view from the opposing length side is a mirror image);

FIG. 50(*d*) shows a side view along a width of the exemplary embodiment of the "diamond gauze" bandage illustrated in FIGS. 50(*a*) and (*b*) (the view from the opposing width side is a mirror image);

FIG. 50(*e*) shows a perspective view of the exemplary embodiment of the "diamond gauze" bandage illustrated in FIGS. 50(*a*) and (*b*);

FIG. 51(*a*) shows a bottom wound-facing side of an exemplary embodiment of a "diamond gauze" bandage according to the present invention;

FIG. 51(*b*) shows a top non-wound-facing side of the exemplary embodiment of the "diamond gauze" bandage illustrated in FIG. 51(*a*);

FIG. 51(*c*) shows a side view along a length tangent 519C of the exemplary embodiment of the "diamond gauze" bandage illustrated in FIGS. 51(*a*) and (*b*) (the view from the opposing length tangent 519A is a mirror image);

FIG. 51(*d*) shows a side view along a width tangent 519B of the exemplary embodiment of the "diamond gauze" bandage illustrated in FIGS. 51(*a*) and (*b*);

FIG. 51(*e*) shows a side view along a width tangent 519D of the exemplary embodiment of the "diamond gauze" bandage illustrated in FIGS. 51(*a*) and (*b*);

FIG. 51(*f*) shows a perspective view of the exemplary embodiment of the "diamond gauze" bandage illustrated in FIGS. 51(*a*) and (*b*);

FIG. 52(*a*) shows a bottom wound-facing side of an exemplary embodiment of a "diamond gauze" bandage according to the present invention;

FIG. 52(*b*) shows a top non-wound-facing side of the exemplary embodiment of the "diamond gauze" bandage illustrated in FIG. 52(*a*);

FIG. 52(*c*) shows a side view along a length tangent 529C of the exemplary embodiment of the "diamond gauze" bandage illustrated in FIGS. 52(*a*) and (*b*) (the view from the opposing length tangent 529A is a mirror image);

FIG. 52(*d*) shows a side view along a width tangent 529B of the exemplary embodiment of the "diamond gauze" bandage illustrated in FIGS. 52(*a*) and (*b*);

FIG. 52(*e*) shows a side view along a width tangent 529D of the exemplary embodiment of the "diamond gauze" bandage illustrated in FIGS. 52(*a*) and (*b*);

FIG. 52(*f*) shows a perspective view of the exemplary embodiment of the "diamond gauze" bandage illustrated in FIGS. 52(*a*) and (*b*);

FIG. 53(*a*) shows a top non-wound-facing view of an exemplary embodiment of a bandage with a wound portal according to the present invention;

FIG. 53(*b*) is a side cross-sectional view of the bandage illustrated in FIG. 53(*a*) taken along line VIII-VIII';

FIG. 53(*c*) is a side cross-sectional view of an alternative configuration of the exemplary embodiment of the bandage with a wound portal illustrated in FIG. 53(*a*);

FIG. 53(*d*) is a side cross-sectional view of an alternative configuration of the exemplary embodiment of the bandage with a wound portal illustrated in FIG. 53(*a*);

FIG. 53(*e*) is a side cross-sectional view of another exemplary embodiment of a bandage with a wound portal according to the present invention with a flap in an open position;

FIG. 53(*f*) is a side cross-sectional view of the exemplary embodiment of a bandage with a wound portal illustrated in FIG. 53(*e*) with the flap in a closed position.

Figure 57:
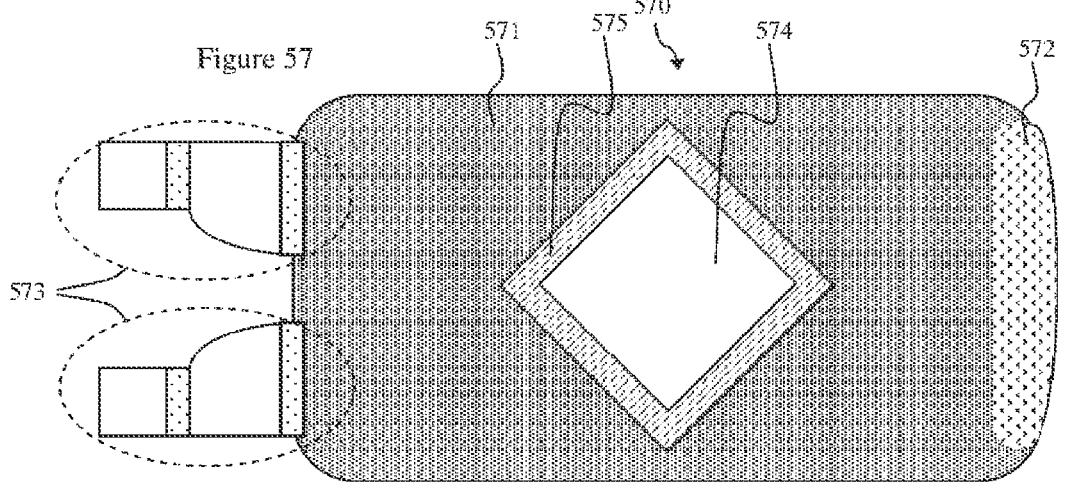
Figure 60:
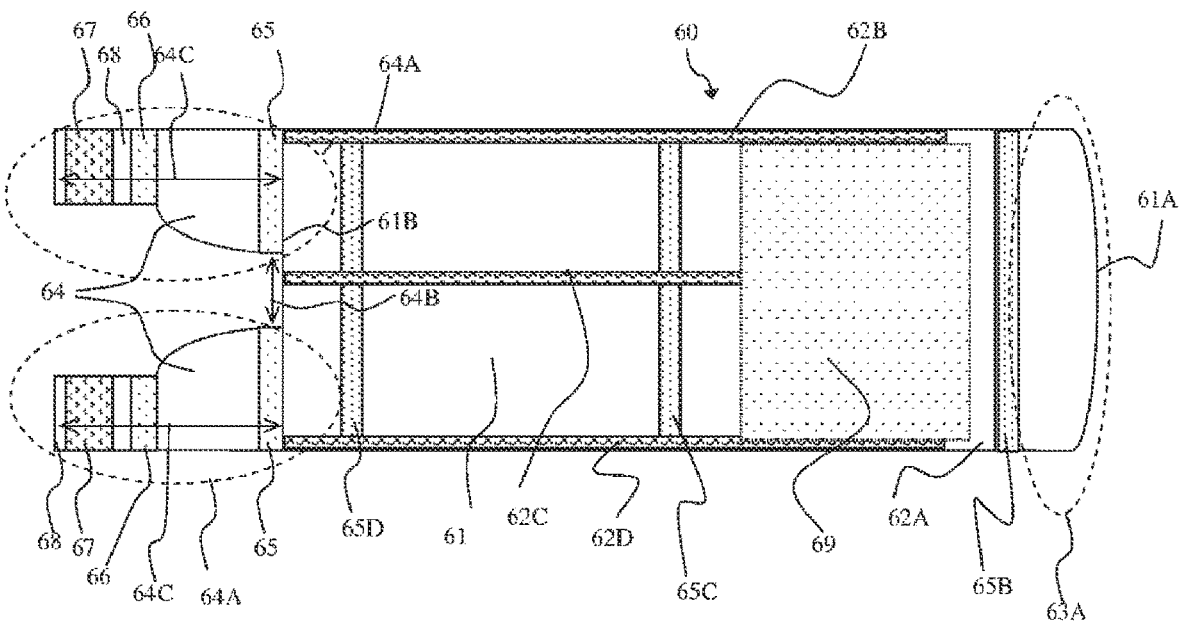
Figure 62A:
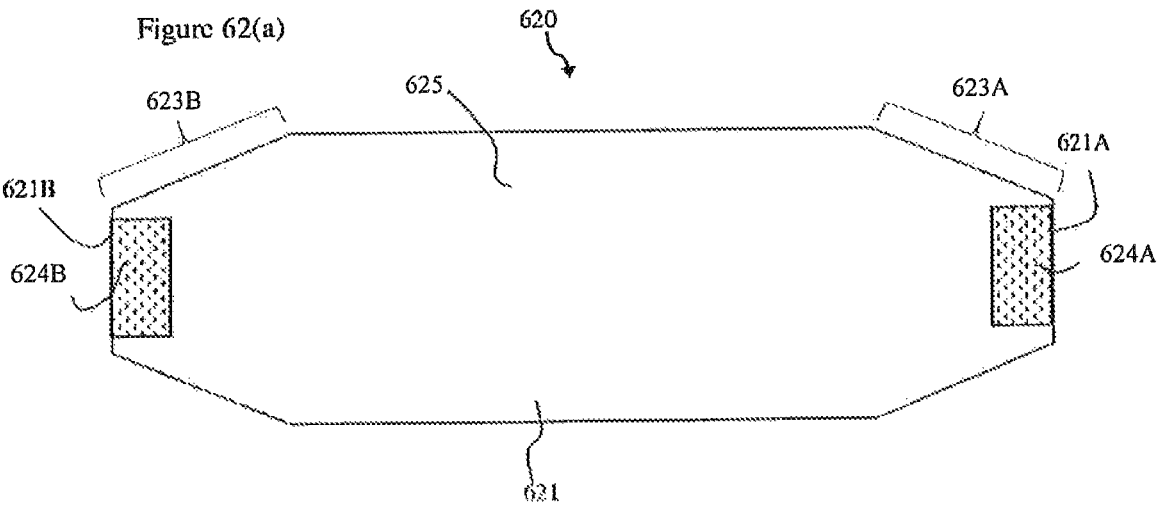
Figure 62B:
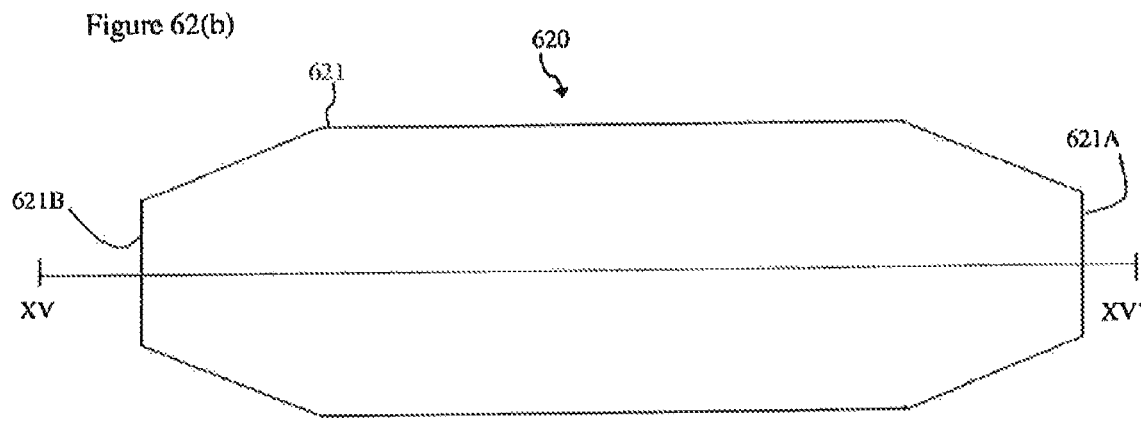
Figure 62C:
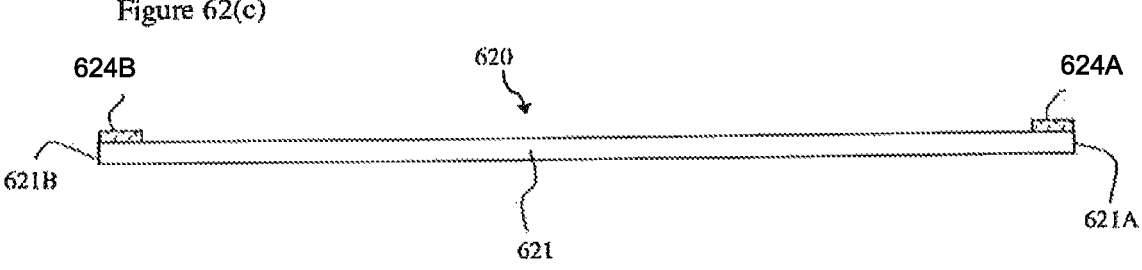
Figure 63A:
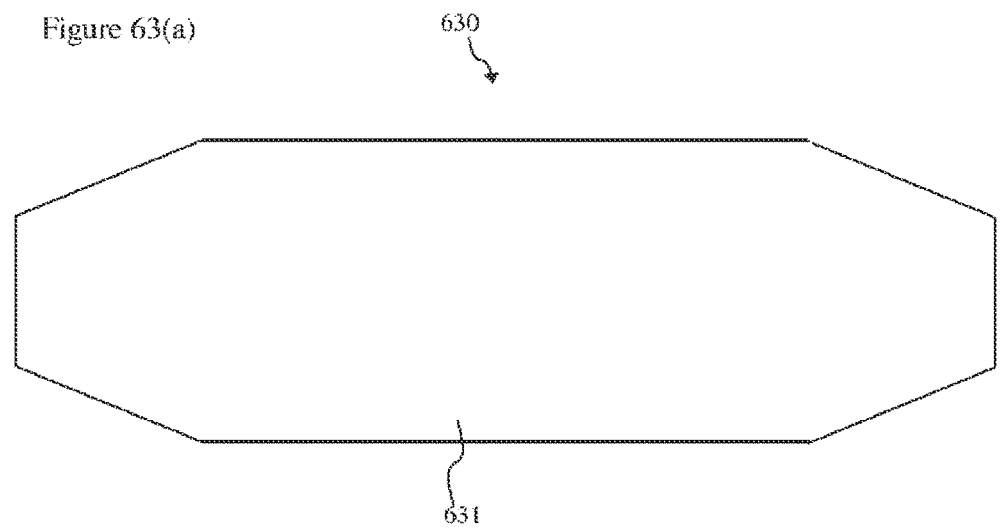
Figure 63B:
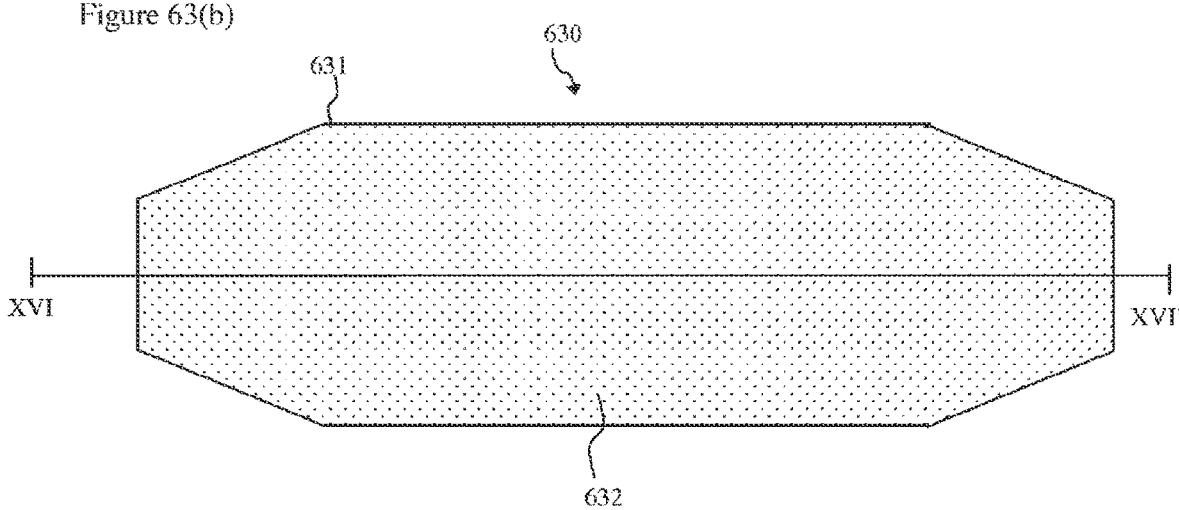
Figure 63C:
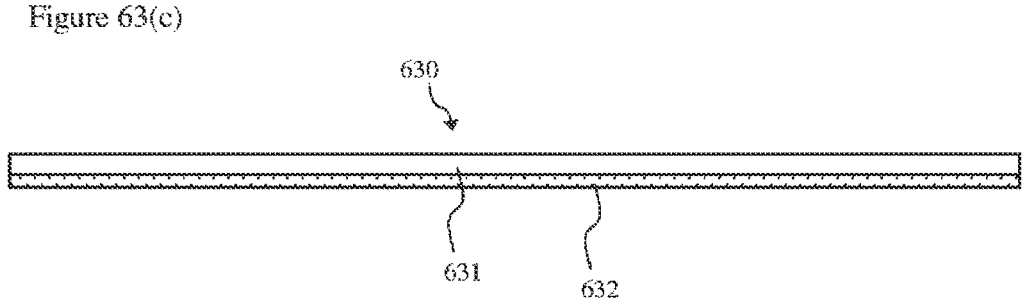

FIG. 54(*a*) shows a top non-wound-facing view of an exemplary embodiment of a bandage with a wound portal according to the present invention;

FIG. 54(*b*) is a side cross-sectional view of the bandage illustrated in FIG. 54(*a*) taken along line IX-IX';

FIG. 55(*a*) shows a top non-wound-facing view of an exemplary embodiment of a bandage with a wound portal according to the present invention;

FIG. 55(*b*) is a side cross-sectional view of the bandage illustrated in FIG. 55(*a*) taken along line X-X';

FIG. 56(*a*) shows a top non-wound-facing view of an exemplary embodiment of a "diamond gauze" bandage with a wound portal according to the present invention;

FIG. 56(*b*) is a side cross-sectional view of the "diamond gauze" bandage illustrated in FIG. 56(*a*) taken along line XI-XI';

FIG. 57 shows a top non-wound-facing view of an exemplary embodiment of a wound/bandage protector with a wound portal and a "diamond gauze" configuration according to the present invention;

FIG. 58(*a*) is a top view of an exemplary embodiment of a frictional gauze pad according to the present invention;

FIG. 58(*b*) is a side cross-sectional view of the frictional gauze pad illustrated in FIG. 58(*a*) taken along line XII-XII';

FIG. 59(*a*) is a top view of an exemplary embodiment of a frictional gauze pad according to the present invention;

FIG. 59(*b*) is a first exemplary cross-sectional view of the frictional gauze pad illustrated in FIG. 59(*a*) taken along line XIII-XIII';

FIG. 59(*c*) is a second exemplary cross-sectional view of the frictional gauze pad illustrated in FIG. 59(*a*) taken along line XIII-XIII';

FIG. 59(*d*) is a third exemplary cross-sectional view of the frictional gauze pad illustrated in FIG. 59(*a*) taken along line XIII-XIII';

FIG. 59(*e*) is an alternative exemplary cross-sectional view of the frictional gauze pad according to the present invention;

FIG. 60 is an alternative bottom wound facing side view of the exemplary embodiment of the wound/bandage protector illustrated in FIG. 6(*a*);

FIG. 61(*a*) is a top non-wound facing side view of an exemplary embodiment of a wound/bandage protector according to the present invention;

FIG. 61(*b*) is a bottom wound facing side view of the exemplary embodiment of the wound/bandage protector illustrated in FIG. 61(*a*);

FIG. 61(*c*) is a side cross-sectional view of the exemplary embodiment of the wound/bandage protector illustrated in FIGS. 61(*a*) and (*b*) taken along the line XIV-XIV' in FIG. 61(*b*);

FIG. 62(*a*) is a top non-wound facing side view of an exemplary embodiment of a bandage wrap protector/holder according to the present invention;

FIG. 62(*b*) is a bottom wound facing side view of the exemplary embodiment of the bandage wrap protector/holder illustrated in FIG. 62(*a*);

FIG. 62(*c*) is a side cross-sectional view of the exemplary embodiment of the bandage wrap protector/holder illustrated in FIGS. 62(*a*) and (*b*) taken along the line XV-XV' in FIG. 62(*b*);

FIG. 63(*a*) is a top non-wound facing side view of an exemplary embodiment of a fastening base according to the present invention;

FIG. 63(*b*) is a bottom wound facing side view of the exemplary embodiment of the fastening base illustrated in FIG. 63(*a*);

FIG. 63(*c*) is a side cross-sectional view of the exemplary embodiment of the fastening base illustrated in FIGS. 63(*a*) and (*b*) taken along the line XVI-XVI' in FIG. 63(*b*).

Figure 64A:
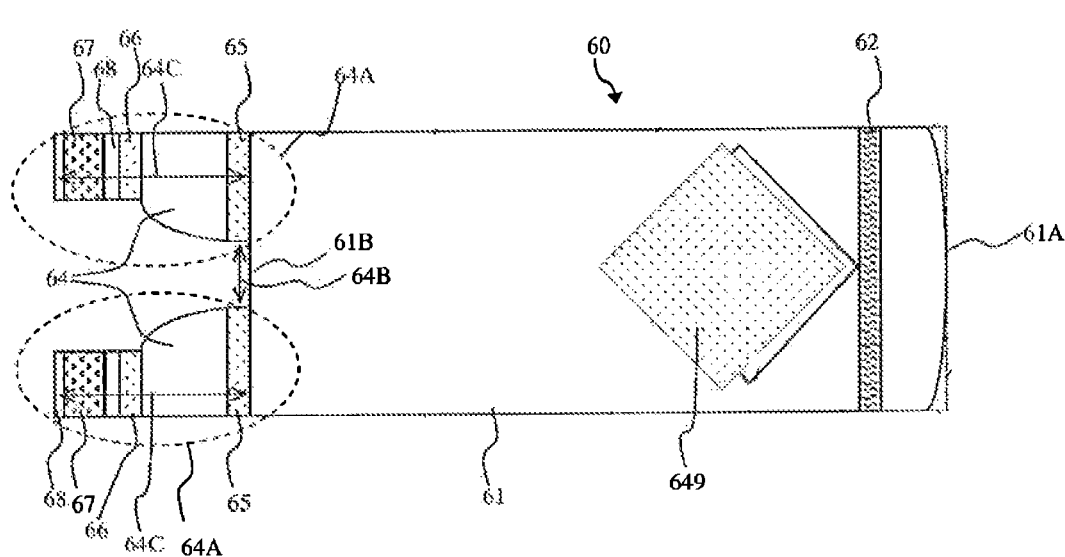
Figure 64B:
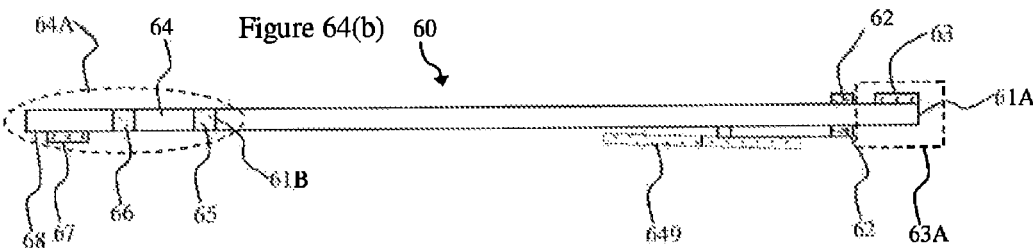
Figure 65A:
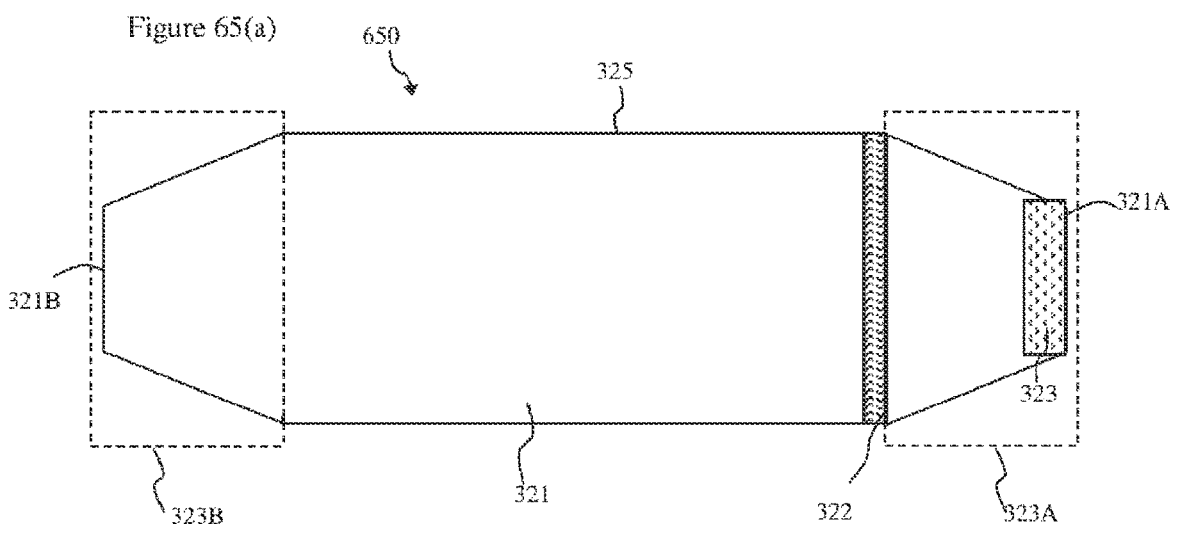
Figure 65B:
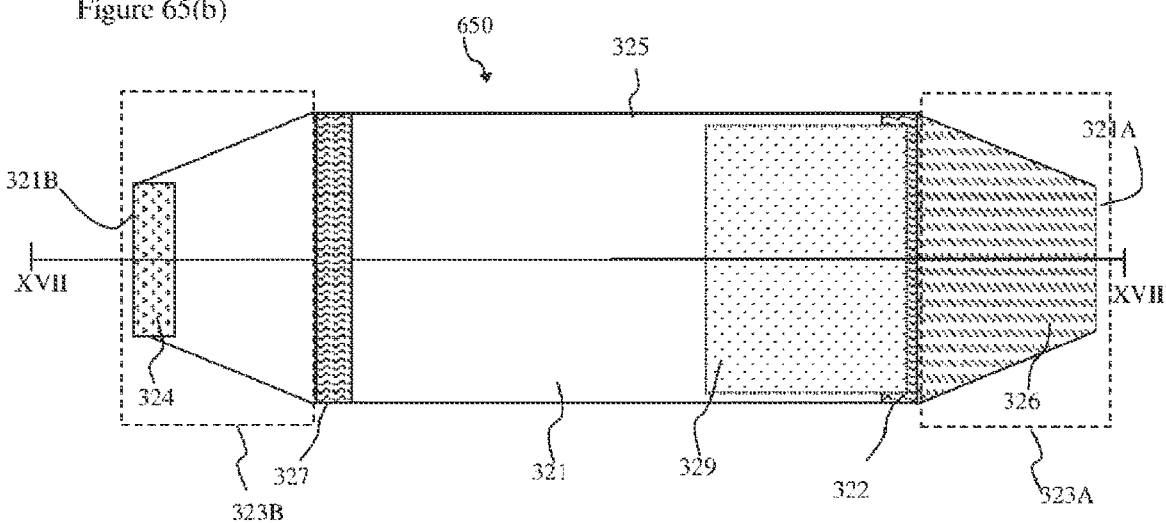
Figure 65C:
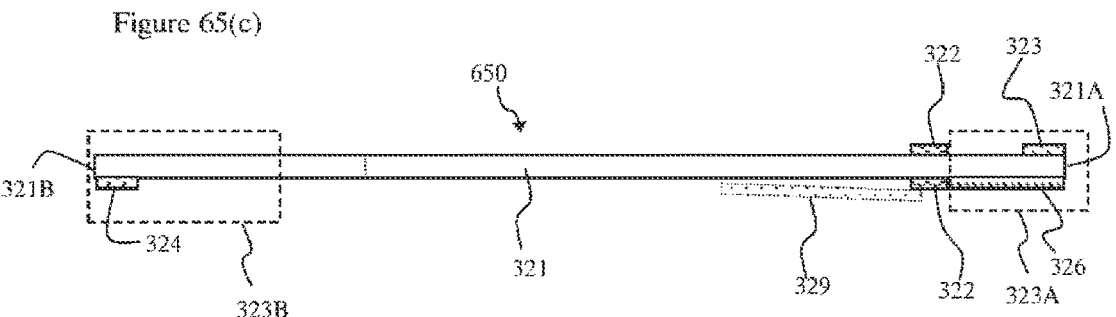

FIG. 64(*a*) is a bottom wound facing side view of an alternative exemplary embodiment of the wound/bandage protector of FIG. 6 with a "diamond gauze configuration" according to the present invention;

FIG. 64(*b*) is a side view of the exemplary embodiment of the wound/bandage protector illustrated in FIG. 64(*a*);

FIG. 65(*a*) is a top non-wound facing side view of an exemplary embodiment of an alternative arrangement according to the present invention for the wound/bandage protector illustrated in FIGS. 61(*a*)-(*c*);

FIG. 65(*b*) is a bottom wound facing side view of an exemplary embodiment of the alternative arrangement according to the present invention for the wound/bandage protector illustrated in FIGS. 61(*a*)-(*c*);

FIG. 65(*c*) is a side cross-sectional view of the exemplary embodiment of the wound/bandage protector illustrated in FIGS. 65(*a*) and (*b*) taken along the line XVII-XVII' in FIG. 65(*b*);

FIG. 66(*a*) is a top non-wound facing side view of an exemplary embodiment of a wound/bandage protector according to the present invention;

FIG. 66(*b*) is a bottom wound facing side view of the exemplary embodiment of the wound/bandage protector illustrated in FIG. 66(*a*);

FIG. 66(*c*) is a side view of the exemplary embodiment of the wound/bandage protector illustrated in FIGS. 66(*a*) and (*b*).

MODES FOR CARRYING OUT THE
INVENTION

FIG. 1 shows a super-stretch tube 1 that is part of the bandaging system according to the present invention. The super-stretch tube 1 may be used for protecting a wound or for covering one of the bandages disclosed below. The super-stretch tube 1 has a tube body portion 2 which may be made of a stretchable material such as an elastic non-woven that is found in the side portions of Huggies® brand Little Swimmers® and Pull-Ups® or Pampers® Easy Ups® Cruisers®. Alternatively, the tube body portion 2 may be made of other materials with similar elasticity properties that provide a comparable amount of stretchability and tension.

According to one exemplary embodiment of the invention, the stretchable material of the tube body portion 2, when extended to its full capacity, can stretch to more than double the tube body portion's 2 un-extended size. In the context of this application, "super stretchable" material refers to material that can resiliently stretch to a length that is equal to or greater than one and a half times the length of the material when not under tension. In the context of this application, "stretchable" material refers to material that can resiliently stretch to a length that is at least ten percent greater than the length of the material when not under tension. A material that has "little or no stretch" is one that is not super stretchable. A material that has "no stretch" is one that is not stretchable. A "dead zone" is an area of material that has little or no stretch which may, but not necessarily, be an integral part of an otherwise stretchable material. A dead zone area may be formed in an elastic nonwoven material with an ultrasonic seal, which is generally used when attaching two nonwovens together, by punching, applying pressure and then high frequency vibration, which causes nonwoven materials to melt, to an overlapping connecting portion of the two nonwovens. Alternatively, particularly when forming a dead zone in a single piece of nonwoven fabric, the dead zone may be formed by simply applying the pressure and high frequency vibration without punching. The "stretching resistance", "elastic modulus" or Young's modulus, refers to a ratio of stretching force on a particular area along a particular axis over a ratio of change in the length of the material along the particular axis due to the applied stretching force. Thus, a material that can be "easily" stretched has a lower elastic modulus than a material that is "hard" to stretch. The stretchable material of the tube body portion 2 at least provides stretching capacity in a manner that allows a circumference of the super-stretch tube 1 to vary. The stretchable material of the tube body portion 2 may, alternatively, provide stretching capacity that allows both the circumference and a length of the tube body portion 2 to vary. Preferably, the super-stretch material of the tube body portion 2 is very thin, being less than $\frac{1}{16}$th of an inch thick when in the un-extended position and provides some breathability as well as good water resistance.

The super-stretch tube 1 has a strip 4 that extends along a length 7 of the super-stretch tube 1 from a first open end 6 of the super-stretch tube 1 to a second open end 8 of the super-stretch tube 1 at least along an inside surface 3 of the super-stretch tube 1. The strip 4 may be positioned along or over a seam 5 that may extend the length of the super-stretch tube 1. The strip 4 has one or more threads made of a rubberized material provided in such a manner that the rubberized material threads are exposed at least on an inner side of the super-stretch tube 1. The strip 4 may be made from an elastic material used in some larger hair bands that includes rubberized material threads. The rubberized material is not necessarily exposed on the exterior side 9 of the stretch tube 1. Alternatively, the strip 4 may be comprised of stretch non-slip medical grade silicone or similar, preferably latex free, material. The non-slip silicone may be applied in a continuous or discontinuous manner to form the strip 4. Alternatively, the entire inside of the tube may be coated with low tack non-slip silicone or similar, preferably latex free, material.

Although not depicted in FIGS. 1(a) and 1(b) of the super-stretch tube 1, in an alternative exemplary embodiment of the super-stretch tube 1 according to the present invention, there may also be one or more super-stretch tube fastening straps attached to an exterior surface 9 of the super-stretch tube 1. The one or more super-stretch tube fastening straps may be configured in a similar fashion as fastening strap 23A shown in FIGS. 2(a) and 2(b) and discussed below. Preferably, a first fastening strap of the one or more super-stretch tube fastening straps may be provided in close proximity to the first open end 6 of the super-stretch tube 1 and a second fastening strap of the one or more of the super-stretch tube fastening straps may be provided in close proximity to the to the second open end 8 of the super-stretch tube 1.

FIG. 2(a) shows an exemplary embodiment of a wound/bandage protector 20, according to the present invention. The wound/bandage protector 20 is configured as a "sock/mitten", with a body 21 that has a first end 21A that is open and a second end 21B that is closed. The body 21 may be made of super-stretchable or stretchable material similar to the material of the super-stretch tube 1, discussed above and shown in FIG. 1 and at least a portion of the non-wound facing side of the body 21 may be configured as a Velcro® loop type fastener. The stretchable material of the body 21 of the wound/bandage protector 20 at least provides such stretching capacity in a manner that allows a circumference of the body 21 to vary. The stretchable material of the body 21 may, alternatively, provide such stretching capacity that allows both the circumference and a length of the body 21 to vary.

The body 21 has a panel 22 which may be made of material that has little or no stretch. The panel 22 is shown in FIG. 2(a), which illustrates an outside side view showing a portion of an external non-wound facing surface of the wound/bandage protector 20. However, the panel 22 is not necessarily visibly distinguishable from the rest of the body 21, particularly on the external non-wound facing surface of the wound/bandage protector 20. A gauze pad (not specifically illustrated in FIG. 2(a) may be affixed to the panel 22 on an internal wound-facing side. Alternatively, the gauze pad may be attached to the panel 22 in a temporary fashion such as via use of a Velcro® type fastening system or a reusable pressure sensitive adhesive such as that used in Post-it® notes. In another alternative embodiment, the panel 22 and the gauze pad is made of stretchable or super-stretchable material. In this embodiment, the entire body 21 may be configured to function as the panel 22.

In the context of this specification, gauze, or gauze pad, refers to any material or composite of material that may be therapeutically used as a pad over a wound. For example, the gauze pad may be made of cotton or a polyester blend fabric. The fabric may be covered with a plastic porous film such as Telfa® which prevents or minimizes wound adhesion. Furthermore, the gauze pad may be backed with a film that prevents body fluids from penetrating through the gauze pad to the bandage.

The body 21 has an external non-wound facing surface and an internal wound-facing surface. Attached to the external non-wound facing surface of the body 21 proximate to the first end 21A is a fastening strap 23A. The fastening strap 23A, as illustrated in FIG. 2(a) has a first strap part 23 that may be attached to the body 21 via a first attachment region 24. The first strap part 23 may be comprised of a stretchable or super stretchable material similar to the material used in the super-stretch tube 1. The material of the first strap part 23 preferably provides a stretching resistance that is greater than the stretching resistance of the body 21. The material of the first strap part 23 at least provides such stretching capacity in a manner that allows the length of the fastening strap 23A to vary. The first attachment region 24 is preferably configured as a dead zone to provide no stretch and may be comprised of a composite of the material of the first strap part 23 and the body 21 of the wound/bandage protector 20 and may be attached by a punch and melt heat seal. Alternatively, the first strap part 23 is directly attached to the body 21 without the first attachment region 24 intervening therebetween.

A second strap part 27 is attached to the first strap part 23 via a second attachment region 25. The second attachment region 25 is preferably configured as a dead zone to provide no stretch and may be comprised of a composite of the material of the first strap part 23 and the second strap part 27 and may be attached by a punch and melt heat seal. Alternatively, the second strap part 27 is directly attached to the first strap part 23 without the second attachment region 25 intervening therebetween. The fastening strap 23A has a wound facing side, which may be seen in FIG. 2(a). The second strap part 27 has a portion 26 that includes a Velcro® hook type material, such as Velcro USA HTH 819 natural, on a wound-facing side of the fastening strap 23A. Alternatively, the second strap part 27 or the entire fastening strap 23A may be comprised of a cohesive material such as Coban™ so that the fastening strap 23A when wrapped around can fasten to itself.

On the internal wound-facing surface of the of the body 21 proximate to the first end 21A is a strip 21C, which may be similar in configuration to the strip 4 in the super-stretch tube 1, having one or more threads made of a rubberized material that provides a moderate amount of friction interwoven in the strip 21C in such a manner that the rubberized material threads are exposed. Alternatively, the strip 21C may be made of stretch non-slip silicone or similar, preferably latex free, material that provides a frictional surface. The non-slip silicone may be applied in a continuous or discontinuous manner to form the strip 21C. Preferably, the amount of friction provided by the frictional surface of the strip 21C should be one that does not cause discomfort when the wound/bandage protector 20 is worn. For purposes of this application indication of "rubberized material" without further limitation refers to any material that provides a frictional surface, including non-slip silicone and Coban™.

Figures 2C, 2D, 2E, 2F:
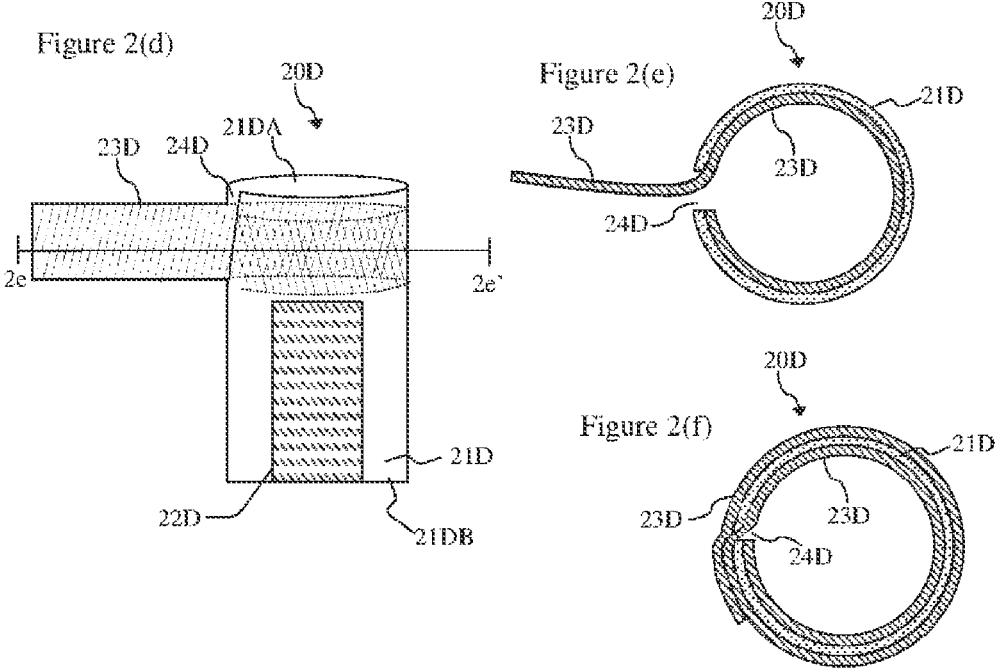
FIG. 2(c) is a side view of the exemplary embodiment of the wound/bandage protector illustrated in FIG. 2(a) illustrating the process of securing the wound/bandage protector.
FIG. 2(d) is a side view of an exemplary embodiment of a wound/bandage protector according to the present invention.
FIG. 2(e) is a top cross-sectional view of the wound/bandage protector illustrated in FIG. 2(d) taken along line 2e-2e' with a strap in an open position.
FIG. 2(f) is a top cross-sectional view of the wound/bandage protector illustrated in FIG. 2(d) with the strap portion in a closed position.

FIG. 2(c) illustrates the process of securing the wound/bandage protector 20 of FIG. 2(a) by showing the fastening strap 23A in an intermediate position, as the fastening strap 23A is being extended around the external non-wound facing surface of the wound/bandage protector 20 in the direction indicated by arrow 27A. The fastening strap 23A has a non-wound facing side, which may be seen in FIG. 2(c). The first strap part 23 may be configured to act as a loop portion of a Velcro® type fastener on the non-wound facing side of the first strap part 23. The second strap part 27 may be configured as a loop portion of a Velcro® type fastener on the non-wound facing side of the fastening strap 23A.

The wound/bandage protector 20 may be slipped onto an appendage through the opening on the first end 21A of the body 21 so that the gauze pad that is affixed to the panel 22 of the wound/bandage protector 20 covers a wound on the appendage, and the wound/bandage protector 20 is then secured in place by wrapping the fastening strap 23A around the outside of the wound/bandage protector 20 and affixing the Velcro hook fastener portion 26 of the second strap part 27 to the loop portion of the first strap part 23, the body 21, or the loop portion of the second strap part 27.

FIG. 2(d) shows another exemplary embodiment of a wound/bandage protector 20D, according to the present invention, that is configured as a "sock/mitten". The wound/bandage protector 20D has a body 21D that may be configured as described above for the body 21. The body 21D has a first end 21DA that is open and a second end 21DB that is closed and a panel 22D where a gauze pad may be permanently or detachably affixed. The wound/bandage protector 20D, however, has a strap 23D located proximate to the first end 21DA that is comprised of a cohesive material such as Coban™. The strap 23D, instead of attaching to an external non-wound facing surface of the body 21D, extends through a slit 24D that allows the strap 23D to extend onto an internal wound-facing surface of the body 21D. FIG. 2(e) is a top cross-sectional view taken along the line 2e-2e' illustrating how the strap 23D attaches to the internal wound-facing surface of the body 21D and extends entirely around a circumference of the body 21D or alternatively around a portion of the circumference. FIGS. 2(d) and 2(e) illustrate the wound/bandage protector 20D with the strap 23D in an open position. FIG. 2(f) illustrates a top cross-sectional view of the wound/bandage protector 20D in a closed position. As is illustrated, the portion of the strap 23D that is not attached to the internal wound-facing side of the body 21D is of sufficient length to extend around the outside circumference of the wound/bandage protector 20D and to overlap on itself so as to securely affix the strap 23D to itself. Alternatively, a portion of the outside circumference of the wound/bandage protector 20D may be covered with the cohesive material so that the strap 23D can securely fasten to the outside circumference of the wound/bandage protector 20D rather than having the strap 23D extending around onto itself.

FIG. 3(a) shows an exemplary embodiment of a wound/bandage protector 30, according to the present invention. The wound/bandage protector 30 is configured as a sock/mitten similar to the wound/bandage protector 20 in FIG. 2(a). The wound/bandage protector 30 has a body 31 that has a first end 31A that is open and a second end 31B that is closed. However, the body 21 of the wound/bandage protector 20 has a uniform circumference from the open end 21A to the closed end 21B and a panel 22, which has a uniform width. In contrast, the body 31 of the wound/bandage protector 30 is tapered from the open end 31A to the closed end 31B so that one end is larger than the other, and a panel 32 is also tapered. Alternatively, the panel 32 may also have a uniform width, regardless of the shape or circumference of the body 31. The body 31 and the panel 32 are otherwise similarly configured to the body 21 and the panel 22.

The body 31 has an external non-wound facing surface and an internal wound-facing surface. Attached to the external non-wound facing surface of the body 31 proximate to the first end 31A is a fastening strap 33A. The fastening strap 33A has a first strap part 33, a second strap part 37, a portion 36 of the second strap part 37, a first attachment region 34 and a second attachment region 35 that are configured similar to the corresponding components of the fastening strap 23A in FIG. 2(*a*).

FIG. 2(*b*) illustrates a first alternative embodiment of a protective sheath 28 and FIG. 3(*b*) illustrates a second alternative embodiment of a protective sheath 38. Both the protective sheath 28 and the protective sheath 38 may each be used in conjunction with either the wound/bandage protector 20 or the wound/bandage protector 30. Each of the protective sheaths 28, 38 has a body 28A, 38A with an opening on a first end 28B, 38B and a second end 28C, 38C that is closed. The bodies 28A, 38A are configured to fit snugly over the exterior of the wound/bandage protector 20, 30. The bodies 28A, 38A may be comprised of a waterproof or water resistant material such as the plastic material used in Playtex® bottle liners or vinyl, or a waterproof or water resistant non-woven material, and may be configured with a plastic backing and/or with the capability of being stretchable or super stretchable. Alternatively, the bodies 28A, 38A may be comprised of a composite of materials, preferably one that will provide a waterproof or water-resistant barrier. The protective sheath 28 has a slit 29 and the protective sheath 38 has a slot 39. Both the slit 29 and the slot 39 are sized and positioned to allow the fastening strap 23A, 33A of the wound/bandage protector 20,30 to fit through so that the fastening strap 23A, 33A can extend around the outside of the sheath and secure both the wound/bandage protector 20,30 as well as the sheath to an appendage being bandaged. On the wound facing side of the fastening strap 23A, 33A may be a tacky surface, which may be comprised of a pressure sensitive adhesive, or rubberized surface, or self-adherent surface material with a corresponding self-adherent surface material on the protective sheath 28,38. Preferably, the tacky surface of the fastening strap 23A, 33A is on the first and/or second attachment regions 24, 34 and 25, 35.

FIG. 4 shows an exemplary embodiment of a wound/bandage protector 40 according to the present invention. The wound/bandage protector 40 is configured as a sock/mitten similar to the wound/bandage protector 30 in FIG. 3(*a*). The wound/bandage protector 40 has a body 41 that has a first end 41A that is open and a second end 41B that is closed. However, the wound/bandage protector 30 has a panel 32 whereas the wound/bandage protector 40 does not have a panel.

The body 41 is otherwise similarly configured to the body 31. The body 41 has an external non-wound facing surface and an internal wound-facing surface. Attached to the external non-wound facing surface of the body 41 proximate to the first end 41A is a fastening strap 43A. The fastening strap 43A has a first strap part 43, a second strap part 47, a portion 46 of the second strap part 47, a first attachment region 44 and a second attachment region 45 that are configured similar to the corresponding components of the fastening strap 33A in FIG. 3(*a*).

The wound/bandage protector 40 may be slipped onto an appendage through the wound/bandage protector opening 41A so that it covers a wound or a bandage on the appendage, or another wound/bandage protector such as the exemplary embodiments in FIGS. 2(*a*) and 3(*a*). The wound/bandage protector 40 is then secured in place by wrapping the fastening strap 43A around the outside of the wound/bandage protector 40 and affixing the Velcro hook fastener portion 46 of the second strap part 47 to the loop portion of the first strap part 43, the body 41 or the loop portion of the second strap part 47.

FIG. 5 shows an exemplary embodiment of a wound/bandage protector 50 according to the present invention. The wound/bandage protector 50 is configured as a sock/mitten similar to the wound/bandage protector 20 in FIG. 2(*a*). The wound/bandage protector 50 has a body 51 that has a first end 51A that is open and a second end 51B that is closed. However, the wound/bandage protector 20 has a panel 22 whereas the wound/bandage protector 50 does not have a panel.

The body 51 is otherwise similarly configured to the body 21. The body 51 has an external non-wound facing surface and an internal wound-facing surface. Attached to the external non-wound facing surface of the body 51 proximate to the first end 51A is a fastening strap 53A. The fastening strap 53A has a first strap part 53, a second strap part 57, a portion 56 of the second strap part 57, a first attachment region 54 and a second attachment region 55 that are configured similar to the corresponding components of the fastening strap 23A in FIG. 2(*a*).

The wound/bandage protector 50 may be slipped onto an appendage through the wound/bandage protector opening 51A so that it covers a wound or a bandage on the appendage, or another wound/bandage protector such as the exemplary embodiments in FIGS. 2(*a*) and 3(*a*), and the wound/bandage protector 50 is then secured in place by wrapping the Velcro stretch strap around the outside of the wound/bandage protector 50 and affixing the Velcro hook fastener portion 56 of the second strap part 57 to the loop portion of the first strap part 53, the body 51 or the loop portion of the second strap part 57.

FIGS. 6(*a*)-6(*c*) are, respectively, a top non-wound-facing view, a bottom wound facing view, and a cross-sectional side view taken along the line II-II' of a wound/bandage protector 60 according to the present invention. The exemplary embodiment of the wound/bandage protector 60 has a body portion 61 that is configured as a wrap which may be comprised of super-stretch material similar to the super-stretch material used in the body 21, 31 of the bandage mittens/socks 20, 30. The body portion 61 is configured to act as a loop portion of a Velcro® type fastener on both the bottom wound-facing side of the wound/bandage protector 60 and the top non-wound facing side of the wound/bandage protector 60. The body portion 61 has a length that runs from a first end 61A to a second end 61B. The stretchable material of the body portion 61 at least provides such stretching capacity in a manner that allows the length of the body portion 61 to vary. The stretchable material of the body portion 61 may, alternatively, provide such stretching capacity that allows both the length of the body portion 61 as well as a width of the body portion 61 which is perpendicular to the length of the body portion 61 to vary.

A gauze port 62A is positioned on or integrated into the body portion 61 proximal to the first end of the body portion 61A. The gauze port 62A is an area where a gauze pad 69 may be attached or removably attached to the wound-facing side of the body portion 61. The gauze port 62A may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, both the gauze port 62A and the gauze pad 69 may have a low tack adhesive, such as a low tack silicone adhesive. The low tack adhesive may be on the entire non-wound facing side of the gauze pad 69, or may be just on a portion of the non-wound facing side of the gauze pad 69. Another possibility is that the surface of the gauze port 62A may be comprised of an adhesive that allows for the permanent attachment of the gauze pad 69. The gauze port 62A may be used to attach different sized gauze pads 69 as well as to periodically replace the gauze pad 69 in the wound/bandage protector 60 shown in this embodiment. The gauze port 62A may be sized and/or configured so as to attach to all, a substantial portion, or a small portion as illustrated in the FIGS. 6(b) and 6(c), such as one side of the gauze pad 69.

In closer proximity to the first end 61A of the body portion 61 of the wound/bandage protector 60 than the gauze port 62A, is a strip 62, which may be similar in configuration to the strip 4 in the first embodiment, having one or more threads made of a rubberized material that provides a moderate amount of friction interwoven in the strip 62 in such a manner that the rubberized material threads are exposed. Alternatively, the strip 62 may be made of stretch non-slip silicone or similar, preferably latex free, material that provides a frictional surface. The non-slip silicone may be applied in a continuous or discontinuous manner to form the strip 62. Preferably, the amount of friction provided by the frictional surface of the strip 62 should be one that does not cause discomfort when the wound/bandage protector 60 is worn. The strip 62 could be configured so that it is not stretchable in either one or both of the length or the width directions. The strip 62 may be provided along the top non-wound facing side of the wound/bandage protector 60 and/or the bottom wound facing side of the wound/bandage protector 60. Moreover, the strip 62 may extend around sides of the wound/bandage protector 60 and along both the top non-wound facing side of the wound/bandage protector 60 and the bottom wound facing side of the wound/bandage protector 60 so as to form an annular shape.

A region 63A of the body portion 61 extends from the strip 62 to the first end of the body portion 61. On the end region 63A of the first end of the body portion 61A, although not necessarily on the entire end region 63A, is a first-catch fastening surface 63 on the top non-wound-facing side of the wound/bandage protector 60. The first end of the body portion 61A may be curved as shown in FIGS. 4(a) and 4(b) or straight or any other configuration.

Attached to the second end of the body portion 61B are two fastening straps 64A. Each of the fastening straps 64A may be comprised of two parts. A first strap part 64 is attached to the second end of the wound/bandage protector body portion 61B and is made out of a super-stretch material which may be adapted to function as a loop portion of a Velcro®-type fastener on both the top non-wound facing side and the bottom wound-facing side of the wound/bandage protector 60. The super-stretch material of the first strap part 64 preferably provides a stretching resistance that is greater than the stretching resistance of the body portion 61. The first strap part 64 may be attached to the second end of the wound/bandage protector body portion 61B via an attachment region 65 which is preferably configured as a dead zone to provide no stretch. The attachment region 65 may be comprised of a composite of the material of the first strap part 64 and the body portion 61 of the wound/bandage protector 60 and may be attached by a punch and melt heat seal. Alternatively, the first strap part 64 is directly attached to the body portion 61 without an attachment region 65 intervening therebetween.

A second strap part 68 is attached to the first strap part 64 via an attachment region 66. The attachment region 66 is preferably configured as a dead zone to provide no stretch and may be comprised of a composite of the material of the first strap part 64 and the second strap part 68 and may be attached by a punch and melt heat seal. The second strap part 68 has a portion 67 which includes a Velcro® hook type material on the bottom wound-facing side of each of the fastening straps 64A. Alternatively, the second strap part 68 is directly attached to the first strap part 64 without an attachment region 66 intervening therebetween. There may be a spacing 64B between inner sides of the two fastening straps 64A at the second end of the wound/bandage protector body portion 61B. The shape of the inner sides of the two fastening straps 64A may be comprised of an arc, an arc combined with a straight line, an angled line, or any other embodiment which would allow for a distance between the two inner sides of the two fastening straps 64A. The magnitude of the spacing 64B may increase along a length of the fastening straps 64A running from the first strap part 64 to the second strap part 68. The two fastening straps 64A have lengths 64C running from the second end of the wound/bandage protector body portion 61B to the second strap part 68 which may run parallel to each other. The outer sides of the two fastening straps 64A may run parallel to each other and may continue the straight lines formed by the sides of the body portion 61 of the wound/bandage protector 60.

FIG. 60 shows an alternative exemplary configuration of a bottom view of the wound/bandage protector 60 according to the present invention. In this configuration, instead of the vertical strip 62, there may be a horizontal strip 62B along or proximal to an upper edge of the wound/bandage protector 60, there may be a horizontal strip 62D along or proximal to a lower edge of the wound/bandage protector 60, and there may be a horizontal strip 62C at another position between the strips 62B and 62D of the wound/bandage protector 60. There may also be any combination of these strips, i.e. only strips 62B and 62D, or 62B and 62C, or 62C and 62D, or any one of the strips 62B, 62C or 62D. In an alternative embodiment not shown in the figure, there may be one or more vertical strips along the bottom wound-facing side of wound/bandage 60 rather than horizontal strips. In another alternative embodiment not shown in the figure, rather than vertical or horizontal strips, the entire wound-facing side of the body portion 61 may be provided with a low tack non-slip silicone coating or similar material. According to this exemplary embodiment, there may be a dead zone 65B at or proximal to the first end 61A, there may be a dead zone 65D at or proximal to the second end 61B, and there may be a dead zone 65C preferably at or proximal to the middle of the body portion 61 or at some other position between the dead zone 65B and the dead zone 65D. Alternatively, instead of or in addition to the strips 62B, 62C and 62D, the dead zones 65B, 65C and 65D may be configured as strips as well.

Figures 7A, 7B, 7C:
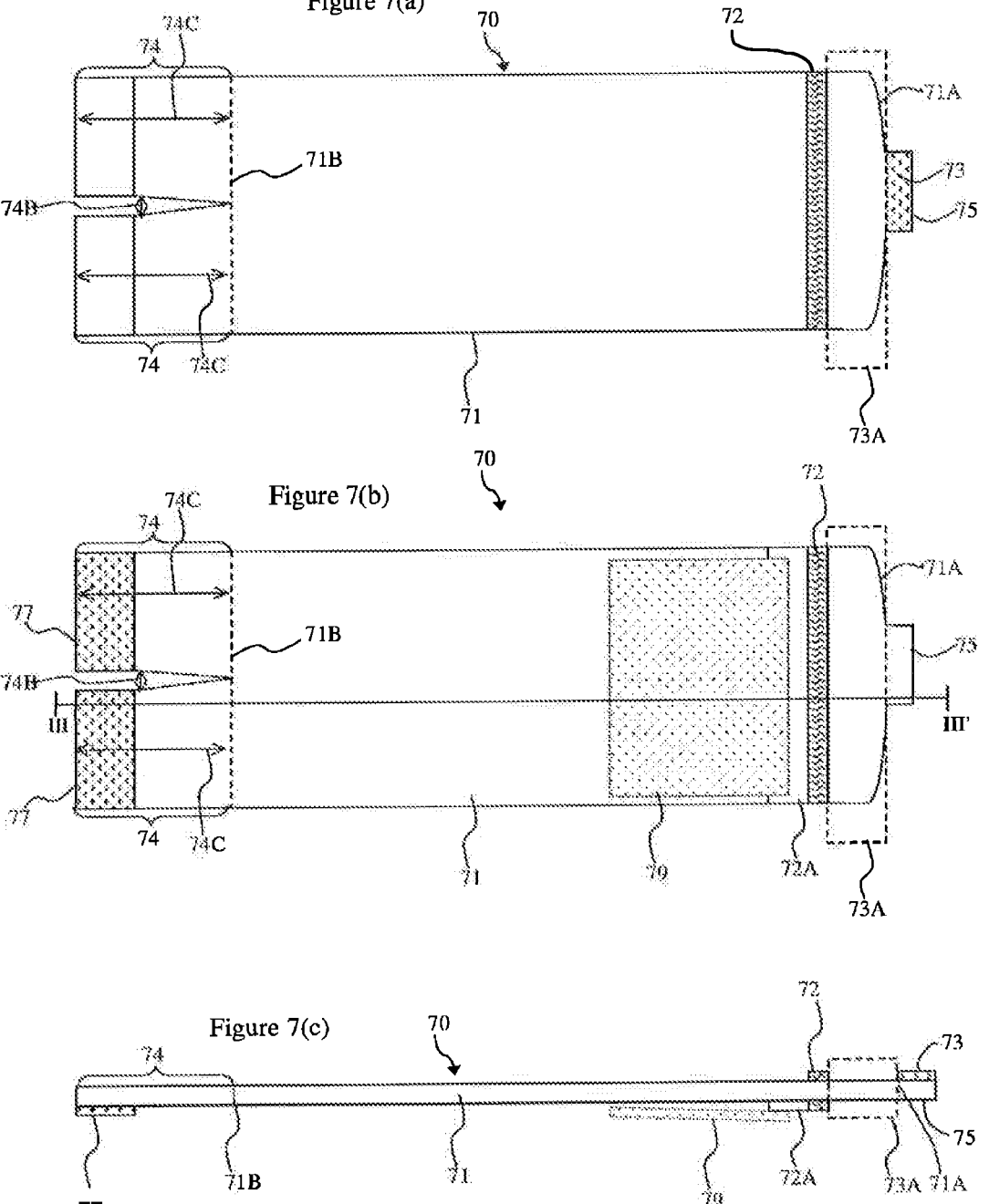
FIG. 7(*a*) is a top non-wound facing side view of an exemplary embodiment of a wound/bandage protector according to the present invention.

FIGS. 7(a)-7(c) are, respectively, a top non-wound-facing view, a bottom wound facing view, and a cross-sectional side view taken along the line III-III' of a wound/bandage protector 70 according to the present invention. The exemplary embodiment of the wound/bandage protector 70 has a body portion 71 that is configured as a wrap which may be comprised of super-stretch material similar to the super-stretch material used in the body 21, 31 of the bandage mittens/socks 20, 30. The body portion 71 is configured to act as a loop portion of a Velcro® type fastener on both the bottom wound-facing side of the wound/bandage protector 70 and the top non-wound facing side of the wound/bandage protector 70. The body portion 71 has a length that runs from a first end 71A to a second end 71B. The stretchable material of the body portion 71 at least provides such stretching capacity in a manner that allows the length of the body portion 71 to vary. The stretchable material of the body portion 71 may, alternatively, provide such stretching capacity that allows both the length of the body portion 71 as well as a width of the body portion 71 which is perpendicular to the length of the body portion 71 to vary.

A gauze port 72A is positioned on or integrated into the body portion 71 proximal to the first end 71A of the body portion 71. The gauze port 72A is an area where a gauze pad 79 may be attached or removably attached to the wound-facing side of the body portion 71. The gauze port 72A may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze port 72A may be comprised of an adhesive that allows for the permanent attachment of the gauze pad 79. The gauze port 72A may be used to attach different sized gauze pads 79 as well as to periodically replace the gauze pad 79 in the wound/bandage protector 70 shown in this embodiment. The gauze port 72A may be sized and or configured so as to attach to all, a substantial portion, or a small portion such as one side of the gauze pad 79.

In closer proximity to the first end 71A of the body portion 71 of the wound/bandage protector 70 than the gauze port 72A, is a strip 72, which may be similar in configuration to the strip 4 in the first embodiment, having one or more threads made of a rubberized material that provides a moderate amount of friction interwoven in the strip 72 in such a manner that the rubberized material threads are exposed. Alternatively, the strip 72 may be made of other material that provides a frictional surface. Preferably, the amount of friction provided by the frictional surface of the strip 72 should be one that does not cause discomfort when the wound/bandage protector 70 is worn. The strip 72 could be configured so that it is not stretchable in either one or both of the length or the width directions. The strip 72 may be provided along the top non-wound facing side of the wound/bandage protector 70 and/or the bottom wound facing side of the wound/bandage protector 70. Moreover, the strip 72 may extend around sides of the wound/bandage protector 70 and along both the top non-wound facing side of the wound/bandage protector 70 and the bottom wound facing side of the wound/bandage protector 70 so as to form an annular shape.

An end region 73A of the body portion 71 extends from the strip 72 to the first end 71A of the body portion 71. A portion of the end region 73A may be tapered so as to provide a gradual diminution in the width of the body portion 71 toward the first end 71A. A tab 75 extends from the first end 71A of the body portion 71. The tab 75 may be centered along the outer edge of the first end 71A. On the tab 75 is a first catch fastening surface 73 on the top non-wound-facing side of the wound/bandage protector 70. The first catch fastening surface 73 may also extend onto the end region 73A.

On the second end of the body portion 71B are two fastening straps 74. The two fastening straps 74 are a continuation of the same piece of super-stretch material as the body portion 71. There may be a spacing 74B between inner sides of the two fastening straps 74 at the second end of the wound/bandage protector body portion 71B. The shape of the inner sides of the two fastening straps 74 may be an angled line as shown in FIGS. 5(*a*) &5(*b*), an arc, an arc combined with a straight line, or any other configuration which would allow for a distance between the two inner sides of the two fastening straps 74. The magnitude of the spacing 74B may increase along a length of the fastening straps 74. The two fastening straps 74 have lengths 74C running from the second end of the wound/bandage protector body portion 71B to the second strap part 78 which may run parallel to each other. Outer sides of the two fastening straps 74 may run parallel to each other and may continue straight lines formed by the sides of the body portion 71 of the wound/bandage protector 70, as shown in FIGS. 5(*a*) &5(*b*). Alternatively, the outer sides of the two fastening straps 74 may assume a shape that tapers inwardly, toward the inner sides of the fastening straps 74, or outwardly, away from the inner sides of the fastening straps 74. An end portion 77 of each of the two fastening straps 74 has a Velcro® hook type material on the bottom wound-facing side of the wound/bandage protector 70.

Figures 8A, 8B, 8C:
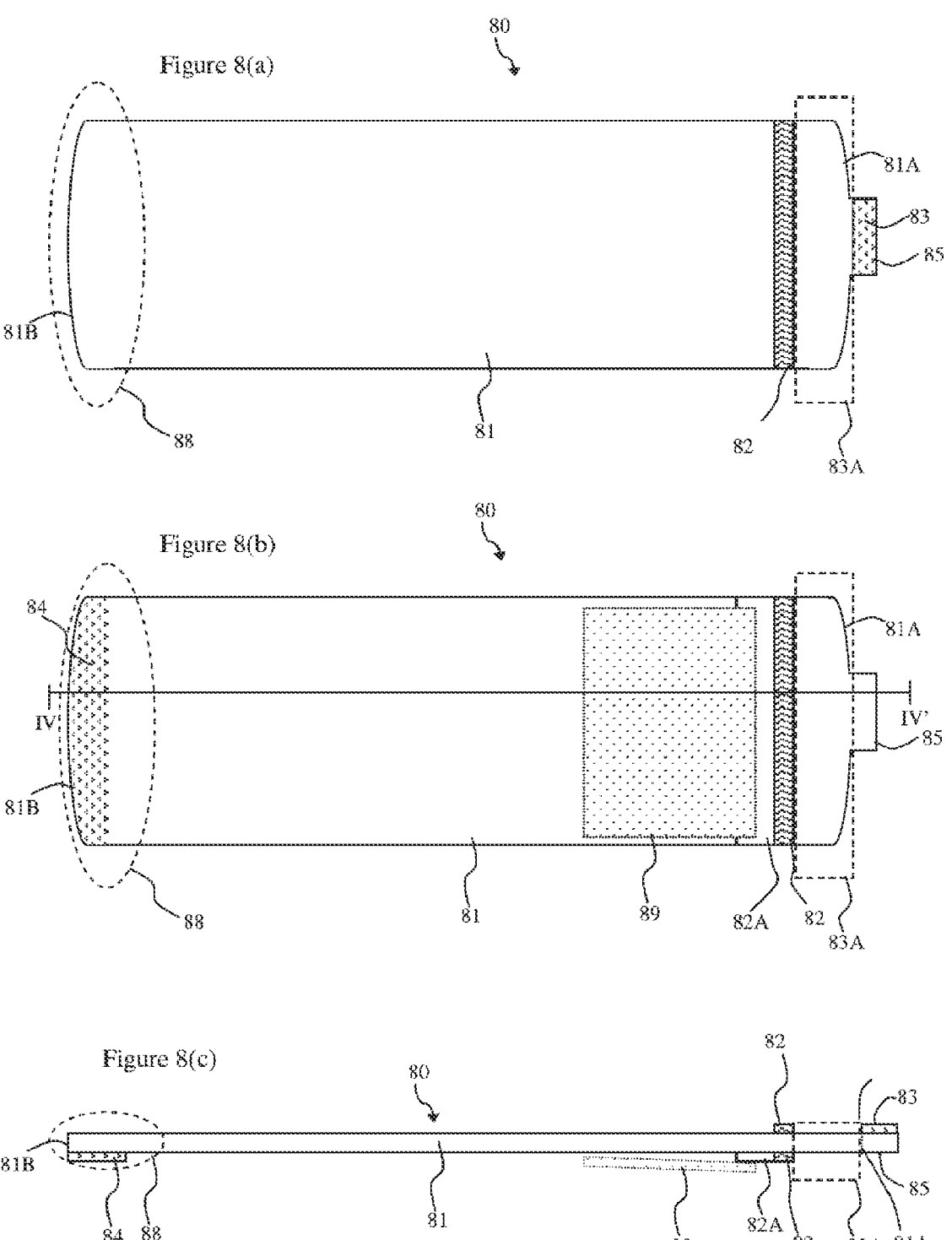
FIG. 8(*a*) is a top non-wound facing side view of an exemplary embodiment of a wound/bandage protector according to the present invention.

FIGS. 8(*a*)-8(*c*) are, respectively, a top non-wound-facing view, a bottom wound facing view, and a cross-sectional side view taken along the line IV-IV' of a wound/bandage protector 80 according to the present invention. The exemplary embodiment of the wound/bandage protector 80 has a body portion 81 that is configured as a wrap which may be comprised of super-stretch material similar to the super-stretch material used in the body 21, 31 of the bandage mittens/socks 20, 30. The body portion 81 is configured to act as a loop portion of a Velcro® type fastener on both the bottom wound-facing side of the wound/bandage protector 80 and the top non-wound facing side of the wound/bandage protector 80. The body portion 81 has a length that runs from a first end 81A to a second end 81B. The stretchable material of the body portion 81 at least provides such stretching capacity in a manner that allows the length of the body portion 81 to vary. The stretchable material of the body portion 81 may, alternatively, provide such stretching capacity that allows both the length of the body portion 81 as well as a width of the body portion 81 which is perpendicular to the length of the body portion 81 to vary.

A gauze port 82A is positioned on or integrated into the body portion 81 proximal to the first end 81A of the body portion 81. The gauze port 82A is an area where a portion of a gauze pad 89 may be attached or removably attached to the wound-facing side of the body portion 81. The gauze port 82A may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze port 82A may be comprised of an adhesive that allows for the permanent attachment of the gauze pad 89. The gauze port 82A may be used to attach different sized gauze pads 89 as well as to periodically replace the gauze pad 89 in the wound/bandage protector 80 shown in this embodiment. The gauze port 82A may be sized and or configured so as to attach to all, a substantial portion, or a small portion such as one side of the gauze pad 89.

In closer proximity to the first end 81A of the body portion 81 of the wound/bandage protector 80 than the gauze port 82A, is a strip 82, which may be similar in configuration to the strip 4 in the first embodiment, having one or more threads made of a rubberized material that provides a moderate amount of friction interwoven in the strip 82 in such a manner that the rubberized material threads are exposed. Alternatively, the strip 82 may be made of other material that provides a frictional surface. Preferably, the amount of friction provided by the frictional surface of the strip 82 should be one that does not cause discomfort when the wound/bandage protector 80 is worn. The strip 82 could be configured so that it is not stretchable in either one or both of the length or the width directions. The strip 82 may be provided along the top non-wound facing side of the wound/bandage protector 80 and/or the bottom wound facing side of the wound/bandage protector 80. Moreover, the strip 82 may extend around sides of the wound/bandage protector 80 and along both the top non-wound facing side of the wound/bandage protector 80 and the bottom wound facing side of the wound/bandage protector 80 so as to form an annular shape.

An end region 83A of the body portion 81 extends from the strip 82 to the first end 81A of the body portion 81. A portion of the end region 83A may be tapered so as to provide a gradual diminution in the width of the body portion 81 toward the first end 81A. A tab 85 extends from the first end 81A of the body portion 81. The tab 85 may be centered along the outer edge of the first end 81A. On the tab 85 is a first catch fastening surface 83 on the top non-wound-facing side of the wound/bandage protector 80. The first catch fastening surface 83 may also extend onto the end region 83A.

A second end region 88 extends along the body portion 81 from a point along the length of the body portion 81 that is proximal to the second end 81B of the body portion 81, to the second end 81B. A portion of the end region 88 may be tapered so as to provide a gradual diminution in the width of the body portion 81 toward the second end 81B. On the second end region 88, although not necessarily on the entire second end region 88, is a fastening portion 84 that can engage and hold fast to the body portion 81 on the top non-wound facing side of the wound/bandage protector 80, or a portion thereof. The fastening portion 84 may be made of a Velcro® hook type material provided on the bottom wound-facing side of the wound/bandage protector 80.

Figures 9A, 9B, 9C:
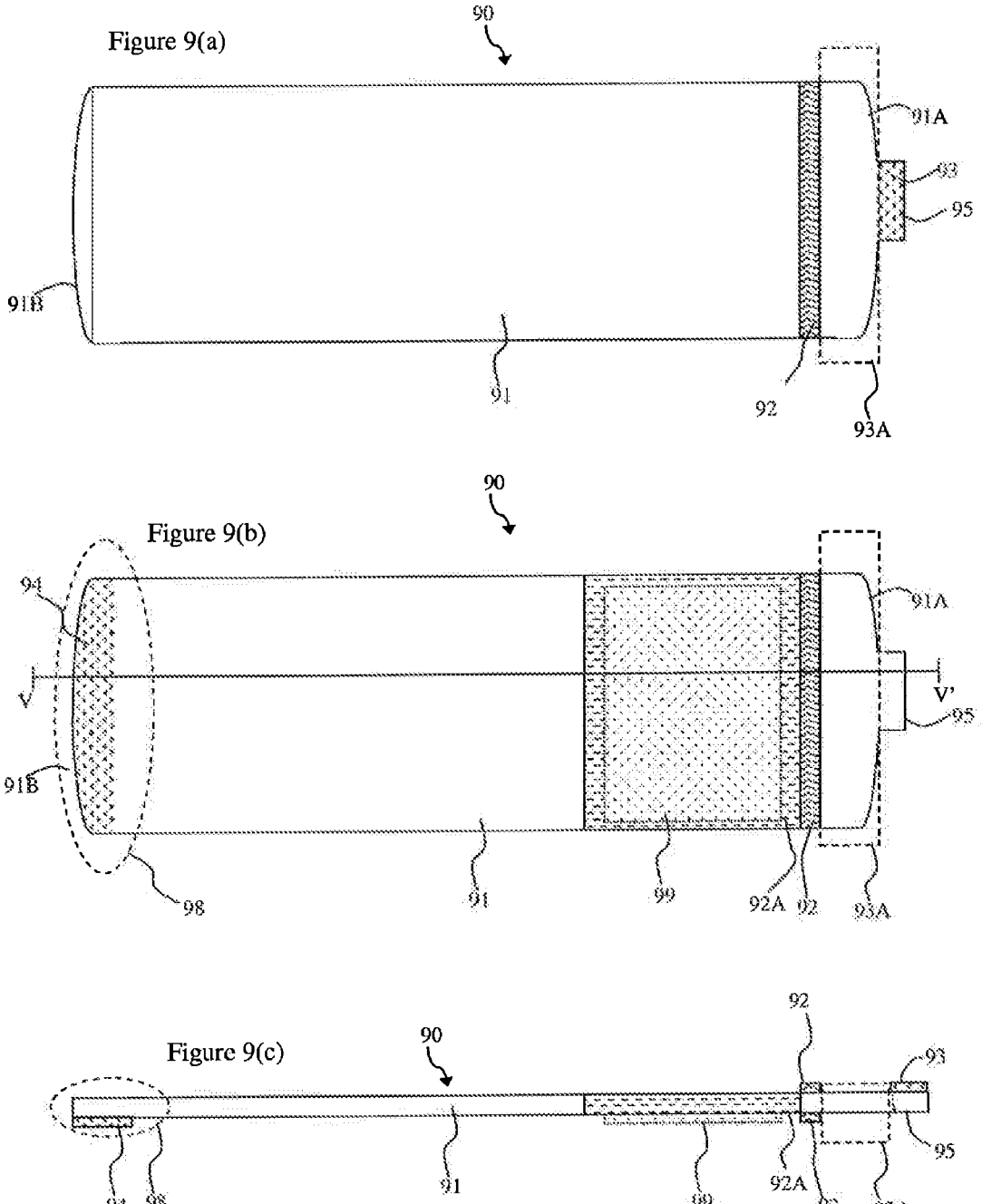
FIG. 9(*a*) is a top non-wound facing side view of an exemplary embodiment of a wound/bandage protector according to the present invention.

FIGS. 9(*a*)-9(*c*) are, respectively, a top non-wound-facing view, a bottom wound facing view, and a cross-sectional side view taken along the line V-V' of a wound/bandage protector 90 according to the present invention. The exemplary embodiment of the wound/bandage protector 90 has a body portion 91 that is configured as a wrap which may be comprised of super-stretch material similar to the super-stretch material used in the body 21, 31 of the bandage mittens/socks 20, 30. The body portion 91 is configured to act as a loop portion of a Velcro® type fastener on both the bottom wound-facing side of the wound/bandage protector 90 and the top non-wound facing side of the wound/bandage protector 90. The body portion 91 has a length that runs from a first end 91A to a second end 91B. The stretchable material of the body portion 91 at least provides such stretching capacity in a manner that allows the length of the body portion 91 to vary. The stretchable material of the body portion 91 may, alternatively, provide such stretching capacity that allows both the length of the body portion 91 as well as a width of the body portion 91 which is perpendicular to the length of the body portion 91 to vary.

A gauze panel 92A is positioned on or integrated into the body portion 91 proximal to the first end 91A of the body portion 91. The gauze panel 92A is an area where all or substantially all of a gauze pad 99 may be attached or removably attached to the wound-facing side of the body portion 91. The gauze panel 92A may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze panel 92A may be comprised of an adhesive that allows for the permanent attachment of the gauze pad 99. The gauze panel 92A may be used to attach different sized gauze pads 99 as well as to periodically replace the gauze pad 99 in the wound/bandage protector 90 shown in this embodiment.

In closer proximity to the first end 91A of the body portion 91 of the wound/bandage protector 90 than the gauze panel 92A, may be a strip 92, which may be similar in configuration to the strip 4 in the first embodiment, having one or more threads made of a rubberized material that provides a moderate amount of friction interwoven in the strip 92 in such a manner that the rubberized material threads are exposed. Alternatively, the strip 92 may be made of other material that provides a frictional surface. Preferably, the amount of friction provided by the frictional surface of the strip 92 should be one that does not cause discomfort when the wound/bandage protector 90 is worn. The strip 92 could be configured so that it is not stretchable in either one or both of the length or the width directions. The strip 92 may be provided along the top non-wound facing side of the wound/bandage protector 90 and/or the bottom wound facing side of the wound/bandage protector 90. Moreover, the strip 92 may extend around sides of the wound/bandage protector 90 and along both the top non-wound facing side of the wound/bandage protector 90 and the bottom wound facing side of the wound/bandage protector 90 so as to form an annular shape.

An end region 93A of the body portion 91 extends from the strip 92 to the first end 91A of the body portion 91. A portion of the end region 93A may be tapered so as to provide a gradual diminution in the width of the body portion 91 toward the first end 91A. A tab 95 extends from the first end 91A of the body portion 91. The tab 95 may be centered along the outer edge of the first end 91A. On the tab 95 is a first catch fastening surface 93 on the top non-wound-facing side of the wound/bandage protector 90. The first catch fastening surface 93 may also extend onto the end region 93A.

A second end region 98 extends along the body portion 91 from a point along the length of the body portion 91 that is proximal to the second end 91B of the body portion 91, to the second end 91B. A portion of the end region 98 may be tapered so as to provide a gradual diminution in the width of the body portion 91 toward the second end 91B. On the second end region 98, although not necessarily on the entire second end region 98, is a fastening portion 94 that can engage and hold fast to the body portion 91 on the top non-wound facing side of the wound/bandage protector 90, or a portion thereof. The fastening portion 94 may be made of a Velcro® hook type material provided on the bottom wound-facing side of the wound/bandage protector 90.

Figure 10A:
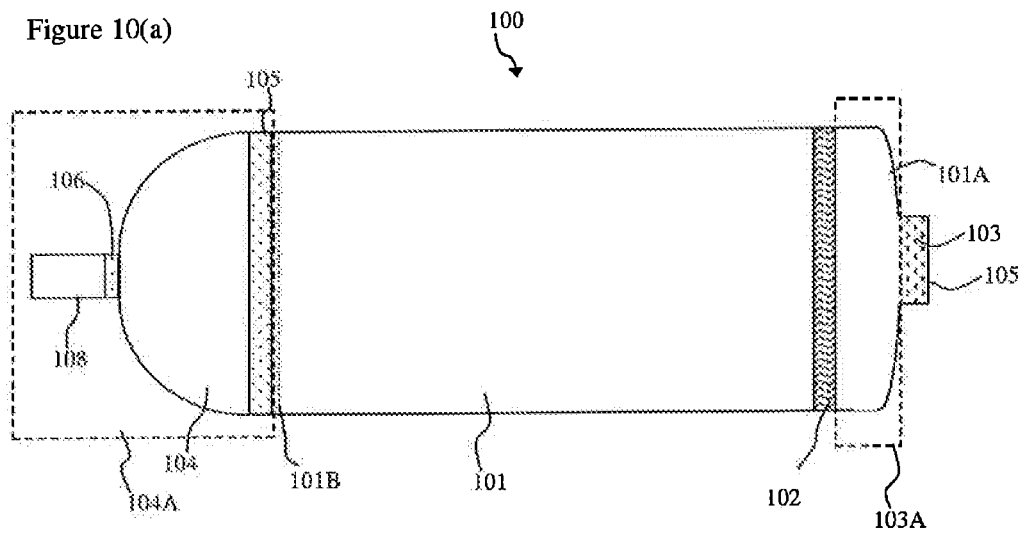
FIG. 10(*a*) is a top non-wound facing side view of a exemplary embodiment of a wound/bandage protector according to the present invention.
Figure 10B:
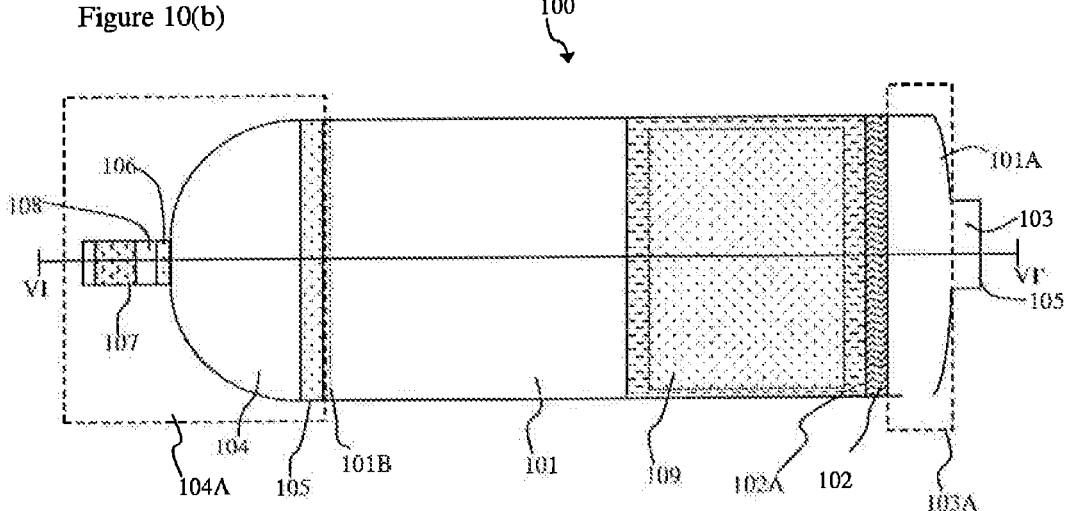
Figure 10C:
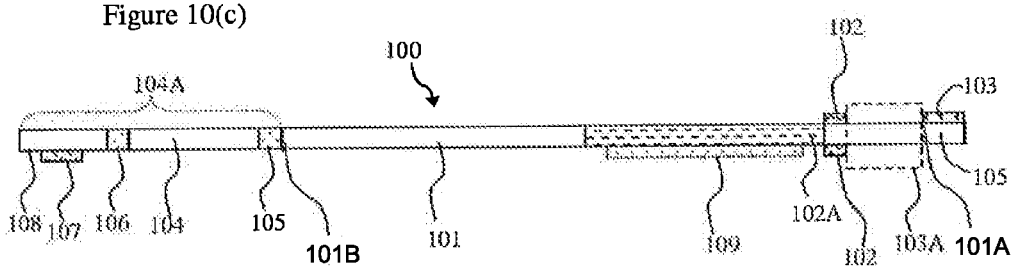

FIGS. 10(*a*)-10(*c*) are, respectively, a top non-wound-facing view, a bottom wound facing view, and a cross-sectional side view taken along the line VI-VI' of a wound/bandage protector 100 according to the present invention. The exemplary embodiment of the wound/bandage protector 100 has a body portion 101 that is configured as a wrap, which may be comprised of super-stretch material similar to the super-stretch material used in the body 21, 31 of the bandage mittens/socks 20, 30. The body portion 101 is configured to act as a loop portion of a Velcro® type fastener on both the bottom wound-facing side of the wound/bandage protector 100 and the top non-wound facing side of the wound/bandage protector 100. The body portion 101 has a length that runs from a first end 101A to a second end 101B. The stretchable material of the body portion 101 at least provides such stretching capacity in a manner that allows the length of the body portion 101 to vary. The stretchable material of the body portion 101 may, alternatively, provide such stretching capacity that allows both the length of the body portion 101 as well as a width of the body portion 101 which is perpendicular to the length of the body portion 101 to vary.

A gauze panel 102A is positioned on or integrated into the body portion 101 proximal to the first end 101A of the body portion 101. The gauze panel 102A is an area where all or substantially all of a gauze pad 109 may be attached or removably attached to the wound-facing side of the body portion 101. The gauze panel 102A may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze panel 102A may be comprised of an adhesive that allows for the permanent attachment of the gauze pad 109. The gauze panel 102A may be used to attach different sized gauze pads 109 as well as to periodically replace the gauze pad 109 in the wound/bandage protector 100 shown in this embodiment.

In closer proximity to the first end 101A of the body portion 101 of the wound/bandage protector 100 than the gauze panel 102A, may be a strip 102, which may be similar in configuration to the strip 4 in the first embodiment, having one or more threads made of a rubberized material that provides a moderate amount of friction interwoven in the strip 102 in such a manner that the rubberized material threads are exposed. Alternatively, the strip 102 may be made of other material that provides a frictional surface. Preferably, the amount of friction provided by the frictional surface of the strip 102 should be one that does not cause discomfort when the wound/bandage protector 100 is worn. The strip 102 could be configured so that it is not stretchable in either one or both of the length or the width directions. The strip 102 may be provided along the top non-wound facing side of the wound/bandage protector 100 and/or the bottom wound facing side of the wound/bandage protector 100. Moreover, the strip 102 may extend around sides of the wound/bandage protector 100 and along both the top non-wound facing side of the wound/bandage protector 100 and the bottom wound facing side of the wound/bandage protector 100 so as to form an annular shape.

An end region 103A of the body portion 101 extends from the strip 102 to the first end 101A of the body portion 101. A portion of the end region 103A may be tapered so as to provide a gradual diminution in the width of the body portion 101 toward the first end 101A. A tab 105 extends from the first end 101A of the body portion 101. The tab 105 may be centered along the outer edge of the first end 101A. On the tab 105 is a first catch fastening surface 103 on the top non-wound-facing side of the wound/bandage protector 100. The first catch fastening surface 103 may also extend onto the end region 103A.

Attached to the second end of the body portion 101B is a fastening strap 104A. The fastening strap 104A may be comprised of two parts. A first strap part 104 is attached to the second end of the wound/bandage protector body portion 101B and is made out of a super-stretch material which may be adapted to function as a loop portion of a Velcro®-type fastener on both the top non-wound facing side and the bottom wound-facing side of the wound/bandage protector 100. The super-stretch material of the first strap part 104 preferably provides a stretching resistance that is greater than the stretching resistance of the body portion 101. The first strap part 104 may be attached to the second end of the wound/bandage protector body portion 101B via an attachment region 105 which is preferably configured to provide no stretch. The attachment region 105 may be comprised of a composite of the material of the first strap part 104 and the body portion 101 of the wound/bandage protector 100 and may be attached by a punch and melt heat seal. Alternatively, the first strap part 104 is directly attached to the body portion 101 without an attachment region 105 intervening therebetween. A second strap part 108 is attached to the first strap part 104 via an attachment region 106. The attachment region 106 may be comprised of a composite of the material of the first strap part 104 and the second strap part 108 and may be attached by a punch and melt heat seal. The second strap part 108 has a portion 107 which includes a Velcro® hook type material on the bottom wound-facing side of the fastening strap 104A. Alternatively, the second strap part 108 is directly attached to the first strap part 104 without an attachment region 106 intervening therebetween.

Figure 11A:
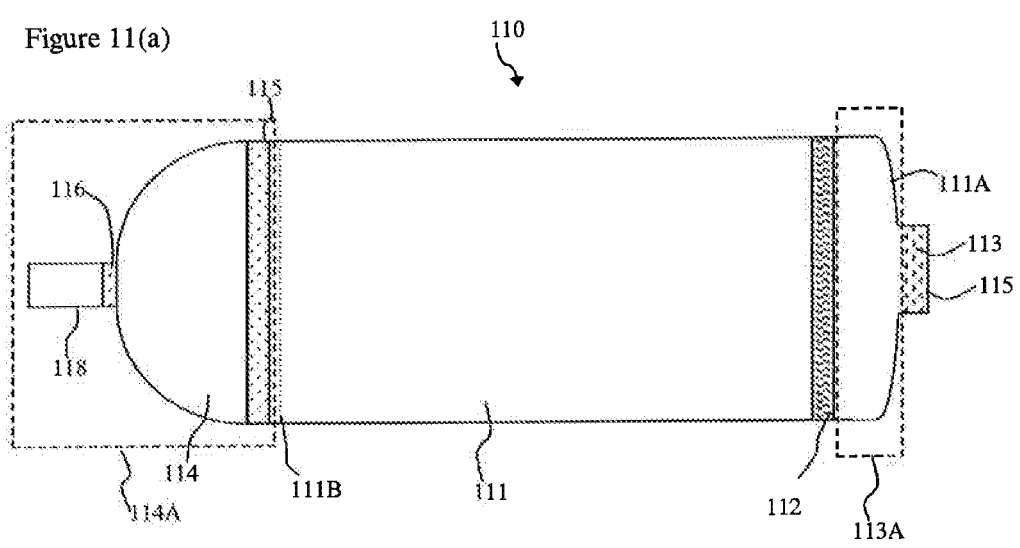
FIG. 11(*a*) is a top non-wound facing side view of an exemplary embodiment of a wound/bandage protector according to the present invention.
Figure 11B:
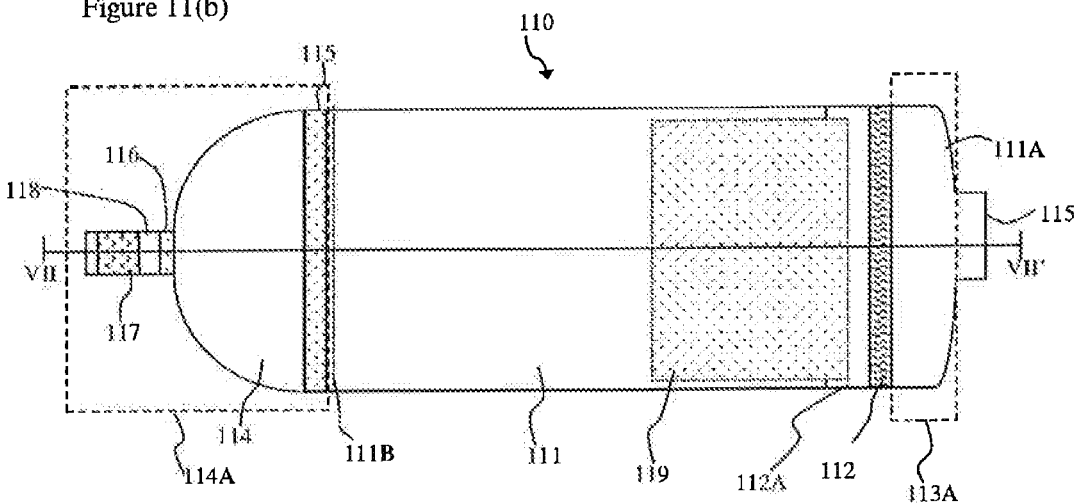
Figure 11C:
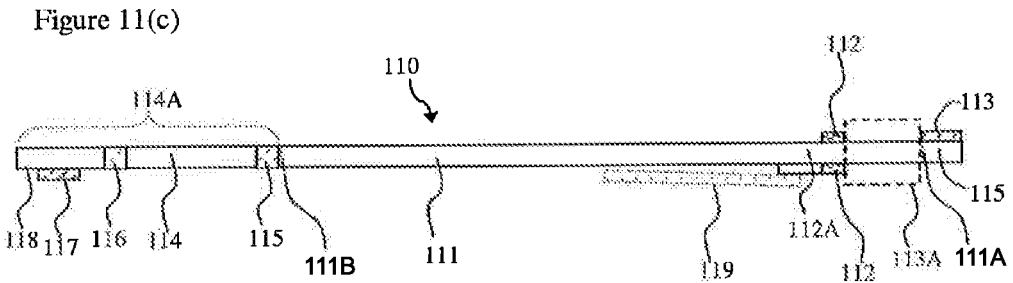

FIGS. 11(a)-11(c) are, respectively, a top non-wound-facing view, a bottom wound facing view, and a cross-sectional side view taken along the line VII-VII' of a wound/bandage protector 110 according to the present invention. The exemplary embodiment of the wound/bandage protector 110 has a body portion 111 that is configured as a wrap, which may be comprised of super-stretch material similar to the super-stretch material used in the body 21, 31 of the bandage mittens/socks 20, 30. The body portion 111 is configured to act as a loop portion of a Velcro® type fastener on both the bottom wound-facing side of the wound/bandage protector 110 and the top non-wound facing side of the wound/bandage protector 110. The body portion 111 has a length that runs from a first end 111A to a second end 111B. The stretchable material of the body portion 111 at least provides such stretching capacity in a manner that allows the length of the body portion 111 to vary. The stretchable material of the body portion 111 may, alternatively, provide such stretching capacity that allows both the length of the body portion 111 as well as a width of the body portion 111 which is perpendicular to the length of the body portion 111 to vary.

A gauze port 112A is attached to the body portion 111 proximal to the first end 111A of the body portion 111. The gauze port 112A is an area where a portion of a gauze pad 119 may be attached or removably attached to the wound-facing side of the body portion 111. The gauze port 112A may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze port 112A may be comprised of an adhesive that allows for the permanent attachment of the gauze pad 119. The gauze port 112A may be used to attach different sized gauze pads 119 as well as to periodically replace the gauze pad 119 in the wound/bandage protector 110 shown in this embodiment. The gauze port 112A may be sized and or configured so as to attach to all, a substantial portion, or a small portion such as one side of the gauze pad 119.

In closer proximity to the first end 111A of the body portion 111 of the wound/bandage protector 110 than the gauze port 112A, may be a strip 112, which may be similar in configuration to the strip 4 in the first embodiment, having one or more threads made of a rubberized material that provides a moderate amount of friction interwoven in the strip 112 in such a manner that the rubberized material threads are exposed. Alternatively, the strip 112 may be made of other material that provides a frictional surface. Preferably, the amount of friction provided by the frictional surface of the strip 112 should be one that does not cause discomfort when the wound/bandage protector 110 is worn. The strip 112 could be configured so that it is not stretchable in either one or both of the length or the width directions. The strip 112 may be provided along the top non-wound facing side of the wound/bandage protector 110 and/or the bottom wound facing side of the wound/bandage protector 110. Moreover, the strip 112 may extend around sides of the wound/bandage protector 110 and along both the top non-wound facing side of the wound/bandage protector 110 and the bottom wound facing side of the wound/bandage protector 110 so as to form an annular shape.

An end region 113A of the body portion 111 extends from the strip 112 to the first end 111A of the body portion 111. A portion of the end region 113A may be tapered so as to provide a gradual diminution in the width of the body portion 111 toward the first end 111A. A tab 115 extends from the first end 111A of the body portion 111. The tab 115 may be centered along the outer edge of the first end 111A. On the tab 115 is a first catch fastening surface 113 on the top non-wound-facing side of the wound/bandage protector 110. The first catch fastening surface 113 may also extend onto the end region 113A.

Attached to the second end of the body portion 111B is a fastening strap 114A. The fastening strap 114A may be comprised of two parts. A first strap part 114 is attached to the second end of the wound/bandage protector body portion 111B and is made out of a super-stretch material which may be adapted to function as a loop portion of a Velcro®-type fastener on both the top non-wound facing side and the bottom wound-facing side of the wound/bandage protector 110. The super-stretch material of the first strap part 114 preferably provides a stretching resistance that is greater than the stretching resistance of the body portion 111. The first strap part 114 may be attached to the second end of the wound/bandage protector body portion 111B via an attachment region 115 which is preferably configured to provide no stretch. The attachment region 115 may be comprised of a composite of the material of the first strap part 114 and the body portion 111 of the wound/bandage protector 110 and may be attached by a punch and melt heat seal. Alternatively, the first strap part 114 is directly attached to the body portion 111 without an attachment region 115 intervening therebetween. A second strap part 118 is attached to the first strap part 114 via an attachment region 116. The attachment region 116 may be comprised of a composite of the material of the first strap part 114 and the second strap part 118 and may be attached by a punch and melt heat seal. The second strap part 118 has a portion 117 which includes a Velcro® hook type material on the bottom wound-facing side of the fastening strap 114A. Alternatively, the second strap part 118 is directly attached to the first strap part 114 without an attachment region 116 intervening therebetween.

In certain situations, it may be preferable to apply an adhesive bandage to a wound, particularly on joints, whose constant movement may cause the gauze to move. In those situations, according to the present invention, a "diamond gauze", "triangle gauze" or "stretchable gauze" adhesive bandage, as discussed below, are preferably utilized as they have been found to have advantages over other bandages known in the art. One of the advantages of the "diamond gauze", "triangle gauze" and "stretchable gauze" bandages is that they can provide superior adherence and conformability to a wound area with a maximal area of gauze, particularly for wounds on joints. The "diamond gauze", "triangle gauze", and "stretchable gauze" adhesive bandages may be used alone or in conjunction with the super-stretch tube in FIG. 1 or a bandage wound/protector such as those shown in FIGS. 2 through 11, preferably without the gauze pad which may be shown as an alternative in those figures. In addition, the "diamond gauze", "triangle gauze" and "stretchable gauze" configurations discussed below may be integrated with a bandage wound/protector such as those shown in FIGS. 2 through 11 without the use of a separate adhesive bandage. Moreover, the "diamond gauze" and "triangle gauze" bandages may concurrently be configured as "stretchable gauze" bandages. A "stretchable gauze" bandage is any bandage with a stretchable body portion and a stretchable gauze pad affixed to the wound-facing side of the body portion. The body portion may have adhesive on at least a portion of a wound facing side or, alternatively, the body portion may include self adherent material, such as the nonwoven laminate used in 3M™ Coban™ Self-Adherent Wrap.

FIGS. 66(*a*)-66(*c*) are, respectively, a top non-wound-facing view, a bottom wound facing view, and a side view of a wound/bandage protector 660 according to the present invention. The exemplary embodiment of the wound/bandage protector 660 has a body portion 661 that is configured as a wrap which may be comprised of super-stretch material similar to the super-stretch material used in the body 21, 31 of the bandage mittens/socks 20, 30. The body portion 661 is configured to act as a loop portion of a Velcro® type fastener on both the bottom wound-facing side of the wound/bandage protector 660 and the top non-wound facing side of the wound/bandage protector 660. The body portion 661 has a length that runs from a first end 661A to a second end 661B. The stretchable material of the body portion 661 at least provides such stretching capacity in a manner that allows the length of the body portion 661 to vary. The stretchable material of the body portion 661 may, alternatively, provide such stretching capacity that allows both the length of the body portion 661 as well as a width of the body portion 661 which is perpendicular to the length of the body portion 661 to vary.

A gauze port 662 is positioned on or integrated into the body portion 661 proximal to the first end of the body portion 661A. The gauze port 662A is an area where a gauze pad 669 may be attached or removably attached to the wound-facing side of the body portion 661. The gauze port 662 may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, both the gauze port 662 and the gauze pad 669 may have a low tack adhesive, such as a low tack silicone adhesive. The low tack adhesive may be on the entire non-wound facing side of the gauze pad 669, or may be just on a portion of the non-wound facing side of the gauze pad 669. Another possibility is that the surface of the gauze port 662 may be comprised of an adhesive that allows for the permanent attachment of the gauze pad 669. The gauze port 662 may be used to attach different sized gauze pads 669 as well as to periodically replace the gauze pad 669 in the wound/bandage protector 660 shown in this embodiment. The gauze port 662 may be sized and/or configured so as to attach to all, a substantial portion, or a small portion as illustrated in the FIGS. 66(*b*) and 66(*c*), such as one side of the gauze pad 669.

In closer proximity to the first end 661A of the body portion 661 of the wound/bandage protector 660 than the gauze port 662A, is a strip 668, which may be similar in configuration to the strip 4 in the first embodiment, having one or more threads made of a rubberized material that provides a moderate amount of friction interwoven in the strip 668 in such a manner that the rubberized material threads are exposed. Alternatively, the strip 668 may be made of stretch non-slip silicone or similar, preferably latex free, material that provides a frictional surface. The non-slip silicone may be applied in a continuous or discontinuous manner to form the strip 668. Preferably, the amount of friction provided by the frictional surface of the strip 668 should be one that does not cause discomfort when the wound/bandage protector 660 is worn. The strip 668 could be configured so that it is not stretchable in either one or both of the length or the width directions. The strip 668 may be provided along the top non-wound facing side of the wound/bandage protector 660 and/or the bottom wound facing side of the wound/bandage protector 660. Moreover, the strip 668 may extend around sides of the wound/bandage protector 660 and along both the top non-wound facing side of the wound/bandage protector 660 and the bottom wound facing side of the wound/bandage protector 660 so as to form an annular shape.

A first strap 664A extends from the first end 661A of the body portion 661 along, or proximal and substantially with, a line tangential to a lower side 661C of the body portion 661. On the wound facing side of the first strap 664A is a first-attachment region 666 that preferably extends to or proximal to an end of the first strap 664A that is distal to the body portion 661. The first-attachment region 666 is capable of fastening to a portion of the non-wound facing side of the body portion 661. A second strap 664B extends from the second end 661A of the body portion 661 along, or proximal and substantially with, a line tangential to an upper side 661D of the body portion 661. On the wound facing side of the second strap 664A is a second-attachment region 667 that preferably extends to or proximal to an end of the second strap 664B that is distal to the body portion 661. The second-attachment region 666 is capable of fastening to a portion of the non-wound facing side of the body portion 661. In the wound/bandage protector 660 the first and second straps 664A, 664B are made of the same integral piece of material as the body portion. However, in other alternative embodiments the first and second straps 664A, 664B may be constructed in the manner described herein by straps in other exemplary embodiments of the wound bandage protector. The first-attachment region 666 and second attachment region 667 are preferably a hook portion of a Velcro®-type fastener, while the non-wound facing side of the body portion 661 preferably acts as a loop portion of a Velcro®-type fastener. On the top non-wound-facing side of the wound/bandage protector 660 proximal or adjacent to the first end 661A of the body portion is a first-catch fastening surface 663. The first-catch fastening surface 663 extends between the upper side 661D and the lower side 661C at least along a portion that is opposing the second strap 664B, such that when the wound/bandage protector 660 is wrapped around a limb a portion of the wound facing side of the second strap 664B may fasten to the first-catch fastening surface 663. The first-catch fastening surface 663 is preferably a hook portion of a Velcro®-type fastener, while the wound facing side of the second strap 664B preferably acts as a loop portion of a Velcro®-type fastener.

FIGS. 12(*a*)-12(*f*) are, respectively, a bottom wound-facing view, a top non-wound facing view, two side views and two perspective views of an exemplary embodiment of a "diamond gauze" bandage 120 according to the present invention. The "diamond gauze" bandage 120 has a body portion 121 in a square shape, preferably with rounded corners, which may be made of any suitable material, preferably a stretchable and breathable material, which is known in the art to be used for bandaging wounds.

A gauze pad 122 is attached to the wound-facing side of the body portion 121. In the context of this specification, gauze, or gauze pad, refers to any material or composite of material that may be therapeutically used as a pad over a wound. For example, the gauze pad may be made of cotton or a polyester blend fabric. The fabric may be covered with a plastic porous film such as Telfa® which prevents or minimizes wound adhesion. Furthermore, the gauze pad may be backed with a film that prevents body fluids from penetrating through the gauze pad and then through the body portion of the bandage.

FIGS. 25(*a*)-(*k*) show several exemplary gauze pad configurations 250A, 250B, 250C, 250D, 250E, 250F, 250G, 250H, 250I, 250J, 250K for "diamond gauze" bandages according to the present invention. The gauze pad 122, as shown in FIGS. 12(*a*)-12(*f*), has a square shape equivalent to the gauze pad configuration 250E. Alternatively, the gauze pad 122 may be configured in the shape of a diamond or rhombus as exemplified by the gauze pad configuration 250G, in a "kite shape" (quadrilateral with two distinct pairs of equal adjacent sides) as exemplified by the gauze pad configuration 250H, a rectangle as exemplified by the gauze pad configuration 250I, or in the shape of an "offset diamond" (parallelogram with opposing sides of equal length, adjacent sides of unequal length and corner angles not equal to 90 degrees) as exemplified by the gauze pad configuration 250F. One or more corners of the gauze pad 122 may be rounded, as exemplified by the corners of gauze pad configuration 250D, or one or more corners of the gauze pad 122 may be cut off, as exemplified by corners of gauze pad configurations 250J and 250K. Furthermore, sides 124 of the gauze pad 122 need not be straight. For example, one or more of the sides 124 of the gauze pad 122 may be a convex or concave curve, as exemplified by the sides of gauze pad configurations 250A and 250B, respectively, or an undulating line, as exemplified by the sides of the gauze pad configuration 250C. Any combination of side and corner configurations, such as the exemplary ones shown herein, may be applied to the gauze pad 122. However, all possible shape configurations of a gauze pad in "diamond gauze" bandages should have four "primary corners", i.e. the four corners of a quadrilateral or any four locations on a polygon where the polygon narrows and that would together approximate a quadrilateral with sides defined by sides of the gauze pad between the primary corners. Where a corner is cut off or rounded, the narrowing of the polygon to the corner should be substantial in order for the corner to be a "primary corner", i.e. the narrowing should be greater than 50% and more preferably greater than 75%, and even more preferably 85% and even more preferably 95%. Thus, for example, a length 251L of a cut off corner 251K in gauze pad configuration 250D should be less than 50% of the length of a parallel line 251M drawn between the two opposing corners that are adjacent to the cut off corner 251K or more preferably the length of the cut off corner 251K should be less than 25% and even more preferably less than 15% of the length of the parallel line 251M drawn between the two opposing corners that are adjacent to the cut off corner 251K. Similarly, with a rounded corner 251D, the diameter of a circle 251N, which is partially comprised of the arc of the rounded corner 251D, should be less than 50% of the length of a line 251P drawn between the two opposing corners that are adjacent to the rounded corner 251D or more preferably the diameter of a circle 251N should be less than 25% and even more preferably less than 15% of the length of the parallel line 251P drawn between the two opposing corners that are adjacent to the rounded corner 251D. In the exemplary gauze pad configurations 250A, 250B, 250C, 250D, 250E, 250F, 250G, 250H, 250I, 250J, 250K, there are four primary corners 251, identified by circles, and they are oriented as indicated by directional arrows associated with each of the primary corners 251.

The primary corners of the gauze pad 122 are offset from the corners of the body portion 121 such that the sides 124 of the gauze pad 122 are not parallel to edges 123 of the body portion 121. Preferably, the gauze pad 122 is oriented so that each of the sides of the gauze pad 122 is parallel to a hypotenuse of an isosceles right triangle formed with two adjacent edges 123 of the body portion 121.

In regard to the "diamond gauze" bandages disclosed herein, length and width tangents of a body portion may be defined by the edges of the body portion such as the edges 123 of the body portion 121. Thus, where a body portion as illustrated herein is square or rectangular, the length and width tangents are not explicitly defined as they are the edges of the body portion itself. Similarly, in exemplary embodiments of "diamond gauze" bandages where the body portion has a different shape but one of the length or width tangents is completely or almost completely contiguous with the body portion, the tangent line is not explicitly defined, such as for the "diamond gauze" bandage 120. Otherwise, the length and width tangents are a set of explicitly defined tangents that are tangential to the body portion edges and form a square or rectangular shape. For purposes of the discussion herein, length 252 is defined along the horizontal axis and width 253 is defined along the vertical axis, as shown in FIG. **25(*l*). Each of the primary corners of the gauze pad 122 is oriented towards a different length or width tangent of the body portion 121**. Similarly, for other embodiments of a "diamond gauze" bandage, each of the primary corners is oriented towards a different length or width tangent of the body portion.

The gauze pad 122 may have the same center point as the body portion 121, and/or each of the primary corners of the gauze pad 122 may be oriented toward a mid-point or midsection of one of the edges 123, which in this case are essentially equivalent to the length or width tangents of the body portion 121. The midsection of a length or width tangent is a portion of the length or width tangent preferably equal to half of the length or width tangent and centered on the midpoint of the length or width tangent. More preferably, the midsection may be a third, a quarter, or an eighth, or another fraction of the length or width tangent that is less than half of the length or width tangent.

FIG. **25(*m*) illustrates an exemplary preferred range of gauze pad orientation for a "diamond gauze" bandage according to the present invention. Preferably, all primary corners of a gauze pad in a "diamond gauze" bandage should be oriented towards the midpoints of the length and width tangents. Of course, this is not always practical, given the varied shapes, functions, and other limiting factors of the specific bandage configurations. Line 254 represents an exemplary length or width tangent that is divided into equal sub-lengths defined by tick-marks, and a preferable orientation range 257 is indicated by the thicker portion of the line 254. A gauze pad 255** with four primary corners indicated by circles with orientations indicated by their associated arrows is positioned so that one of the primary corners is oriented towards an upper limit of the preferable orientation range

257, while a gauze pad 255' is oriented so that one of the primary corners is oriented towards a lower limit of the preferable orientation range 257. The preferable orientation range 257 may represent the midsection of the line 254, as discussed above. Alternatively, the preferable range of gauze pad orientation may be defined by a minimal angle formed by the intersection of a length or width tangent and a ray that extends in the direction that a primary corner is oriented, where the angle is on the side of the ray that is proximate to the point where the ray would form a right angle with the length or width tangent. In FIG. **25(*m*), angles 258, 258' are formed by the intersection of the line 254 and rays 256, 256' that extend in the direction that the primary corner of gauze pads 255, 255' are oriented. In this instance, the orientation range 257 of the line 254 is defined by a minimal value for the angles 258, 258'. The orientation range 257 in this instance is not necessarily centered on the midpoint of the line 254. The angles 258, 258' preferably have a range from a minimal value of 55° to a maximal value of 90° at the right angled intersection of the line 254 and the rays 256, 256'. More preferably, the angles 258, 258'** have a minimal value of 65°, 75°, or 85°.

The size of the gauze pad 122 is such that the primary corners of the gauze pad 122 do not reach the edges 123 of the body portion 121. Alternatively, the gauze pad 122 may be sized shaped and/or positioned in such manner that one or more of the primary corners of the gauze pad reach the edges 123 of the body portion 121. The gauze pad 122 may be sized and positioned so as to substantially define four equal quadrants on the wound facing side of the body portion 121, i.e. each side of the gauze pad 132 defines the majority of one edge of one of the quadrants, the quadrants being areas of the wound facing side of the body portion 121 that are not covered by the gauze pad 122. The bottom wound-facing side of the body portion 121 may have adhesive as those used for bandages in the art, or alternatively, the body portion may include self adherent material, such as the nonwoven laminate used in 3M™ Coban™ Self-Adherent Wrap. The adhesive may be applied to all or part of the bottom wound-facing side of the body portion 121. The gauze pad 122 may or may not be affixed to the body portion 121 via the same adhesive as that which is used to affix the "diamond gauze" bandage 120 to a patient.

FIGS. **13(*a*)-13(*f*) are, respectively, a bottom wound-facing view, a top non-wound facing view, two side views and two perspective views of an exemplary embodiment of a "diamond gauze" bandage 130 according to the present invention. In contrast to "diamond gauze" bandage 120, the size of gauze pad 132 in the "diamond gauze" bandage 130 is such that the primary corners of the gauze pad 132 reach edges 133 of a body portion 131 of the "diamond gauze" bandage 130. The gauze pad 132 may be sized and positioned so as to define four equal quadrants on the wound facing side of the body portion 131. In an alternative exemplary embodiment, the gauze pad 132 may be sized and positioned so as to substantially define four equal quadrants on the wound facing side of the body portion 131. In all other respects, the configuration of the "diamond gauze" bandage 130 is comparable to the configuration of the "diamond gauze" bandage 120. Thus, the discussion above by "diamond gauze" bandage 120 regarding issues such as gauze pad shape, positioning and orientation as well as body portion materials, adhesive type and placement are applicable to the "diamond gauze" bandage 130** as well to other "diamond gauze" bandages, including the exemplary embodiments of a "diamond gauze" bandage discussed below.

FIGS. 14(*a*) through 14(*e*) are, respectively, a bottom wound-facing view, a top non-wound facing view, two side views and one perspective view of an exemplary embodiment of a "diamond gauze" bandage 140 according to the present invention. In the "diamond gauze" bandage 140, a body portion 141 has a rectangular shape, preferably with rounded corners. A gauze pad 142 is configured in a square shape and is oriented with respect to the body portion 141 such that the sides of the gauze pad 142 are not parallel to the edges of the body portion 141. The gauze pad 142 may be sized so that two opposing primary corners may touch two opposing edges of the body portion 141 while the remaining primary corners of the gauze pad 142 do not touch the remaining edges of the body portion 141. Moreover, for any "diamond gauze" bandages, according to the present invention, the gauze pads may be sized so that two opposing primary corners may touch two opposing edges of the body portions. The gauze pad 142 may have the same center point as the body portion 141 and/or each of the primary corners of the gauze pad 142 may be oriented toward a mid-point of one of the edges of body portion 141.

FIGS. 18(*a*) through 18(*e*) are, respectively, a bottom wound-facing view, a top non-wound facing view, two side views and one perspective view of an exemplary embodiment of a "diamond gauze" bandage 180 according to the present invention. In the "diamond gauze" bandage 180, a body portion 181 has a rectangular shape, preferably with rounded corners. A gauze pad 182 is configured in the shape of a diamond, with two opposing primary corners of the gauze pad 182 touching two opposing length edges of the body portion 181. In all other respects, the configuration of the "diamond gauze" bandage 180 is comparable to the configuration of the "diamond gauze" bandage 140.

FIGS. 50(*a*) through 50(*e*) are, respectively, a bottom wound-facing view, a top non-wound facing view, two side views and one perspective view of an exemplary embodiment of a "diamond gauze" bandage 500 according to the present invention. In the "diamond gauze" bandage 500, a body portion 501 has a rectangular shape, preferably with rounded corners. A gauze pad 502 is configured in the shape of a diamond, with all four primary corners of the gauze pad 502 touching all four edges of the body portion 501. In all other respects, the configuration of the "diamond gauze" bandage 500 is comparable to the configuration of the "diamond gauze" bandage 180. Moreover, for any of the "diamond gauze" bandages, according to the present invention, the gauze pad may be sized and positioned so that some or all of the gauze pad corners extend to the edges of the body portion.

FIGS. 15(*a*)-15(*e*) are, respectively, a bottom wound-facing view, a top non-wound facing view, two side views and one perspective view of another exemplary embodiment of a "diamond gauze" bandage 150 according to the present invention. The body portion 151 of the "diamond gauze" bandage 150 is an "almond" shape which among other bandaging uses may be particularly useful for bandaging a finger tip or similar appendage. The gauze pad 152 is oriented with respect to the body portion 151 of the "diamond gauze" bandage 150 such that the sides of the gauze pad 152 are not parallel to length tangents 159A, 159C and width tangents 159B, 159D of the body portion 151. The gauze pad 152 may have the same center point as the body portion 151 and/or each of the corners of the gauze pad 152 may be oriented toward a mid-point of one of the length tangents 159A, 159C or width tangents 159B, 159D.

FIGS. 16(*a*)-16(*e*) are, respectively, a bottom wound-facing view, a top non-wound facing view, two side views and one perspective view of another exemplary embodiment of a "diamond gauze" bandage 160 according to the present invention. The body portion 161 of the "diamond gauze" bandage 160 is an oval shape which among other bandaging uses may be particularly useful for bandaging a finger tip or similar appendage. The gauze pad 162 is oriented with respect to the body portion 161 such that the sides of the gauze pad 162 are not parallel to length tangents 169A, 169C and width tangents 169B, 169D of the body portion 161. The gauze pad 162 may have the same center point as the body portion 161 and/or each of the corners of the gauze pad 162 may be oriented toward a mid-point of one of the length tangents 169A. 169C or width tangents 169B, 169D.

FIGS. 17(*a*)-17(*e*) are, respectively, a bottom wound-facing view, a top non-wound facing view, two side views and one perspective view of another exemplary embodiment of a "diamond gauze" bandage 170 according to the present invention. The body portion 171 of the "diamond gauze" bandage 170 is a "bowtie" or "hourglass" shape which among other bandaging uses may be particularly useful for bandaging a finger tip or similar appendage. The gauze pad 172 is oriented with respect to the body portion 171 of the "diamond gauze" bandage 170 such that the sides of the gauze pad 172 are not parallel to the length tangents 179A, 179B and edges 179C and 179D of the body portion 171, the edges 179C and 179D being essentially equivalent to width tangents in this exemplary embodiment. The gauze pad 172 may have the same center point as the body portion 171, and/or each of the corners of the gauze pad 172 may be oriented toward a mid-point of one of the tangents 179A and 179B and edges 179C and 179D of the body portion 171 of the "diamond gauze" bandage 170.

Figure 19A:
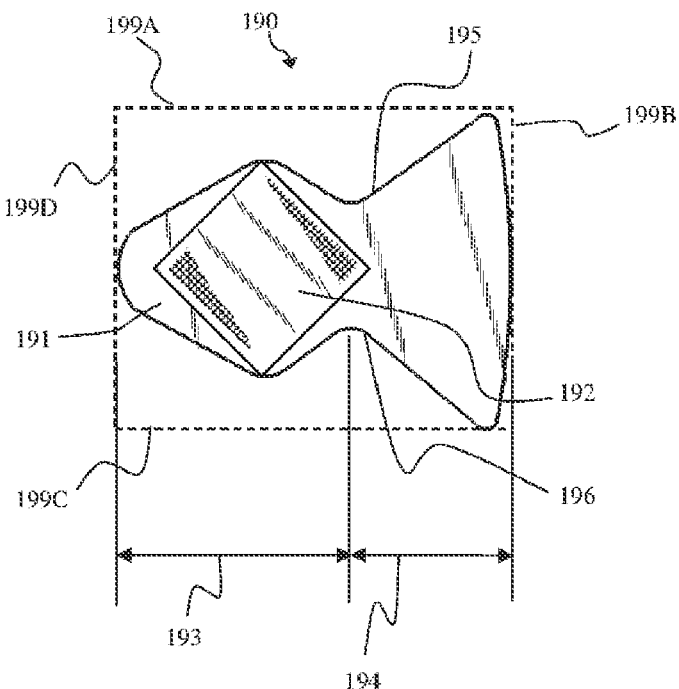
FIG. 19(a) shows a bottom wound-facing side of an exemplary embodiment of a "diamond gauze" adhesive bandage according to the present invention.
Figure 19B:
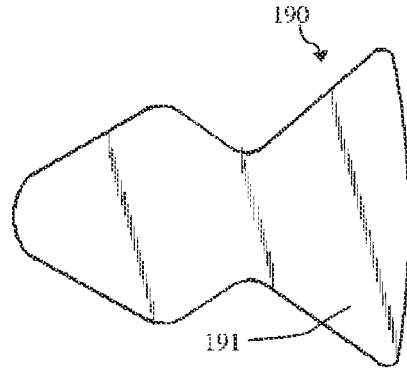
FIG. 19(b) shows a top non-wound-facing side of the exemplary embodiment of the "diamond gauze" adhesive bandage illustrated in FIG. 19(a)
Figures 20A, 20B, 20C, 20D, 20E, 20F, 20G:
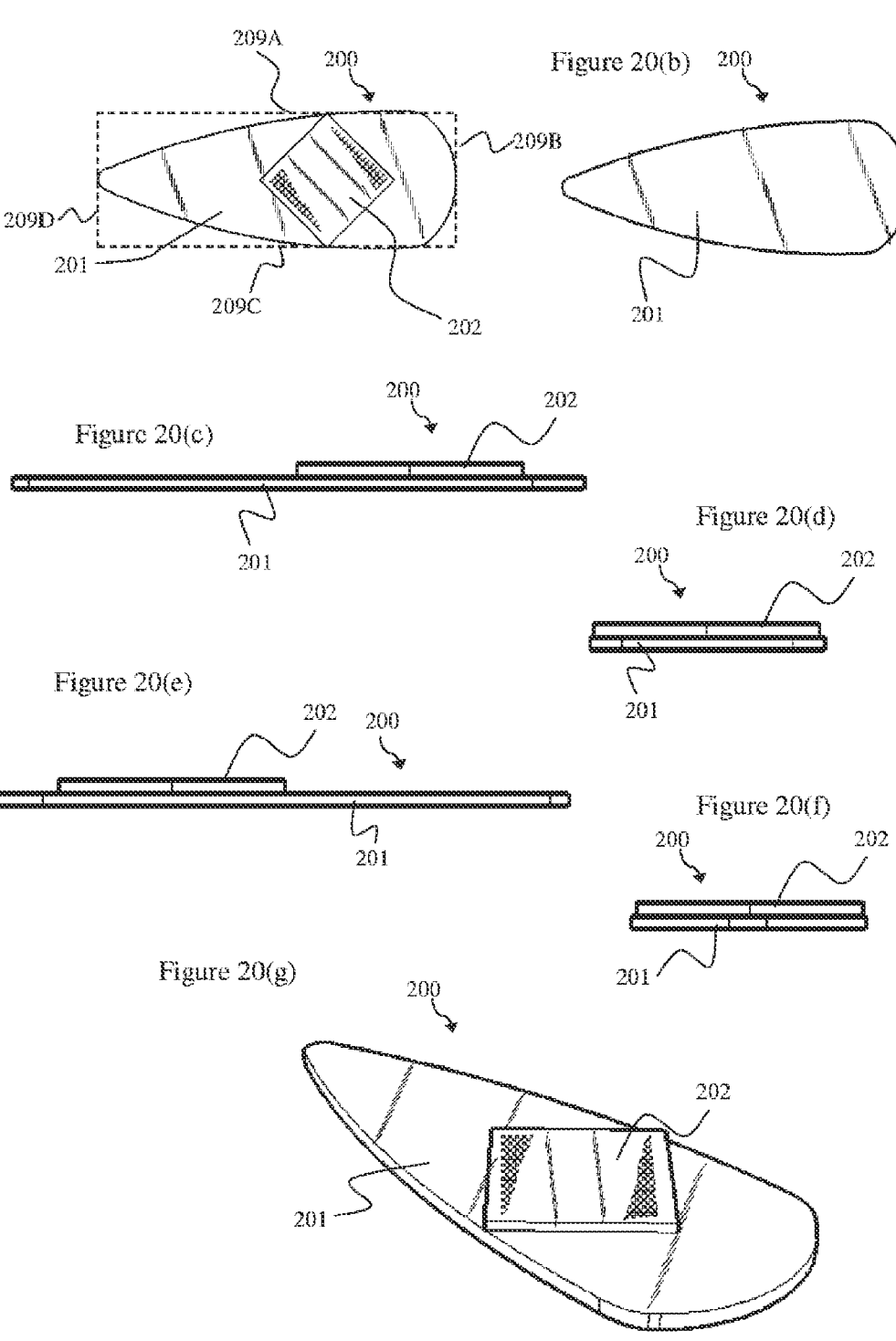
FIG. 20(a) shows a bottom wound-facing side of an exemplary embodiment of a "diamond gauze" adhesive bandage according to the present invention.
FIG. 20(b) shows a top non-wound-facing side of the exemplary embodiment of the "diamond gauze" adhesive bandage illustrated in FIG. 20(a)
FIG. 20(c) shows a first side view of the exemplary embodiment of the "diamond gauze" adhesive bandage illustrated in FIGS. 20(a) and (b)
FIG. 20(d) shows a second side view of the exemplary embodiment of the "diamond gauze" adhesive bandage illustrated in FIGS. 20(a) and (b)
FIG. 20(e) shows a first end view of the exemplary embodiment of the "diamond gauze" adhesive bandage illustrated in FIGS. 20(a) and (b)
FIG. 20(f) shows a second end view of the exemplary embodiment of the "diamond gauze" adhesive bandage illustrated in FIGS. 20(a) and (b)
FIG. 20(g) shows a perspective view of the exemplary embodiment of the "diamond gauze" adhesive bandage illustrated in FIGS. 20(a) and (b)

FIGS. 19(*a*)-19(*g*) are, respectively, a bottom wound-facing view, a top non-wound facing view, four side views and one perspective view of another exemplary embodiment of a "diamond gauze" bandage 190 according to the present invention. The body portion 191 of the "diamond gauze" bandage 190 has a "knuckle" shape which among other bandaging uses may be particularly useful for bandaging a knuckle as well as a finger tip, or similar appendage. The body portion 191 has a head portion 193 and a tail portion 194. The head portion 193 may be a truncated oval, diamond, almond or similar shape that is possibly asymmetrically shortened on a first side of the head portion 193 where the head portion 193 connects to the tail portion 194. The tail portion 194 flares out with a width that increases as the tail extends lengthwise from the first side of the head portion 193 forming concavities with the head portion 193 along a top edge 195 and bottom edge 196 of the body portion 191 that are preferably smooth curves. The gauze pad 192 is substantially positioned in the head portion 193, and is oriented with respect to the body portion 191 such that the sides of the gauze pad 192 are not parallel to the length tangents 199A, 199C or width tangents 199B, 199D of the body portion 191.

FIGS. 24(*a*)-24(*f*) are, respectively, a bottom wound-facing view, a top non-wound facing view, one perspective view, and three side views of another exemplary embodiment of a "diamond gauze" bandage. The body portion 241 of the "diamond gauze" bandage 240 has a "knuckle" shape similar to that of "diamond gauze" bandage 190. The gauze pad 242 is oriented with respect to the "knuckle" shaped body portion 241 such that the sides of the gauze pad 242 are parallel to length tangents 249A, 249C and width tangents 249B, 249D. In all other respects, the "diamond gauze" bandage 240 may be configured in the same manner as "diamond gauze" bandage 190.

Figures 26A, 26B, 26C, 26D, 26E, 26F:
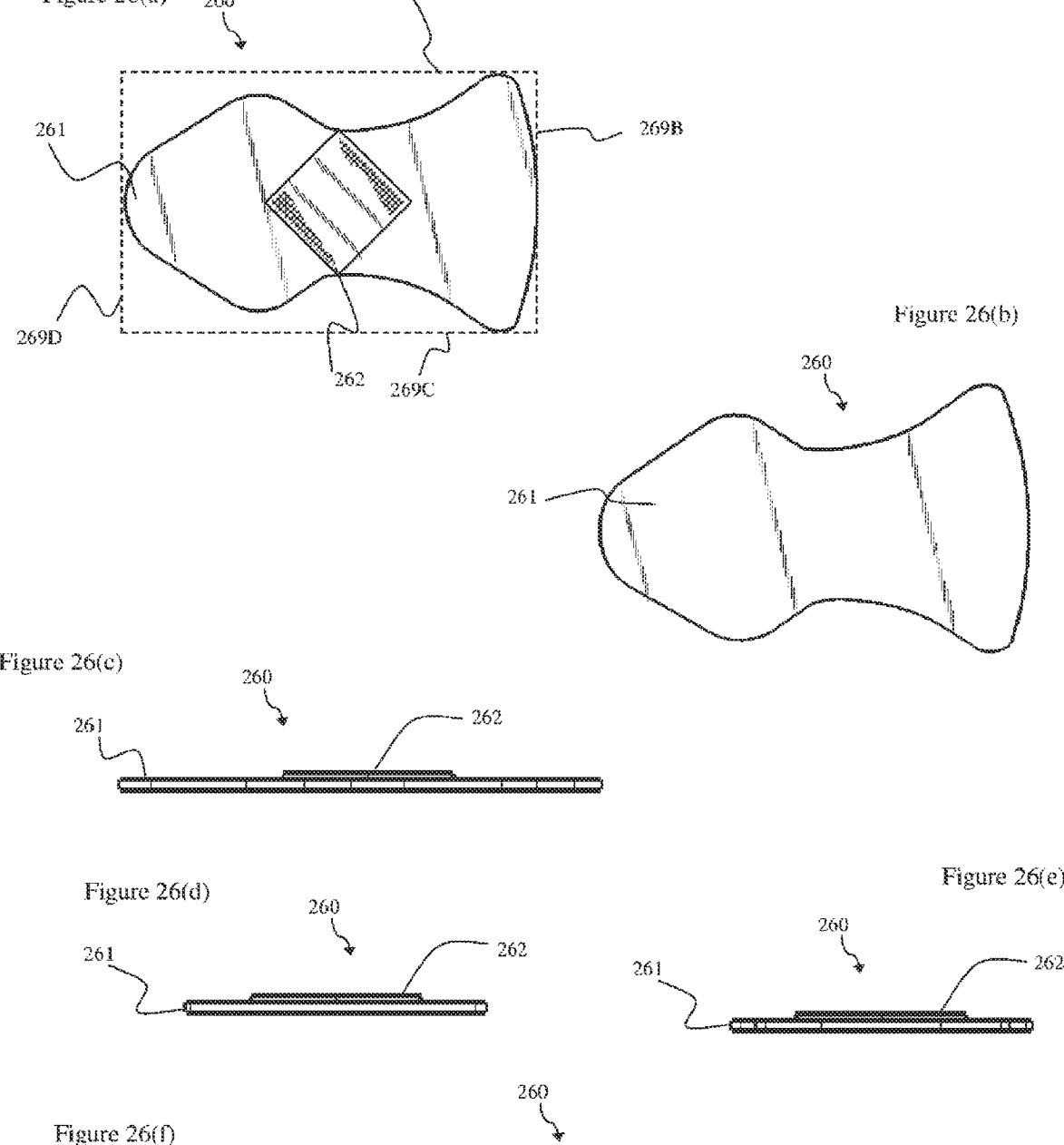

FIGS. 26(a)-26(f) are, respectively, a bottom wound-facing view, a top non-wound facing view, three side views and one perspective view of another exemplary embodiment of a "diamond gauze" bandage. In FIG. 26(a), 269A and 269C indicate length tangents of the exemplary embodiment of the "diamond gauze" bandage, and 269B and 269D indicate width tangents of the exemplary embodiment of the "diamond gauze" bandage. The body portion 261 of the "diamond gauze" bandage 260 has a "knuckle" shape similar to that of "diamond gauze" bandage 190. The gauze pad 262 is positioned so that the center of the gauze pad 262 corresponds to a position along concavities formed by a head portion 263 and a tail portion 264. In all other respects, the "diamond gauze" bandage 260 may be configured in the same manner as "diamond gauze" bandage 190.

FIGS. 20(a)-20(g) are, respectively, a bottom wound-facing view, a top non-wound facing view, four side views and one perspective view of another exemplary embodiment of a "diamond gauze" bandage 200 according to the present invention. The body portion 201 of the "diamond gauze" bandage 200 has a shape which among other bandaging uses may be particularly useful as a finger wrap. The body portion 201 of the "diamond gauze" bandage 200 may be comprised of self-adherent material, as discussed above by "diamond gauze" bandage 120, so that when it is wrapped around a finger or other appendage, a wound facing side of the bandage that is distal to the gauze pad adheres to the non-wound facing side of the body portion 201 so as to secure the wrap in place. Similarly, all the other "diamond gauze" bandages, particularly when used to wrap around an appendage, may be made with such self-adherent material. The gauze pad 202 is oriented with respect to the body portion 201 such that the sides of the gauze pad 202 are not parallel to length tangents 209A, 209C and width tangents 209B, 209D. The gauze pad 202 is preferably positioned proximate to the width tangent 209B. Alternatively, the "diamond gauze" bandage 200 may be used with the gauze pad 202 not oriented as a diamond shape, but rather in the standard rectangular or square orientation that parallels the length of the bandage, particularly when the "diamond gauze" bandage 200 is configured with self-adherent material or other material for the purpose of resealing the bandage.

FIGS. 21(a)-21(e) are, respectively, a bottom wound-facing view, a top non-wound facing view, two side views and one perspective view of another exemplary embodiment of a "diamond gauze" bandage 210 according to the present invention. The body portion 211 of the "diamond gauze" bandage 210 is an elongated octagonal shape. The gauze pad 212 is oriented with respect to the body portion 211 such that the sides of the gauze pad 212 are not parallel to length tangents 219A, 219C and width tangents 219B, 219D. The gauze pad 212 may have the same center point as the body portion 211 and/or each of the corners of the gauze pad 212 may be oriented toward a mid-point of one of the length tangents 219A, 219C or width tangents 219B, 219D. Alternatively, the body portion 211 may be an octagonal shape with eight equal sides. FIGS. 27(a)-27(e) are, respectively, a bottom wound-facing view, a top non-wound facing view, two side views and one perspective view of another exemplary embodiment of a "diamond gauze" bandage 270 according to the present invention. A body portion 271 of the "diamond gauze" bandage 270 has a central almond or oval shaped portion 273 similar to the configuration of the bandages in FIG. 15 or 16 and bulbous side portions 274, 275. The gauze pad 272 is oriented with respect to the body portion 271 such that the sides of the gauze pad 272 are not parallel to length tangents 279A, 279C, and width tangents 279B, 279D. The gauze pad 272 may have the same center point as the body portion 271 and/or each of the corners of the gauze pad 272 may be oriented toward a mid-point of one of the length tangents 279A, 279C or width tangents 279B, 279D. Midpoints of the central portion 273 are preferably positioned to correspond with the midpoints of the length tangents 279A, 279C.

FIGS. 28(a)-28(e) are, respectively, a bottom wound-facing view, a top non-wound facing view, two side views and one perspective view of another exemplary embodiment of a "diamond gauze" bandage 280 according to the present invention. A body portion 281 of the "diamond gauze" bandage 280 has a central narrow portion 283 and side regions 284 and 285 that initially widen, moving along the length from the central narrow portion 283, and then narrowing again in straight or substantially straight lines to rounded ends, where the portions of the side regions 284 and 285 that widen are connected to the portions of the side regions 284 and 285 that narrow by rounded angles. The body portion 281 has a "bowtie" or "hourglass" shape. The gauze pad 282 is oriented with respect to the body portion 281 such that the sides of the gauze pad 282 are not parallel to the length tangents 289A, 289C and width tangents 289B, 289D. The gauze pad 282 may have the same center point as the body portion 281 and/or each of the corners of the gauze pad 282 may be oriented toward a mid-point of one of the length tangents 289A, 289C or width tangents 289B, 289D. The central narrow portion 283 is preferably positioned to correspond with the midpoints of the length tangents 289A, 289C.

FIGS. 29(a)-29(f) are, respectively, a bottom wound-facing view, a top non-wound facing view, three side views and one perspective view of another exemplary embodiment of a "diamond gauze" bandage 290 according to the present invention. A body portion 291 of the "diamond gauze" bandage 290 has a central portion 293 that lengthwise terminates on a first side with a rounded end, and on a second side has legs 294, 295 that extend from the body portion 291 substantially in the lengthwise direction, the legs 294, 295 terminating with rounded ends distal to the central portion 293. The body portion 291 forms an "arch" shape defined by two parallel arcs or parabolas that are connected at each of their respective proximate ends distal to the central portion 293 by a third and fourth curve forming convexities on the terminating ends of the legs 294, 295. Alternatively, the body portion 291 may be formed with straight or wavy sides rather than the parabolas and may include squared off ends rather than the convexities on the ends of the legs 294, 295 and the central portion 293. The legs 294, 295 are spaced apart from each other at the central portion 293 and preferably extend out at diverging angles from the central portion 293. The diverging angles should preferably allow the legs 294, 295 to extend around a limb to which the "diamond gauze" bandage 290 is being applied and to have the bottom wound-facing side of the legs 294, 295 slightly overlap on top of the top non-wound facing side of the central portion 295. Thus, the body portion 291 has a shape which among other bandaging uses may be particularly useful as a finger wrap. The gauze pad 292 is oriented with respect to the body portion 291 such that the sides of the gauze pad 292 are not parallel to length tangents 299A, 299C and width tangents 299B, 299D. The gauze pad 292 may have the same center point as the central body portion 293 and/or corners of the gauze pad 292 may be oriented toward a mid-point of one of the width tangents 299B, 299D.

FIGS. 30(*a*)-30(*e*) are, respectively, a bottom wound-facing view, a top non-wound facing view, two side views and one perspective view of another exemplary embodiment of a "diamond gauze" bandage 300 according to the present invention. A body portion 301 of the "diamond gauze" bandage 300 has a central portion 303 that has flattened top and bottom edges 306A, 306B, resulting in a uniform or substantially uniform width for the central portion 303. The body portion 301 of the "diamond gauze" bandage 300 also has side regions 304 and 305 that, moving along the length from the central portion 303, narrow in straight or substantially straight lines to rounded ends, where the central portion 303 transitions to the side regions 304 and 305 by rounded angles. The gauze pad 302 is oriented with respect to the body portion 301 such that the sides of the gauze pad 302 are not parallel to length tangents 309A, 309C and width tangents 309B, 309D. The gauze pad 302 may have the same center point as the body portion 301 and/or each of the corners of the gauze pad 302 may be oriented toward a mid-point of one of the length tangents 309A, 309C or width tangents 309B, 309D. Midpoints of the central portion 303 are preferably positioned to correspond with the midpoints of the length tangents 309A, 309C.

FIGS. 31(*a*)-31(*e*) are, respectively, a bottom wound-facing view, a top non-wound facing view, two side views and one perspective view of another exemplary embodiment of a "diamond gauze" bandage 310 according to the present invention. A body portion 311 of the "diamond gauze" bandage 310 has a central narrow portion 313 and side regions 314 and 315 that initially widen, moving along the length from the central narrow portion 313, and then narrowing again in straight or substantially lines to rounded ends. The "diamond gauze" bandage 310 has a body portion that has a "bowtie" or "hourglass" shape. The gauze pad 312 is oriented with respect to the body portion 311 such that the sides of the gauze pad 312 are not parallel to length tangents 319A, 319C and width tangents 319B, 319D. The gauze pad 312 may have the same center point as the body portion 311 and/or each of the corners of the gauze pad 312 may be oriented toward a mid-point of one of the length tangents 319A, 319C or width tangents 319B, 319D. The central narrow portion 313 is preferably positioned to correspond with the midpoints of the length tangents 319A, 319C.

FIGS. 32(*a*)-32(*e*) are, respectively, a bottom wound-facing view, a top non-wound facing view, two side views and one perspective view of another exemplary embodiment of a "diamond gauze" bandage 320 according to the present invention. A body portion 321 of the "diamond gauze" bandage 320 has a central narrow portion 323 and side regions 324 and 325 that initially widen, moving along the length from the central narrow portion 323, and then narrowing again in straight or substantially lines to rounded ends. The "diamond gauze" bandage 320 has a body portion that has a "bowtie" or "hourglass" shape. The gauze pad 322 is oriented with respect to the body portion 321 such that the sides of the gauze pad 322 are not parallel to length tangents 329A, 329C and width tangents 329B, 329D. The gauze pad 322 may have the same center point as the body portion 321 and/or each of the corners of the gauze pad 322 may be oriented toward a mid-point of one of the length tangents 329A, 329C or width tangents 329B, 329D. The central narrow portion 323 is preferably positioned to correspond with the midpoints of the length tangents 329A, 329C.

FIGS. 33(*a*)-33(*e*) are, respectively, a bottom wound-facing view, a top non-wound facing view, two side views and one perspective view of another exemplary embodiment of a "diamond gauze" bandage 330 according to the present invention. A body portion 331 of the "diamond gauze" bandage 330 has a central narrow portion 333 and side regions 334 and 335 that widen in straight or substantially straight lines to rounded ends. The "diamond gauze" bandage 330 has a body portion that has a "bowtie" or "hourglass" shape. The gauze pad 332 is oriented with respect to the body portion 331 such that the sides of the gauze pad 332 are not parallel to length tangents 339A. 339C and width tangents 339B, 339D. The gauze pad 332 may have the same center point as the body portion 331 and/or each of the corners of the gauze pad 332 may be oriented toward a mid-point of one of the length tangents 339A, 339C or width tangents 339B, 339D. The central narrow portion 333 is preferably positioned to correspond with the midpoints of the length tangents 339A, 339C.

FIGS. 34(*a*)-34(*e*) are, respectively, a bottom wound-facing view, a top non-wound facing view, two side views and one perspective view of another exemplary embodiment of a "diamond gauze" bandage 340 according to the present invention. A body portion 341 of the "diamond gauze" bandage 340 has a central narrow portion 343 and side regions 344 and 345 that widen in straight or substantially straight lines to rounded ends. The "diamond gauze" bandage 340 has a body portion that has a "bowtie" or "hourglass" shape. The gauze pad 342 is oriented with respect to the body portion 341 such that the sides of the gauze pad 342 are not parallel to length tangents 349A. 349C and width tangents 349B, 349D. The gauze pad 342 may have the same center point as the body portion 341 and/or each of the corners of the gauze pad 342 may be oriented toward a mid-point of one of the length tangents 349A, 349C or width tangents 349B, 349D. The central narrow portion 343 is preferably positioned to correspond with the midpoints of the length tangents 349A, 349C.

FIGS. 35(*a*)-35(*e*) are, respectively, a bottom wound-facing view, a top non-wound facing view, two side views and one perspective view of another exemplary embodiment of a "diamond gauze" bandage 350 according to the present invention. A body portion 351 of the "diamond gauze" bandage 350 has a central narrow portion 353 and side regions 354 and 355 that are formed by circular or elliptical arcs. The "diamond gauze" bandage 350 has a body portion that has a "bowtie" or "hourglass" shape. The gauze pad 352 is oriented with respect to the body portion 351 such that the sides of the gauze pad 352 are not parallel to length tangents 359A, 359C and width tangents 359B, 359D. The gauze pad 352 may have the same center point as the body portion 351 and/or each of the corners of the gauze pad 352 may be oriented toward a mid-point of one of the length tangents 359A, 359C or width tangents 359B, 359D. The central narrow portion 353 is preferably positioned to correspond with the midpoints of the length tangents 359A, 359C.

FIGS. 36(*a*)-36(*e*) are, respectively, a bottom wound-facing view, a top non-wound facing view, two side views and one perspective view of another exemplary embodiment of a "diamond gauze" bandage 360 according to the present invention. A body portion 361 of the "diamond gauze" bandage 360 has a central narrow portion 363 and side regions 364 and 365 that are formed by circular or elliptical arcs. The "diamond gauze" bandage 360 has a body portion that has a "bowtie" or "hourglass" shape. The gauze pad 362 is oriented with respect to the body portion 361 such that the sides of the gauze pad 362 are not parallel to length tangents 369A, 369C and width tangents 369B, 369D. The gauze pad 362 may have the same center point as the body portion 361 and/or each of the corners of the gauze pad 362 may be oriented toward a mid-point of one of the length tangents 369A, 369C or width tangents 369B, 369D. The central narrow portion 363 is preferably positioned to correspond with the midpoints of the length tangents 369A, 369C.

FIGS. 37(a)-37(e) are, respectively, a bottom wound-facing view, a top non-wound facing view, two side views and one perspective view of another exemplary embodiment of a "diamond gauze" bandage 370 according to the present invention. A body portion 371 of the "diamond gauze" bandage 370 has a central narrow portion 373 and side regions 374 and 375 that widen in straight or substantially straight lines to straight or substantially straight ends, connected by rounded corners. The "diamond gauze" bandage 370 has a body portion that has a "bowtie" or "hourglass" shape with flattened ends. The gauze pad 372 is oriented with respect to the body portion 371 such that the sides of the gauze pad 372 are not parallel to length tangents 379A, 379C and width tangents 379B, 379D. The gauze pad 372 may have the same center point as the body portion 371 and/or each of the corners of the gauze pad 372 may be oriented toward a mid-point of one of the length tangents 379A, 379C or width tangents 379B, 379D. The central narrow portion 373 is preferably positioned to correspond with the midpoints of the length tangents 379A, 379C.

FIGS. 38(a)-38(e) are, respectively, a bottom wound-facing view, a top non-wound facing view, two side views and one perspective view of another exemplary embodiment of a "diamond gauze" bandage 380 according to the present invention. A body portion 381 of the "diamond gauze" bandage 380 has a central narrow portion 383 and side regions 384 and 385 that widen in straight or substantially straight lines to straight or substantially straight ends, connected by rounded corners. The "diamond gauze" bandage 380 has a body portion that has a "bowtie" or "hourglass" shape with flattened ends. The gauze pad 382 is oriented with respect to the body portion 381 such that the sides of the gauze pad 382 are not parallel to length tangents 389A, 389C and width tangents 389B, 389D. The gauze pad 382 may have the same center point as the body portion 381 and/or each of the corners of the gauze pad 382 may be oriented toward a mid-point of one of the length tangents 389A, 389C or width tangents 389B, 389D. The central narrow portion 383 is preferably positioned to correspond with the midpoints of the length tangents 389A, 389C.

FIGS. 39(a)-39(e) are, respectively, a bottom wound-facing view, a top non-wound facing view, two side views and one perspective view of another exemplary embodiment of a "diamond gauze" bandage 390 according to the present invention. A body portion 391 of the "diamond gauze" bandage 390 has a central narrow portion 393 and side regions 394 and 395 that widen in curved lines to straight or substantially straight ends, connected by rounded corners. The "diamond gauze" bandage 390 has a body portion that has a "bowtie" or "hourglass" shape with flattened ends. The gauze pad 392 is oriented with respect to the body portion 391 such that the sides of the gauze pad 392 are not parallel to length tangents 399A, 399C and width tangents 399B, 399D. The gauze pad 392 may have the same center point as the body portion 391 and/or each of the corners of the gauze pad 392 may be oriented toward a mid-point of one of the length tangents 399A, 399C or width tangents 399B, 399D. The central narrow portion 393 is preferably positioned to correspond with the midpoints of the length tangents 399A, 399C.

FIGS. 40(a)-40(e) are, respectively, a bottom wound-facing view, a top non-wound facing view, two side views and one perspective view of another exemplary embodiment of a "diamond gauze" bandage 400 according to the present invention. A body portion 401 of the "diamond gauze" bandage 400 has a central narrow portion 403 and side regions 404 and 405 that widen in curved lines to straight or substantially straight ends, connected by rounded corners. The "diamond gauze" bandage 400 has a body portion that has a "bowtie" or "hourglass" shape with flattened ends. The gauze pad 402 is oriented with respect to the body portion 401 such that the sides of the gauze pad 402 are not parallel to length tangents 409A, 409C and width tangents 409B, 409D. The gauze pad 402 may have the same center point as the body portion 401 and/or each of the corners of the gauze pad 402 may be oriented toward a mid-point of one of the length tangents 409A, 409C or width tangents 409B, 409D. The central narrow portion 403 is preferably positioned to correspond with the midpoints of the length tangents 409A, 409C.

FIGS. 41(a)-41(f) are, respectively, a bottom wound-facing view, an exploded bottom wound-facing view, a top non-wound facing view, two side views and one perspective view of another exemplary embodiment of a "diamond gauze" bandage 410 according to the present invention. A body portion 411 of the "diamond gauze" bandage 410 has a central narrow portion 413 and side regions 414A, 414B that widen with straight or substantially straight side lines 415A, 415B, 415E, 415F as the side regions extend to rounded corners 416A, 416B, 416C, 416D. The rounded corners 416A, 416B, 416C, 416D transition to straight or substantially straight end lines 415C, 415D, 415G, 415H that are oriented so as to taper or decrease the length of the body portion 411 as the substantially straight end lines 415C, 415D, 415G, 415H extend toward inflection points 417A, 417B. The inflection points 417A, 417B are preferably at midpoints between corresponding rounded corners 416A, 416B, 416C, 416D. The side lines 415A, 415B, 415E, 415F are preferably equal in length, and longer than the end lines 415H, 415C, 415D, 415G, respectively, which are also preferably equal in length. The "diamond gauze" bandage 410 has a body portion that has a "bowtie" or "hourglass" shape. The gauze pad 412 is oriented with respect to the body portion 411 such that the sides of the gauze pad 412 are not parallel to length tangents 419A, 419C and width tangents 419B, 419D. The gauze pad 412 may have the same center point as the body portion 411 and/or each of the corners of the gauze pad 412 may be oriented toward a mid-point of one of the length tangents 419A, 419C or width tangents 419B, 419D. The central narrow portion 413 is preferably positioned to correspond with the midpoints of the length tangents 419A, 419C.

FIGS. 42(a)-42(e) are, respectively, a bottom wound-facing view, a top non-wound facing view, two side views and one perspective view of another exemplary embodiment of a "diamond gauze" bandage 420 according to the present invention. A body portion 421 of the "diamond gauze" bandage 420 has a central narrow portion 423 and side regions 424 and 425 that initially widen, moving along the length from the central narrow portion 423, and then narrowing again in straight or substantially straight lines to rounded ends, where the portions of the side regions 424 and 425 that widen are connected to the portions of the side regions 424 and 425 that narrow by rounded angles. The body portion 421 has a "bowtie" or "hourglass" shape. The gauze pad 422 is oriented with respect to the body portion 421 such that the sides of the gauze pad 422 are not parallel to length tangents 429A, 429C and width tangents 429B, 429D. The gauze pad 422 may have the same center point as the body portion 421 and/or each of the corners of the gauze pad 422 may be oriented toward a mid-point of one of the length tangents 429A, 429C or width tangents 429B, 429D. The central narrow portion 423 is preferably positioned to correspond with the midpoints of the length tangents 429A, 429C.

FIGS. 43(a)-43(e) are, respectively, a bottom wound-facing view, a top non-wound facing view, two side views and one perspective view of another exemplary embodiment of a "diamond gauze" bandage 430 according to the present invention. A body portion 431 of the "diamond gauze" bandage 430 has a central narrow portion 433 and side regions 434 and 435 that initially widen, moving along the length from the central narrow portion 433, and then narrowing again in straight or substantially straight lines to rounded ends, where the portions of the side regions 434 and 435 that widen are connected to the portions of the side regions 434 and 435 that narrow by rounded angles. The body portion 431 has a "bowtie" or "hourglass" shape. The gauze pad 432 is oriented with respect to the body portion 431 such that the sides of the gauze pad 432 are not parallel to length tangents 439A, 439C and width tangents 439B, 439D. The gauze pad 432 may have the same center point as the body portion 431 and/or each of the corners of the gauze pad 432 may be oriented toward a mid-point of one of the length tangents 439A, 439C or width tangents 439B, 439D. The central narrow portion 433 is preferably positioned to correspond with the midpoints of the length tangents 439A, 439C.

FIGS. 44(a)-44(e) are, respectively, a bottom wound-facing view, a top non-wound facing view, two side views and one perspective view of another exemplary embodiment of a "diamond gauze" bandage 440 according to the present invention. A body portion 441 of the "diamond gauze" bandage 440 has a central narrow portion 443 and side regions 444 and 445 that initially widen, moving along the length from the central narrow portion 443, and then narrowing again in straight or substantially straight lines to straight or substantially straight ends connected by first rounded angles, where the portions of the side regions 444 and 445 that widen are connected to the portions of the side regions 444 and 445 that narrow by second rounded angles. The body portion 441 has a "bowtie" or "hourglass" shape with flattened ends. The gauze pad 442 is oriented with respect to the body portion 441 such that the sides of the gauze pad 442 are not parallel to length tangents 449A, 449C and width tangents 449B, 449D. The gauze pad 442 may have the same center point as the body portion 441 and/or each of the corners of the gauze pad 442 may be oriented toward a mid-point of one of the length tangents 449A, 449C or width tangents 449B, 449D. The central narrow portion 443 is preferably positioned to correspond with the midpoints of the length tangents 449A, 449C.

FIGS. 45(a) through 45(e) are, respectively, a bottom wound-facing view, a top non-wound facing view, two side views and one perspective view of an exemplary embodiment of a "diamond gauze" bandage 450 according to the present invention. The "diamond gauze" bandage 450 has a body portion 451 with a central portion 453 that has flattened top and bottom edges 456A, 456B, resulting in a uniform or substantially uniform width for the central portion 453. Oval shaped side regions 455A and 455B connect to the central portion 453 via narrow portions 454A and 454B. The narrow portions 454A and 454B preferably narrow in straight or substantially straight lines from a wider end connected to the central portion 453 and a narrower end connected to the oval shaped side regions 455A and 455B. A gauze pad 452 is oriented with respect to the body portion 451 such that the sides of the gauze pad 452 are not parallel to length tangents 459A, 459C and width tangents 459B, 459D. The gauze pad 452 may have the same center point as the body portion 451 and/or each of the corners of the gauze pad 452 may be oriented toward a mid-point of one of the length tangents 459A, 459C or width tangents 459B, 459D. The central portion 453 is preferably positioned to correspond with the midpoints of the length tangents 459A, 459C.

FIGS. 46(a)-46(d) are, respectively, a bottom wound-facing view, a top non-wound facing view, one side view and one perspective view of another exemplary embodiment of a "diamond gauze" bandage 460 according to the present invention. A body portion 461 of the "diamond gauze" bandage 460 has a central narrow portion 463 and side regions 464A, 464B. Side region 464A has edges defined by two circular or elliptical arcs 465A, 465A' that extend from opposing sides of the central narrow portion 463 and meet at an inflection point 466A. Side region 464B has edges defined by two circular or elliptical arcs 465B, 465B' that extend from opposing sides of the narrow portion 463 and meet at an inflection point 466B. The gauze pad 462 is oriented with respect to the body portion 461 such that the sides of the gauze pad 462 are not parallel to length tangents 469A, 469C and width tangents 469B, 469D. The gauze pad 462 may have the same center point as the body portion 461 and/or each of the corners of the gauze pad 462 may be oriented toward a mid-point of one of the length tangents 469A, 469C or width tangents 469B, 469D. The inflection points 466A, 466B preferably correspond to midpoints of the width tangents 469D, 469B, respectively. The circular or elliptical arcs 465A, 465A', 465B, 465B', are preferably equivalently or similarly sized, and are preferably oriented at a 90 degree angle in relation to adjacent arcs. The central narrow portion 463 is preferably positioned to correspond with the midpoints of the length tangents 469A, 469C.

FIGS. 47(a) through 47(e) are, respectively, a bottom wound-facing view, a top non-wound facing view, two side views and one perspective view of an exemplary embodiment of a "diamond gauze" bandage 470 according to the present invention. The "diamond gauze" bandage 470 has a body portion 471 with a central portion 473 that has top and bottom edges 476A, 476B and oval or bulbous shaped side regions 475A, 475B. The "diamond gauze" bandage 470 has a width that is defined by the distance between the top edge 476A and the bottom edge 476B. The top and bottom edges 476A, 476B may be substantially straight, resulting in a uniform or substantially uniform width for the central portion 473. Alternatively, the top and bottom edges 476A, 476B may be concave edges, resulting in a widening width from the middle of the central portion 473 to the oval shaped side regions 475A, 475B. The oval shaped side regions 475A, 475B have a width that is wider than the widest width of the central portion 473. A gauze pad 472 is oriented with respect to the body portion 471 such that the sides of the gauze pad 472 are not parallel to length tangents 479A, 479C and width tangents 479B, 479D. The gauze pad 472 may have the same center point as the body portion 471 and/or each of the corners of the gauze pad 472 may be oriented toward a mid-point of one of the length tangents 479A, 479C or width tangents 479B, 479D. The central portion 473 is preferably positioned to correspond with the midpoints of the length tangents 479A, 479C.

FIGS. 48(a)-48(e) are, respectively, a bottom wound-facing view, a top non-wound facing view, two side views and one perspective view of another exemplary embodiment of a "diamond gauze" bandage 480 according to the present invention. A body portion 481 of the "diamond gauze" bandage 480 has a central portion 483 that has flattened top and bottom edges 486A, 486B, resulting in a uniform or substantially uniform width for the central portion 483. The body portion 481 also has side regions 484 and 485 that, moving along the length from the central portion 483, narrow in straight or substantially lines to rounded ends, where the central portion 483 transitions to the side regions 484 and 485 by sharp angles. The gauze pad 482 is oriented with respect to the body portion 481 such that the sides of the gauze pad 482 are not parallel to length tangents 489A, 489C and width tangents 489B, 489D. The gauze pad 482 may have the same center point as the body portion 481 and/or each of the corners of the gauze pad 482 may be oriented toward a mid-point of one of the length tangents 489A, 489C or width tangents 489B, 489D. Midpoints of the central portion 483 are preferably positioned to correspond with the midpoints of the length tangents 489A, 489C.

FIGS. 49(a)-49(f) are, respectively, a bottom wound-facing view, an exploded bottom wound-facing view, a top non-wound facing view, two side views and one perspective view of another exemplary embodiment of a "diamond gauze" bandage 490 according to the present invention. A body portion 491 of the "diamond gauze" bandage 490 has a central narrow portion 493 and side regions 494A, 494B that widen with straight, substantially straight, or slightly curved side lines 495A, 495B, 495E, 495F as the side regions 494A, 494B extend to rounded corners 496A, 496B, 496C, 496D. The rounded corners 496A, 496B, 496C, 496D transition to straight, substantially straight, or slightly curved end lines 495C, 495D, 495G, 495H that are oriented so as to taper or decrease a length of the body portion 491 as the end lines 495C, 495D, 495G, 495H extend toward inflection points 497A, 497B. The inflection points 497A, 497B are preferably at midpoints between corresponding rounded corners 496A, 496B, 496C, 496D. The side lines 495A, 495B, 495E, 495F are preferably equal in length and shape to the end lines 495H, 495C, 495D, 495G, respectively. The gauze pad 492 is oriented with respect to the body portion 491 such that the sides of the gauze pad 492 are not parallel to length tangents 499A, 499C and width tangents 499B, 499D. The gauze pad 492 may have the same center point as the body portion 491 and/or each of the corners of the gauze pad 492 may be oriented toward a mid-point of one of the length tangents 499A, 499C or width tangents 499B, 499D. The central narrow portion 493 is preferably positioned to correspond with the midpoints of the length tangents 499A, 499C.

FIGS. 51(a)-51(f) are, respectively, a bottom wound-facing view, a top non-wound facing view, three side views and one perspective view of another exemplary embodiment of a "diamond gauze" bandage 510 according to the present invention. A body portion 511 of the "diamond gauze" bandage 510 has a central narrow portion 513 and side regions 514A, 514B that have widening portions 515A, 515B, that extend from the central narrow portion 513 to narrowing portions 516A, 516B in straight or substantially straight lines. The narrowing portions 516A, 516B extend to rounded ends in straight or substantially straight lines. The widening portions 515A, 515B are connected to the narrowing portions 516A, 516B by rounded angles. The body portion 511 has a "bowtie" or "hourglass" shape with the narrowing portion 516B having a greater length than the narrowing portion 516A. The gauze pad 512 is oriented with respect to the body portion 511 such that the sides of the gauze pad 512 are not parallel to length tangents 519A, 519C and width tangents 519B, 519D. The corners of the gauze pad 512 oriented toward the width tangents 519B, 519D may be oriented toward the mid-points of the width tangents 519B, 519D. The corners of the gauze pad 512 oriented toward the length tangents 519A, 519C may be oriented toward a midpoint between the rounded angles that connect the widening portions 515A, 515B with the narrowing portions 516A, 516B. Due to the asymmetrical lengths of the side regions 514A, 514B, a midpoint of the central narrow portion 513 does not correspond to the midpoint of the length tangents 519A, 519C.

FIGS. 52(a)-52(f) are, respectively, a bottom wound-facing view, a top non-wound facing view, three side views and one perspective view of another exemplary embodiment of a "diamond gauze" bandage 520 according to the present invention. A body portion 521 of the "diamond gauze" bandage 520 is similar to the configuration of the body portion 511 in FIG. 51. The body portion 521 of the "diamond gauze" bandage 520 has a central narrow portion 523 and side regions 524A, 524B that have widening regions 525A, 525B, that extend from the central narrow portion 523 to narrowing portions 526A, 526B in straight or substantially straight lines. The narrowing portions 526A, 526B extend to rounded ends in straight or substantially straight lines. The widening portions 525A, 525B are connected to the narrowing portions 526A, 526B by rounded angles. The body portion 521 has a "bowtie" or "hourglass" shape with the narrowing portion 526B having a greater length than the narrowing portion 526A. The gauze pad 522 is oriented with respect to the body portion 521 such that the sides of the gauze pad 522 are not parallel to length tangents 529A, 529C and width tangents 529B, 529D. The corners of the gauze pad 522 oriented toward the width tangents 529B, 529D may be oriented toward the mid-points of the width tangents 529B, 529D. Due to the asymmetrical lengths of the side regions 524A, 524B, a midpoint of the central narrow portion 523 does not correspond to the midpoint of the length tangents 529A, 529C. However, the corners of the gauze pad 522 oriented toward the length tangents 529A, 529C may be oriented toward a midpoint between the rounded angles that connect the widening portions 525A, 525B with the narrowing portions 526A, 526B. In contrast to the shape of the gauze pad 512 for bandage 510, which has equal sides, the gauze pad 522 for bandage 520 has a "kite-shape". The "kite shape" may be formed by configuring the sides of the gauze pad 522 that correspond or extend into the side region 524B to be "stretched" to have an increased length corresponding to the increased length in the narrowing portion 526B relative to the length of narrowing portion 526A. Moreover, a kite-shaped gauze pad and/or an increase in length for a single side region may be applied to any "diamond gauze" bandage such as the other exemplary embodiments of a "diamond gauze" bandage described above.

According to the present invention, an alternative to the "diamond gauze" configuration of a bandage is a "triangular gauze" bandage, as discussed below. The "triangular gauze" configuration provides similar advantages to the "diamond gauze" particularly superior adherence and conformability to a wound area with a maximal area of gauze. The "triangular gauze" configuration may be especially useful in bandaging smaller wounds.

FIGS. 22(a)-22(g) are, respectively, a bottom wound-facing view, a top non-wound facing view, four side views and one perspective view of an exemplary embodiment of a "triangular gauze" bandage 220 according to the present invention. The "triangular gauze" bandage 220 has a body portion 221 in a circular shape, which may be made of any suitable material, preferably a stretchable and breathable material, which is known in the art to be used for bandages.

A gauze pad 222 is attached to the wound-facing side of the body portion 221. The gauze pad 222 is a triangular shape, preferably an equilateral triangular shape, but the gauze pad 222 may alternatively be configured as an isosceles, right or other triangular shape and may have rounded or flattened corners. Moreover, just as in the "diamond gauze" bandages, the corners may be rounded and the sides need not be straight but may, for example, be concave or convex curves or wavy lines. The gauze pad 222 may be positioned so as to have the same center point as the body portion 221, with each of the corners of the gauze pad 222 extending to the edges of body portion 221. Alternatively, the gauze pad 222 may be sized so that the corners of the gauze pad 222 do not reach the edges of the body portion 221. The gauze pad 222 may be sized and positioned so as to substantially define three equal quadrants, on the "non-gauze portion" of the wound facing side of the body portion 221, i.e. on the wound facing side of the body portion 221 that is not covered by the gauze pad 222. The bottom wound-facing side of the body portion 221 of the "triangular gauze" bandage 220 may have adhesive as those used for bandages in the art. The adhesive may be applied to all or part of the bottom wound-facing side of the body portion 221 of the "triangular gauze" bandage 220. The gauze pad 222 may or may not be affixed to the body portion 221 of the "triangular gauze" bandage 220 via the same adhesive as that which is used to affix the "triangular gauze" bandage 220 to a patient.

Figures 23A, 23B, 23C, 23D, 23E, 23F, 23G:
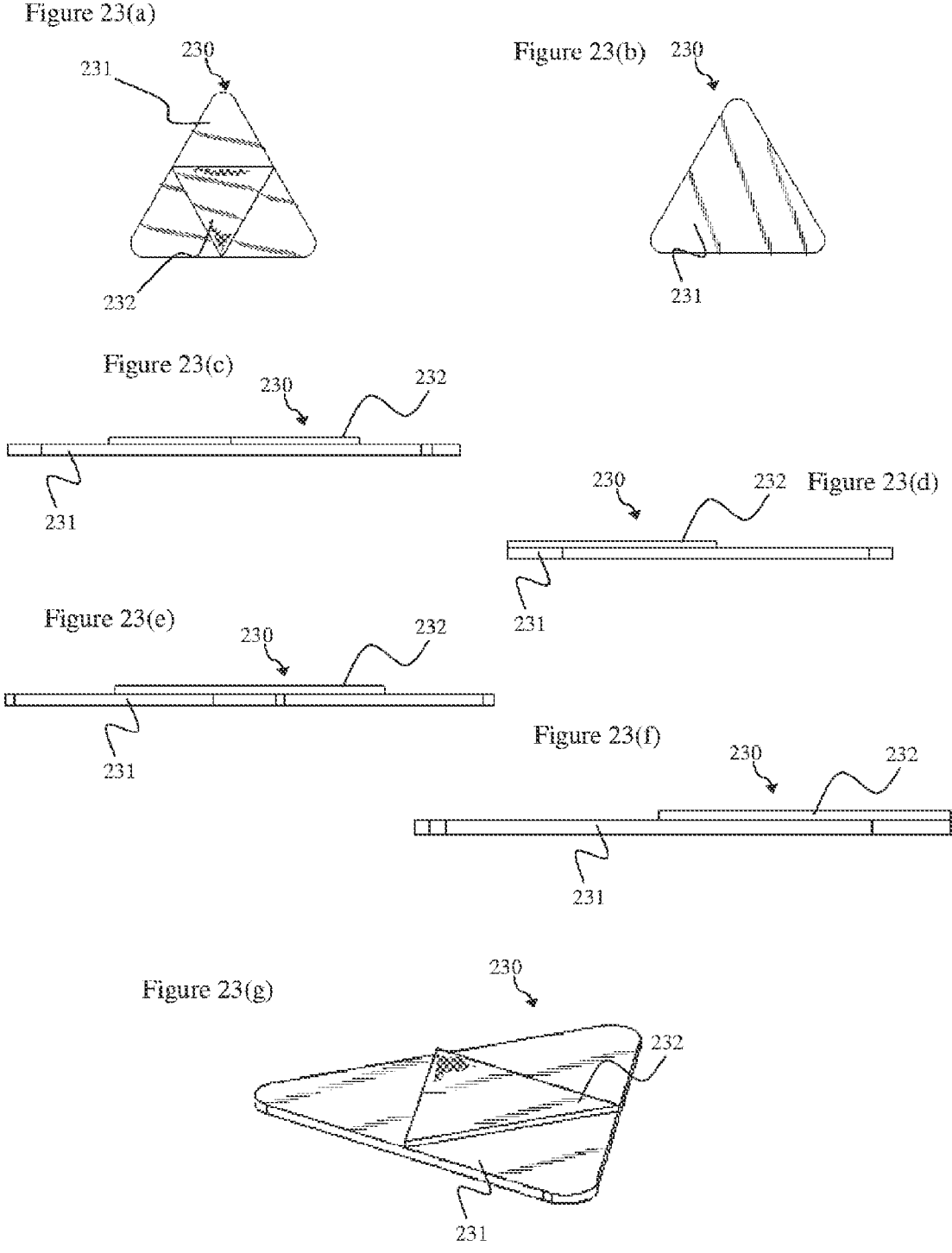
FIG. 23(a) shows a bottom wound-facing side of an exemplary embodiment of a "triangular gauze" adhesive bandage according to the present invention.
Figures 25A, 25B, 25C:
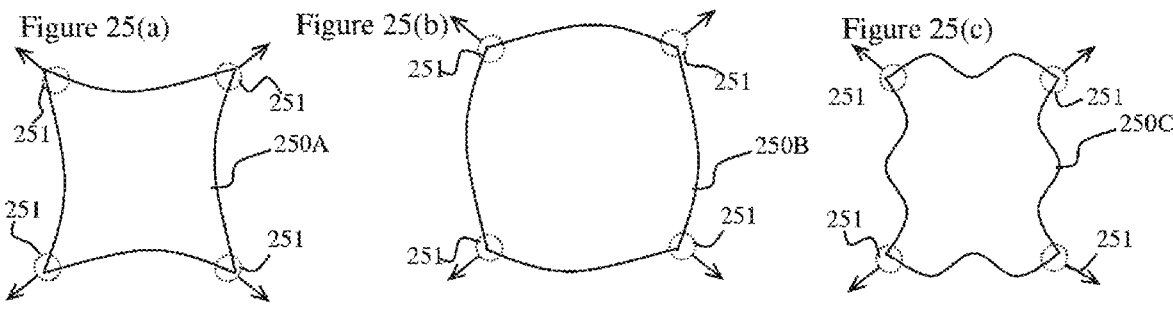
FIG. 25(*a*) shows a top view of an exemplary gauze pad configuration with concave sides for a "diamond gauze" bandage according to the present invention.
Figure 25D:
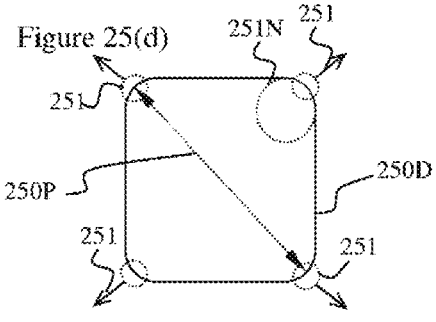
Figure 25E:
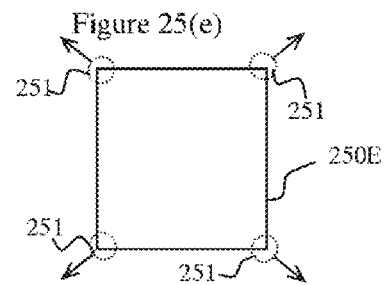
Figure 25F:
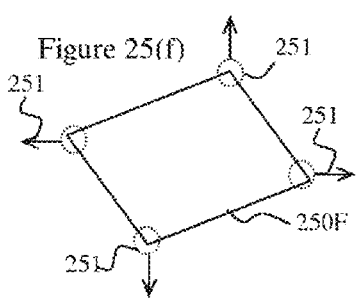
Figure 25G:
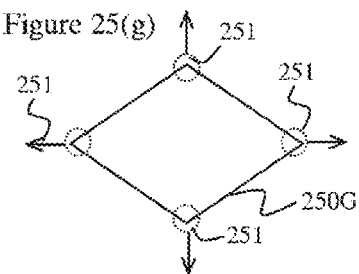
Figure 25H:
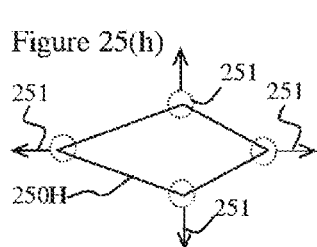
Figure 25I:
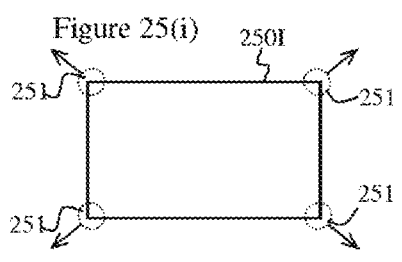
Figure 25J:
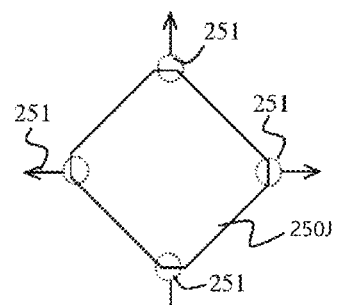
Figure 25K:
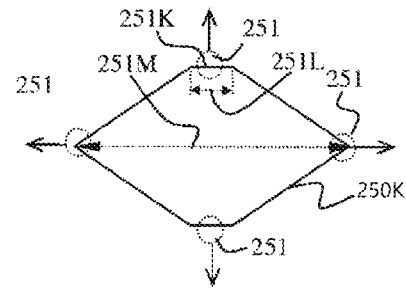
Figure 25L:
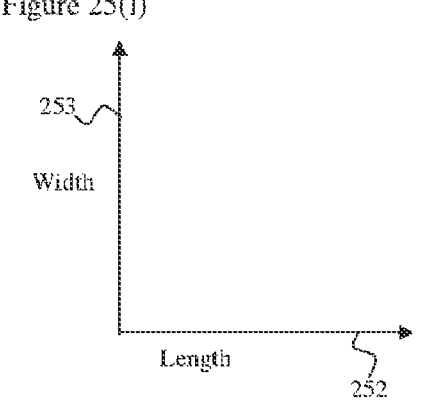
Figure 25M:
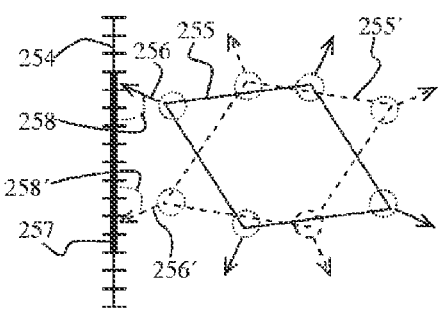

FIGS. 23(*a*)-23(*g*) are, respectively, a bottom wound-facing view, a top non-wound facing view, four side views and one perspective view of another exemplary embodiment of a "triangular gauze" bandage 230 according to the present invention. The "triangular gauze" bandage 230 has a body portion 231 in a triangular shape, preferably with rounded corners, and may be made of any suitable material, preferably a stretchable and breathable material, which is known in the art to be used for bandages. The gauze pad 232 is a triangular shape, preferably an equilateral triangular shape, but the gauze pad 232 may alternatively be configured as an isosceles, right or other triangular shape and may have rounded or flattened corners. The gauze pad 232 may be positioned so as to have the same center point as the body portion 231, with each of the corners of the gauze pad 232 extending to the edges of body portion 231. Alternatively, the gauze pad 232 may be sized so that the corners of the gauze pad 232 do not reach the edges of the body portion 231. The gauze pad 232 may be sized and positioned so as to substantially define three equal quadrants on the wound facing side of the body portion 231. The bottom wound-facing side of the body portion 231 of the "triangular gauze" bandage 230 may have adhesive as those used for bandages in the art. The adhesive may be applied to all or part of the bottom wound-facing side of the body portion 231 of the "triangular gauze" bandage 230. The gauze pad 232 may or may not be affixed to the body portion 231 of the "triangular gauze" bandage 230 via the same adhesive as that which is used to affix the "triangular gauze" bandage 230 to a patient FIGS. 53(*a*) and 53(*b*) are, respectively, a top non-wound facing view and a cross-sectional side view taken along the line VIII-VIII' of an exemplary embodiment of a bandage 530 with a wound portal according to the present invention. The bandage 530 has a body portion 531 with an aperture 533. The aperture 533 is preferably sized to be greater than the size of a wound it is intended to bandage. The body portion 531 preferably has a shelf 532 surrounding the aperture 533. A cover 534, which is only shown in FIG. 53(*b*), is sized to substantially fill the aperture 533 and to extend at least partially onto the shelf 532. Preferably, the thickness of the cover 534 and the shelf 532 together should be approximately equal to or less than the thickness of the body portion 531 immediately surrounding the shelf 532 so that the top of the cover 534 will be flush or lower than portions of the body portion 531 that surround the shelf 532 and the aperture 533. The cover 534 may be held in place via an adhesive suitable for bandages as is known in the art that is either applied to the shelf 532 or to the cover 534. The adhesive may be a reusable pressure sensitive adhesive such as that used in post-it notes. Alternatively, the cover 534 may be held in place by some other fastening system such as a Velcro® type fastening system.

A gauze pad 535 may be placed within the aperture 533 to cover a wound. The gauze pad 535 may be attached to the cover 534 via a reusable pressure sensitive adhesive such as that used in post-it notes or by some other fastening system such as a Velcro® type fastening system or by a more permanent form of fastening. Alternatively, the gauze pad 535 may not be attached to the cover 534 and may instead be held in place by the cover 534 and/or by the sides of the aperture 533 without use of adhesive.

In another alternative configuration of the wound portal as shown in FIG. 53(*c*), a bandage 530C has a body portion comprised a top layer 531C and a bottom layer 531D. The top and bottom layers 531C, 531D are affixed to each other and are sized such that the bottom layer 531D forms a shelf 532C around an aperture 533C. Similar to the cross-section shown in FIG. 53(*b*), a cover 534C is sized to substantially cover the aperture 533C and preferably extends at least partially onto the shelf 532C. Similar to the cross-section in FIG. 53(*b*), the gauze pad 535C that is within the aperture 533C may be attached to the cover 534C. Alternatively, the gauze pad 535C may not be attached to the cover 534C and may instead be held in place by the cover 534C and/or by the sides of the aperture 533C without use of adhesive.

In a further alternative configuration of the wound portal as shown in FIG. 53(*d*), similar to the configuration of the bandage 530C shown in FIG. 53(*c*), the bandage 530D has a body portion comprising a top layer 531E and a bottom layer 531F. The top and bottom layers 531E, 531F are affixed to each other and are sized such that the bottom layer 531F forms a shelf 532D around an aperture 533D. A cover 534D is sized to substantially cover the aperture 533D and preferably extends at least partially onto the shelf 532D. A gauze port 536 may be a separate piece of material attached to the bottom layer 531F or may be an integral protuberance of the bottom layer 531F. The gauze port 536 has an area either on a top non-wound facing side and/or a bottom wound facing side where a gauze pad 535D may be attached or removably attached. The top non-wound facing side of the gauze port 536 is the side facing the cover 534D where the gauze pad 535D is attached in FIG. 53(*d*). The bottom wound facing side of the gauze port 536 is the opposing side. The gauze port 536 may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze port 536 may be comprised of an adhesive that allows for the permanent attachment of the gauze pad 535D. The gauze port 536 may be used to attach different sized gauze pads 535D as well as to periodically replace the gauze pad 535D in the bandage 530D shown in this embodiment. The gauze port 536 may be sized and or configured so as to attach to all, a substantial portion, or a small portion such as one side of the gauze pad 535D.

Figures 53E, 53F, 54A, 54B:
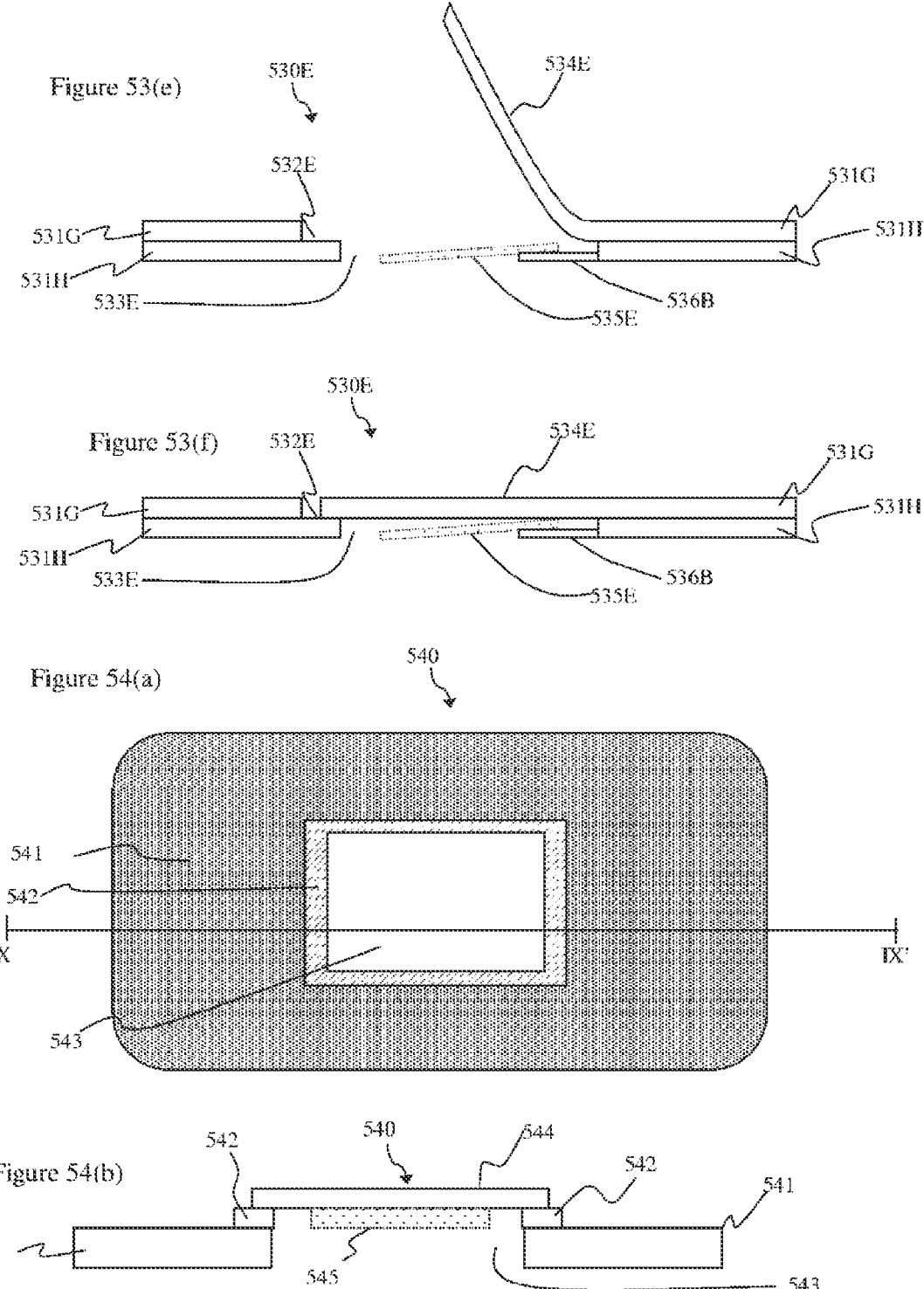

In a further alternative configuration of the wound portal as shown in FIGS. 53(e) and 53(f), similar to the configuration of the bandage 530C shown in FIG. 53(c), the bandage 530E has a body portion comprising a top layer 531G and a bottom layer 531H. The top and bottom layers 531G, 531H are affixed to each other. An aperture 533E is formed in the bottom layer 531H and the top layer 531G has a flap 534E that covers the aperture 533E in the bottom layer 531H. The flap 534E preferably extends at least partially onto a shelf 532E that is formed at least partially around the aperture 533E. The flap 534E is sized so as to allow for the placement of a gauze pad 535E in the aperture 533E. In FIG. 53(e), the flap 534E is shown in an open position so as to access the gauze pad 535E, and in FIG. 53(f), the flap 534E is shown in a closed position. A gauze port 536B may be a separate piece of material attached to the bottom layer 531H or may be an integral protuberance of the bottom layer 531H. The gauze port 536B has an area either on a top non-wound facing side and/or a bottom wound facing side where a gauze pad 535E may be attached or removably attached. The top non-wound facing side of the gauze port 536B is the side facing the cover 534E where the gauze pad 535E is attached in FIGS. 53(e) and 53(f). The bottom wound facing side of the gauze port 536B is the opposing side. The gauze port 536B may be comprised of non-stretchable material and may have a surface that is configured for repeated removal and attachment of gauze by having either a hook or loop Velcro® type fastening surface or a surface that provides a good bond with a re-stickable adhesive such as that found in Post-it® notes. Alternatively, the surface of the gauze port 536B may be comprised of an adhesive that allows for the permanent attachment of the gauze pad 535E. The gauze port 536B may be used to attach different sized gauze pads 535E as well as to periodically replace the gauze pad 535E in the bandage 530E shown in this embodiment. The gauze port 536B may be sized and or configured so as to attach to all, a substantial portion, or a small portion such as one side of the gauze pad 535E. Alternatively, instead of the gauze pad 535E attaching to the gauze port 536B, the gauze pad 535E may be unattached and held in place by the cover 534E, or the gauze port 536B may be attached to the cover 534E.

FIGS. 54(a) and 54(b) are, respectively, a top non-wound facing view and a cross-sectional side view taken along the line IX-IX' of another exemplary embodiment of a bandage 540 with a wound portal according to the present invention. The bandage 540 has a body portion 541 with an aperture 543. The aperture 543 is preferably sized to be greater than the size of a wound it is intended to bandage. Affixed to the body portion 541 around the perimeter of the aperture 543 is a flexible, yet non-stretchable or substantially non-stretchable rim 542, which may be made of a material such as silicone rubber. The rim 542 may be affixed to the non-wound facing side of the body portion 541, as shown in FIG. 54(b), or on the edges of the body portion 541 that surround and form the walls of the aperture 543 (not shown). The rim 542 is sized and configured so as to allow for removable attachment of a cover 544. The cover 544, which is only shown in FIG. 54(b), is sized to extend at least partially onto the rim 542 so as to close the aperture 543. A gauze pad 545 may be permanently or removably attached to the bottom wound-facing side of the cover 544. Alternatively, the gauze pad 545 may not be attached to the cover 544 and may instead be held in place by the cover 544 and/or by the sides of the aperture 543 without use of adhesive. The cover 544 may be held in place via an adhesive suitable for bandages as is known in the art that is either applied to the rim 542 or to the cover 544. The adhesive may be a reusable pressure sensitive adhesive such as that used in Post-it® notes. Alternatively, the cover 544 may be held in place by some other fastening system such as a Velcro® type fastening system.

Figure 55A:
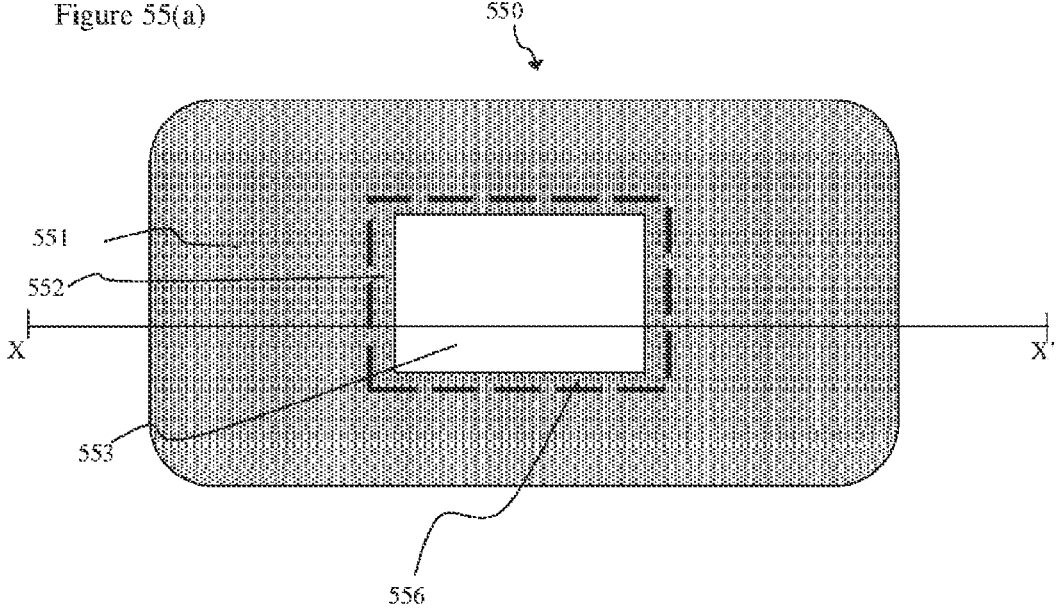
Figure 55B:
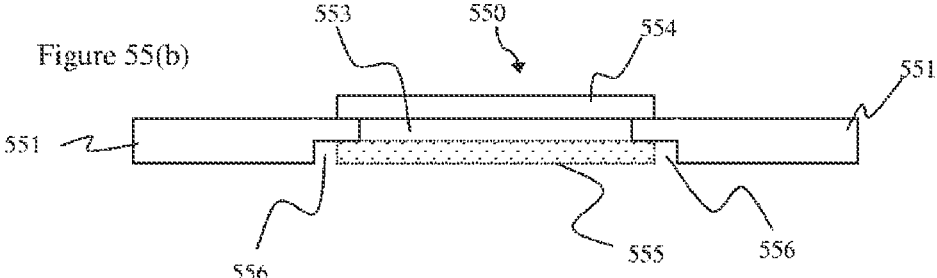

FIGS. 55(a) and 55(b) are, respectively, a top non-wound facing view and a cross-sectional side view taken along the line X-X' of another exemplary embodiment of a bandage 550 with a wound portal according to the present invention. The bandage 550 has a body portion 551 with an aperture 553. The aperture 553 is preferably sized to be greater than the size of a wound it is intended to bandage. The body portion 551 has a recess 552/556 in a bottom portion around the aperture 553. Although the recess 552/556 is not visible from the top non-wound facing view of the bandage 550, the recess 552/556 is indicated by a dashed line. The cover 554, shown only in FIG. 55(b) affixes to the top non-wound-facing surface of the body portion 551. As shown in FIG. 55(b), the gauze 555 that is within the aperture 553 is not attached to the cover 554 and is instead held in place by a protuberance from the top portion of the body portion 551 formed above the recess 552/556 around the aperture 553. However, as in previous embodiments of the bandages with a wound portal, the gauze 555 may be attached in some manner similar to that discussed by the gauze 545.

Figure 56A:
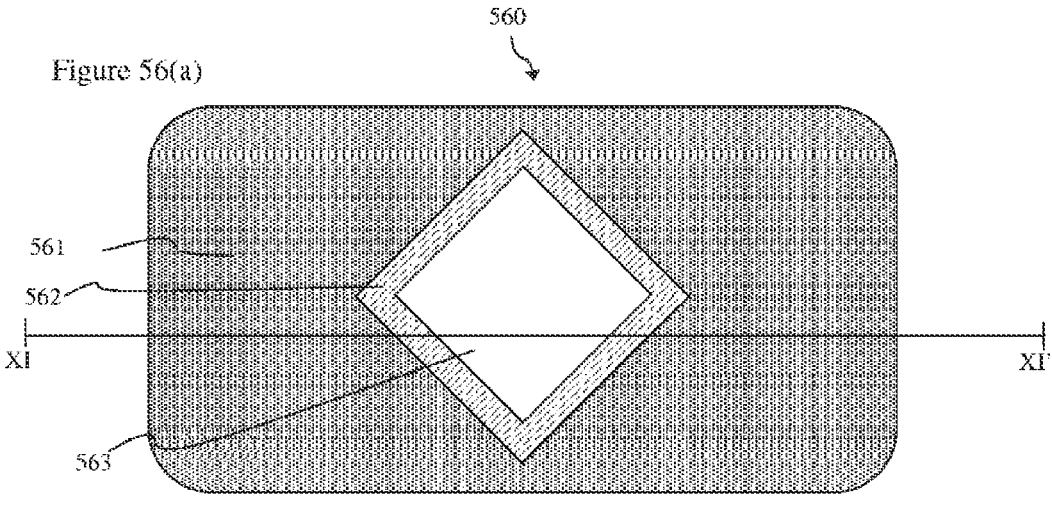
Figure 56B:
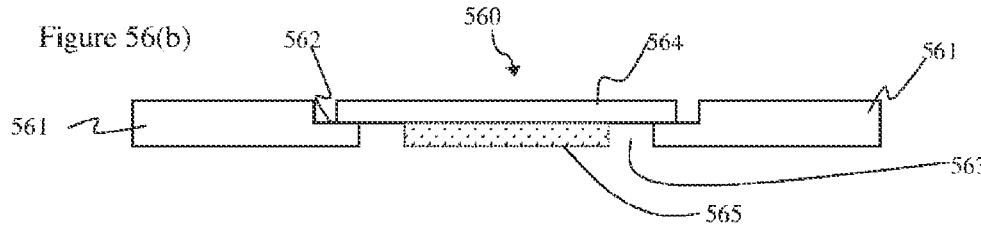

FIGS. 56(a) and 56(b) are, respectively, a top non-wound facing view and a cross-sectional side view taken along the line XI-XI' of an exemplary embodiment of a bandage 560 with a wound portal with a "diamond gauze" configuration according to the present invention. It should be noted that the bandage 560 incorporates a "diamond gauze" configuration, comparable to that of the bandage 140, with the wound portal configuration of the bandage 530. However, other wound portal configurations such as those in the bandages 530C, 530D, 530E may, alternatively, be used in the bandage 560. Moreover, all "diamond gauze" and "triangle gauze" bandage configurations may incorporate wound portals with configurations such as those shown in the bandages 530, 530C, 530D, and 530E.

The bandage 560 has a body portion 561 with an aperture 563 that is a square shape. Alternatively, the aperture 563 may be configured in the shape of a diamond or rhombus. Corners of the aperture 563 are offset from the corners of the body portion 561 such that the sides of the aperture 563 are not parallel to the sides of the body portion 561. The aperture 563 may have the same center point as the body portion 561, and/or each of the corners of the aperture 563 may be oriented toward a mid-point of one of the sides of body portion 561. A bottom wound-facing side of the body portion 561 may have adhesive such as those used for bandages in the art. The aperture 563 is preferably sized to be greater than the size of a wound it is intended to bandage. The body portion 561 preferably has a shelf 562 surrounding the aperture 563.

A cover 564, which is only shown in FIG. 56(b), is sized to substantially fill the aperture 563 and to extend at least partially onto the shelf 562. Preferably, the thickness of the cover 564 and the shelf 562 together should be approximately equal to or less than the thickness of the body portion 561 immediately surrounding the shelf 562 so that the top of the cover 564 will be flush or lower than portions of the body portion 561 that surround the shelf 562 and the aperture 563. The cover 564 may be held in place via an adhesive suitable for bandages as is known in the art that is either applied to the shelf 562 or to the cover 564. The adhesive may be a reusable pressure sensitive adhesive such as that used in Post-it® notes. Alternatively, the cover 564 may be held in place by some other fastening system such as a Velcro® type fastening system.

A gauze pad 565 may be placed within the aperture 563 to cover a wound. The gauze pad 565 may be attached to the cover 564 via a reusable pressure sensitive adhesive such as that used in Post-it® notes or by some other fastening system such as a Velcro® type fastening system or by a more permanent form of fastening. Alternatively, the gauze pad 565 may not be attached to the cover 564 and may instead be held in place by the cover 564 and/or by the sides of the aperture 563 without use of adhesive.

FIG. 57 is a top non-wound facing view of an exemplary embodiment of a bandage 570, according to the present invention. The bandage 570 incorporates the wound portal configuration of the bandage 270 into the wound/bandage protector 60. In other words, the bandage 570 has a body portion 571 that is configured as a wrap, first-catch fastening surface 572 and two fastening straps 573 that are configured in the same manner as in the wound/bandage protector 60 with an aperture 574, shelf 575, cover (not shown in figure) and gauze pad (not shown in figure) configured in the same manner as in the bandage 570. All of the exemplary embodiments of wound portal bandage configurations discussed above such as those shown in the exemplary embodiments of bandages shown in FIGS. 53-56 may be incorporated into any of the exemplary wound/bandage protectors shown in FIGS. 2-11, 61, 65 and 66 and/or with any of the exemplary "diamond gauze" and "triangular gauze" bandages shown in FIGS. 12-23, 26-52 and 64. Moreover, any of the exemplary wound/bandage protectors shown in FIGS. 2-11, 61, 65 and 66 may be combined with any of the "diamond gauze" and "triangular gauze" bandages shown in FIGS. 12-23, 26-52 without a wound portal configuration. For example, FIGS. 63(a)-63(b) show respectively, a bottom wound facing view and a side view of an alternative exemplary configuration of the wound/bandage protector 60 according to the present invention. In this configuration, instead of the gauze pad 69, a gauze pad 639 is attached or removably attached to the wound-facing side of the body portion 61 in a "diamond gauze" configuration. Moreover, instead of the gauze port 62A, a gauze port 632A may be configured in a "v" shape (as shown), to follow a portion of the perimeter of the gauze pad 639 or may have any other configuration that provides for attachment of all or a portion of the gauze pad 639.

FIGS. 58(a) and 58(b) are, respectively, a top view and a side cross-sectional view taken along line XII-XII' of an exemplary embodiment of a frictional gauze pad 580 according to the present invention. The frictional gauze pad 580 has a pad portion 581 and a frame 582. The pad portion 581 may be comprised of materials similar to that of the frictional gauze pads discussed above. The frame 582 is attached to and extends from the edge of the pad portion 581. The frame 582 may be comprised of a self-adherent material or a rubberized or tacky material and may have a similar configuration as the strip 62 in FIG. 6(a) above. The frictional gauze pad 580 can be used instead of a gauze port or similar method of securing the gauze in place by providing a frictional or similar resistance between the frame 582 of the frictional gauze pad 580 and a bandage and/or a frictional or similar resistance between the frictional gauze pad 580 and the area surrounding the wound. Thus, for example, in the wound/bandage protector 60, in lieu of providing a gauze port 62A, one may use the frictional gauze pad 580. In addition, the wound/bandage protector 60 may be further configured to include a corresponding self-adherent material or a rubberized or tacky surface on the wound facing side of the body portion 61 to further enhance the frictional or similar resistance between the wound/bandage protector 60 and the frictional gauze pad 580. One skilled in the art would understand that this frictional gauze pad 580 may be applied to any and all of the bandages discussed above as well as to other bandages known in the art.

FIGS. 59(a)-(e) show alternative exemplary embodiments of a frictional gauze pad according to the present invention. FIG. 59(a) may be a top view and/or a bottom view of a gauze pad 590 with a pad portion 591 and a frame 592. The pad portion 591 may be comprised of materials similar to that of the frictional gauze pad 290, discussed above. The frame 592 may be affixed to the top and/or bottom surface of the pad portion 591. Alternatively, the frame 592 may be attached to and extend from the edge of the pad portion 591. The frame 592 may be comprised of a self-adherent material or a rubberized or tacky material. FIG. 59(b) is a side cross-sectional view of one alternative embodiment of a frictional gauze pad 300B, with a frame 592B, that has the same configuration as the frame 592, attached to the top surface of a pad portion 591B of the frictional gauze pad 300B. FIG. 59(c) is a side cross-sectional view of another alternative embodiment of a frictional gauze pad 590C, with a frame 592C, that has the same configuration as the frame 592, attached to the bottom surface of a pad portion 591C of the frictional gauze pad 590C. FIG. 59(d) is a side cross-sectional view of another alternative embodiment of a frictional gauze pad 590D, with a frame 592D, that has the same configuration as the frame 592, attached to both the top surface and the bottom surface of a pad portion 591D of the frictional gauze pad 590D. FIG. 59(e) is a side cross-sectional view of another alternative embodiment of a frictional gauze pad 590E in which a frame 592E is extended to cover the entire top surface of a pad portion 591E. This embodiment may be combined with the frictional gauze pad 590C in which the frame 592C is attached to the bottom of the pad portion 591C.

Figure 61A:
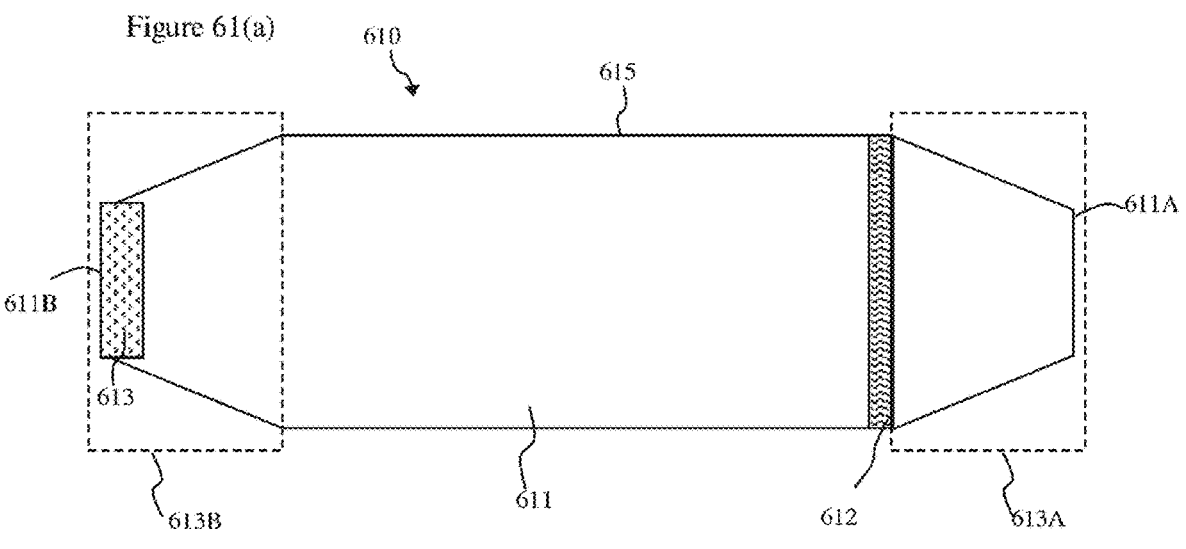
Figure 61B:
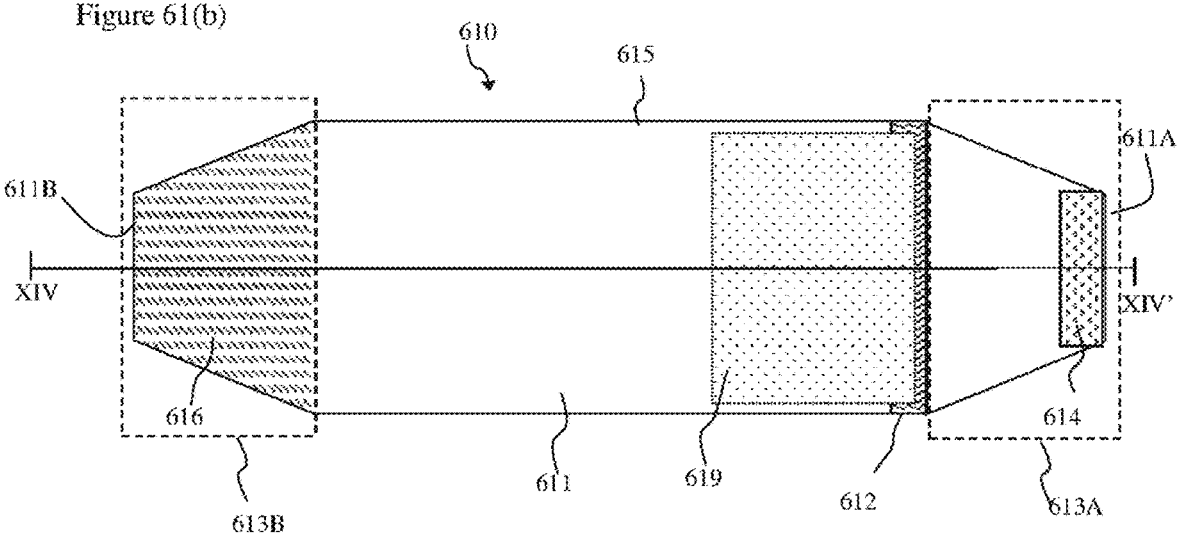
Figure 61C:
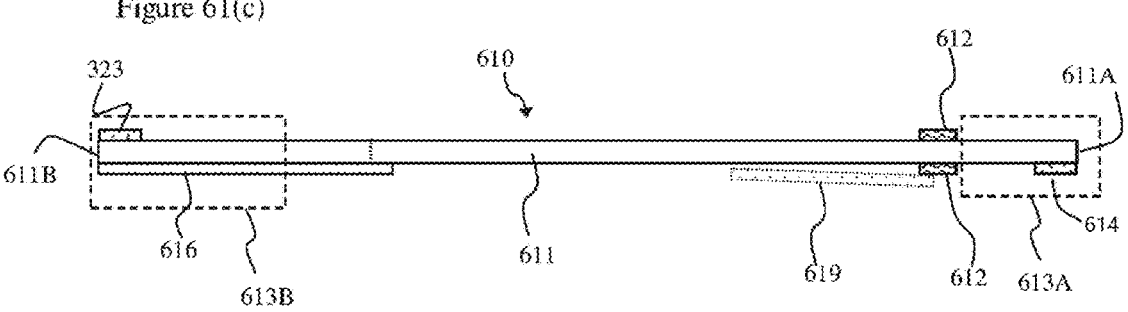

FIGS. 61(a)-61(c) are, respectively, a top non-wound facing view, a bottom wound facing view, and a cross-sectional side view taken along the line XIV-XIV' of an exemplary embodiment of a wound/bandage protector 610 according to the present invention. The exemplary embodiment of the wound/bandage protector 610 has a body portion 611 that is configured as a wrap which may be comprised of super-stretch material similar to the super-stretch material used in the body 21, 31 of the bandage mittens/socks 20, 30. The body portion 611 is configured to act as a loop portion of a Velcro® type fastener on both the bottom wound-facing side of the wound/bandage protector 610 and the top non-wound facing side of the wound/bandage protector 610. The body portion 611 has a length that runs from a first end 611A to a second end 611B with a first end region 613A that extends along the length of the body portion 611 from the first end 611A to a central region 615, the central region extending along the length of the body portion from the first end region 613A to a second end region 613B, and the second end region extending along the length of the body portion from the central region 615 to the second end 611B. The stretchable material of the body portion 611 at least provides such stretching capacity in a manner that allows the length of the body portion 611, i.e. the distance between the first end 611A and the second end 611B, to vary. The stretchable material of the body portion 611 may alternatively provide such stretching capacity that allows both the length of the body portion 611 as well as a width of the body portion 611, which is perpendicular to the length of the body portion 611, to vary.

A gauze port 612 is preferably positioned on or integrated into the central region 615 of the body portion 611 adjacent or proximal to the first end region 613A. The gauze port 612 is an area where a portion of a gauze pad 619 may be attached or removably attached to the wound-facing side of the body portion 611. The gauze port 612 may be comprised of non-stretchable material and may have a surface at least on the wound facing side of the wound/bandage protector 610 that is configured for repeated removal and attachment of gauze by having either a hook or loop Velcro® type fastening surface or that provides a good bond with a re-stickable adhesive such as that found in Post-it® notes. Alternatively, the surface of the gauze port 612 at least on the wound facing side of the wound/bandage protector 610 may be configured for permanent attachment of the gauze pad 619 to the body portion such as by permanent adhesive. The gauze port 612 may be used to attach different sized gauze pads 619 as well as to periodically replace the gauze pad 619 in the wound/bandage protector 610 shown in this embodiment. The gauze port 612 may be sized and/or configured so as to attach to all, a substantial portion, or a small portion such as one side of the gauze pad 619.

The first end region 613A is tapered so as to provide a gradual diminution in the width of the body portion 611 as the first end region extends in a length direction toward the first end 611A. On the first end region 613A, although not necessarily on the entire first end region 613A, is a fastening portion 614 that can engage and hold fast to the body portion 611 on the top non-wound facing side of the wound/bandage protector 610, or a portion thereof. The fastening portion 614 may be made of a Velcro® hook type material provided on the bottom wound-facing side of the wound/bandage protector 610. The fastening portion 614 preferably extends to the first end 611A.

The second end region 613B is tapered so as to provide a gradual diminution in the width of the body portion 611 as the second end region extends in a length direction toward the second end 611B. On the wound facing side of the second end region 613B is a frictional portion 616 that provides resistance to motion between the wound/bandage protector 610 and a surface to which it is applied, such as skin, hair, or fur. The frictional portion 616 may have one or more threads made of a rubberized material that provides a moderate amount of friction interwoven in the frictional portion 616 in such a manner that the rubberized material threads are exposed. Alternatively, the frictional portion 616 may be made of a material or a coating that provides a frictional surface. Preferably, the amount of friction provided by the frictional surface of the frictional portion 616 should be one that does not cause discomfort when the wound/bandage protector 610 is worn. The frictional portion 616 may, alternatively, be positioned between the gauze port 612 and the first end region 613A, similar to the strip # in the exemplary wound/bandage protector # as well as other exemplary embodiments of wound/bandage protectors provided herein. Alternatively, the frictional portion 616 may be provided on another portion of the wound-facing side of the wound/bandage protector 610 that does not conflict with the gauze pad 619, the gauze port 612, or the fastening portion 614. Similarly, the other exemplary embodiments of wound/bandage protectors provided herein may have a frictional portion positioned in a similar or equivalent manner as that of wound/bandage protector 610. In addition, the frictional portion 616 of wound/bandage protector 610 may be provided along the top non-wound facing side of the wound/bandage protector 610 and/or the bottom wound facing side of the wound/bandage protector 610.

On the second end region 613B is a first catch fastening surface 613 on the non-wound-facing side of the wound/bandage protector 610. The first catch fastening surface 613 preferably extends to the second end 611B. The first catch fastening surface 613 may be made of a Velcro® hook type material so that the first catch fastening surface 613 may securely fasten to a portion of the wound facing side of the body portion 611 when the wound/bandage protector 610 is being secured. Thus the first catch fastening surface 613, as in all the exemplary wound/bandage protector embodiments disclosed herein, allows for initially securing the wound/bandage protector 610 around a limb and then for further tightening and/or securing of the wound/bandage protector 610 by fastening the fastening portion 614 to a portion of the non-wound facing side of the body portion 611.

FIGS. 65(*a*)-(*c*) illustrate a top non-wound-facing view, a bottom wound facing view, and a cross-sectional side view taken along the line XVII-XVII' of a wound/bandage protector 650 having a first end 321A and a second end 321B, an attachment region 327, and a gauze pad 329, which is an alternative arrangement for the wound/bandage protector 610. In this alternative arrangement, all the elements and structural limitations are the same, except that the frictional portion 326 is positioned on the bottom wound facing side of the wound/bandage protector 650 between the gauze port 322 and the first end 321A, i.e. preferably within the first end region 323A and the first catch fastening surface 323 on the non-wound-facing side of the wound/bandage protector 610 within the first end region 323A, while the fastening portion 324 is positioned on the wound-facing side of the wound/bandage protector 610 within the second end region 323B. In addition, a portion of the frictional portion 326 may also provide the necessary functionality of the gauze port 322.

FIGS. 62(*a*)-62(*c*) are, respectively, a top non-wound-facing view, a bottom wound facing view, and a cross-sectional side view taken along the line XV-XV' of an exemplary bandage wrap protector/holder 620 according to the present invention. The exemplary embodiment of the bandage wrap protector/holder 620 has a body portion 621 that is preferably comprised of super-stretch material similar to the super-stretch material used in the body 21, 31 of the bandage mittens/socks 20, 30. If the bandage wrap protector/holder 620 is primarily intended to be used as a bandage holder, then the super-stretch material of the body portion 621 may have a relatively high elastic modulus. If the bandage wrap protector/holder 620 is primarily intended to be used as a bandage protector, then the super-stretch material of the body portion 621 may have a relatively low elastic modulus. In the exemplary embodiment, the body portion 621 is configured to act as a loop portion of a Velcro® type fastener on both the bottom wound-facing side of the bandage wrap protector/holder 620 and the top non-wound facing side of the bandage wrap protector/holder 620. Alternatively, the bandage wrap protector/holder 620 may be configured to act as a loop portion of a Velcro® type fastener only on the top non-wound facing side of the bandage wrap protector/holder 620 or the bandage wrap protector/holder 620 may not be configured to act as a loop portion of a Velcro® type fastener at all. The body portion 621 has a length that runs from a first end 621A to a second end 621B with a first end region 623A that extends along the length of the body portion 621 from the first end 621A to a central region 625, the central region 625 extending along the length of the body portion from the first end region 623A to a second end region 623B, and the second end region extending along the length of the body portion from the central region 625 to the second end 621B. The stretchable material of the body portion 621 at least provides such stretching capacity in a manner that allows the length of the body portion 621 to vary. The stretchable material of the body portion 621 may, alternatively, provide such stretching capacity that allows both the length of the body portion 621 as well as a width of the body portion 621 which is perpendicular to the length of the body portion 621 to vary. Both the first end region 623A and the second end region 623B are preferably tapered so as to provide a gradual diminution in the width of the body portion 621 as the first and second end regions 623A, 623B extend lengthwise from the central region 625. On the wound facing side of the bandage wrap protector/holder 620 both the first and second end regions 623A, 623B have fastening portions 624A, 624B that are configured as hook portions of a Velcro® type fastener. The fastening portions 624A, 624B preferably extend to the first and second ends 621A, 621B, respectively.

The exemplary bandage wrap protector/holder 620 may be used in several ways. First, the bandage wrap protector/holder 620 may be used as bandage holder. For example, a limb with a wound that is wrapped with a bandaging material wrap (similar to a regular Ace-type bandage) that can act as a loop portion of a Velcro® type fastener on a non-wound/limb facing side of the bandaging material wrap may be kept closed by the bandage wrap protector/holder 620. (For all exemplary embodiments described herein, other types of fasteners may be implemented and, therefore, for whatever type of fastener is implemented for the bandage wrap protector/holder 620, a complementary fastener would be implemented on the bandaging material wrap.) In such a case, the bandage wrap protector/holder 620 may be secured by one of the fastening portions 624A, 624B to a non-wound/limb facing side of the bandaging material wrap on or close to the external/exposed end of the bandaging material wrap. The wrap protector/holder 620 then is extended rotationally around the bandaging material wrap in the same direction as the bandaging material wrap was wound around the limb and then the other one of the fastening portions 624A, 624B may then be secured to another external/exposed portion of the bandaging material wrap. Alternatively, the wrap protector/holder 620 may be extended entirely around the circumference of the limb and then the other one of the fastening portions 624A, 624B may then be secured to a non-wound facing side of the body portion 621 of the wrap protector/holder 620. In this case, the body portion 621 preferably has a width that is greater than the width of the bandaging material wrap so as to completely cover and protect the bandaging material wrap. It is also preferable in this case that the body portion 621 of the wrap protector/holder 620 be comprised of material that is breathable and water resistant.

Alternatively, the wrap protector/holder 620 may be used as a first catch fastener/holder for the bandaging material wrap by securing one of the fastening portions 624A, 624B to the wound/limb facing side of the bandaging material wrap on or close to the internal/covered end of the bandaging material wrap. The bandaging material wrap may then be wrapped around the circumference of the limb by first extending length-wise away from the body portion 621 and attaching to the wrap protector/holder 620 via the other one of the fastening portions 624A, 624B.

Furthermore, the wrap protector/holder 620 may be used in conjunction with one or more fastening bases to cover a wound/bandage. FIGS. 63(*a*)-63(*c*) are respectively an exemplary embodiment of a non-wound/limb facing side, a wound/limb facing side and a cross-sectional side view taken along the line XVI-XVI' of an exemplary embodiment of a fastening base 630 according to the present invention. On the non-wound/limb facing side of the body portion 631, all or a portion of the body portion 631 of the fastening base 630 is configured to act as a loop portion of a Velcro® type fastener. On the wound/limb facing side of the body portion 631, all or a portion of the body portion 631 of the fastening base 630 has an adhesive 632 known in the art of bandaging for adhering to skin, hair, fur, etc. The fastening base 630 may, for example, be adhesively attached to a limb, positioned away from a wound/bandage on the limb via the adhesive 632. The wrap protector/holder 620 may then be coupled to the fastening base 630 by fastening one of the fastening portions 624A, 624B of the wrap protector/holder 620 to the non-wound facing side of the fastening base 630, then extending the body portion 621 of the wrap protector/holder 620 over the wound and then fastening the other one of the fastening portions 624A, 624B to the fastening base 630 on the other side of the wound. Together, the wrap protector/holder 620 and the fastening base 630 thereby traverse the entire circumference of the limb. Alternatively, two fastening bases may be adhesively attached to the limb, positioned on opposing sides of a wound/bandage via an adhesive on the wound/limb facing side of the fastening base so as to allow for fastening the protector/holder 620 to the limb with one of the fastening portions 624A, 624B fastened to one of the fastening bases and the other one of the fastening portions 624A, 624B attached to the second fastening base and the body portion 621 of the wrap protector/holder 620 extending over the wound/bandage, without the need to traverse the entire circumference of the limb.

The embodiments of the invention described herein are exemplary in nature, and therefore, the spirit and the scope of the invention are by no means restricted to what is described above or intended to represent every possible embodiment of the invention. For example, when Velcro is mentioned, the hook portion could be the loop portion and the loop portion could be the hook portion, or it could be a different type of fastening system altogether such as reusable adhesive with a surface that can adhere well to a reusable adhesive or magnetic fasteners, or a self adhering material surfaces, snaps, buttons. Moreover, where reusable adhesive is mentioned, could also be any other form of fastening, or releasable fastening, and in cases where permanent fastening is a possibility, use of other methods of attachment such as heat and punch, radio frequency sealing, ultrasonic sealing or bonding or sewing may also be used. A gauze pad does not need to be square or rectangular it may be any shape that is sufficient to treat a particular wound. The wound/bandage protectors may or may not be configured with a first catch tab and the tab may or may not be configured with a fastener or fastening surface. Likewise, structural limitations discussed by one exemplary embodiment of a wound/bandage protector or sock/mitten or bandage or adhesive bandage may be applied to other exemplary embodiments of the wound/bandage protector or sock/mitten or bandage or adhesive bandage.

What is claimed is:

1. A wrapping, comprising:
   a body configured as a sock/mitten having a first end that is open, a second end that is closed, an internal side, and an external side; and
   a fastening strap attached to the body and having an internal side and an external side,
   wherein a non-slip grip material is disposed on the internal side of the body,
   wherein the fastening strap extends entirely or partially around the external side of the body and fastens to at least one of the external side of the body and the external side of the fastening strap upon the fastening strap being wrapped around a body part and fastened, wherein the non-slip grip material is adapted to contact the body part upon the fastening strap being wrapped around the body part and fastened, wherein an end of the fastening strap is attached to the body at an attachment region, and the attachment region is a dead zone that provides little to no stretch at a point of attachment of the fastening strap, wherein the attachment region is disposed at a fixed location on the body at a location such that an entirety of the fastening strap entirely overlaps the external side of the body upon the fastening strap being wrapped around the body part and fastened, wherein the body comprises a breathable material.

2. The wrapping of claim 1, wherein the body comprises a stretchable material.

3. The wrapping of claim 2, wherein the body comprising the stretchable material is stretchable to at least double an un-extended size of the body.

4. The wrapping of claim 1, wherein the non-slip grip material is positioned to be on an internal side of the wrapping at a portion aligned with an upper half of the wrapping and is fixed so that the non-slip grip material makes contact with the body part and the internal side of wrapping upon the fastening strap being wrapped around the body part and fastened.

5. The wrapping of claim 1, wherein an entirety of the wrapping is a dead zone having little to no stretch.

6. The wrapping of claim 1, wherein the non-slip grip material is further disposed on the external side of the body.

7. A wrapping, comprising:

a body configured as a sock/mitten having a first end that is open, a second end that is closed, an internal side, and an external side, wherein the body is tapered from the second end to the first end such that the second end is larger than the first end, wherein the body comprises a first side portion, a second side portion opposing the first side portion, a third side portion, and a fourth side portion opposing the third side portion, wherein the first side portion connects the first end to the third side portion, and the second side portion connects the first end to the fourth side portion, wherein the first and second side portions are straight and run parallel to each other, wherein the third and fourth side portions are curved, wherein among the first to fourth side portions, the first and second side portions are the only side portions that run parallel to each other, wherein a non-slip grip material is disposed on the internal side of the body, wherein the non-slip grip material comprises a rubberized material, wherein the body comprises a stretchable material.

8. The wrapping of claim 7, further comprising:

a fastening strap attached to the body and having an internal side and an external side.

9. The wrapping of claim 8, wherein the fastening strap is attached to the body at the first side portion of the body.

10. The wrapping of claim 8, wherein the fastening strap extends around the external side of the body and fastens to the external side of the fastening strap upon the fastening strap being wrapped around a body part and fastened, wherein the fastening strap is attached to the body at a location on the body such that an entirety of the fastening strap entirely overlaps the external side of the body upon the fastening strap being wrapped around the body part and fastened.

11. The wrapping of claim 8, wherein the non-slip grip material is positioned to be on an internal side of the wrapping at a portion aligned with an upper half of the wrapping and is fixed so that the non-slip grip material makes contact with a body part and the internal side of wrapping upon the fastening strap being wrapped around the body part and fastened.

12. The wrapping of claim 7, wherein the body comprises a water resistant material.

13. The wrapping of claim 7, wherein the body comprises a waterproof material.

14. The wrapping of claim 7, wherein the body comprising the stretchable material is stretchable to at least double an un-extended size of the body.

15. The wrapping of claim 7, wherein the non-slip grip material is further disposed on at least a portion of the external side of the body.

16. A wrapping, comprising:

a body configured as a sock/mitten having a first end that is open, a second end that is closed, an internal side, and an external side, wherein the body is tapered from the second end to the first end such that the second end is larger than the first end, wherein the body comprises a first side portion, a second side portion opposing the first side portion, a third side portion, and a fourth side portion opposing the third side portion, wherein the first side portion connects the first end to the third side portion, and the second side portion connects the first end to the fourth side portion, wherein the first and second side portions are straight and run parallel to each other, wherein the third and fourth side portions are curved, wherein among the first to fourth side portions, the first and second side portions are the only side portions that run parallel to each other, wherein a non-slip grip material is disposed on the internal side of the body, wherein the non-slip grip material comprises a rubberized material, wherein the body comprises a breathable material.

* * * * *